US011013796B2

(12) United States Patent
Gauger et al.

(10) Patent No.: US 11,013,796 B2
(45) Date of Patent: May 25, 2021

(54) PORCINE PARAINFLUENZA VIRUS TYPE 1 ISOLATES AND IMMUNOGENIC COMPOSITIONS THEREFROM

(71) Applicant: Iowa State University Research Foundation, Inc., Ames, IA (US)

(72) Inventors: Phillip Gauger, Ames, IA (US); Jie Yeun Park, Ames, IA (US); Karen M. Harmon, Ames, IA (US); Jianqiang Zhang, Ames, IA (US); Pablo Pineyro, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 16/557,177

(22) Filed: Aug. 30, 2019

(65) Prior Publication Data

US 2020/0069789 A1 Mar. 5, 2020

Related U.S. Application Data

(60) Provisional application No. 62/724,713, filed on Aug. 30, 2018.

(51) Int. Cl.

*A61K 39/155* (2006.01)
*C12N 7/00* (2006.01)
*C12Q 1/70* (2006.01)
*A61K 39/00* (2006.01)

(52) U.S. Cl.

CPC .............. *A61K 39/155* (2013.01); *C12N 7/00* (2013.01); *C12Q 1/701* (2013.01); *A61K 2039/5254* (2013.01); *A61K 2039/545* (2013.01); *A61K 2039/552* (2013.01); *A61K 2039/575* (2013.01); *C12N 2760/18621* (2013.01); *C12N 2760/18634* (2013.01); *C12N 2760/18664* (2013.01); *C12Q 2600/112* (2013.01)

(58) Field of Classification Search

None

See application file for complete search history.

(56) References Cited

U.S. PATENT DOCUMENTS

| | | | |
|---|---|---|---|
| 2016/0206722 A1 | 7/2016 | Hayes et al. |
| 2017/0065709 A1 | 3/2017 | Burgard et al. |
| 2018/0064804 A1 | 3/2018 | Zhang et al. |
| 2018/0133309 A1 | 5/2018 | Bucklin et al. |

FOREIGN PATENT DOCUMENTS

WO WO/2017/120168 * 7/2017

OTHER PUBLICATIONS

Lytle and Sagripanti, Predicted Inactivation of Viruses of Relevance to Biodefense by Solar Radiation, 2005, Journal of Virology, vol. 79, No. 22, pp. 14244-14252.*

Gauger, Phillip, "Pathogenesis of a parainfluenza virus associated with respiratory disease in swine", BMS Seminar Cosponsored by Neuroscience, Flyer, 1 page Nov. 2, 2017.

Gauger, Phillip, "Pathogenesis of Porcine Parainfluenza Virus type 1 & Iowa State University Veterinary Diagnostic Laboratory" Powerpoint, 46 pages, Nov. 2, 2017.

"Porcine respirovirus 1 strain USA/MN25890NS/2016 complete genome", Genbank: MF681710.1, 7 pages, Sep. 4, 2017.

Lau et al., "Identification and characterization of a novel paramyxovirus, porcine parainfluenza virus 1, from deceased pigs", Journal of General Virology, vol. 94, pp. 2184-2190, Jul. 26, 2013.

Palinski et al., "Widespread detection and characterization of porcine parainfluenza virus 1 in pigs in the USA", Journal of General Virology, vol. 97, pp. 281-286, 2016.

Park et al., "Complete Genome Sequence of Porcine respirovirus 1 Strain USA/MN25890NS/2016, Isolated in the United States", Genome Announcements, vol. 5, Issue 42, 2 pages, Oct. 19, 2017.

Welch et al., "Porcine Parainfluenza Virus Type-1 (PPIV-1) in weaned and CDCD Piglets", Iowa State University, Dept of Veterinary Diagnostic and Production Animal Medicine, Powerpoint, 21 pages, Nov. 2, 2018.

Welch et al., "Pathogenesis of a Porcine Parainfluenza Virus-1 isolate in conventional and caesarean derived colostrum deprived piglets", Iowa State University, Dept. of Veterinary Diagnostic and Production Animal Medicine, Jowerpoint, 1 page, Jan. 5, 2018.

Welch et al., "Pathogenesis and transmission of a novel Porcine Parainfluenza Virus Isolate (MN25890NS/2016) in weaned and CDCD piglets", Iowa State University, Veterinary Diagnostic and Production Animal Medicine, 1 page, Jun. 11, 2018.

Welch et al., "Porcine Parainfluenza Virus Type 1 (PPIV-1) in U.S. Swine: Summary of Veterinary Diagnostic Laboratory Data", Iowa State University Animal Industry Report, 4 pages, 2017.

Welch et al., "Pathogenesis and Transmission of a Porcine Parainfluenza Virus-1 Isolate (MN25890NS/2016) in Growing Pigs", Iowa State University, Dept. of Veterinary Diagnostic and Preventive Animal Medicine, 3 pages, Nov. 2, 2017.

Welch et al., "Pathogenesis of a porcine parainfluenza virus-1 isolate (USA/MN25890NS/2016) in conventional and CDCD piglets", Iowa State University, Dept. of Veterinary Diagnostic and Preventive Animal Medicine, 3 pages, Mar. 3, 2017.

* cited by examiner

*Primary Examiner* — Benjamin P Blumel

(74) *Attorney, Agent, or Firm* — McKee, Voorhees & Sease, PLC

(57) ABSTRACT

The present invention is directed to novel nucleotide and amino acid sequences of Porcine Parainfluenza Virus Type 1 ("PPIV-1"), including novel genotypes thereof, all of which are useful in the preparation of immunogenic compositions and vaccines for treating and preventing disease in swine.

45 Claims, 11 Drawing Sheets

Specification includes a Sequence Listing.

A

B

SEQUENCE LISTING

```
<160> NUMBER OF SEQ ID NOS: 15

<210> SEQ ID NO 1
<211> LENGTH: 15334
<212> TYPE: DNA
<213> ORGANISM: Porcine respirovirus 1

<400> SEQUENCE: 1
ggttaaagta ttaacctcaa aaggacagat caggaacttt gatttcttag catagtgcca     60
aaatggcagg gttattaagt gtctttgaca catttagttc taaaaggagt gaaagcataa    120
atagaggagg tggtggtgcg gttatacctg gacaaaagaa caccgtctca gtatttgtcc    180
tagggtcaag tattgtagac gacagcgata agttagctat agcactcatg tttttaacac    240
atgctcttga tactgacaag caacactcac aaagaagcgg tttcctggtt tcattaatgg    300
caatggcata tagtagtcct gaattatatc taacaactaa tggagttaat gcagatgtta    360
agtatgttat ctacacaatt gagcatgatc cccagaggac aacccataat gggttcattg    420
ttaggacaag agatatggac tatgaaaaga caacagagtg gctattcagc cgtataacta    480
ataaataccc actacttcag ggacaaaaag acactcatga tccagaatca ctactccaga    540
cttatggata tccctcatgt ttaggagcat tgataatcca ggtttggatt gtcttggtca    600
aagcaattac aagtagtgct ggattgaaga aaggattctt caatagactt gaagccttca    660
ggcaggatgg aacagttaga agctcactag tcttcagtgg ggagacagtt gaggggattg    720
ggtcagtgat gagatctcag cagagtttgg tgtccttaat ggtagagact ctagttacca    780
tgaacacggc cagatctgac ttgaccactc tagaaaagaa tattcagatt gttgggaatt    840
acatcaggga tgcaggtctt gcttcattca tgaacacgat tagatatggt gtggagacta    900
agatggcagc acttacatta tctaatctta gacctgatat taataaacta aagagtctaa    960
ttgacatcta cttatccaaa ggtgcaagag ccccccttcat atgcatatta cgtgatccgg   1020
tacacggaga atttgctcct ggaaattatc cagcattgtg gagttatgct atgggggtcg   1080
cagtagtcca gaacaaagcc atgcagcagt atgtgacagg gaggacttat ctggatatgg   1140
aaatgttcct tcttggtcaa gcagtagcta aagacgcaga atctaagatc agtaatgcat   1200
```

-continued

```
tagaggatga attaggtata actgaaaatg ccaaagacag gctcaaacat catcttgcta   1260
acctttctgg aggtgatgga gcttatcaca aacccactgg tggaggagca atagaagtta   1320
taattgacaa tgcagacata gatctcagga cagaggaaac cacagaagaa tcttcaatca   1380
ggctttccaa tattagagaa aacaaaggga gaatagcaga cgggcagagg agatgggaaa   1440
caaccagatc cattggtgat gaccccaatc cagacaacac cactgacgat gaagtatccg   1500
ccgcagaaag gaggattgca gaaagactgg caaaaaagga ggggaagaat accaggtcgg   1560
atatactcat taccgatggt atgactgaag atacagataa cgatgatgat ataatgagaa   1620
tgaatgcact aggaggaata taataaatcc aaacaaaggg ttttatatat tggttagtaa   1680
gaaaaactta gggtgaaaga atagctccta gatactagga actctatcac tcccaaagac   1740
aggatctcaa actggccacc cacaaaagaa tcccccaaaa tccagatacc aaatggatca   1800
agatgccctc ttttctgaag aatctatgga ggatcagaag gagggacact caacaaccag   1860
cacactcacc agtgcagtcg gactcattga catcatcctt gccagtgagc ccacagacat   1920
tagaaaagac agaaaacacc tatgtgagcc catcacagcc tggggaaaat cagaagcaag   1980
caagatttcc aaggatacag tctgtgaaga aaacccaaga acagaaaggg aagattatgg   2040
acaaagtaaa aagagtggaa ttcctaggga gtcaaacaag ttcgaagcag aagtttcttt   2100
tagagaaact catagctcag gtacatcatg gagggcttgg agaagaagta gtgcaaactc   2160
tatacttgag aatatgggca atggatccga ctcctatggc aacgaaatta ctggaaatgg   2220
aggaggaaac cagagacaaa gtcctgaagc taaagttgga gagatggatc cgagttctaa   2280
tacgaggaga aaagacaaaa ctgagggact tccagaagag atacgaggag gttcacccat   2340
atctaatgac ggagaaggtg gaagaaataa taatggagga agcctggagt ctgtcagcac   2400
acataatcca agagtagaaa acaacattat ggatccaact catcatcttg aagaagaggt   2460
acttaagagg aacaagccac gggagatgaa tgctacaagt caatggtcgg gtggatacaa   2520
gactgatcaa caagacggta aacatgaatt gataaccaat ccaatatttt caaatcaaaa   2580
taggtcacag gacacaaaaa agggaaaagg gaaagaatca actgtaaagc ccaagaccag   2640
aaaatctaaa atatcctttg aagacacaag aagcacagat cacatctacg aagactctca   2700
agaacataca agaagaaaga aaacagacaa cgaaccatca caaaagattg gtaaaaaggg   2760
cacagaagag aataccttat atacagaaga ggtgatcaaa ttgttagtga gtcttggtgt   2820
aatcccatct gtagccgcat tcaaccaatc ccgaaacata tgccatgtat ttgcaaaacg   2880
tgtcctcaat tctgtgaact ctgcagaaat gacagctaat atgtgcggat tattgctgtc   2940
tgttgagaaa tcagtatcag accatattga agaaaataag acactaataa atcagattat   3000
aagtgattta agtacaggta gggaagtgca gaaacgtttc actgagtatc aaaaggaaca   3060
gaattcattg attatgtcaa atctggcgac acttcatatc ataacagata gaggaggaaa   3120
gaacaacagc atggatacag gggagaggac accatcaatc aggaccaagg ggaaggagcc   3180
aacacagaga acacaaagat ttgatccatc tatggaattc accgaggaga ttaagtacaa   3240
gcccgatcta tacagggaag acacattgag acaaagaata acaaaccctg ttcttgatga   3300
gagcgcagag agaatcgaca attcgaatgc cgcgagactg ataccttgca aagaaaaatc   3360
aacactgcgt tcactcaaat taattattga gaacagcaat ttgagcagag cagacaaaat   3420
tgcctatatc aggtcattat caaaatgcaa agatgacaaa gaggtagaat cagtaatgaa   3480
actatttgaa gaagatatag aatcaagtaa tgaataatca ctgatcagta tatccagaaa   3540
```

-continued acgtcaagac aagagtgtac tgtgatgagt aatgactctc caaataccta ataagaaaaa 3600
cttagggtgc aagactcacc aaccaagcca agcaaatggc cgagatctac aagttcccca 3660
agctatcata tgaggaacat ggatatatgg aacctctacc actaaggact ggcccagata 3720
agaaggcagt cccacatata aggataatca agataggggga cccaccgaag catggaaatc 3780
gatatcttga tattctctta cttgggtttt atgagatacc caaagaagtt ggaacatacg 3840
gtagtgtatc agatttgacg agacccacgg gatacacaat ctgcggttca ggatcattac 3900
ctattggaat tgctaggtac ttaggtacag atcaggaact actcaaagca tcagtagagc 3960
taaaagtgac agtgagaagg acagtaaggt caagtgagat gattgtgtat atggtagata 4020
ccataccacc agcaatgatg gcttgggctt ccaggttgaa acgaggcatg atattcaatg 4080
cgaataaagt agctctagct cctcaatgtc tacctataga taaagatata agattcagag 4140
ttgtctttgt caatggcact tctctaggtt ccatcacaat agcaaaagtt cccaagacat 4200
tagccgatct tgctttaccg aattccatat cggtcaattt aatggtctca ctcaagactg 4260
gtgcgtcaac tgagtccaag ggcattattc ctacgctaaa cgaaaagggc gacaaggtac 4320
taaactttat ggtacacctt ggattaatac ataggaaagt cggaagggtg tattcaatgg 4380
agtattgcaa gggtaaaata gagaagatgc ggctgatctt ctcattagga ctggttggag 4440
gaatcagttt ccatgttcag cttacaggtg tggtatctaa atcctttgtt ggtcagcttg 4500
gagggaggaa ggaaatatgt taccctttga tggatgtaaa cccacacatg aatttagtta 4560
tctgggctgc ttccgttgaa atcactggcg tggatgctgt tttccaacct tccataccaa 4620
gagatttcaa atactacccg aatgtggtgg caaaaaatat tgggaaaata aaagcttaga 4680
gatccaaagc cactgtaacc ccagacatcc caacactaga ctggtaagtg tcattatatg 4740
atcagcatca ttcatcagaa ataagaaaaa cttagggtac aagttatcca aaaaagacag 4800
aacagaacaa acagatcaag acaagacatc acaaaatgca aatcatcatc ctcagaccag 4860
ccataatact aagcatagta ctattagtga ccagtcaagt ccctagagat aaactagcca 4920
atttagggat catcattaag gacagcaaag cactcaaaat tgcaggatct tatgaaaaca 4980
gatacatagt cttaaacctt gtaccaacaa tagaaaatgt gggtgggtgt ggttccatcc 5040
aaatagcaaa atataaagag atgcttgaaa ggttgttaat accgataaaa gatgcactag 5100
atttacaaga gtctttgata atgattgata atgaaaccgt caacaacaat tatcgtcctc 5160
agtatagatt tgttggtgca attattggga ctatagccct tggggtagca actgcggccc 5220
aagttacagc aggggtggca ctgatggagg caagagaggc caaaagagat atatcagtgt 5280
taaaagaagc aattggaaag actcaaaact caattgaaaa attacagaat tctgcaggtg 5340
aacagatact ggctctcaaa atgctccagg attatgtcaa tggagagatt aaaccagcta 5400
ttgaagaact tggatgtgag actgctgcac ttaaattagg aattgcactt acacaacact 5460
acacagagct cacaaatgcc tttgggtcga atctaggttc cataggagag aagagcttaa 5520
cattacaggc cctatcatca ttatacaaga ccaatataac tgatatactg acaacaacta 5580
atctcgggaa aacagatatt tatgatatta tatatgctga gcaagttaaa ggaagagtaa 5640
tagatgtcga tcttagacga tatatggtta caatatctgt taagatacca atattatcag 5700
aaataccagg agtattgatc tatgaagtct cctctatatc ttataatata gatggaacag 5760
aatggtatgc cgctgtacct gaccacatat taagtaaatc cgcatatata gggggtgcag 5820
atataagtga ttgtatagaa tctggattga catatatttg tccgcgagat cctgctcaga 5880
ttatagcgga taaccaacag caatgttttt taggtcatct tgacaagtgc cctataacta 5940

```
aagtagttga taatcttgtg cctaaatttg cattcataaa tggtggagta gttgcaaact   6000
gtatagcctc tacatgtacc tgtggagaag agagggtcca ggtctctcaa gatagaaata   6060
aaggagtaac ctttttgact cataataatt gtggattaat agggataaac gggatggaat   6120
ttcatgctaa caagaaaggg agtgatgcta cttggaatgt ctcccccata agagcagggc   6180
cagcggtatc gttaagacca gtagatatat ctttacaaat agtttctgct actaattttc   6240
taaactcatc aagaaaagat cttatgaagg caaaagagat cttaaaccag gtaggaaatc   6300
ttagagattt aaccgtcata acgataatta atatagtaat tatagctgta ttacttatat   6360
gtgtaactgg attaggcgta ctgtatcacc aattgagaag tgcactagtg atgagagaca   6420
agatgtcagt attaaataat agttcctatt ctttagaacc aagaaccacc caggtacaag   6480
taattaagcc tactagtttc atgagataaa ctataaaaat atattttaat ccatcctcat   6540
taatcaaagt aaagaaaact tagggtgcac gacagtaact caccaccaaa ggagaaatag   6600
atcagagacc aacacaccaa gagatggaag gggccaaagt taagacatca gggtactggg   6660
ccaagagtcc tcaaattcac gcaacaaata atcctaacgt acaaaacaga gagaagatca   6720
aggaaacatt aacaatttta atatcattca tttctttcct atctcttgta ctggttatag   6780
ctgtactgat aatgcaatct ttacataacg gcacaatact aaggtgtaaa gatgtaggcc   6840
tagaatctat caataaatcc acttactcta tatctaatgc aattctggat gtcatcaaac   6900
aagagctgat aactcgtata ataaatactc aaagttctgt gcaggtagcc ctcccggtct   6960
taattaacaa gaaaatccag gatctctcac taaccattga gaaaagttca aaagtgcatc   7020
aaaattctcc tacttgtagt ggtgtggctg ccctgacaca tgtggaaggg ataaaacctt   7080
tggatccaga cgattactgg aggtgtccaa gtggggaacc atatctagag gatgaattga   7140
cattaagtct tatccctgga cctagtatgc tagctggaac ctctaccatc gatggctgtg   7200
taagattacc atctcttgca ataggaaaat cgctatatgc ctatagttcc aaccttataa   7260
ctaagggttg tcaagatata gggaaatcct atcaagtgct acagttaggt attataactc   7320
tgaattcaga cttacatcct gatttaaatc ctataatatc acatacttat gatataaatg   7380
ataatagaaa gtcctgttct gttgctgtat cagaaactaa aggataccaa ttatgctcga   7440
tgccgcgtgt caatgaaaaa acagattaca ctagtgatgg tattgaagat atagtttttg   7500
atgtacttga tctcaaaggg tcctctagaa gtttcaaatt ttcaaacaat gatataaact   7560
ttgatcatcc tttttcagcg ttataccccta gtgtaggaag tggtattata tgggaaaatg   7620
aactgtattt cctaggttac ggggctctga caactgcact tcaagggaat acaaaatgta   7680
atttaatggg atgtccagga gcaacacaaa acaactgcaa caagttcatc tctagttcat   7740
ggttatacag caaacagatg gttaatgtac tgatacaggt taaggggtat ttatctaaca   7800
agccaagtat tatagttaga acaatcccaa taacggaaaa ttatgtagga gcagaaggga   7860
aactagtggg aacacgtgag agaatatata tatatacaag atcaacgggt tggcatgcca   7920
atttacaaat aggagtactt aatataaatc atccaataac cataacttgg aaagatcaca   7980
aagtactatc aagaccagga agaagtcctt gtgcctggaa taacaaatgc cctagaaatt   8040
gtactactgg tgtatacaca gatgcttatc ctatatcgcc tgatgctaat tatgttgcta   8100
cagttactct attatctaat tcaacacgaa ctaatcctac tattatgtat tcatcttctg   8160
atagagtata taacatgtta agattaagaa atactgaatt agaagctgca tacacaacca   8220
cgtcttgtat tgtccacttt gatagaggtt attgttttca tattatagaa attaatcaaa   8280
```

-continued

```
aaggactgaa tacactacag cctatgctct ttaagactgc aattcctaaa gcttgcagga   8340
taagcaattt ataagacacc cattgaaata ataatttgta tctaattact taaaagggtg   8400
actgtgcatg acttagagat aagtgacctg tggacataaa tcatacaggt cattaaatag   8460
catataatac acctaataag aaaaacttag gttgaatgcc aaagcattca gccagaatgg   8520
atcatttcaa tatgtctcaa aatccaagtg atatactata ccctgaatgc cacttgaact   8580
ctccagttgt gaaagggaag atcgctcagc tacatgtctt gttagatatt aatcagccgt   8640
atgaaatgag ggaccctagt ataatagaaa tcacaaaagt taaaattaaa tctggagggt   8700
taaatcaaag gttaatcaga atcagatctt tagggaaaga gatgaggaga atcatatttg   8760
attttgataa gtatacattc gaaccttacc caatattttc taaagaatta tttagattag   8820
agataccaga gatttgtgat aaaattcaat cagtttttgc agtgtcggat aggttaagca   8880
aagatatatc ccagccatta caatacttat ggagagatgt gcgtaggcag ttgggagggg   8940
attgttccaa ggatctttct aacaatgaga ttgatataca caaaattcct gaaatccata   9000
ctaaattcac cagaaataac tggtataaac cattcatgac atggtttagt attaaatatg   9060
atatgagaag atgtcaaaag aatagggaaa acataaactt agacagtagg caatcatata   9120
attatcttaa ctgtaaatac tattttataa ttatccaccc ggatctctta atgatattgg   9180
acaagatcaa atacacggga tacttactga caccagaatt agtgctaatg tactgtgatg   9240
tggtcgaagg tagatggaat atgtctgctg ctggacaatt agatgacaaa tcacacaaaa   9300
taacattgaa aggagaagaa ttgtggggca ggatagatga attattcaag ataatcgggg   9360
aagagacatt taatatcata tcactattgg agccattatc tttagcattg atacaattaa   9420
cagatcctgt tatgtcttta aaaggtgcat ttatgagaca tgtcatctca gaaatgagtg   9480
aaatattggg taaatgtgga aatctaactg aacttgaggt ggatcacata atggattcaa   9540
tccttaacat ttttatggat acaacagtag atgagaaagc agagatattc tccttcttta   9600
ggacatttgg tcatcctagc cttgaggcct ccatagctgc tgaaaaagtt aggcaacata   9660
tgtatgcgca gaaaagtata aaatataaga ccttatgtga gtgtcacgct atattttgta   9720
caattataat aaacggatat agagacagac atggaggaca gtggcccccc tgtcagttcc   9780
cagatcatgt gtgtcaagaa ctcagaaatt ctcaaggatc taattcagct atatcttatg   9840
aaacagccgt tgacaatttc gagagcttta taggtttcag attcgagaag ttcatagacc   9900
ctcaattaga tgaagatctc actatttaca tgagagataa agcattgtct ccaagaagag   9960
aagcctggga ttctgtgtat ccagatggca atctgctgta taaagtgccg ttctctgaag  10020
aaacaaggag attgatagaa gtctttatta gtgattctaa tttcaatcca gaagacatta  10080
tacaatatgt agagacagga gaatggttga acgatgatac tttcaacata tcttatagcc  10140
taaaagaaaa ggagatcaaa caagagggtc gattgtttgc caagatgaca tacaaaatga  10200
gagcagtcca agtattggca gaaactttgc tagcaaaagg aataggggggt ttatttaatg  10260
aaaatggtat ggttaaaggt gaaatcgatt tactaaagag tctaactact ttatctatat  10320
caggagttcc aaggactagc gagatttata atgaatcagt tagtgaagaa gctgatagga  10380
gaagatggga aagggaaaat tcctcatact attgggataa aagaaaaaaa tcaaaacatg  10440
agttcaaagc cacagactca tctactaacg gctatgagac tctaagctgt tttcttacta  10500
cggacttgaa aaaatattgt ctaaattgga ggtttgagag tacatctcta ttcgggcaga  10560
gatgtaacga aatatttggg ttcaagagat tcttcaactg gatgcatcct gtattggaag  10620
aatgtacaat atatgtgggt gatccttact gtcccgtgcc cgataaaatc cacaagaatt  10680
```

-continued

```
tagaagatca tgaagattca ggcatcttta tacatagacc gaggggtggg atagaaggtt  10740
attgtcaaaa actttggact ctcatatcca taagtgcaat tcatctagct gctgtcaagg  10800
tcggggttag agtatcagct atggtacaag gtgacaacca agcaattgcc gtgacatcta  10860
gggtaccagt gacggccacg tataagttca aaaaagagca ggtatatacg gagatcacta  10920
agtattttag gtctttaaga gatgtgatgt ctgatttagg acatgaactc aaactcaacg  10980
agacaattat aagtagcaag atgttcgtgt atagtaagcg gatatattat gatggtaaaa  11040
tactacccca atgtttaaaa gcacttacaa ggtgtgtttt ttggtctgag accttggtgg  11100
atgaaaacag gtctgcttgt tccaatcttg caactgctat agccaaagct atagaaaatg  11160
gctattcacc aatattaggt tactcaatag ctctgtataa gacttgtcag caagtatgta  11220
tctcattagg gatgactatc aatcctacaa taacacctaa tataagagac caatattatt  11280
tagggaagaa ttggcttaga tgtgcagttt tgatacctgc taatgttggg ggatttaact  11340
acatggcaat gtctagatgc ttcgtcagaa atataggcga ccctgcagta gctgctctag  11400
cagacctcaa aaggtttatc cgagcaggac tattggacaa gcagattttg taccgtgtaa  11460
tgaatcaaga atctggggag tctaatttct tagactgggc atctgatcca tactcatgta  11520
atttaccaca ttcgcagagt atcacaacaa ttataaagaa tattacagct cgttcagttc  11580
tccaagagtc accaaatcct ctactgtcag gtttatttac atgtgacagt aaagaagaag  11640
acttaaattt agcgacattt ctgatggaca ggaaggtcat attgccaaga gttgcacatg  11700
agatactaga caactctttg acagggatca gagaatccat cgcaggaatg ctggatacta  11760
caaaatcatt agtacgggtt agtattagaa aaggggggttt atcatacaat ctcttaagaa  11820
agctgataaa ttatgactta ttacaatatg aaacattaac caggacttta aggaaagtcg  11880
tcacaaataa cattgaatat gaatatatgt gttctgtgga attagcaatt ggattaaggc  11940
aaaaaatgtg gtcacatcta acatatggga gacctataca tggattagaa acacctgatc  12000
ctctagaact ccttaaagga acattcatca aaggatctga ggtttgcaaa atatgcaggt  12060
ctgaaggtga taatcctata tatacttggt tttatttacc tgaggaaata gatctggata  12120
acctagaaca aggaaatcca tctataagaa taccttactt tgggtctact actgacgaaa  12180
gatcagaagc acaactgggt tatgttaaaa cactgagtaa acctgctaaa gcagcgatta  12240
ggattgctat gatatatact tgggcttatg gtactgatga gatatcatgg atggaagcgg  12300
ctcagattgc acaaacaaga gcaaatttaa gtcttgataa tttgaaactt ctgactccgg  12360
tatcaacatc tacaaatctg tcccatagat taaaggacac tgctacccag atgaaattct  12420
caagtgcaac tctagttaga gctagtagat ttattactat atcaaatgat aagatggctc  12480
tgaaggaggc aggtgagaca aaggatacta atttaatata tcagcagata atgttgacag  12540
gacttagtgt ttttgaattc aataccagat acattaaagg taagactaaa caaccaatga  12600
tcctacactt acatttaaac aatggctgct gcattatgga atcaccacaa gagacttgta  12660
tccctcctaa atctactcta gacttagagg taaccaatga agaaaataaa ttaatatatg  12720
ataataatcc attaaaaaat gttgatctcg gtattttcca aaaaattaga gatatcgtac  12780
acactgtaga tatgactttc tggtctgatt tggaaataat gagagcagtt actatttgta  12840
catctatgac aatagcagac accatgtctc aattggatag agataacctt aaagaagtaa  12900
ttgttcttgc gaatgatgat gacattaata gcttaataac agagtttatg ataatagaca  12960
tcccgctctt ttgctcaaca ttcggaggaa tcttagtaaa tcagtttgcc tatgcattat  13020
```

-continued

```
acggtctaaa tataagaggt agagaagaaa tatggggtta cattacacgg actttgaaag  13080
atacttctca tgctgtgtta aaggtacttg ctaatgcatt atcacatcca aaggtgttca  13140
agagattctg ggatttcggt attttagagc ctgtatatgg acctaattta tccaaccaag  13200
ataagataat gttagcatta tctgtttgtg agtactcaat agacttattc atgagggact  13260
ggcaaagcgg aatacctcta gaaaccttta tatgtgacaa tgatccagaa gtagttgaat  13320
taagaaaagg tgcctacttg gcaagacatt tagcatattt atgcagctta ggagagattt  13380
cctcatatgg tcctagatta gaaactctaa catcattaga aaggttagag gttcttaaaa  13440
gctacctaga gatatcttgt ttagaggatc caacattgag atacagtcag gttacagggc  13500
tggtattaaa agtgttccca tcaacagtag tatatatcag gaagttagct ataaagatgt  13560
tgaggattag gggcataggg gtgccagagg tgttagaaga ctgggatccc agtcatgaac  13620
aagctctact agataatata gctcaagaga tccaacataa tatcccaata aaccaatcta  13680
tcaagacacc tttctggggg ctcaaagtca ataattccca agtcttacgt ctaaggggat  13740
ataaggaggt taaggatagg aaatcagggc gatcaggagt aggtctaaca cttccatgtg  13800
ataataggta cttatcccat cagataagac ttttcgggat taatagtact agctgcctga  13860
aagctttgga gttaacatat ttaataggac cattgataga taaaagtaaa gatagattat  13920
tcttagggga aggtgcaggt gctatgttgt catgttatga tgcaacgtta ggaccttcaa  13980
tgaactatta taactcaggt gtctcatcat atgatataaa tggtcagagg gaattaggga  14040
tctatccatc tgaggctgca ttagtggcaa agaaattgaa taatgtaact aatttgggtc  14100
agagaattaa ggtgctgttc aacggaaacc ctgggtctac atgggttggc aaccaggaat  14160
gcgaaacatt aatttggagt gaattacagg acaaatcaat cggcttgata cattgtgacc  14220
tagaaggtgg agaactaaaa gatacacaaa cagtactgca tgaacattat agcataatta  14280
ggatagcata cttagtagga gataacgatg ttttattagt gactaaaatt gcacctaaat  14340
tgggtacaga ttggactcag caactatgct tgtatctaag atattggaat gaagtcaatt  14400
tagttgttct taagacatct aatccttctt ctactgagat gtatttgtta tcaaggaatc  14460
caagtaaaga tgtgattgaa gatagtctaa cagtaatctc agacctaaag ccattgtcta  14520
aaaaagatag tatacaatta gaaaagtgga ttttggttga gaaagacaaa gttaaggaat  14580
ggctaattaa agaattaaga gagggagaac taatgtcagg ttcacttagg ccttatcacc  14640
aagcacttca gatttttgga tttgaggcca acttgcacaa attgtgtaga gacttcttat  14700
caactatgag tatttcagat atccagatgt gtataaattc attctacaga gttttaaagg  14760
acacaatatt tgagtggagt cgggtaacaa atgatcataa gacatgtaaa ctcacaggga  14820
aatatgagtt atatcctata agagacagtg gaaagttgaa agtgatatca agaaggctta  14880
taatatcctg gattgcttta tccatgtcta ctagactgtt aacaggcgct ttccctgata  14940
ttaagtttga gtccagattg aatataggtt tagtctcctt atctacgaat gagatcaaat  15000
cacttaaact tatatccaag gctacggtgg ataggtttca agaagtgatt cacagtgtat  15060
cctacagatt cttgactaaa gaaattaaaa tactcatgaa gatacttgga gctgttaaat  15120
tatttggtgc aagacagact tataaccatt tagctttaac accagaacct ctatctgata  15180
tagagggata tttagatgat tagctcgaat atcaacagta aacagctaag aatcattaag  15240
aagactatct ggatccagac ctaaatgaaa gaataagaaa aacttattta aacaatcaaa  15300
gatccaagca aaatgatatg tcttaaactc ttgt                              15334
```

<210> SEQ ID NO 2
<211> LENGTH: 1581
<212> TYPE: DNA
<213> ORGANISM: Porcine respirovirus 1

<400> SEQUENCE: 2
atggcagggt tattaagtgt ctttgacaca tttagttcta aaaggagtga aagcataaat 60
agaggaggtg gtggtgcggt tatacctgga caaaagaaca ccgtctcagt atttgtccta 120
gggtcaagta ttgtagacga cagcgataag ttagctatag cactcatgtt tttaacacat 180
gctcttgata ctgacaagca acactcacaa agaagcggtt tcctggtttc attaatggca 240
atggcatata gtagtcctga attatatcta acaactaatg gagttaatgc agatgttaag 300
tatgttatct acacaattga gcatgatccc cagaggacaa cccataatgg gttcattgtt 360
aggacaagag atatggacta tgaaaagaca acagagtggc tattcagccg tataactaat 420
aaatacccac tacttcaggg acaaaaagac actcatgatc cagaatcact actccagact 480
tatggatatc cctcatgttt aggagcattg ataatccagg tttggattgt cttggtcaaa 540
gcaattacaa gtagtgctgg attgaagaaa ggattcttca atagacttga agccttcagg 600
caggatggaa cagttagaag ctcactagtc ttcagtgggg agacagttga ggggattggg 660
tcagtgatga gatctcagca gagtttggtg tccttaatgg tagagactct agttaccatg 720
aacacggcca gatctgactt gaccactcta gaaaagaata ttcagattgt tgggaattac 780
atcagggatg caggtcttgc ttcattcatg aacacgatta gatatggtgt ggagactaag 840
atggcagcac ttacattatc taatcttaga cctgatatta ataaactaaa gagtctaatt 900
gacatctact tatccaaagg tgcaagagcc cccttcatat gcatattacg tgatccggta 960
cacggagaat ttgctcctgg aaattatcca gcattgtgga gttatgctat gggggtcgca 1020
gtagtccaga acaaagccat gcagcagtat gtgacaggga ggacttatct ggatatggaa 1080
atgttccttc ttggtcaagc agtagctaaa gacgcagaat ctaagatcag taatgcatta 1140
gaggatgaat taggtataac tgaaaatgcc aaagacaggc tcaaacatca tcttgctaac 1200
ctttctggag gtgatggagc ttatcacaaa cccactggtg gaggagcaat agaagttata 1260
attgacaatg cagacataga tctcaggaca gaggaaacca cagaagaatc ttcaatcagg 1320
ctttccaata ttagagaaaa caaagggaga atagcagacg ggcagaggag atgggaaaca 1380
accagatcca ttggtgatga ccccaatcca gacaacacca ctgacgatga agtatccgcc 1440
gcagaaagga ggattgcaga aagactggca aaaaaggagg ggaagaatac caggtcggat 1500
atactcatta ccgatggtat gactgaagat acagataacg atgatgatat aatgagaatg 1560
aatgcactag gaggaatata a 1581

<210> SEQ ID NO 3
<211> LENGTH: 526
<212> TYPE: PRT
<213> ORGANISM: Porcine respirovirus 1

<400> SEQUENCE: 3

Met Ala Gly Leu Leu Ser Val Phe Asp Thr Phe Ser Ser Lys Arg Ser
1 5 10 15

Glu Ser Ile Asn Arg Gly Gly Gly Gly Ala Val Ile Pro Gly Gln Lys
20 25 30

Asn Thr Val Ser Val Phe Val Leu Gly Ser Ser Ile Val Asp Asp Ser
35 40 45

Asp Lys Leu Ala Ile Ala Leu Met Phe Leu Thr His Ala Leu Asp Thr

-continued

```
    50                  55                  60

Asp Lys Gln His Ser Gln Arg Ser Gly Phe Leu Val Ser Leu Met Ala
65                  70                  75                  80

Met Ala Tyr Ser Ser Pro Glu Leu Tyr Leu Thr Thr Asn Gly Val Asn
                85                  90                  95

Ala Asp Val Lys Tyr Val Ile Tyr Thr Ile Glu His Asp Pro Gln Arg
            100                 105                 110

Thr Thr His Asn Gly Phe Ile Val Arg Thr Arg Asp Met Asp Tyr Glu
        115                 120                 125

Lys Thr Thr Glu Trp Leu Phe Ser Arg Ile Thr Asn Lys Tyr Pro Leu
    130                 135                 140

Leu Gln Gly Gln Lys Asp Thr His Asp Pro Glu Ser Leu Leu Gln Thr
145                 150                 155                 160

Tyr Gly Tyr Pro Ser Cys Leu Gly Ala Leu Ile Ile Gln Val Trp Ile
                165                 170                 175

Val Leu Val Lys Ala Ile Thr Ser Ser Ala Gly Leu Lys Lys Gly Phe
            180                 185                 190

Phe Asn Arg Leu Glu Ala Phe Arg Gln Asp Gly Thr Val Arg Ser Ser
        195                 200                 205

Leu Val Phe Ser Gly Glu Thr Val Glu Gly Ile Gly Ser Val Met Arg
    210                 215                 220

Ser Gln Gln Ser Leu Val Ser Leu Met Val Glu Thr Leu Val Thr Met
225                 230                 235                 240

Asn Thr Ala Arg Ser Asp Leu Thr Thr Leu Glu Lys Asn Ile Gln Ile
                245                 250                 255

Val Gly Asn Tyr Ile Arg Asp Ala Gly Leu Ala Ser Phe Met Asn Thr
            260                 265                 270

Ile Arg Tyr Gly Val Glu Thr Lys Met Ala Ala Leu Thr Leu Ser Asn
        275                 280                 285

Leu Arg Pro Asp Ile Asn Lys Leu Lys Ser Leu Ile Asp Ile Tyr Leu
    290                 295                 300

Ser Lys Gly Ala Arg Ala Pro Phe Ile Cys Ile Leu Arg Asp Pro Val
305                 310                 315                 320

His Gly Glu Phe Ala Pro Gly Asn Tyr Pro Ala Leu Trp Ser Tyr Ala
                325                 330                 335

Met Gly Val Ala Val Val Gln Asn Lys Ala Met Gln Gln Tyr Val Thr
            340                 345                 350

Gly Arg Thr Tyr Leu Asp Met Glu Met Phe Leu Leu Gly Gln Ala Val
        355                 360                 365

Ala Lys Asp Ala Glu Ser Lys Ile Ser Asn Ala Leu Glu Asp Glu Leu
    370                 375                 380

Gly Ile Thr Glu Asn Ala Lys Asp Arg Leu Lys His His Leu Ala Asn
385                 390                 395                 400

Leu Ser Gly Gly Asp Gly Ala Tyr His Lys Pro Thr Gly Gly Gly Ala
                405                 410                 415

Ile Glu Val Ile Ile Asp Asn Ala Asp Ile Asp Leu Arg Thr Glu Glu
            420                 425                 430

Thr Thr Glu Glu Ser Ser Ile Arg Leu Ser Asn Ile Arg Glu Asn Lys
        435                 440                 445

Gly Arg Ile Ala Asp Gly Gln Arg Arg Trp Glu Thr Thr Arg Ser Ile
    450                 455                 460

Gly Asp Asp Pro Asn Pro Asp Asn Thr Thr Asp Asp Glu Val Ser Ala
465                 470                 475                 480
```

-continued

Ala Glu Arg Arg Ile Ala Glu Arg Leu Ala Lys Lys Glu Gly Lys Asn
485 490 495

Thr Arg Ser Asp Ile Leu Ile Thr Asp Gly Met Thr Glu Asp Thr Asp
500 505 510

Asn Asp Asp Asp Ile Met Arg Met Asn Ala Leu Gly Gly Ile
515 520 525

<210> SEQ ID NO 4
<211> LENGTH: 1725
<212> TYPE: DNA
<213> ORGANISM: Porcine respirovirus 1

<400> SEQUENCE: 4
atggatcaag atgccctctt ttctgaagaa tctatggagg atcagaagga gggacactca 60
acaaccagca cactcaccag tgcagtcgga ctcattgaca tcatccttgc cagtgagccc 120
acagacatta gaaaagacag aaaacaccta tgtgagccca tcacagcctg ggaaaatca 180 gaagcaagca agatttccaa ggatacagtc tgtgaagaaa acccaagaac agaaagggaa 240
gattatggac aaagtaaaaa gagtggaatt cctagggagt caaacaagtt cgaagcagaa 300
gtttctttta gagaaactca tagctcaggt acatcatgga gggcttggag aagaagtagt 360
gcaaactcta tacttgagaa tatgggcaat ggatccgact cctatggcaa cgaaattact 420
ggaaatggag gaggaaacca gagacaaagt cctgaagcta aagttggaga gatggatccg 480
agttctaata cgaggagaaa agacaaaact gagggacttc cagaagagat acgaggaggt 540
tcacccatat ctaatgacgg agaaggtgga agaaataata atggaggaag cctggagtct 600
gtcagcacac ataatccaag agtagaaaac aacattatgg atccaactca tcatcttgaa 660
gaagaggtac ttaagaggaa caagccacgg gagatgaatg ctacaagtca atggtcgggt 720
ggatacaaga ctgatcaaca agacggtaaa catgaattga taaccaatcc aatattttca 780
aatcaaaata ggtcacagga cacaaaaaag ggaaaaggga aagaatcaac tgtaaagccc 840
aagaccagaa aatctaaaat atcctttgaa gacacaagaa gcacagatca catctacgaa 900
gactctcaag aacatacaag aagaaagaaa acagacaacg aaccatcaca aaagattggt 960
aaaaagggca cagaagagaa taccttatat acagaagagg tgatcaaatt gttagtgagt 1020
cttggtgtaa tcccatctgt agccgcattc aaccaatccc gaaacatatg ccatgtattt 1080
gcaaaacgtg tcctcaattc tgtgaactct gcagaaatga cagctaatat gtgcggatta 1140
ttgctgtctg ttgagaaatc agtatcagac catattgaag aaaataagac actaataaat 1200
cagattataa gtgatttaag tacaggtagg gaagtgcaga aacgtttcac tgagtatcaa 1260
aaggaacaga attcattgat tatgtcaaat ctggcgacac ttcatatcat aacagataga 1320
ggaggaaaga acaacagcat ggatacaggg gagaggacac catcaatcag gaccaagggg 1380
aaggagccaa cacagagaac acaaagattt gatccatcta tggaattcac cgaggagatt 1440
aagtacaagc ccgatctata cagggaagac acattgagac aaagaataac aaaccctgtt 1500
cttgatgaga gcgcagagag aatcgacaat tcgaatgccg cgagactgat accttgcaaa 1560
gaaaaatcaa cactgcgttc actcaaatta attattgaga acagcaattt gagcagagca 1620
gacaaaattg cctatatcag gtcattatca aaatgcaaag atgacaaaga ggtagaatca 1680
gtaatgaaac tatttgaaga agatatagaa tcaagtaatg aataa 1725

<210> SEQ ID NO 5
<211> LENGTH: 574

<212> TYPE: PRT
<213> ORGANISM: Porcine respirovirus 1

<400> SEQUENCE: 5

```
Met Asp Gln Asp Ala Leu Phe Ser Glu Glu Ser Met Glu Asp Gln Lys
1               5                   10                  15

Glu Gly His Ser Thr Thr Ser Thr Leu Thr Ser Ala Val Gly Leu Ile
            20                  25                  30

Asp Ile Ile Leu Ala Ser Glu Pro Thr Asp Ile Arg Lys Asp Arg Lys
        35                  40                  45

His Leu Cys Glu Pro Ile Thr Ala Trp Gly Lys Ser Glu Ala Ser Lys
    50                  55                  60

Ile Ser Lys Asp Thr Val Cys Glu Glu Asn Pro Arg Thr Glu Arg Glu
65                  70                  75                  80

Asp Tyr Gly Gln Ser Lys Lys Ser Gly Ile Pro Arg Glu Ser Asn Lys
                85                  90                  95

Phe Glu Ala Glu Val Ser Phe Arg Glu Thr His Ser Ser Gly Thr Ser
            100                 105                 110

Trp Arg Ala Trp Arg Arg Ser Ser Ala Asn Ser Ile Leu Glu Asn Met
        115                 120                 125

Gly Asn Gly Ser Asp Ser Tyr Gly Asn Glu Ile Thr Gly Asn Gly Gly
    130                 135                 140

Gly Asn Gln Arg Gln Ser Pro Glu Ala Lys Val Gly Glu Met Asp Pro
145                 150                 155                 160

Ser Ser Asn Thr Arg Arg Lys Asp Lys Thr Glu Gly Leu Pro Glu Glu
                165                 170                 175

Ile Arg Gly Gly Ser Pro Ile Ser Asn Asp Gly Glu Gly Gly Arg Asn
            180                 185                 190

Asn Asn Gly Gly Ser Leu Glu Ser Val Ser Thr His Asn Pro Arg Val
        195                 200                 205

Glu Asn Asn Ile Met Asp Pro Thr His His Leu Glu Glu Glu Val Leu
    210                 215                 220

Lys Arg Asn Lys Pro Arg Glu Met Asn Ala Thr Ser Gln Trp Ser Gly
225                 230                 235                 240

Gly Tyr Lys Thr Asp Gln Gln Asp Gly Lys His Glu Leu Ile Thr Asn
                245                 250                 255

Pro Ile Phe Ser Asn Gln Asn Arg Ser Gln Asp Thr Lys Lys Gly Lys
            260                 265                 270

Gly Lys Glu Ser Thr Val Lys Pro Lys Thr Arg Lys Ser Lys Ile Ser
        275                 280                 285

Phe Glu Asp Thr Arg Ser Thr Asp His Ile Tyr Glu Asp Ser Gln Glu
    290                 295                 300

His Thr Arg Arg Lys Lys Thr Asp Asn Glu Pro Ser Gln Lys Ile Gly
305                 310                 315                 320

Lys Lys Gly Thr Glu Glu Asn Thr Leu Tyr Thr Glu Glu Val Ile Lys
                325                 330                 335

Leu Leu Val Ser Leu Gly Val Ile Pro Ser Val Ala Ala Phe Asn Gln
            340                 345                 350

Ser Arg Asn Ile Cys His Val Phe Ala Lys Arg Val Leu Asn Ser Val
        355                 360                 365

Asn Ser Ala Glu Met Thr Ala Asn Met Cys Gly Leu Leu Leu Ser Val
    370                 375                 380

Glu Lys Ser Val Ser Asp His Ile Glu Glu Asn Lys Thr Leu Ile Asn
385                 390                 395                 400
```

-continued

```
Gln Ile Ile Ser Asp Leu Ser Thr Gly Arg Glu Val Gln Lys Arg Phe
                405                 410                 415

Thr Glu Tyr Gln Lys Glu Gln Asn Ser Leu Ile Met Ser Asn Leu Ala
            420                 425                 430

Thr Leu His Ile Ile Thr Asp Arg Gly Gly Lys Asn Asn Ser Met Asp
        435                 440                 445

Thr Gly Glu Arg Thr Pro Ser Ile Arg Thr Lys Gly Lys Glu Pro Thr
    450                 455                 460

Gln Arg Thr Gln Arg Phe Asp Pro Ser Met Glu Phe Thr Glu Glu Ile
465                 470                 475                 480

Lys Tyr Lys Pro Asp Leu Tyr Arg Glu Asp Thr Leu Arg Gln Arg Ile
                485                 490                 495

Thr Asn Pro Val Leu Asp Glu Ser Ala Glu Arg Ile Asp Asn Ser Asn
            500                 505                 510

Ala Ala Arg Leu Ile Pro Cys Lys Glu Lys Ser Thr Leu Arg Ser Leu
        515                 520                 525

Lys Leu Ile Ile Glu Asn Ser Asn Leu Ser Arg Ala Asp Lys Ile Ala
    530                 535                 540

Tyr Ile Arg Ser Leu Ser Lys Cys Lys Asp Asp Lys Glu Val Glu Ser
545                 550                 555                 560

Val Met Lys Leu Phe Glu Glu Asp Ile Glu Ser Ser Asn Glu
                565                 570
```

<210> SEQ ID NO 6
<211> LENGTH: 1044
<212> TYPE: DNA
<213> ORGANISM: Porcine respirovirus 1

<400> SEQUENCE: 6

```
atggccgaga tctacaagtt ccccaagcta tcatatgagg aacatggata tatggaacct     60

ctaccactaa ggactggccc agataagaag gcagtcccac atataaggat aatcaagata    120

ggggacccac cgaagcatgg aaatcgatat cttgatattc tcttacttgg gttttatgag    180

atacccaaag aagttggaac atacggtagt gtatcagatt tgacgagacc cacgggatac    240

acaatctgcg gttcaggatc attacctatt ggaattgcta ggtacttagg tacagatcag    300

gaactactca aagcatcagt agagctaaaa gtgacagtga gaaggacagt aaggtcaagt    360

gagatgattg tgtatatggt agataccata ccaccagcaa tgatggcttg ggcttccagg    420

ttgaaacgag gcatgatatt caatgcgaat aaagtagctc tagctcctca atgtctacct    480

atagataaag atataagatt cagagttgtc tttgtcaatg gcacttctct aggttccatc    540

acaatagcaa aagttcccaa gacattagcc gatcttgctt taccgaattc catatcggtc    600

aatttaatgg tctcactcaa gactggtgcg tcaactgagt ccaagggcat tattcctacg    660

ctaaacgaaa agggcgacaa ggtactaaac tttatggtac accttggatt aatacatagg    720

aaagtcggaa gggtgtattc aatggagtat tgcaagggta aaatagagaa gatgcggctg    780

atcttctcat taggactggt tggaggaatc agtttccatg ttcagcttac aggtgtggta    840

tctaaatcct ttgttggtca gcttggaggg aggaaggaaa tatgttaccc tttgatggat    900

gtaaacccac acatgaattt agttatctgg gctgcttccg ttgaaatcac tggcgtggat    960

gctgttttcc aaccttccat accaagagat ttcaaatact acccgaatgt ggtggcaaaa   1020

aatattggga aaataaaagc ttag                                          1044
```

<210> SEQ ID NO 7
<211> LENGTH: 347
<212> TYPE: PRT
<213> ORGANISM: Porcine respirovirus 1

<400> SEQUENCE: 7

```
Met Ala Glu Ile Tyr Lys Phe Pro Lys Leu Ser Tyr Glu Glu His Gly
1               5                   10                  15

Tyr Met Glu Pro Leu Pro Leu Arg Thr Gly Pro Asp Lys Lys Ala Val
            20                  25                  30

Pro His Ile Arg Ile Ile Lys Ile Gly Asp Pro Pro Lys His Gly Asn
        35                  40                  45

Arg Tyr Leu Asp Ile Leu Leu Leu Gly Phe Tyr Glu Ile Pro Lys Glu
    50                  55                  60

Val Gly Thr Tyr Gly Ser Val Ser Asp Leu Thr Arg Pro Thr Gly Tyr
65                  70                  75                  80

Thr Ile Cys Gly Ser Gly Ser Leu Pro Ile Gly Ile Ala Arg Tyr Leu
                85                  90                  95

Gly Thr Asp Gln Glu Leu Leu Lys Ala Ser Val Glu Leu Lys Val Thr
            100                 105                 110

Val Arg Arg Thr Val Arg Ser Ser Glu Met Ile Val Tyr Met Val Asp
        115                 120                 125

Thr Ile Pro Pro Ala Met Met Ala Trp Ala Ser Arg Leu Lys Arg Gly
    130                 135                 140

Met Ile Phe Asn Ala Asn Lys Val Ala Leu Ala Pro Gln Cys Leu Pro
145                 150                 155                 160

Ile Asp Lys Asp Ile Arg Phe Arg Val Val Phe Val Asn Gly Thr Ser
                165                 170                 175

Leu Gly Ser Ile Thr Ile Ala Lys Val Pro Lys Thr Leu Ala Asp Leu
            180                 185                 190

Ala Leu Pro Asn Ser Ile Ser Val Asn Leu Met Val Ser Leu Lys Thr
        195                 200                 205

Gly Ala Ser Thr Glu Ser Lys Gly Ile Ile Pro Thr Leu Asn Glu Lys
    210                 215                 220

Gly Asp Lys Val Leu Asn Phe Met Val His Leu Gly Leu Ile His Arg
225                 230                 235                 240

Lys Val Gly Arg Val Tyr Ser Met Glu Tyr Cys Lys Gly Lys Ile Glu
                245                 250                 255

Lys Met Arg Leu Ile Phe Ser Leu Gly Leu Val Gly Gly Ile Ser Phe
            260                 265                 270

His Val Gln Leu Thr Gly Val Val Ser Lys Ser Phe Val Gly Gln Leu
        275                 280                 285

Gly Gly Arg Lys Glu Ile Cys Tyr Pro Leu Met Asp Val Asn Pro His
    290                 295                 300

Met Asn Leu Val Ile Trp Ala Ala Ser Val Glu Ile Thr Gly Val Asp
305                 310                 315                 320

Ala Val Phe Gln Pro Ser Ile Pro Arg Asp Phe Lys Tyr Tyr Pro Asn
                325                 330                 335

Val Val Ala Lys Asn Ile Gly Lys Ile Lys Ala
            340                 345
```

<210> SEQ ID NO 8
<211> LENGTH: 1671
<212> TYPE: DNA
<213> ORGANISM: Porcine respirovirus 1

<400> SEQUENCE: 8

```
atgcaaatca tcatcctcag accagccata atactaagca tagtactatt agtgaccagt     60
caagtcccta gagataaact agccaattta gggatcatca ttaaggacag caaagcactc    120
aaaattgcag gatcttatga aaacagatac atagtcttaa accttgtacc aacaatagaa    180
aatgtgggtg ggtgtggttc catccaaata gcaaaatata aagagatgct tgaaaggttg    240
ttaataccga taaaagatgc actagattta caagagtctt tgataatgat tgataatgaa    300
accgtcaaca acaattatcg tcctcagtat agatttgttg gtgcaattat tgggactata    360
gcccttgggg tagcaactgc ggcccaagtt acagcagggg tggcactgat ggaggcaaga    420
gaggccaaaa gagatatatc agtgttaaaa gaagcaattg gaaagactca aaactcaatt    480
gaaaaattac agaattctgc aggtgaacag atactggctc tcaaaatgct ccaggattat    540
gtcaatggag agattaaacc agctattgaa gaacttggat gtgagactgc tgcacttaaa    600
ttaggaattg cacttacaca acactacaca gagctcacaa atgcctttgg gtcgaatcta    660
ggttccatag gagagaagag cttaacatta caggccctat catcattata caagaccaat    720
ataactgata tactgacaac aactaatctc gggaaaacag atatttatga tattatatat    780
gctgagcaag ttaaaggaag agtaatagat gtcgatctta gacgatatat ggttacaata    840
tctgttaaga taccaatatt atcagaaata ccaggagtat tgatctatga agtctcctct    900
atatcttata atatagatgg aacagaatgg tatgccgctg tacctgacca catattaagt    960
aaatccgcat atataggggg tgcagatata agtgattgta tagaatctgg attgacatat   1020
atttgtccgc gagatcctgc tcagattata gcggataacc aacagcaatg ttttttaggt   1080
catcttgaca agtgccctat aactaaagta gttgataatc ttgtgcctaa atttgcattc   1140
ataaatggtg gagtagttgc aaactgtata gcctctacat gtacctgtgg agaagagagg   1200
gtccaggtct ctcaagatag aaataaagga gtaacctttt tgactcataa taattgtgga   1260
ttaataggga taaacgggat ggaatttcat gctaacaaga aagggagtga tgctacttgg   1320
aatgtctccc ccataagagc agggccagcg gtatcgttaa gaccagtaga tatatcttta   1380
caaatagttt ctgctactaa ttttctaaac tcatcaagaa aagatcttat gaaggcaaaa   1440
gagatcttaa accaggtagg aaatcttaga gatttaaccg tcataacgat aattaatata   1500
gtaattatag ctgtattact tatatgtgta actggattag gcgtactgta tcaccaattg   1560
agaagtgcac tagtgatgag agacaagatg tcagtattaa ataatagttc ctattcttta   1620
gaaccaagaa ccacccaggt acaagtaatt aagcctacta gtttcatgag a            1671
```

<210> SEQ ID NO 9
<211> LENGTH: 557
<212> TYPE: PRT
<213> ORGANISM: Porcine respirovirus 1

<400> SEQUENCE: 9

```
Met Gln Ile Ile Ile Leu Arg Pro Ala Ile Ile Leu Ser Ile Val Leu
1               5                   10                  15

Leu Val Thr Ser Gln Val Pro Arg Asp Lys Leu Ala Asn Leu Gly Ile
            20                  25                  30

Ile Ile Lys Asp Ser Lys Ala Leu Lys Ile Ala Gly Ser Tyr Glu Asn
        35                  40                  45

Arg Tyr Ile Val Leu Asn Leu Val Pro Thr Ile Glu Asn Val Gly Gly
    50                  55                  60

Cys Gly Ser Ile Gln Ile Ala Lys Tyr Lys Glu Met Leu Glu Arg Leu
```

-continued

```
65                  70                  75                  80

Leu Ile Pro Ile Lys Asp Ala Leu Asp Leu Gln Glu Ser Leu Ile Met
                85                  90                  95

Ile Asp Asn Glu Thr Val Asn Asn Asn Tyr Arg Pro Gln Tyr Arg Phe
            100                 105                 110

Val Gly Ala Ile Ile Gly Thr Ile Ala Leu Gly Val Ala Thr Ala Ala
        115                 120                 125

Gln Val Thr Ala Gly Val Ala Leu Met Glu Ala Arg Glu Ala Lys Arg
    130                 135                 140

Asp Ile Ser Val Leu Lys Glu Ala Ile Gly Lys Thr Gln Asn Ser Ile
145                 150                 155                 160

Glu Lys Leu Gln Asn Ser Ala Gly Glu Gln Ile Leu Ala Leu Lys Met
                165                 170                 175

Leu Gln Asp Tyr Val Asn Gly Glu Ile Lys Pro Ala Ile Glu Glu Leu
            180                 185                 190

Gly Cys Glu Thr Ala Ala Leu Lys Leu Gly Ile Ala Leu Thr Gln His
        195                 200                 205

Tyr Thr Glu Leu Thr Asn Ala Phe Gly Ser Asn Leu Gly Ser Ile Gly
    210                 215                 220

Glu Lys Ser Leu Thr Leu Gln Ala Leu Ser Ser Leu Tyr Lys Thr Asn
225                 230                 235                 240

Ile Thr Asp Ile Leu Thr Thr Thr Asn Leu Gly Lys Thr Asp Ile Tyr
                245                 250                 255

Asp Ile Ile Tyr Ala Glu Gln Val Lys Gly Arg Val Ile Asp Val Asp
            260                 265                 270

Leu Arg Arg Tyr Met Val Thr Ile Ser Val Lys Ile Pro Ile Leu Ser
        275                 280                 285

Glu Ile Pro Gly Val Leu Ile Tyr Glu Val Ser Ser Ile Ser Tyr Asn
    290                 295                 300

Ile Asp Gly Thr Glu Trp Tyr Ala Ala Val Pro Asp His Ile Leu Ser
305                 310                 315                 320

Lys Ser Ala Tyr Ile Gly Gly Ala Asp Ile Ser Asp Cys Ile Glu Ser
                325                 330                 335

Gly Leu Thr Tyr Ile Cys Pro Arg Asp Pro Ala Gln Ile Ile Ala Asp
            340                 345                 350

Asn Gln Gln Gln Cys Phe Leu Gly His Leu Asp Lys Cys Pro Ile Thr
        355                 360                 365

Lys Val Val Asp Asn Leu Val Pro Lys Phe Ala Phe Ile Asn Gly Gly
    370                 375                 380

Val Val Ala Asn Cys Ile Ala Ser Thr Cys Thr Cys Gly Glu Glu Arg
385                 390                 395                 400

Val Gln Val Ser Gln Asp Arg Asn Lys Gly Val Thr Phe Leu Thr His
                405                 410                 415

Asn Asn Cys Gly Leu Ile Gly Ile Asn Gly Met Glu Phe His Ala Asn
            420                 425                 430

Lys Lys Gly Ser Asp Ala Thr Trp Asn Val Ser Pro Ile Arg Ala Gly
        435                 440                 445

Pro Ala Val Ser Leu Arg Pro Val Asp Ile Ser Leu Gln Ile Val Ser
    450                 455                 460

Ala Thr Asn Phe Leu Asn Ser Ser Arg Lys Asp Leu Met Lys Ala Lys
465                 470                 475                 480

Glu Ile Leu Asn Gln Val Gly Asn Leu Arg Asp Leu Thr Val Ile Thr
                485                 490                 495
```

```
Ile Ile Asn Ile Val Ile Ile Ala Val Leu Leu Ile Cys Val Thr Gly
            500                 505                 510

Leu Gly Val Leu Tyr His Gln Leu Arg Ser Ala Leu Val Met Arg Asp
        515                 520                 525

Lys Met Ser Val Leu Asn Asn Ser Ser Tyr Ser Leu Glu Pro Arg Thr
    530                 535                 540

Thr Gln Val Gln Val Ile Lys Pro Thr Ser Phe Met Arg
545                 550                 555


<210> SEQ ID NO 10
<211> LENGTH: 1731
<212> TYPE: DNA
<213> ORGANISM: Porcine respirovirus 1

<400> SEQUENCE: 10

atggaagggg ccaaagttaa gacatcaggg tactgggcca agagtcctca aattcacgca     60

acaaataatc ctaacgtaca aaacagagag aagatcaagg aaacattaac aattttaata    120

tcattcattt ctttcctatc tcttgtactg gttatagctg tactgataat gcaatcttta    180

cataacggca caatactaag gtgtaaagat gtaggcctag aatctatcaa taaatccact    240

tactctatat ctaatgcaat tctggatgtc atcaaacaag agctgataac tcgtataata    300

aatactcaaa gttctgtgca ggtagccctc ccggtcttaa ttaacaagaa aatccaggat    360

ctctcactaa ccattgagaa aagttcaaaa gtgcatcaaa attctcctac ttgtagtggt    420

gtggctgccc tgacacatgt ggaagggata aaacctttgg atccagacga ttactggagg    480

tgtccaagtg gggaaccata tctagaggat gaattgacat taagtcttat ccctggacct    540

agtatgctag ctggaacctc taccatcgat ggctgtgtaa gattaccatc tcttgcaata    600

ggaaaatcgc tatatgccta tagttccaac cttataacta agggttgtca agatataggg    660

aaatcctatc aagtgctaca gttaggtatt ataactctga attcagactt acatcctgat    720

ttaaatccta taatatcaca tacttatgat ataaatgata atagaaagtc ctgttctgtt    780

gctgtatcag aaactaaagg ataccaatta tgctcgatgc cgcgtgtcaa tgaaaaaaca    840

gattacacta gtgatggtat tgaagatata gtttttgatg tacttgatct caaagggtcc    900

tctagaagtt tcaaattttc aaacaatgat ataaactttg atcatccttt ttcagcgtta    960

taccctagtg taggaagtgg tattatatgg gaaaatgaac tgtatttcct aggttacggg   1020

gctctgacaa ctgcacttca agggaataca aaatgtaatt taatgggatg tccaggagca   1080

acacaaaaca actgcaacaa gttcatctct agttcatggt tatacagcaa acagatggtt   1140

aatgtactga tacaggttaa ggggtattta tctaacaagc caagtattat agttagaaca   1200

atcccaataa cggaaaatta tgtaggagca gaagggaaac tagtgggaac acgtgagaga   1260

atatatatat atacaagatc aacgggttgg catgccaatt tacaaatagg agtacttaat   1320

ataaatcatc caataaccat aacttggaaa gatcacaaag tactatcaag accaggaaga   1380

agtccttgtg cctggaataa caaatgccct agaaattgta ctactggtgt atacacagat   1440

gcttatccta tatcgcctga tgctaattat gttgctacag ttactctatt atctaattca   1500

acacgaacta atcctactat tatgtattca tcttctgata gagtatataa catgttaaga   1560

ttaagaaata ctgaattaga agctgcatac acaaccacgt cttgtattgt ccactttgat   1620

agaggttatt gttttcatat tatagaaatt aatcaaaaag gactgaatac actacagcct   1680

atgctcttta agactgcaat tcctaaagct tgcaggataa gcaatttata a            1731
```

<210> SEQ ID NO 11
<211> LENGTH: 576
<212> TYPE: PRT
<213> ORGANISM: Porcine respirovirus 1

<400> SEQUENCE: 11

```
Met Glu Gly Ala Lys Val Lys Thr Ser Gly Tyr Trp Ala Lys Ser Pro
1               5                   10                  15

Gln Ile His Ala Thr Asn Asn Pro Asn Val Gln Asn Arg Glu Lys Ile
            20                  25                  30

Lys Glu Thr Leu Thr Ile Leu Ile Ser Phe Ile Ser Phe Leu Ser Leu
        35                  40                  45

Val Leu Val Ile Ala Val Leu Ile Met Gln Ser Leu His Asn Gly Thr
    50                  55                  60

Ile Leu Arg Cys Lys Asp Val Gly Leu Glu Ser Ile Asn Lys Ser Thr
65                  70                  75                  80

Tyr Ser Ile Ser Asn Ala Ile Leu Asp Val Ile Lys Gln Glu Leu Ile
                85                  90                  95

Thr Arg Ile Ile Asn Thr Gln Ser Ser Val Gln Val Ala Leu Pro Val
            100                 105                 110

Leu Ile Asn Lys Lys Ile Gln Asp Leu Ser Leu Thr Ile Glu Lys Ser
        115                 120                 125

Ser Lys Val His Gln Asn Ser Pro Thr Cys Ser Gly Val Ala Ala Leu
    130                 135                 140

Thr His Val Glu Gly Ile Lys Pro Leu Asp Pro Asp Asp Tyr Trp Arg
145                 150                 155                 160

Cys Pro Ser Gly Glu Pro Tyr Leu Glu Asp Glu Leu Thr Leu Ser Leu
                165                 170                 175

Ile Pro Gly Pro Ser Met Leu Ala Gly Thr Ser Thr Ile Asp Gly Cys
            180                 185                 190

Val Arg Leu Pro Ser Leu Ala Ile Gly Lys Ser Leu Tyr Ala Tyr Ser
        195                 200                 205

Ser Asn Leu Ile Thr Lys Gly Cys Gln Asp Ile Gly Lys Ser Tyr Gln
    210                 215                 220

Val Leu Gln Leu Gly Ile Ile Thr Leu Asn Ser Asp Leu His Pro Asp
225                 230                 235                 240

Leu Asn Pro Ile Ile Ser His Thr Tyr Asp Ile Asn Asp Asn Arg Lys
                245                 250                 255

Ser Cys Ser Val Ala Val Ser Glu Thr Lys Gly Tyr Gln Leu Cys Ser
            260                 265                 270

Met Pro Arg Val Asn Glu Lys Thr Asp Tyr Thr Ser Asp Gly Ile Glu
        275                 280                 285

Asp Ile Val Phe Asp Val Leu Asp Leu Lys Gly Ser Ser Arg Ser Phe
    290                 295                 300

Lys Phe Ser Asn Asn Asp Ile Asn Phe Asp His Pro Phe Ser Ala Leu
305                 310                 315                 320

Tyr Pro Ser Val Gly Ser Gly Ile Ile Trp Glu Asn Glu Leu Tyr Phe
                325                 330                 335

Leu Gly Tyr Gly Ala Leu Thr Thr Ala Leu Gln Gly Asn Thr Lys Cys
            340                 345                 350

Asn Leu Met Gly Cys Pro Gly Ala Thr Gln Asn Asn Cys Asn Lys Phe
        355                 360                 365

Ile Ser Ser Ser Trp Leu Tyr Ser Lys Gln Met Val Asn Val Leu Ile
    370                 375                 380
```

Gln Val Lys Gly Tyr Leu Ser Asn Lys Pro Ser Ile Ile Val Arg Thr
385 390 395 400

Ile Pro Ile Thr Glu Asn Tyr Val Gly Ala Glu Gly Lys Leu Val Gly
405 410 415

Thr Arg Glu Arg Ile Tyr Ile Tyr Thr Arg Ser Thr Gly Trp His Ala
420 425 430

Asn Leu Gln Ile Gly Val Leu Asn Ile Asn His Pro Ile Thr Ile Thr
435 440 445

Trp Lys Asp His Lys Val Leu Ser Arg Pro Gly Arg Ser Pro Cys Ala
450 455 460

Trp Asn Asn Lys Cys Pro Arg Asn Cys Thr Thr Gly Val Tyr Thr Asp
465 470 475 480

Ala Tyr Pro Ile Ser Pro Asp Ala Asn Tyr Val Ala Thr Val Thr Leu
485 490 495

Leu Ser Asn Ser Thr Arg Thr Asn Pro Thr Ile Met Tyr Ser Ser Ser
500 505 510

Asp Arg Val Tyr Asn Met Leu Arg Leu Arg Asn Thr Glu Leu Glu Ala
515 520 525

Ala Tyr Thr Thr Thr Ser Cys Ile Val His Phe Asp Arg Gly Tyr Cys
530 535 540

Phe His Ile Ile Glu Ile Asn Gln Lys Gly Leu Asn Thr Leu Gln Pro
545 550 555 560

Met Leu Phe Lys Thr Ala Ile Pro Lys Ala Cys Arg Ile Ser Asn Leu
565 570 575

<210> SEQ ID NO 12
<211> LENGTH: 6708
<212> TYPE: DNA
<213> ORGANISM: Porcine respirovirus 1

<400> SEQUENCE: 12
atgccaaagc attcagccag aatggatcat ttcaatatgt ctcaaaatcc aagtgatata 60
ctataccctg aatgccactt gaactctcca gttgtgaaag ggaagatcgc tcagctacat 120
gtcttgttag atattaatca gccgtatgaa atgagggacc ctagtataat agaaatcaca 180
aaagttaaaa ttaaatctgg agggttaaat caaaggttaa tcagaatcag atctttaggg 240
aaagagatga ggagaatcat atttgatttt gataagtata cattcgaacc ttacccaata 300
ttttctaaag aattatttag attagagata ccagagattt gtgataaaat tcaatcagtt 360
tttgcagtgt cggataggtt aagcaaagat atatcccagc cattacaata cttatggaga 420
gatgtgcgta ggcagttggg aggggattgt tccaaggatc tttctaacaa tgagattgat 480
atacacaaaa ttcctgaaat ccatactaaa ttcaccagaa ataactggta taaaccattc 540
atgacatggt ttagtattaa atatgatatg agaagatgtc aaaagaatag ggaaaacata 600
aacttagaca gtaggcaatc atataattat cttaactgta aatactattt tataattatc 660
cacccggatc tcttaatgat attggacaag atcaaataca cgggatactt actgacacca 720
gaattagtgc taatgtactg tgatgtggtc gaaggtagat ggaatatgtc tgctgctgga 780
caattagatg acaaatcaca caaaataaca ttgaaaggag aagaattgtg gggcaggata 840
gatgaattat tcaagataat cggggaagag acatttaata tcatatcact attggagcca 900
ttatctttag cattgataca attaacagat cctgttatgt ctttaaaagg tgcatttatg 960
agacatgtca tctcagaaat gagtgaaata ttgggtaaat gtggaaatct aactgaactt 1020

-continued

```
gaggtggatc acataatgga ttcaatcctt aacattttta tggatacaac agtagatgag   1080
aaagcagaga tattctcctt ctttaggaca tttggtcatc ctagccttga ggcctccata   1140
gctgctgaaa aagttaggca acatatgtat gcgcagaaaa gtataaaata taagacctta   1200
tgtgagtgtc acgctatatt ttgtacaatt ataataaacg gatatagaga cagacatgga   1260
ggacagtggc ccccctgtca gttcccagat catgtgtgtc aagaactcag aaattctcaa   1320
ggatctaatt cagctatatc ttatgaaaca gccgttgaca atttcgagag ctttataggt   1380
ttcagattcg agaagttcat agaccctcaa ttagatgaag atctcactat ttacatgaga   1440
gataaagcat tgtctccaag aagagaagcc tgggattctg tgtatccaga tggcaatctg   1500
ctgtataaag tgccgttctc tgaagaaaca aggagattga tagaagtctt tattagtgat   1560
tctaatttca atccagaaga cattatacaa tatgtagaga caggagaatg gttgaacgat   1620
gatactttca acatatctta tagcctaaaa gaaaaggaga tcaaacaaga gggtcgattg   1680
tttgccaaga tgacatacaa aatgagagca gtccaagtat tggcagaaac tttgctagca   1740
aaaggaatag gggtttatt taatgaaaat ggtatggtta aaggtgaaat cgatttacta   1800
aagagtctaa ctactttatc tatatcagga gttccaagga ctagcgagat ttataatgaa   1860
tcagttagtg aagaagctga taggagaaga tgggaaaggg aaaattcctc atactattgg   1920
gataaaagaa aaaaatcaaa acatgagttc aaagccacag actcatctac taacggctat   1980
gagactctaa gctgttttct tactacggac ttgaaaaaat attgtctaaa ttggaggttt   2040
gagagtacat ctctattcgg gcagagatgt aacgaaatat ttgggttcaa gagattcttc   2100
aactggatgc atcctgtatt ggaagaatgt acaatatatg tgggtgatcc ttactgtccc   2160
gtgcccgata aaatccacaa gaatttagaa gatcatgaag attcaggcat ctttatacat   2220
agaccgaggg gtgggataga aggttattgt caaaaacttt ggactctcat atccataagt   2280
gcaattcatc tagctgctgt caaggtcggg gttagagtat cagctatggt acaaggtgac   2340
aaccaagcaa ttgccgtgac atctagggta ccagtgacgg ccacgtataa gttcaaaaaa   2400
gagcaggtat atacggagat cactaagtat tttaggtctt taagagatgt gatgtctgat   2460
ttaggacatg aactcaaact caacgagaca attataagta gcaagatgtt cgtgtatagt   2520
aagcggatat attatgatgg taaaatacta ccccaatgtt taaaagcact tacaaggtgt   2580
gttttttggt ctgagacctt ggtggatgaa aacaggtctg cttgttccaa tcttgcaact   2640
gctatagcca aagctataga aaatggctat tcaccaatat taggttactc aatagctctg   2700
tataagactt gtcagcaagt atgtatctca ttagggatga ctatcaatcc tacaataaca   2760
cctaatataa gagaccaata ttatttaggg aagaattggc ttagatgtgc agttttgata   2820
cctgctaatg ttgggggatt taactacatg gcaatgtcta gatgcttcgt cagaaatata   2880
ggcgaccctg cagtagctgc tctagcagac ctcaaaaggt ttatccgagc aggactattg   2940
gacaagcaga ttttgtaccg tgtaatgaat caagaatctg ggagtctaa tttcttagac    3000
tgggcatctg atccatactc atgtaattta ccacattcgc agagtatcac aacaattata   3060
aagaatatta cagctcgttc agttctccaa gagtcaccaa atcctctact gtcaggttta   3120
tttacatgtg acagtaaaga agaagactta aatttagcga catttctgat ggacaggaag   3180
gtcatattgc caagagttgc acatgagata ctagacaact ctttgacagg gatcagagaa   3240
tccatcgcag gaatgctgga tactacaaaa tcattagtac gggttagtat tagaaaaggg   3300
ggtttatcat acaatctctt aagaaagctg ataaattatg acttattaca atatgaaaca   3360
ttaaccagga ctttaaggaa agtcgtcaca aataacattg aatatgaata tatgtgttct   3420
```

-continued

```
gtggaattag caattggatt aaggcaaaaa atgtggtcac atctaacata tgggagacct   3480
atacatggat tagaaacacc tgatcctcta gaactcctta aaggaacatt catcaaagga   3540
tctgaggttt gcaaaatatg caggtctgaa ggtgataatc ctatatatac ttggttttat   3600
ttacctgagg aaatagatct ggataaccta gaacaaggaa atccatctat aagaatacct   3660
tactttgggt ctactactga cgaaagatca gaagcacaac tgggttatgt taaaacactg   3720
agtaaacctg ctaaagcagc gattaggatt gctatgatat atacttgggc ttatggtact   3780
gatgagatat catggatgga agcggctcag attgcacaaa caagagcaaa tttaagtctt   3840
gataatttga aacttctgac tccggtatca acatctacaa atctgtccca tagattaaag   3900
gacactgcta cccagatgaa attctcaagt gcaactctag ttagagctag tagatttatt   3960
actatatcaa atgataagat ggctctgaag gaggcaggtg agacaaagga tactaattta   4020
atatatcagc agataatgtt gacaggactt agtgtttttg aattcaatac cagatacatt   4080
aaaggtaaga ctaaacaacc aatgatccta cacttacatt taaacaatgg ctgctgcatt   4140
atggaatcac cacaagagac ttgtatccct cctaaatcta ctctagactt agaggtaacc   4200
aatgaagaaa ataaattaat atatgataat aatccattaa aaaatgttga tctcggtatt   4260
ttccaaaaaa ttagagatat cgtacacact gtagatatga ctttctggtc tgatttggaa   4320
ataatgagag cagttactat ttgtacatct atgacaatag cagacaccat gtctcaattg   4380
gatagagata accttaaaga agtaattgtt cttgcgaatg atgatgacat taatagctta   4440
ataacagagt ttatgataat agacatcccg ctcttttgct caacattcgg aggaatctta   4500
gtaaatcagt ttgcctatgc attatacggt ctaaatataa gaggtagaga agaaatatgg   4560
ggttacatta cacggacttt gaaagatact tctcatgctg tgttaaaggt acttgctaat   4620
gcattatcac atccaaaggt gttcaagaga ttctgggatt tcggtatttt agagcctgta   4680
tatggaccta atttatccaa ccaagataag ataatgttag cattatctgt ttgtgagtac   4740
tcaatagact tattcatgag ggactggcaa agcggaatac ctctagaaac ctttatatgt   4800
gacaatgatc cagaagtagt tgaattaaga aaaggtgcct acttggcaag acatttagca   4860
tatttatgca gcttaggaga gatttcctca tatggtccta gattagaaac tctaacatca   4920
ttagaaaggt tagaggttct taaaagctac ctagagatat cttgtttaga ggatccaaca   4980
ttgagataca gtcaggttac agggctggta ttaaaagtgt tcccatcaac agtagtatat   5040
atcaggaagt tagctataaa gatgttgagg attaggggca taggggtgcc agaggtgtta   5100
gaagactggg atcccagtca tgaacaagct ctactagata atatagctca agagatccaa   5160
cataatatcc caataaacca atctatcaag acacctttct gggggctcaa agtcaataat   5220
tcccaagtct tacgtctaag ggatataagg gaggttaagg ataggaaatc agggcgatca   5280
ggagtaggtc taacacttcc atgtgataat aggtacttat cccatcagat aagacttttc   5340
gggattaata gtactagctg cctgaaagct ttggagttaa catatttaat aggaccattg   5400
atagataaaa gtaaagatag attattctta ggggaaggtg caggtgctat gttgtcatgt   5460
tatgatgcaa cgttaggacc ttcaatgaac tattataact caggtgtctc atcatatgat   5520
ataaatggtc agagggaatt agggatctat ccatctgagg ctgcattagt ggcaaagaaa   5580
ttgaataatg taactaattt gggtcagaga attaaggtgc tgttcaacgg aaaccctggg   5640
tctacatggg ttggcaacca ggaatgcgaa acattaattt ggagtgaatt acaggacaaa   5700
tcaatcggct tgatacattg tgacctagaa ggtggagaac taaaagatac acaaacagta   5760
```

ctgcatgaac attatagcat aattaggata gcatacttag taggagataa cgatgtttta 5820
ttagtgacta aaattgcacc taaattgggt acagattgga ctcagcaact atgcttgtat 5880
ctaagatatt ggaatgaagt caatttagtt gttcttaaga catctaatcc ttcttctact 5940
gagatgtatt tgttatcaag gaatccaagt aaagatgtga ttgaagatag tctaacagta 6000
atctcagacc taaagccatt gtctaaaaaa gatagtatac aattagaaaa gtggattttg 6060
gttgagaaag acaaagttaa ggaatggcta attaaagaat taagagaggg agaactaatg 6120
tcaggttcac ttaggcctta tcaccaagca cttcagattt ttggatttga ggccaacttg 6180
cacaaattgt gtagagactt cttatcaact atgagtattt cagatatcca gatgtgtata 6240
aattcattct acagagtttt aaaggacaca atatttgagt ggagtcgggt aacaaatgat 6300
cataagacat gtaaactcac agggaaatat gagttatatc ctataagaga cagtggaaag 6360
ttgaaagtga tatcaagaag gcttataata tcctggattg ctttatccat gtctactaga 6420
ctgttaacag gcgctttccc tgatattaag tttgagtcca gattgaatat aggtttagtc 6480
tccttatcta cgaatgagat caaatcactt aaacttatat ccaaggctac ggtggatagg 6540
tttcaagaag tgattcacag tgtatcctac agattcttga ctaaagaaat taaaatactc 6600
atgaagatac ttggagctgt taaattattt ggtgcaagac agacttataa ccatttagct 6660
ttaacaccag aacctctatc tgatatagag ggatatttag atgattag 6708

<210> SEQ ID NO 13
<211> LENGTH: 2235
<212> TYPE: PRT
<213> ORGANISM: Porcine respirovirus 1

<400> SEQUENCE: 13

Met Pro Lys His Ser Ala Arg Met Asp His Phe Asn Met Ser Gln Asn
1 5 10 15

Pro Ser Asp Ile Leu Tyr Pro Glu Cys His Leu Asn Ser Pro Val Val
20 25 30

Lys Gly Lys Ile Ala Gln Leu His Val Leu Leu Asp Ile Asn Gln Pro
35 40 45

Tyr Glu Met Arg Asp Pro Ser Ile Ile Glu Ile Thr Lys Val Lys Ile
50 55 60

Lys Ser Gly Gly Leu Asn Gln Arg Leu Ile Arg Ile Arg Ser Leu Gly
65 70 75 80

Lys Glu Met Arg Arg Ile Ile Phe Asp Phe Asp Lys Tyr Thr Phe Glu
85 90 95

Pro Tyr Pro Ile Phe Ser Lys Glu Leu Phe Arg Leu Glu Ile Pro Glu
100 105 110

Ile Cys Asp Lys Ile Gln Ser Val Phe Ala Val Ser Asp Arg Leu Ser
115 120 125

Lys Asp Ile Ser Gln Pro Leu Gln Tyr Leu Trp Arg Asp Val Arg Arg
130 135 140

Gln Leu Gly Gly Asp Cys Ser Lys Asp Leu Ser Asn Asn Glu Ile Asp
145 150 155 160

Ile His Lys Ile Pro Glu Ile His Thr Lys Phe Thr Arg Asn Asn Trp
165 170 175

Tyr Lys Pro Phe Met Thr Trp Phe Ser Ile Lys Tyr Asp Met Arg Arg
180 185 190

Cys Gln Lys Asn Arg Glu Asn Ile Asn Leu Asp Ser Arg Gln Ser Tyr
195 200 205

```
Asn Tyr Leu Asn Cys Lys Tyr Tyr Phe Ile Ile Ile His Pro Asp Leu
    210                 215                 220

Leu Met Ile Leu Asp Lys Ile Lys Tyr Thr Gly Tyr Leu Leu Thr Pro
225                 230                 235                 240

Glu Leu Val Leu Met Tyr Cys Asp Val Val Glu Gly Arg Trp Asn Met
                245                 250                 255

Ser Ala Ala Gly Gln Leu Asp Asp Lys Ser His Lys Ile Thr Leu Lys
            260                 265                 270

Gly Glu Glu Leu Trp Gly Arg Ile Asp Glu Leu Phe Lys Ile Ile Gly
        275                 280                 285

Glu Glu Thr Phe Asn Ile Ile Ser Leu Leu Glu Pro Leu Ser Leu Ala
    290                 295                 300

Leu Ile Gln Leu Thr Asp Pro Val Met Ser Leu Lys Gly Ala Phe Met
305                 310                 315                 320

Arg His Val Ile Ser Glu Met Ser Glu Ile Leu Gly Lys Cys Gly Asn
                325                 330                 335

Leu Thr Glu Leu Glu Val Asp His Ile Met Asp Ser Ile Leu Asn Ile
            340                 345                 350

Phe Met Asp Thr Thr Val Asp Glu Lys Ala Glu Ile Phe Ser Phe Phe
        355                 360                 365

Arg Thr Phe Gly His Pro Ser Leu Glu Ala Ser Ile Ala Ala Glu Lys
    370                 375                 380

Val Arg Gln His Met Tyr Ala Gln Lys Ser Ile Lys Tyr Lys Thr Leu
385                 390                 395                 400

Cys Glu Cys His Ala Ile Phe Cys Thr Ile Ile Ile Asn Gly Tyr Arg
                405                 410                 415

Asp Arg His Gly Gly Gln Trp Pro Pro Cys Gln Phe Pro Asp His Val
            420                 425                 430

Cys Gln Glu Leu Arg Asn Ser Gln Gly Ser Asn Ser Ala Ile Ser Tyr
        435                 440                 445

Glu Thr Ala Val Asp Asn Phe Glu Ser Phe Ile Gly Phe Arg Phe Glu
    450                 455                 460

Lys Phe Ile Asp Pro Gln Leu Asp Glu Asp Leu Thr Ile Tyr Met Arg
465                 470                 475                 480

Asp Lys Ala Leu Ser Pro Arg Arg Glu Ala Trp Asp Ser Val Tyr Pro
                485                 490                 495

Asp Gly Asn Leu Leu Tyr Lys Val Pro Phe Ser Glu Glu Thr Arg Arg
            500                 505                 510

Leu Ile Glu Val Phe Ile Ser Asp Ser Asn Phe Asn Pro Glu Asp Ile
        515                 520                 525

Ile Gln Tyr Val Glu Thr Gly Glu Trp Leu Asn Asp Asp Thr Phe Asn
    530                 535                 540

Ile Ser Tyr Ser Leu Lys Glu Lys Glu Ile Lys Gln Glu Gly Arg Leu
545                 550                 555                 560

Phe Ala Lys Met Thr Tyr Lys Met Arg Ala Val Gln Val Leu Ala Glu
                565                 570                 575

Thr Leu Leu Ala Lys Gly Ile Gly Gly Leu Phe Asn Glu Asn Gly Met
            580                 585                 590

Val Lys Gly Glu Ile Asp Leu Leu Lys Ser Leu Thr Thr Leu Ser Ile
        595                 600                 605

Ser Gly Val Pro Arg Thr Ser Glu Ile Tyr Asn Glu Ser Val Ser Glu
    610                 615                 620

Glu Ala Asp Arg Arg Arg Trp Glu Arg Glu Asn Ser Ser Tyr Tyr Trp
```

-continued

```
625                 630                 635                 640

Asp Lys Arg Lys Lys Ser Lys His Glu Phe Lys Ala Thr Asp Ser Ser
                645                 650                 655

Thr Asn Gly Tyr Glu Thr Leu Ser Cys Phe Leu Thr Thr Asp Leu Lys
            660                 665                 670

Lys Tyr Cys Leu Asn Trp Arg Phe Glu Ser Thr Ser Leu Phe Gly Gln
        675                 680                 685

Arg Cys Asn Glu Ile Phe Gly Phe Lys Arg Phe Phe Asn Trp Met His
    690                 695                 700

Pro Val Leu Glu Glu Cys Thr Ile Tyr Val Gly Asp Pro Tyr Cys Pro
705                 710                 715                 720

Val Pro Asp Lys Ile His Lys Asn Leu Glu Asp His Glu Asp Ser Gly
                725                 730                 735

Ile Phe Ile His Arg Pro Arg Gly Gly Ile Glu Gly Tyr Cys Gln Lys
            740                 745                 750

Leu Trp Thr Leu Ile Ser Ile Ser Ala Ile His Leu Ala Ala Val Lys
        755                 760                 765

Val Gly Val Arg Val Ser Ala Met Val Gln Gly Asp Asn Gln Ala Ile
    770                 775                 780

Ala Val Thr Ser Arg Val Pro Val Thr Ala Thr Tyr Lys Phe Lys Lys
785                 790                 795                 800

Glu Gln Val Tyr Thr Glu Ile Thr Lys Tyr Phe Arg Ser Leu Arg Asp
                805                 810                 815

Val Met Ser Asp Leu Gly His Glu Leu Lys Leu Asn Glu Thr Ile Ile
            820                 825                 830

Ser Ser Lys Met Phe Val Tyr Ser Lys Arg Ile Tyr Tyr Asp Gly Lys
        835                 840                 845

Ile Leu Pro Gln Cys Leu Lys Ala Leu Thr Arg Cys Val Phe Trp Ser
    850                 855                 860

Glu Thr Leu Val Asp Glu Asn Arg Ser Ala Cys Ser Asn Leu Ala Thr
865                 870                 875                 880

Ala Ile Ala Lys Ala Ile Glu Asn Gly Tyr Ser Pro Ile Leu Gly Tyr
                885                 890                 895

Ser Ile Ala Leu Tyr Lys Thr Cys Gln Gln Val Cys Ile Ser Leu Gly
            900                 905                 910

Met Thr Ile Asn Pro Thr Ile Thr Pro Asn Ile Arg Asp Gln Tyr Tyr
        915                 920                 925

Leu Gly Lys Asn Trp Leu Arg Cys Ala Val Leu Ile Pro Ala Asn Val
    930                 935                 940

Gly Gly Phe Asn Tyr Met Ala Met Ser Arg Cys Phe Val Arg Asn Ile
945                 950                 955                 960

Gly Asp Pro Ala Val Ala Ala Leu Ala Asp Leu Lys Arg Phe Ile Arg
                965                 970                 975

Ala Gly Leu Leu Asp Lys Gln Ile Leu Tyr Arg Val Met Asn Gln Glu
            980                 985                 990

Ser Gly Glu Ser Asn Phe Leu Asp  Trp Ala Ser Asp Pro  Tyr Ser Cys
        995                 1000                1005

Asn Leu  Pro His Ser Gln Ser  Ile Thr Thr Ile Ile  Lys Asn Ile
    1010                1015                1020

Thr Ala  Arg Ser Val Leu Gln  Glu Ser Pro Asn Pro  Leu Leu Ser
    1025                1030                1035

Gly Leu  Phe Thr Cys Asp Ser  Lys Glu Glu Asp Leu  Asn Leu Ala
    1040                1045                1050
```

```
Thr Phe  Leu Met Asp Arg Lys  Val Ile Leu Pro Arg  Val Ala His
    1055                 1060                 1065

Glu Ile  Leu Asp Asn Ser Leu  Thr Gly Ile Arg Glu  Ser Ile Ala
    1070                 1075                 1080

Gly Met  Leu Asp Thr Thr Lys  Ser Leu Val Arg Val  Ser Ile Arg
    1085                 1090                 1095

Lys Gly  Gly Leu Ser Tyr Asn  Leu Leu Arg Lys Leu  Ile Asn Tyr
    1100                 1105                 1110

Asp Leu  Leu Gln Tyr Glu Thr  Leu Thr Arg Thr Leu  Arg Lys Val
    1115                 1120                 1125

Val Thr  Asn Asn Ile Glu Tyr  Glu Tyr Met Cys Ser  Val Glu Leu
    1130                 1135                 1140

Ala Ile  Gly Leu Arg Gln Lys  Met Trp Ser His Leu  Thr Tyr Gly
    1145                 1150                 1155

Arg Pro  Ile His Gly Leu Glu  Thr Pro Asp Pro Leu  Glu Leu Leu
    1160                 1165                 1170

Lys Gly  Thr Phe Ile Lys Gly  Ser Glu Val Cys Lys  Ile Cys Arg
    1175                 1180                 1185

Ser Glu  Gly Asp Asn Pro Ile  Tyr Thr Trp Phe Tyr  Leu Pro Glu
    1190                 1195                 1200

Glu Ile  Asp Leu Asp Asn Leu  Glu Gln Gly Asn Pro  Ser Ile Arg
    1205                 1210                 1215

Ile Pro  Tyr Phe Gly Ser Thr  Thr Asp Glu Arg Ser  Glu Ala Gln
    1220                 1225                 1230

Leu Gly  Tyr Val Lys Thr Leu  Ser Lys Pro Ala Lys  Ala Ala Ile
    1235                 1240                 1245

Arg Ile  Ala Met Ile Tyr Thr  Trp Ala Tyr Gly Thr  Asp Glu Ile
    1250                 1255                 1260

Ser Trp  Met Glu Ala Ala Gln  Ile Ala Gln Thr Arg  Ala Asn Leu
    1265                 1270                 1275

Ser Leu  Asp Asn Leu Lys Leu  Leu Thr Pro Val Ser  Thr Ser Thr
    1280                 1285                 1290

Asn Leu  Ser His Arg Leu Lys  Asp Thr Ala Thr Gln  Met Lys Phe
    1295                 1300                 1305

Ser Ser  Ala Thr Leu Val Arg  Ala Ser Arg Phe Ile  Thr Ile Ser
    1310                 1315                 1320

Asn Asp  Lys Met Ala Leu Lys  Glu Ala Gly Glu Thr  Lys Asp Thr
    1325                 1330                 1335

Asn Leu  Ile Tyr Gln Gln Ile  Met Leu Thr Gly Leu  Ser Val Phe
    1340                 1345                 1350

Glu Phe  Asn Thr Arg Tyr Ile  Lys Gly Lys Thr Lys  Gln Pro Met
    1355                 1360                 1365

Ile Leu  His Leu His Leu Asn  Asn Gly Cys Cys Ile  Met Glu Ser
    1370                 1375                 1380

Pro Gln  Glu Thr Cys Ile Pro  Pro Lys Ser Thr Leu  Asp Leu Glu
    1385                 1390                 1395

Val Thr  Asn Glu Glu Asn Lys  Leu Ile Tyr Asp Asn  Asn Pro Leu
    1400                 1405                 1410

Lys Asn  Val Asp Leu Gly Ile  Phe Gln Lys Ile Arg  Asp Ile Val
    1415                 1420                 1425

His Thr  Val Asp Met Thr Phe  Trp Ser Asp Leu Glu  Ile Met Arg
    1430                 1435                 1440
```

-continued

Ala Val Thr Ile Cys Thr Ser Met Thr Ile Ala Asp Thr Met Ser
1445 1450 1455

Gln Leu Asp Arg Asp Asn Leu Lys Glu Val Ile Val Leu Ala Asn
1460 1465 1470

Asp Asp Asp Ile Asn Ser Leu Ile Thr Glu Phe Met Ile Ile Asp
1475 1480 1485

Ile Pro Leu Phe Cys Ser Thr Phe Gly Gly Ile Leu Val Asn Gln
1490 1495 1500

Phe Ala Tyr Ala Leu Tyr Gly Leu Asn Ile Arg Gly Arg Glu Glu
1505 1510 1515

Ile Trp Gly Tyr Ile Thr Arg Thr Leu Lys Asp Thr Ser His Ala
1520 1525 1530

Val Leu Lys Val Leu Ala Asn Ala Leu Ser His Pro Lys Val Phe
1535 1540 1545

Lys Arg Phe Trp Asp Phe Gly Ile Leu Glu Pro Val Tyr Gly Pro
1550 1555 1560

Asn Leu Ser Asn Gln Asp Lys Ile Met Leu Ala Leu Ser Val Cys
1565 1570 1575

Glu Tyr Ser Ile Asp Leu Phe Met Arg Asp Trp Gln Ser Gly Ile
1580 1585 1590

Pro Leu Glu Thr Phe Ile Cys Asp Asn Asp Pro Glu Val Val Glu
1595 1600 1605

Leu Arg Lys Gly Ala Tyr Leu Ala Arg His Leu Ala Tyr Leu Cys
1610 1615 1620

Ser Leu Gly Glu Ile Ser Ser Tyr Gly Pro Arg Leu Glu Thr Leu
1625 1630 1635

Thr Ser Leu Glu Arg Leu Glu Val Leu Lys Ser Tyr Leu Glu Ile
1640 1645 1650

Ser Cys Leu Glu Asp Pro Thr Leu Arg Tyr Ser Gln Val Thr Gly
1655 1660 1665

Leu Val Leu Lys Val Phe Pro Ser Thr Val Val Tyr Ile Arg Lys
1670 1675 1680

Leu Ala Ile Lys Met Leu Arg Ile Arg Gly Ile Gly Val Pro Glu
1685 1690 1695

Val Leu Glu Asp Trp Asp Pro Ser His Glu Gln Ala Leu Leu Asp
1700 1705 1710

Asn Ile Ala Gln Glu Ile Gln His Asn Ile Pro Ile Asn Gln Ser
1715 1720 1725

Ile Lys Thr Pro Phe Trp Gly Leu Lys Val Asn Asn Ser Gln Val
1730 1735 1740

Leu Arg Leu Arg Gly Tyr Lys Glu Val Lys Asp Arg Lys Ser Gly
1745 1750 1755

Arg Ser Gly Val Gly Leu Thr Leu Pro Cys Asp Asn Arg Tyr Leu
1760 1765 1770

Ser His Gln Ile Arg Leu Phe Gly Ile Asn Ser Thr Ser Cys Leu
1775 1780 1785

Lys Ala Leu Glu Leu Thr Tyr Leu Ile Gly Pro Leu Ile Asp Lys
1790 1795 1800

Ser Lys Asp Arg Leu Phe Leu Gly Glu Gly Ala Gly Ala Met Leu
1805 1810 1815

Ser Cys Tyr Asp Ala Thr Leu Gly Pro Ser Met Asn Tyr Tyr Asn
1820 1825 1830

Ser Gly Val Ser Ser Tyr Asp Ile Asn Gly Gln Arg Glu Leu Gly

```
    1835                1840                1845

Ile Tyr  Pro Ser Glu Ala Ala  Leu Val Ala Lys Lys  Leu Asn Asn
    1850                1855                1860

Val Thr  Asn Leu Gly Gln Arg  Ile Lys Val Leu Phe  Asn Gly Asn
    1865                1870                1875

Pro Gly  Ser Thr Trp Val Gly  Asn Gln Glu Cys Glu  Thr Leu Ile
    1880                1885                1890

Trp Ser  Glu Leu Gln Asp Lys  Ser Ile Gly Leu Ile  His Cys Asp
    1895                1900                1905

Leu Glu  Gly Gly Glu Leu Lys  Asp Thr Gln Thr Val  Leu His Glu
    1910                1915                1920

His Tyr  Ser Ile Ile Arg Ile  Ala Tyr Leu Val Gly  Asp Asn Asp
    1925                1930                1935

Val Leu  Leu Val Thr Lys Ile  Ala Pro Lys Leu Gly  Thr Asp Trp
    1940                1945                1950

Thr Gln  Gln Leu Cys Leu Tyr  Leu Arg Tyr Trp Asn  Glu Val Asn
    1955                1960                1965

Leu Val  Val Leu Lys Thr Ser  Asn Pro Ser Ser Thr  Glu Met Tyr
    1970                1975                1980

Leu Leu  Ser Arg Asn Pro Ser  Lys Asp Val Ile Glu  Asp Ser Leu
    1985                1990                1995

Thr Val  Ile Ser Asp Leu Lys  Pro Leu Ser Lys Lys  Asp Ser Ile
    2000                2005                2010

Gln Leu  Glu Lys Trp Ile Leu  Val Glu Lys Asp Lys  Val Lys Glu
    2015                2020                2025

Trp Leu  Ile Lys Glu Leu Arg  Glu Gly Glu Leu Met  Ser Gly Ser
    2030                2035                2040

Leu Arg  Pro Tyr His Gln Ala  Leu Gln Ile Phe Gly  Phe Glu Ala
    2045                2050                2055

Asn Leu  His Lys Leu Cys Arg  Asp Phe Leu Ser Thr  Met Ser Ile
    2060                2065                2070

Ser Asp  Ile Gln Met Cys Ile  Asn Ser Phe Tyr Arg  Val Leu Lys
    2075                2080                2085

Asp Thr  Ile Phe Glu Trp Ser  Arg Val Thr Asn Asp  His Lys Thr
    2090                2095                2100

Cys Lys  Leu Thr Gly Lys Tyr  Glu Leu Tyr Pro Ile  Arg Asp Ser
    2105                2110                2115

Gly Lys  Leu Lys Val Ile Ser  Arg Arg Leu Ile Ile  Ser Trp Ile
    2120                2125                2130

Ala Leu  Ser Met Ser Thr Arg  Leu Leu Thr Gly Ala  Phe Pro Asp
    2135                2140                2145

Ile Lys  Phe Glu Ser Arg Leu  Asn Ile Gly Leu Val  Ser Leu Ser
    2150                2155                2160

Thr Asn  Glu Ile Lys Ser Leu  Lys Leu Ile Ser Lys  Ala Thr Val
    2165                2170                2175

Asp Arg  Phe Gln Glu Val Ile  His Ser Val Ser Tyr  Arg Phe Leu
    2180                2185                2190

Thr Lys  Glu Ile Lys Ile Leu  Met Lys Ile Leu Gly  Ala Val Lys
    2195                2200                2205

Leu Phe  Gly Ala Arg Gln Thr  Tyr Asn His Leu Ala  Leu Thr Pro
    2210                2215                2220

Glu Pro  Leu Ser Asp Ile Glu  Gly Tyr Leu Asp Asp
    2225                2230                2235
```

<210> SEQ ID NO 14
<211> LENGTH: 15334
<212> TYPE: DNA
<213> ORGANISM: Porcine respirovirus 1

<400> SEQUENCE: 14
ggttaaagta ttaacctcaa aaggacagat caggaacttt gatttcttag catagtgcca 60
aaatggcagg gttattaagt gtctttgaca catttagttc taaaaggagt gaaagcataa 120
atagaggagg tggtggtgcg gttatacctg gacaaaagaa caccgtctca gtatttgtcc 180
tagggtcaag tattgtagac gacagcgata agttagctat agcactcatg tttttaacac 240
atgctcttga tactgacaag caacactcac aaagaagcgg tttcctggtt tcattaatgg 300
caatggcata tagtagtcct gaattatatc taacaactaa tggagttaat gcagatgtta 360
agtatgttat ctacacaatt gagcatgatc cccagaggac aacccataat gggttcattg 420
ttaggacaag agatatggac tatgaaaaga caacagagtg gctattcagc cgtataacta 480
ataaataccc actacttcag ggacaaaaag acactcatga tccagaatca ctactccaga 540
cttatggata tccctcatgt ttaggagcat tgataatcca ggtttggatt gtcttggtca 600
aagcaattac aagtagtgct ggattgaaga aaggattctt caatagactt gaagccttca 660
ggcaggatgg aacagttaga agctcactag tcttcagtgg ggagacagtt gaggggattg 720
ggtcagtgat gagatctcag cagagtttgg tgtccttaat ggtagagact ctagttacca 780
tgaacacggc cagatctgac ttgaccactc tagaaaagaa tattcagatt gttgggaatt 840
acatcaggga tgcaggtctt gcttcattca tgaacacgat tagatatggt gtggagacta 900
agatggcagc acttacatta tctaatctta gacctgatat taataaacta aagagtctaa 960
ttgacatcta cttatccaaa ggtgcaagag ccccccttcat atgcatatta cgtgatccgg 1020
tacacggaga atttgctcct ggaaattatc cagcattgtg gagttatgct atgggggtcg 1080
cagtagtcca gaacaaagcc atgcagcagt atgtgacagg gaggacttat ctggatatgg 1140
aaatgttcct tcttggtcaa gcagtagcta aagacgcaga atctaagatc agtaatgcat 1200
tagaggatga attaggtata actgaaaatg ccaaagacag gctcaaacat catcttgcta 1260
acctttctgg aggtgatgga gcttatcaca aacccactgg tggaggagca atagaagtta 1320
taattgacaa tgcagacata gatctcagga cagaggaaac cacagaagaa tcttcaatca 1380
ggctttccaa tattagagaa aacaaaggga gaatagcaga cgggcagagg agatgggaaa 1440
caaccagatc cattggtgat gaccccaatc cagacaacac cactgacgat gaagtatccg 1500
ccgcagaaag gaggattgca gaaagactgg caaaaaagga ggggaagaat accaggtcgg 1560
atatactcat taccgatggt atgactgaag atacagataa cgatgatgat ataatgagaa 1620
tgaatgcact aggaggaata taataaatcc aaacaaaggg ttttatatat tggttagtaa 1680
gaaaaactta gggtgaaaga atagctccta gatactagga actctatcac tcccaaagac 1740
aggatctcaa actggccacc cacaaaagaa tcccccaaaa tccagatacc aaatggatca 1800
agatgccctc ttttctgaag aatctatgga ggatcagaag gagggacact caacaaccag 1860
cacactcacc agtgcagtcg gactcattga catcatcctt gccagtgagc ccacagacat 1920
tagaaaagac agaaaacacc tatgtgagcc catcacagcc tggggaaaat cagaagcaag 1980
caagatttcc aaggatacag tctgtgaaga aaacccaaga acagaaaggg aagattatgg 2040
acaaagtaaa aagagtggaa ttcctaggga gtcaaacaag ttcgaagcag aagtttcttt 2100

-continued

```
tagagaaact catagctcag gtacatcatg gagggcttgg agaagaagta gtgcaaactc   2160
tatacttgag aatatgggca atggatccga ctcctatggc aacgaaatta ctggaaatgg   2220
aggaggaaac cagagacaaa gtcctgaagc taaagttgga gagatggatc cgagttctaa   2280
tacgaggaga aaagacaaaa ctgagggact tccagaagag atacgaggag gttcacccat   2340
atctaatgac ggagaaggtg gaagaaataa taatggagga agcctggagt ctgtcagcac   2400
acataatcca agagtagaaa acaacattat ggatccaact catcatcttg aagaagaggt   2460
acttaagagg aacaagccac gggagatgaa tgctacaagt caatggtcgg gtggatacaa   2520
gactgatcaa caagacggta aacatgaatt gataaccaat ccaatatttt caaatcaaaa   2580
taggtcacag gacacaaaaa agggaaaagg gaaagaatca actgtaaagc ccaagaccag   2640
aaaatctaaa atatcctttg aagacacaag aagcacagat cacatctacg aagactctca   2700
agaacataca agaagaaaga aaacagacaa cgaaccatca caaaagattg gtaaaaaggg   2760
cacagaagag aataccttat atacagaaga ggtgatcaaa ttgttagtga gtcttggtgt   2820
aatcccatct gtagccgcat tcaaccaatc ccgaaacata tgccatgtat ttgcaaaacg   2880
tgtcctcaat tctgtgaact ctgcagaaat gacagctaat atgtgcggat tattgctgtc   2940
tgttgagaaa tcagtatcag accatattga agaaaataag acactaataa atcagattat   3000
aagtgattta agtacaggta gggaagtgca gaaacgtttc actgagtatc aaaaggaaca   3060
gaattcattg attatgtcaa atctggcgac acttcatatc ataacagata gaggaggaaa   3120
gaacaacagc atggatacag gggagaggac accatcaatc aggaccaagg ggaaggagcc   3180
aacacagaga acacaaagat ttgatccatc tatggaattc accgaggaga ttaagtacaa   3240
gcccgatcta tacagggaag acacattgag acaaagaata acaaaccctg ttcttgatga   3300
gagcgcagag agaatcgaca attcgaatgc cgcgagactg ataccttgca aagaaaaatc   3360
aacactgcgt tcactcaaat taattattga gaacagcaat ttgagcagag cagacaaaat   3420
tgcctatatc aggtcattat caaaatgcaa agatgacaaa gaggtagaat cagtaatgaa   3480
actatttgaa gaagatatag aatcaagtaa tgaataatca ctgatcagta tatccagaaa   3540
acgtcaagac aagagtgtac tgtgatgagt aatgactctc caaataccta ataagaaaaa   3600
cttagggtgc aagactcacc aaccaagcca agcaaatggc cgagatctac aagttcccca   3660
agctatcata tgaggaacat ggatatatgg aacctctacc actaaggact ggcccagata   3720
agaaggcagt cccacatata aggataatca agatagggga cccaccgaag catggaaatc   3780
gatatcttga tattctctta cttgggtttt atgagatacc caaagaagtt ggaacatacg   3840
gtagtgtatc agatttgacg agacccacgg gatacacaat ctgcggttca ggatcattac   3900
ctattggaat tgctaggtac ttaggtacag atcaggaact actcaaagca tcagtagagc   3960
taaaagtgac agtgagaagg acagtaaggt caagtgagat gattgtgtat atggtagata   4020
ccataccacc agcaatgatg gcttgggctt ccaggttgaa acgaggcatg atattcaatg   4080
cgaataaagt agctctagct cctcaatgtc tacctataga taaagatata agattcagag   4140
ttgtctttgt caatggcact tctctaggtt ccatcacaat agcaaaagtt cccaagacat   4200
tagccgatct tgctttaccg aattccatat cggtcaattt aatggtctca ctcaagactg   4260
gtgcgtcaac tgagtccaag ggcattattc ctacgctaaa cgaaaagggc gacaaggtac   4320
taaactttat ggtacacctt ggattaatac ataggaaagt cggaagggtg tattcaatgg   4380
agtattgcaa gggtaaaata gagaagatgc ggctgatctt ctcattagga ctggttggag   4440
gaatcagttt ccatgttcag cttacaggtg tggtatctaa atcctttgtt ggtcagcttg   4500
```

-continued gagggaggaa ggaaatatgt taccctttga tggatgtaaa cccacacatg aatttagtta 4560
tctgggctgc ttccgttgaa atcactggcg tggatgctgt tttccaacct tccataccaa 4620
gagatttcaa atactacccg aatgtggtgg caaaaaatat tgggaaaata aaagcttaga 4680
gatccaaagc cactgtaacc ccagacatcc caacactaga ctggtaagtg tcattatatg 4740
atcagcatca ttcatcagaa ataagaaaaa cttagggtac aagttatcca aaaaagacag 4800
aacagaacaa acagatcaag acaagacatc acaaaatgca aatcatcatc ctcagaccag 4860
ccataatact aagcatagta ctattagtga ccagtcaagt ccctagagat aaactagcca 4920
atttagggat catcattaag gacagcaaag cactcaaaat tgcaggatct tatgaaaaca 4980
gatacatagt cttaaacctt gtaccaacaa tagaaaatgt gggtgggtgt ggttccatcc 5040
aaatagcaaa atataaagag atgcttgaaa ggttgttaat accgataaaa gatgcactag 5100
atttacaaga gtctttgata atgattgata atgaaaccgt caacaacaat tatcgtcctc 5160
agtatagatt tgttggtgca attattggga ctatagccct tggggtagca actgcggccc 5220
aagttacagc aggggtggca ctgatggagg caagagaggc caaaagagat atatcagtgt 5280
taaaagaagc aattggaaag actcaaaact caattgaaaa attacagaat tctgcaggtg 5340
aacagatact ggctctcaaa atgctccagg attatgtcaa tggagagatt aaaccagcta 5400
ttgaagaact tggatgtgag actgctgcac ttaaattagg aattgcactt acacaacact 5460
acacagagct cacaaatgcc tttgggtcga atctaggttc cataggagag aagagcttaa 5520
cattacaggc cctatcatca ttatacaaga ccaatataac tgatatactg acaacaacta 5580
atctcgggaa aacagatatt tatgatatta tatatgctga gcaagttaaa ggaagagtaa 5640
tagatgtcga tcttagacga tatatggtta caatatctgt taagatacca atattatcag 5700
aaataccagg agtattgatc tatgaagtct cctctatatc ttataatata gatggaacag 5760
aatggtatgc cgctgtacct gaccacatat taagtaaatc cgcatatata gggggtgcag 5820
atataagtga ttgtatagaa tctggattga catatatttg tccgcgagat cctgctcaga 5880
ttatagcgga taaccaacag caatgttttt taggtcatct tgacaagtgc cctataacta 5940
aagtagttga taatcttgtg cctaaatttg cattcataaa tggtggagta gttgcaaact 6000
gtatagcctc tacatgtacc tgtggagaag agagggtcca ggtctctcaa gatagaaata 6060
aaggagtaac ctttttgact cataataatt gtggattaat agggataaac gggatggaat 6120
ttcatgctaa caagaaaggg agtgatgcta cttggaatgt ctcccccata agagcagggc 6180
cagcggtatc gttaagacca gtagatatat ctttacaaat agtttctgct actaattttc 6240
taaactcatc aagaaaagat cttatgaagg caaaagagat cttaaaccag gtaggaaatc 6300
ttagagattt aaccgtcata acgataatta atatagtaat tatagctgta ttacttatat 6360
gtgtaactgg attaggcgta ctgtatcacc aattgagaag tgcactagtg atgagagaca 6420
agatgtcagt attaaataat agttcctatt ctttagaacc aagaaccacc caggtacaag 6480
taattaagcc tactagtttc atgagataaa ctataaaaat atattttaat ccatcctcat 6540
taatcaaagt aaagaaaact tagggtgcac gacagtaact caccaccaaa ggagaaatag 6600
atcagagacc aacacaccaa gagatggaag gggccaaagt taagacatca gggtactggg 6660
ccaagagtcc tcaaattcac gcaacaaata atcctaacgt acaaaacaga gagaagatca 6720
aggaaacatt aacaatttta atatcattca tttctttcct atctcttgta ctggttatag 6780
ctgtactgat aatgcaatct ttacataacg gcacaatact aaggtgtaaa gatgtaggcc 6840

-continued

```
tagaatctat caataaatcc acttactcta tatctaatgc aattctggat gtcatcaaac   6900
aagagctgat aactcgtata ataaatattc aaagttctgt gcaggtagcc ctcccggtct   6960
taattaacaa gaaaatccag gatctctcac taaccattga gaaaagttca aaagtgcatc   7020
aaaattctcc tacttgtagt ggtgtggctg ccctgacaca tgtggaaggg ataaaacctt   7080
tggatccaga cgattactgg aggtgtccaa gtggggaacc atatctagag gatgaattga   7140
cattaagtct tatccctgga cctagtatgc tagctggaac ctctaccatc gatggctgtg   7200
taagattacc atctcttgca ataggaaaat cgctatatgc ctatagttcc aaccttataa   7260
ctaagggttg tcaagatata gggaaatcct atcaagtgct acagttaggt attataactc   7320
tgaattcaga cttacatcct gatttaaatc ctataatatc acatacttat gatataaatg   7380
ataatagaaa gtcctgttct gttgctgtat cagaaactaa aggataccaa ttatgctcga   7440
tgccgcgtgt caatgaaaaa acagattaca ctagtgatgg tattgaagat atagtttttg   7500
atgtacttga tctcaaaggg tcctctagaa gtttcaaatt ttcaaacaat gatataaact   7560
ttgatcatcc tttttcagcg ttatacccta gtgtaggaag tggtattata tgggaaaatg   7620
aactgtattt cctaggttac ggggctctga caactgcact tcaagggaat acaaaaatgta   7680
atttaatggg atgtccagga gcaacacaaa acaactgcaa caagttcatc tctagttcat   7740
ggttatacag caaacagatg gttaatgtac tgatacaggt taaggggtat ttatctaaca   7800
agccaagtat tatagttaga acaatcccaa taacggaaac ttatgtagga gcagaaggga   7860
aactagtggg aacacgtgag agaatatata tatatacaag atcaacgggt tggcatgcca   7920
atttacaaat aggagtactt aatataaatc atccaataac cataacttgg aaagatcaca   7980
aagtactatc aagaccagga agaagtcctt gtgcctggaa taacaaatgc cctagaaatt   8040
gtactactgg tgtatacaca gatgcttatc ctatatcgcc tgatgctaat tatgttgcta   8100
cagttactct attatctaat tcaacacgaa ctaatcctac tattatgtat tcatcttctg   8160
atagagtata taacatgtta agattaagaa atactgaatt agaagctgca tacacaacca   8220
cgtcttgtat tgtccacttt gatagaggtt attgttttca tattatagaa attaatcaaa   8280
aaggactgaa tacactacag cctatgctct ttaagactgc aattcctaaa gcttgcagga   8340
taagcaattt ataagacacc cattgaaata ataatttgta tctaattact taaaagggtg   8400
actgtgcatg acttagagat aagtgacctg tggacataaa tcatacaggt cattaaatag   8460
catataatac acctaataag aaaaacttag gttgaatgcc aaagcattca gccagaatgg   8520
atcatttcaa tatgtctcaa aatccaagtg atatactata ccctgaatgc cacttgaact   8580
ctccagttgt gaaagggaag atcgctcagc tacatgtctt gttagatatt aatcagccgt   8640
atgaaatgag ggaccctagt ataaatagaaa tcacaaaagt taaaattaaa tctggagggt   8700
taaatcaaag gttaatcaga atcagatctt tagggaaaga gatgaggaga atcatatttg   8760
attttgataa gtatacattc gaaccttacc caatattttc taaagaatta tttagattag   8820
agataccaga gatttgtgat aaaaattcaat cagtttttgc agtgtcggat aggttaagca   8880
aagatatatc ccagccatta caatacttat ggagagatgt gcgtaggcag ttgggagggg   8940
attgttccaa ggatctttct aacaatgaga ttgatataca caaaattcct gaaatccata   9000
ctaaattcac cagaaataac tggtataaac cattcatgac atggtttagt attaaatatg   9060
atatgagaag atgtcaaaag aatagggaaa acataaactt agacagtagg caatcatata   9120
attatcttaa ctgtaaatac tattttataa ttatccaccc ggatctctta atgatattgg   9180
acaagatcaa atacacggga tacttactga caccagaatt agtgctaatg tactgtgatg   9240
```

-continued tggtcgaagg tagatggaat atgtctgctg ctggacaatt agatgacaaa tcacacaaaa 9300
taacattgaa aggagaagaa ttgtggggca ggatagatga attattcaag ataatcgggg 9360
aagagacatt taatatcata tcactattgg agccattatc tttagcattg atacaattaa 9420
cagatcctgt tatgtcttta aaaggtgcat ttatgagaca tgtcatctca gaaatgagtg 9480
aaatattggg taaatgtgga aatctaactg aacttgaggt ggatcacata atggattcaa 9540
tccttaacat ttttatggat acaacagtag atgagaaagc agagatattc tccttcttta 9600
ggacatttgg tcatcctagc cttgaggcct ccatagctgc tgaaaaagtt aggcaacata 9660
tgtatgcgca gaaaagtata aaatataaga ccttatgtga gtgtcacgct atattttgta 9720
caattataat aaacggatat agagacagac atggaggaca gtggcccccc tgtcagttcc 9780
cagatcatgt gtgtcaagaa ctcagaaatt ctcaaggatc taattcagct atatcttatg 9840
aaacagccgt tgacaatttc gagagcttta taggtttcag attcgagaag ttcatagacc 9900
ctcaattaga tgaagatctc actatttaca tgagagataa agcattgtct ccaagaagag 9960
aagcctggga ttctgtgtat ccagatggca atctgctgta taaagtgccg ttctctgaag 10020
aaacaaggag attgatagaa gtctttatta gtgattctaa tttcaatcca gaagacatta 10080
tacaatatgt agagacagga gaatggttga acgatgatac tttcaacata tcttatagcc 10140
taaaagaaaa ggagatcaaa caagagggtc gattgtttgc caagatgaca tacaaaatga 10200
gagcagtcca agtattggca gaaactttgc tagcaaaagg aatagggggt ttatttaatg 10260
aaaatggtat ggttaaaggt gaaatcgatt tactaaagag tctaactact ttatctatat 10320
caggagttcc aaggactagc gagatttata atgaatcagt tagtgaagaa gctgatagga 10380
gaagatggga aagggaaaat tcctcatact attgggataa aagaaaaaaa tcaaaacatg 10440
agttcaaagc cacagactca tctactaacg gctatgagac tctaagctgt tttcttacta 10500
cggacttgaa aaaatattgt ctaaattgga ggtttgagag tacatctcta ttcgggcaga 10560
gatgtaacga aatatttggg ttcaagagat tcttcaactg gatgcatcct gtattggaag 10620
aatgtacaat atatgtgggt gatccttact gtcccgtgcc cgataaaatc cacaagaatt 10680
tagaagatca tgaagattca ggcatcttta tacatagacc gaggggtggg atagaaggtt 10740
attgtcaaaa actttggact ctcatatcca taagtgcaat tcatctagct gctgtcaagg 10800
tcggggttag agtatcagct atggtacaag gtgacaacca agcaattgcc gtgacatcta 10860
gggtaccagt gacggccacg tataagttca aaaaagagca ggtatatacg gagatcacta 10920
agtattttag gtctttaaga gatgtgatgt ctgatttagg acatgaactc aaactcaacg 10980
agacaattat aagtagcaag atgttcgtgt atagtaagcg gatatattat gatggtaaaa 11040
tactacccca atgtttaaaa gcacttacaa ggtgtgtttt ttggtctgag accttggtgg 11100
atgaaaacag gtctgcttgt tccaatcttg caactgctat agccaaagct atagaaaatg 11160
gctattcacc aatattaggt tactcaatag ctctgtataa gacttgtcag caagtatgta 11220
tctcattagg gatgactatc aatcctacaa taacacctaa tataagagac caatattatt 11280
tagggaagaa ttggcttaga tgtgcagttt tgatacctgc taatgttggg ggatttaact 11340
acatggcaat gtctagatgc ttcgtcagaa atataggcga ccctgcagta gctgctctag 11400
cagacctcaa aaggtttatc cgagcaggac tattggacaa gcagattttg taccgtgtaa 11460
tgaatcaaga atctggggag tctaatttct tagactgggc atctgatcca tactcatgta 11520
atttaccaca ttcgcagagt atcacaacaa ttataaagaa tattacagct cgttcagttc 11580

-continued

```
tccaagagtc accaaatcct ctactgtcag gtttatttac atgtgacagt aaagaagaag  11640
acttaaattt agcgacattt ctgatggaca ggaaggtcat attgccaaga gttgcacatg  11700
agatactaga caactctttg acagggatca gagaatccat cgcaggaatg ctggatacta  11760
caaaatcatt agtacgggtt agtattagaa aagggggttt atcatacaat ctcttaagaa  11820
agctgataaa ttatgactta ttacaatatg aaacattaac caggacttta aggaaagtcg  11880
tcacaaataa cattgaatat gaatatatgt gttctgtgga attagcaatt ggattaaggc  11940
aaaaaatgtg gtcacatcta acatatggga gacctataca tggattagaa acacctgatc  12000
ctctagaact ccttaaagga acattcatca aaggatctga ggtttgcaaa atatgcaggt  12060
ctgaaggtga taatcctata tatacttggt tttatttacc tgaggaaata gatctggata  12120
acctagaaca aggaaatcca tctataagaa taccttactt tgggtctact actgacgaaa  12180
gatcagaagc acaactgggt tatgttaaaa cactgagtaa acctgctaaa gcagcgatta  12240
ggattgctat gatatatact tgggcttatg gtactgatga gatatcatgg atggaagcgg  12300
ctcagattgc acaaacaaga gcaaatttaa gtcttgataa tttgaaactt ctgactccgg  12360
tatcaacatc tacaaatctg tcccatagat taaaggacac tgctacccag atgaaattct  12420
caagtgcaac tctagttaga gctagtagat ttattactat atcaaatgat aagatggctc  12480
tgaaggaggc aggtgagaca aaggatacta atttaatata tcagcagata atgttgacag  12540
gacttagtgt ttttgaattc aataccagat acattaaagg taagactaaa caaccaatga  12600
tcctacactt acatttaaac aatggctgct gcattatgga atcaccacaa gagacttgta  12660
tccctcctaa atctactcta gacttagagg taaccaatga agaaaataaa ttaatatatg  12720
ataataatcc attaaaaaat gttgatctcg gtattttcca aaaaattaga gatatcgtac  12780
acactgtaga tatgactttc tggtctgatt tggaaataat gagagcagtt actatttgta  12840
catctatgac aatagcagac accatgtctc aattggatag agataacctt aaagaagtaa  12900
ttgttcttgc gaatgatgat gacattaata gcttaataac agagtttatg ataatagaca  12960
tcccgctctt ttgctcaaca ttcggaggaa tcttagtaaa tcagtttgcc tatgcattat  13020
acggtctaaa tataagaggt agagaagaaa tatggggtta cattacacgg actttgaaag  13080
atacttctca tgctgtgtta aaggtacttg ctaatgcatt atcacatcca aaggtgttca  13140
agagattctg ggatttcggt attttagagc ctgtatatgg acctaattta tccaaccaag  13200
ataagataat gttagcatta tctgtttgtg agtactcaat agacttattc atgagggact  13260
ggcaaagcgg aatacctcta gaaaccttta tatgtgacaa tgatccagaa gtagttgaat  13320
taagaaaagg tgcctacttg gcaagacatt tagcatattt atgcagctta ggagagattt  13380
cctcatatgg tcctagatta gaaactctaa catcattaga aaggttagag gttcttaaaa  13440
gctacctaga gatatcttgt ttagaggatc caacattgag atacagtcag gttacagggc  13500
tggtattaaa agtgttccca tcaacagtag tatatatcag gaagttagct ataaagatgt  13560
tgaggattag gggcataggg gtgccagagg tgttagaaga ctgggatccc agtcatgaac  13620
aagctctact agataatata gctcaagaga tccaacataa tatcccaata aaccaatcta  13680
tcaagacacc tttctggggg ctcaaagtca ataattccca agtcttacgt ctaaggggat  13740
ataaggaggt taaggatagg aaatcagggc gatcaggagt aggtctaaca cttccatgtg  13800
ataataggta cttatcccat cagataagac ttttcgggat taatagtact agctgcctga  13860
aagctttgga gttaacatat ttaataggac cattgataga taaaagtaaa gatagattat  13920
tcttagggga aggtgcaggt gctatgttgt catgttatga tgcaacgtta ggaccttcaa  13980
```

```
tgaactatta taactcaggt gtctcatcat atgatataaa tggtcagagg gaattaggga  14040
tctatccatc tgaggctgca ttagtggcaa agaaattgaa taatgtaact aatttgggtc  14100
agagaattaa ggtgctgttc aacggaaacc ctgggtctac atgggttggc aaccaggaat  14160
gcgaaacatt aatttggagt gaattacagg acaaatcaat cggcttgata cattgtgacc  14220
tagaaggtgg agaactaaaa gatacacaaa cagtactgca tgaacattat agcataatta  14280
ggatagcata cttagtagga gataacgatg ttttattagt gactaaaatt gcacctaaat  14340
tgggtacaga ttggactcag caactatgct tgtatctaag atattggaat gaagtcaatt  14400
tagttgttct taagacatct aatccttctt ctactgagat gtatttgtta tcaaggaatc  14460
caagtaaaga tgtgattgaa gatagtctaa cagtaatctc agacctaaag ccattgtcta  14520
aaaaagatag tatacaatta gaaaagtgga ttttggttga gaaagacaaa gttaaggaat  14580
ggctaattaa agaattaaga gagggagaac taatgtcagg ttcacttagg ccttatcacc  14640
aagcacttca gatttttgga tttgaggcca acttgcacaa attgtgtaga gacttcttat  14700
caactatgag tatttcagat atccagatgt gtataaattc attctacaga gttttaaagg  14760
acacaatatt tgagtggagt cggtaacaa atgatcataa gacatgtaaa ctcacaggga  14820
aatatgagtt atatcctata agagacagtg gaaagttgaa agtgatatca agaaggctta  14880
taatatcctg gattgcttta tccatgtcta ctagactgtt aacaggcgct ttccctgata  14940
ttaagtttga gtccagattg aatataggtt tagtctcctt atctacgaat gagatcaaat  15000
cacttaaact tatatccaag gctacggtgg ataggtttca agaagtgatt cacagtgtat  15060
cctacagatt cttgactaaa gaaattaaaa tactcatgaa gatacttgga gctgttaaat  15120
tatttggtgc aagacagact tataaccatt tagctttaac accagaacct ctatctgata  15180
tagagggata tttagatgat tagctcgaat atcaacagta aacagctaag aatcattaag  15240
aagactatct ggatccagac ctaaatgaaa gaataagaaa aacttattta aacaatcaaa  15300
gatccaagca aaatgatatg tcttaaactc ttgt                              15334
```

```
<210> SEQ ID NO 15
<211> LENGTH: 15334
<212> TYPE: DNA
<213> ORGANISM: Porcine respirovirus 1

<400> SEQUENCE: 15

ggttaaagta ttaacctcaa aaggacagat caggaacttt gatttcttag catagtgcca     60
aaatggcagg gttattaagt gtctttgaca catttagttc taaaaggagt gaaagcataa    120
atagaggagg tggtggtgcg gttatacctg gacaaaagaa caccgtctca gtatttgtcc    180
tagggtcaag tattgtagac gacagcgata agttagctat agcactcatg tttttaacac    240
atgctcttga tactgacaag caacactcac aaagaagcgg tttcctggtt tcattaatgg    300
caatggcata tagtagtcct gaattatatc taacaactaa tggagttaat gcagatgtta    360
agtatgttat ctacacaatt gagcatgatc cccagaggac aacccataat gggttcattg    420
ttaggacaag agatatggac tatgaaaaga caacagagtg gctattcagc cgtataacta    480
ataaataccc actacttcag ggacaaaaag acactcatga tccagaatca ctactccaga    540
cttatggata tccctcatgt ttaggagcat tgataatcca ggtttggatt gtcttggtca    600
aagcaattac aagtagtgct ggattgaaga aaggattctt caatagactt gaagccttca    660
ggcaggatgg aacagttaga agctcactag tcttcagtgg ggagacagtt gaggggattg    720
```

ggtcagtgat gagatctcag cagagtttgg tgtccttaat ggtagagact ctagttacca 780
tgaacacggc cagatctgac ttgaccactc tagaaaagaa tattcagatt gttgggaatt 840
acatcaggga tgcaggtctt gcttcattca tgaacacgat tagatatggt gtggagacta 900
agatggcagc acttacatta tctaatctta gacctgatat taataaacta aagagtctaa 960
ttgacatcta cttatccaaa ggtgcaagag ccccccttcat atgcatatta cgtgatccgg 1020
tacacggaga atttgctcct ggaaattatc cagcattgtg gagttatgct atgggggtcg 1080
cagtagtcca gaacaaagcc atgcagcagt atgtgacagg gaggacttat ctggatatgg 1140
aaatgttcct tcttggtcaa gcagtagcta aagacgcaga atctaagatc agtaatgcat 1200
tagaggatga attaggtata actgaaaatg ccaaagacag gctcaaacat catcttgcta 1260
acctttctgg aggtgatgga gcttatcaca aacccactgg tggaggagca atagaagtta 1320
taattgacaa tgcagacata gatctcagga cagaggaaac cacagaagaa tcttcaatca 1380
ggctttccaa tattagagaa aacaaaggga gaatagcaga cgggcagagg agatgggaaa 1440
caaccagatc cattggtgat gaccccaatc cagacaacac cactgacgat gaagtatccg 1500
ccgcagaaag gaggattgca gaaagactgg caaaaaagga ggggaagaat accaggtcgg 1560
atatactcat taccgatggt atgactgaag atacagataa cgatgatgat ataatgagaa 1620
tgaatgcact aggaggaata taataaatcc aaacaaaggg ttttatatat tggttagtaa 1680
gaaaaactta gggtgaaaga atagctccta gatactagga actctatcac tcccaaagac 1740
aggatctcaa actggccacc cacaaaagaa tcccccaaaa tccagatacc aaatggatca 1800
agatgccctc ttttctgaag aatctatgga ggatcagaag gagggacact caacaaccag 1860
cacactcacc agtgcagtcg gactcattga catcatcctt gccagtgagc ccacagacat 1920
tagaaaagac agaaaacacc tatgtgagcc catcacagcc tggggaaaat cagaagcaag 1980
caagatttcc aaggatacag tctgtgaaga aaacccaaga acagaaaggg aagattatgg 2040
acaaagtaaa aagagtggaa ttcctaggga gtcaaacaag ttcgaagcag aagtttcttt 2100
tagagaaact catagctcag gtacatcatg gagggcttgg agaagaagta gtgcaaactc 2160
tatacttgag aatatgggca atggatccga ctcctatggc aacgaaatta ctggaaatgg 2220
aggaggaaac cagagacaaa gtcctgaagc taaagttgga gagatggatc cgagttctaa 2280
tacgaggaga aaagacaaaa ctgagggact tccagaagag atacgaggag gttcacccat 2340
atctaatgac ggagaaggtg gaagaaataa taatggagga agcctggagt ctgtcagcac 2400
acataatcca agagtagaaa acaacattat ggatccaact catcatcttg aagaagaggt 2460
acttaagagg aacaagccac gggagatgaa tgctacaagt caatggtcgg gtggatacaa 2520
gactgatcaa caagacggta aacatgaatt gataaccaat ccaatatttt caaatcaaaa 2580
taggtcacag gacacaaaaa agggaaaagg gaaagaatca actgtaaagc ccaagaccag 2640
aaaatctaaa atatcctttg aagacacaag aagcacagat cacatctaca aagactctca 2700
agaacataca agaagaaaga aaacagacaa cgaaccatca caaaagattg gtaaaaaggg 2760
cacagaagag aataccttat atacagaaga ggtgatcaaa ttgttagtga gtcttggtgt 2820
aatcccatct gtagccgcat tcaaccaatc ccgaaacata tgccatgtat ttgcaaaacg 2880
tgtcctcaat tctgtgaact ctgcagaaat gacagctaat atgtgcggat tattgctgtc 2940
tgttgagaaa tcagtatcag accatattga agaaaataag acactaataa atcagattat 3000
aagtgattta agtacaggta gggaagtgca gaaacgtttc actgagtatc aaaaggaaca 3060
gaattcattg attatgtcaa atctggcgac acttcatatc ataacagata gaggaggaaa 3120
gaacaacagc atggatacag gggagaggac accatcaatc aggaccaagg ggaaggagcc 3180
aacacagaga acacaaagat ttgatccatc tatggaattc accgaggaga ttaagtacaa 3240
gcccgatcta tacagggaag acacattgag acaaagaata acaaaccctg ttcttgatga 3300
gagcgcagag agaatcgaca attcgaatgc cgcgagactg ataccttgca aagaaaaatc 3360
aacactgcgt tcactcaaat taattattga gaacagcaat ttgagcagag cagacaaaat 3420
tgcctatatc aggtcattat caaaatgcaa agatgacaaa gaggtagaat cagtaatgaa 3480
actatttgaa gaagatatag aatcaagtaa tgaataatca ctgatcagta tatccagaaa 3540
acgtcaagac aagagtgtac tgtgatgagt aatgactctc caaataccta ataagaaaaa 3600
cttagggtgc aagactcacc aaccaagcca agcaaatggc cgagatctac aagttcccca 3660
agctatcata tgaggaacat ggatatatgg aacctctacc actaaggact ggcccagata 3720
agaaggcagt cccacatata aggataatca agataggga cccgccgaag catggaaatc 3780
gatatcttga tattctctta cttgggtttt atgagatacc caaagaagtt ggaacatacg 3840
gtagtgtatc agatttgacg agacccacgg gatacacaat ctgcggttca ggatcattac 3900
ctattggaat tgctaggtac ttaggtacag atcaggaact actcaaagca tcagtagagc 3960
taaaagtgac agtgagaagg acagtaaggt caagtgagat gattgtgtat atggtagata 4020
ccataccacc agcaatgatg gcttgggctt ccaggttgaa acgaggcatg atattcaatg 4080
cgaataaagt agctctagct cctcaatgtc tacctataga taaagatata agattcagag 4140
ttgtctttgt caatggcact tctctaggtt ccatcacaat agcaaaagtt cccaagacat 4200
tagccgatct tgctttaccg aattccatat cggtcaattt aatggtctca ctcaagactg 4260
gtgcgtcaac tgagtccaag ggcattattc ctacgctaaa cgaaaagggc gacaaggtac 4320
taaactttat ggtacacctt ggattaatac ataggaaagt cggaagggtg tattcaatgg 4380
agtattgcaa gggtaaaata gagaagatgc ggctgatctt ctcattagga ctggttggag 4440
gaatcagttt ccatgttcag cttacaggtg tggtatctaa atcctttgtt ggtcagcttg 4500
gagggaggaa ggaaatatgt taccctttga tggatgtaaa cccacacatg aatttagtta 4560
tctgggctgc ttccgttgaa atcactggcg tggatgctgt tttccaacct tccataccaa 4620
gagatttcaa atactacccg aatgtggtgg caaaaaatat tgggaaaata aaagcttaga 4680
gatccaaagc cactgtaacc ccagacatcc caacactaga ctggtaagtg tcattatatg 4740
atcagcatca ttcatcagaa ataagaaaaa cttagggtac aagttatcca aaaaagacag 4800
aacagaacaa acagatcaag acaagacatc acaaaatgca aatcatcatc ctcagaccag 4860
ccataatact aagcatagta ctattagtga ccagtcaagt ccctagagat aaactagcca 4920
atttagggat catcattaag gacagcaaag cactcaaaat tgcaggatct tatgaaaaca 4980
gatacatagt cttaaacctt gtaccaacaa tagaaaatgt gggtgggtgt ggttccatcc 5040
aaatagcaaa atataaagag atgcttgaaa ggttgttaat accgataaaa gatgcactag 5100
atttacaaga gtctttgata atgattgata atgaaaccgt caacaacaat tatcgtcctc 5160
agtatagatt tgttggtgca attattggga ctatagccct tggggtagca actgcggccc 5220
aagttacagc aggggtggca ctgatggagg caagagaggc caaaagagat atatcagtgt 5280
taaaagaagc aattggaaag actcaaaact caattgaaaa attacagaat tctgcaggtg 5340
aacagatact ggctctcaaa atgctccagg attatgtcaa tggagagatt aaaccagcta 5400
ttgaagaact tggatgtgag actgctgcac ttaaattagg aattgcactt acacaacact 5460

-continued acacagagct cacaaatgcc tttgggtcga atctaggttc cataggagag aagagcttaa 5520
cattacaggc cctatcatca ttatacaaga ccaatataac tgatatactg acaacaacta 5580
atctcgggaa aacagatatt tatgatatta tatatgctga gcaagttaaa ggaagagtaa 5640
tagatgtcga tcttagacga tatatggtta caatatctgt taagatacca atattatcag 5700
aaataccagg agtattgatc tatgaagtct cctctatatc ttataatata gatggaacag 5760
aatggtatgc cgctgtacct gaccacatat taagtaaatc cgcatatata gggggtgcag 5820
atataagtga ttgtatagaa tctggattga catatatttg tccgcgagat cctgctcaga 5880
ttatagcgga taaccaacag caatgttttt taggtcatct tgacaagtgc cctataacta 5940
aagtagttga taatcttgtg cctaaatttg cattcataaa tggtggagta gttgcaaact 6000
gtatagcctc tacatgtacc tgtggagaag agagggtcca ggtctctcaa gatagaaata 6060
aaggagtaac ctttttgact cataataatt gtggattaat agggataaac gggatggaat 6120
ttcatgctaa caagaaaggg agtgatgcta cttggaatgt ctccccccata agagcagggc 6180 cagcggtatc gttaagacca gtagatatat ctttacaaat agtttctgct actaattttc 6240
taaactcatc aagaaaagat cttatgaagg caaaagagat cttaaaccag gtaggaaatc 6300
ttagagattt aaccgtcata acgataatta atatagtaat tatagctgta ttacttatat 6360
gtgtaactgg attaggcgta ctgtatcacc aattgagaag tgcactagtg atgagagaca 6420
agatgtcagt attaaataat agttcctatt ctttagaacc aagaaccacc caggtacaag 6480
taattaagcc tactagtttc atgagataaa ctataaaaat atattttaat ccatcctcat 6540
taatcaaagt aaagaaaact tagggtgcac gacagtaact caccaccaaa ggagaaatag 6600
atcagagacc aacacaccaa gagatggaag gggccaaagt taagacatca gggtactggg 6660
ccaagagtcc tcaaattcac gcaacaaata atcctaacgt acaaaacaga gagaagatca 6720
aggaaacatt aacaatttta atatcattca tttctttcct atctcttgta ctggttatag 6780
ctgtactgat aatgcaatct ttacataacg gcacaatact aaggtgtaaa gatgtaggcc 6840
tagaatctat caataaatcc acttactcta tatctaatgc aattctggat gtcatcaaac 6900
aagagctgat aactcgtata ataaatattc aaagttctgt gcaggtagcc ctcccggtct 6960
taattaacaa gaaaatccag gatctctcac taaccattga gaaaagttca aaagtgcatc 7020
aaaattctcc tacttgtagt ggtgtggctg ccctgacaca tgtggaaggg ataaaacctt 7080
tggatccaga cgattactgg aggtgtccaa gtggggaacc atatctagag gatgaattga 7140
cattaagtct tatccctgga cctagtatgc tagctggaac ctctaccatc gatggctgtg 7200
taagattacc atctcttgca ataggaaaat cgctatatgc ctatagttcc aaccttataa 7260
ctaagggttg tcaagatata gggaaatcct atcaagtgct acagttaggt attataactc 7320
tgaattcaga cttacatcct gatttaaatc ccataatatc acatacttat gatataaatg 7380
ataatagaaa gtcctgttct gttgctgtat cagaaactaa aggataccaa ttatgctcga 7440
tgccgcgtgt caatgaaaaa acagattaca ctagtgatgg tattgaagat atagtttttg 7500
atgtacttga tctcaaaggg tcctctagaa gtttcaaatt ttcaaacaat gatataaact 7560
ttgatcatcc tttttcagcg ttataccccta gtgtaggaag tggtattata tgggaaaatg 7620
aactgtattt cctaggttac ggggctctga caactgcact tcaaggggat acaaaatgta 7680
atttaatggg atgtccagga gcaacacaaa acaactgcaa caagttcatc tctagttcat 7740
ggttatacag caaacagatg gttaatgtac tgatacaggt taaggggtat ttatctaaca 7800
agccaagtat tatagttaga acaatcccaa taacggaaac ttatgtagga gcagaaggga 7860

```
aactagtggg aacacgtgag agaatatata tatatacaag atcaacgggt tggcatgcca   7920
atttacaaat aggagtactt aatataaatc atccaataac cataacttgg aaagatcaca   7980
aagtactatc aagaccagga ataagtcctt gtgcctggaa taacaaatgc cctagaaatt   8040
gtactactgg tgtatacaca gatgcttatc ctatatcgcc tgatgctaat tatgttgcta   8100
cagttactct attatctaat tcaacacgaa ctaatcctac tattatgtat tcatcttctg   8160
atagagtata taacatgtta agattaagaa atactgaatt agaagctgca tacacaacca   8220
cgtcttgtat tgtccacttt gatagaggtt attgttttca tattatagaa attaatcaaa   8280
aaggactgaa tacactacag cctatgctct ttaagactgc aattcctaaa gcttgcagga   8340
taagcaattt ataagacacc cattgaaata ataatttgta tctaattact taaaagggtg   8400
actgtgcatg acttagagat aagtgacctg tggacataaa tcatacaggt cattaaatag   8460
catataatac acctaataag aaaaacttag gttgaatgcc aaagcattca gccagaatgg   8520
atcatttcaa tatgtctcaa aatccaagtg atatactata ccctgaatgc cacttgaact   8580
ctccagttgt gaaagggaag atcgctcagc tacatgtctt gttagatatt aatcagccgt   8640
atgaaatgag ggaccctagt ataatagaaa tcacaaaagt taaaattaaa tctggagggt   8700
taaatcaaag gttaatcaga atcagatctt tagggaaaga gatgaggaga atcatatttg   8760
attttgataa gtatacattc gaaccttacc caatattttc taaagaatta tttagattag   8820
agataccaga gatttgtgat aaaattcaat cagtttttgc agtgtcggat aggttaagca   8880
aagatatatc ccagccatta caatacttat ggagagatgt gcgtaggcag ttgggagggg   8940
attgttccaa ggatctttct aacaatgaga ttgatataca caaaattcct gaaatccata   9000
ctaaattcac cagaaataac tggtataaac cattcatgac atggtttagt attaaatatg   9060
atatgagaag atgtcaaaag aatagggaaa acataaactt agacagtagg caatcatata   9120
attatcttaa ctgtaaatac tattttataa ttatccaccc ggatctctta atgatattgg   9180
acaagatcaa atacacggga tacttactga caccagaatt agtgctaatg tactgtgatg   9240
tggtcgaagg tagatggaat atgtctgctg ctggacaatt agatgacaaa tcacacaaaa   9300
taacattgaa aggagaagaa ttgtggggca ggatagatga attattcaag ataatcgggg   9360
aagagacatt taatatcata tcactattgg agccattatc tttagcattg atacaattaa   9420
cagatcctgt tatgtcttta aaaggtgcat ttatgagaca tgtcatctca gaaatgagtg   9480
aaatattggg taaatgtgga aatctaactg aacttgaggt ggatcacata atggattcaa   9540
tccttaacat ttttatggat acaacagtag atgagaaagc agagatattc tccttcttta   9600
ggacatttgg tcatcctagc cttgaggcct ccatagctgc tgaaaaagtt aggcaacata   9660
tgtatgcgca gaaaagtata aaatataaga ccttatgtga gtgtcacgct atattttgta   9720
caattataat aaacggatat agagacagac atggaggaca gtggcccccc tgtcagttcc   9780
cagatcatgt gtgtcaagaa ctcagaaatt ctcaaggatc taattcagct atatcttatg   9840
aaacagccgt tgacaatttc gagagcttta taggtttcag attcgagaag ttcatagacc   9900
ctcaattaga tgaagatctc actatttaca tgagagataa agcattgtct ccaagaagag   9960
aagcctggga ttctgtgtat ccagatggca atctgctgta taaagtgccg ttctctgaag  10020
aaacaaggag attgatagaa gtctttatta gtgattctaa tttcaatcca gaagacatta  10080
tacaatatgt agagacagga gaatggttga acgatgatac tttcaacata tcttatagcc  10140
taaaagaaaa ggagatcaaa caagagggtc gattgtttgc caagatgaca tacaaaatga  10200
```

-continued

```
gagcagtcca agtattggca gaaactttgc tagcaaaagg aatagggggt ttatttaatg  10260
aaaatggtat ggttaaaggt gaaatcgatt tactaaagag tctaactact ttatctatat  10320
caggagttcc aaggactagc gagatttata atgaatcagt tagtgaagaa gctgatagga  10380
gaagatggga aagggaaaat tcctcatact attgggataa aagaaaaaaa tcaaaacatg  10440
agttcaaagc cacagactca tctactaacg gctatgagac tctaagctgt tttcttacta  10500
cggacttgaa aaaatattgt ctaaattgga ggtttgagag tacatctcta ttcgggcaga  10560
gatgtaacga aatatttggg ttcaagagat tcttcaactg gatgcatcct gtattggaag  10620
aatgtacaat atatgtgggt gatccttact gtcccgtgcc cgataaaatc cacaagaatt  10680
tagaagatca tgaagattca ggcatcttta tacatagacc gaggggtggg atagaaggtt  10740
attgtcaaaa actttggact ctcatatcca taagtgcaat tcatctagct gctgtcaagg  10800
tcggggttag agtatcagct atggtacaag gtgacaacca agcaattgcc gtgacatcta  10860
gggtaccagt gacggccacg tataagttca aaaaagagca ggtatatacg gagatcacta  10920
agtattttag gtctttaaga gatgtgatgt ctgatttagg acatgaactc aaactcaacg  10980
agacaattat aagtagcaag atgttcgtgt atagtaagcg gatatattat gatggtaaaa  11040
tactacccca atgtttaaaa gcacttacaa ggtgtgtttt ttggtctgag accttggtgg  11100
atgaaaacag gtctgcttgt tccaatcttg caactgctat agccaaagct atagaaaatg  11160
gctattcacc aatattaggt tactcaatag ctctgtataa gacttgtcag caagtatgta  11220
tctcattagg gatgactatc aatcctacaa taacacctaa tataagagac caatattatt  11280
tagggaagaa ttggcttaga tgtgcagttt tgatacctgc taatgttggg ggatttaact  11340
acatggcaat gtctagatgc ttcgtcagaa atataggcga ccctgcagta gctgctctag  11400
cagacctcaa aaggtttatc cgagcaggac tattggacaa gcagattttg taccgtgtaa  11460
tgaatcaaga atctggggag tctaatttct tagactgggc atctgatcca tactcatgta  11520
atttaccaca ttcgcagagt atcacaacaa ttataaagaa tattacagct cgttcagttc  11580
tccaagagtc accaaatcct ctactgtcag gtttatttac atgtgacagt aaagaagaag  11640
acttaaattt agcgacattt ctgatggaca ggaaggtcat attgccaaga gttgcacatg  11700
agatactaga caactctttg acagggatca gagaatccat cgcaggaatg ctggatacta  11760
caaaatcatt agtacgggtt agtattagaa aaggggggtt atcatacaat ctcttaagaa  11820
agctgataaa ttatgactta ttacaatatg aaacattaac caggacttta aggaaagtcg  11880
tcacaaataa cattgaatat gaatatatgt gttctgtgga attagcaatt ggattaaggc  11940
aaaaaatgtg gtcacatcta acatatggga gacctataca tggattagaa acacctgatc  12000
ctctagaact ccttaaagga acattcatca aaggatctga ggtttgcaaa atatgcaggt  12060
ctgaaggtga taatcctata tatacttggt tttatttacc tgaggaaata gatctggata  12120
acctagaaca aggaaatcca tctataagaa taccttactt tgggtctact actgacgaaa  12180
gatcagaagc acaactgggt tatgttaaaa cactgagtaa acctgctaaa gcagcgatta  12240
ggattgctat gatatatact tgggcttatg gtactgatga gatatcatgg atggaagcgg  12300
ctcagattgc acaaacaaga gcaaatttaa gtcttgataa tttgaaactt ctgactccgg  12360
tatcaacatc tacaaatctg tcccatagat taaaggacac tgctacccag atgaaattct  12420
caagtgcaac tctagttaga gctagtagat ttattactat atcaaatgat aagatggctc  12480
tgaaggaggc aggtgagaca aaggatacta atttaatata tcagcagata atgttgacag  12540
gacttagtgt ttttgaattc aataccagat acattaaagg taagactaaa caaccaatga  12600
```

```
tcctacactt acatttaaac aatggctgct gcattatgga atcaccacaa gagacttgta  12660
tccctcctaa atctactcta gacttagagg taaccaatga agaaaataaa ttaatatatg  12720
ataataatcc attaaaaaat gttgatctcg gtattttcca aaaaattaga gatatcgtac  12780
acactgtaga tatgactttc tggtctgatt tggaaataat gagagcagtt actatttgta  12840
catctatgac aatagcagac accatgtctc aattggatag agataacctt aaagaagtaa  12900
ttgttcttgc gaatgatgat gacattaata gcttaataac agagtttatg ataatagaca  12960
tcccgctctt ttgctcaaca ttcggaggaa tcttagtaaa tcagtttgcc tatgcattat  13020
acggtctaaa tataagaggt agagaagaaa tatggggtta cattacacgg actttgaaag  13080
atacttctca tgctgtgtta aaggtacttg ctaatgcatt atcacatcca aaggtgttca  13140
agagattctg ggatttcggt attttagagc ctgtatatgg acctaattta tccaaccaag  13200
ataagataat gttagcatta tctgtttgtg agtactcaat agacttattc atgagggact  13260
ggcaaagcgg aatacctcta gaaaccttta tatgtgacaa tgatccagaa gtagttgaat  13320
taagaaaagg tgcctacttg gcaagacatt tagcatattt atgcagctta ggagagattt  13380
cctcatatgg tcctagatta gaaactctaa catcattaga aaggttagag gttcttaaaa  13440
gctacctaga gatatcttgt ttagaggatc caacattgag atacagtcag gttacagggc  13500
tggtattaaa agtgttccca tcaacagtag tatatatcag gaagttagct ataaagatgt  13560
tgaggattag gggcataggg gtgccagagg tgttagaaga ctgggatccc agtcatgaac  13620
aagctctact agataatata gctcaagaga tccaacataa tatcccaata aaccaatcta  13680
tcaagacacc tttctggggg ctcaaagtca ataattccca agtcttacgt ctaaggggat  13740
ataaggaggt taaggatagg aaatcagggc gatcaggagt aggtctaaca cttccatgtg  13800
ataataggta cttatcccat cagataagac ttttcgggat taatagtact agctgcctga  13860
aagctttgga gttaacatat ttaataggac cattgataga taaaagtaaa gatagattat  13920
tcttagggga aggtgcaggt gctatgttgt catgttatga tgcaacgtta ggaccttcaa  13980
tgaactatta taactcaggt gtctcatcat atgatataaa tggtcagagg gaattaggga  14040
tctatccatc tgaggctgca ttagtggcaa agaaattgaa taatgtaact aatttgggtc  14100
agagaattaa ggtgctgttc aacggaaacc ctgggtctac atgggttggc aaccaggaat  14160
gcgaaacatt aatttggagt gaattacagg acaaatcaat cggcttgata cattgtgacc  14220
tagaaggtgg agaactaaaa gatacacaaa cagtactgca tgaacattat agcataatta  14280
ggatagcata cttagtagga gataacgatg ttttattagt gactaaaatt gcacctaaat  14340
tgggtacaga ttggactcag caactatgct tgtatctaag atattggaat gaagtcaatt  14400
tagttgttct taagacatct aatccttctt ctactgagat gtatttgtta tcaaggaatc  14460
caagtaaaga tgtgattgaa gatagtctaa cagtaatctc agacctaaag ccattgtcta  14520
aaaaagatag tatacaatta gaaaagtgga ttttggttga gaaagacaaa gttaaggaat  14580
ggctaattaa agaattaaga gagggagaac taatgtcagg ttcacttagg ccttatcacc  14640
aagcacttca gatttttgga tttgaggcca acttgcacaa attgtgtaga gacttcttat  14700
caactatgag tatttcagat atccagatgt gtataaattc attctacaga gttttaaagg  14760
acacaatatt tgagtggagt cgggtaacaa atgatcataa gacatgtaaa ctcacaggga  14820
aatatgagtt atatcctata agagacagtg gaaagttgaa agtgatatca agaaggctta  14880
taatatcctg gattgcttta tccatgtcta ctagactgtt aacaggcgct ttccctgata  14940
```

-continued

```
ttaagtttga gtccagattg aatataggtt tagtctcctt atctacgaat gagatcaaat  15000

cacttaaact tatatccaag gctacggtgg ataggtttca agaagtgatt cacagtgtat  15060

cctacagatt cttgactaaa gaaattaaaa tactcatgaa gatacttgga gctgttaaat  15120

tatttggtgc aagacagact tataaccatt tagctttaac accagaacct ctatctgata  15180

tagagggata tttagatgat tagctcgaat atcaacagta aacagctaag aatcattaag  15240

aagactatct ggatccagac ctaaatgaaa gaataagaaa aacttattta aacaatcaaa  15300

gatccaagca aaatgatatg tcttaaactc ttgt                              15334
```

PORCINE PARAINFLUENZA VIRUS TYPE 1 ISOLATES AND IMMUNOGENIC COMPOSITIONS THEREFROM

CROSS REFERENCE TO RELATED APPLICATIONS

This application claims priority to provisional application U.S. Ser. No. 62/724,713, filed Aug. 30, 2018, which is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Aug. 23, 2019, is named GAUGER_P12113US01_SEQ_LISTING 08-23-19_ST25.txt and is 121,928 bytes in size.

FIELD OF THE INVENTION

This invention relates generally to novel immunogenic compositions that protect swine from disease caused by Porcine Parainfluenza Virus Type 1 (PPIV-1).

BACKGROUND OF THE INVENTION

Respiratory disease is a major health concern to the United States swine industry due to poor growth performance, increased antimicrobial use, and added vaccination costs. Several viruses play a role in the porcine respiratory disease complex (PRDC) and most often include porcine reproductive and respiratory syndrome virus (PRRSV) and influenza A virus (IAV). However, diagnostic investigations have demonstrated that clinical respiratory disease in swine is often polymicrobial involving coinfections with different viruses and bacteria. Specific respiratory pathogens in swine can also be regarded as primary agents capable of causing disease as a single infection or may be classified as secondary pathogens that are considered opportunistic infections when they occur as a coinfection with a primary agent. Pathogens of minor significance include the Paramyxoviridae family consisting of several genera that may contribute to porcine respiratory disease (PRD) in specific geographic regions but uncommon in the United States. Among these, porcine rubulavirus and Nipah virus have been documented in affected pig populations playing a significant role in porcine respiratory disease. In addition to the Nipah virus, Menangle virus and Newcastle disease virus have also been detected in swine. Pigs are the primary reservoir of porcine rubulavirus and cross-species transmission of paramyxoviruses from host to swine have been documented. A new Paramyxovirus detected in swine in Hong Kong and now the United States was designated porcine parainfluenza virus type 1 (PPIV-1) (taxonomic name Porcine Respirovirus type 1) and has been regarded as a potential respiratory pathogen in nursery and grow-finish pigs.

Parainfluenza virus is a member of the Paramyxoviridae family, subfamily Paramyxovirinae, and the genus Respirovirus. This genus consists of five recognized species: bovine parainfluenza virus 3 (BPIV-3), human parainfluenza virus 1 (HPIV-1), human parainfluenza virus 3 (HPIV-3), Sendai Virus (SeV), Simian virus 10, and PPIV-1.

Parainfluenza viruses are rarely detected in pigs. There are reports of swine experiencing respiratory disease and demonstrating neurological clinical signs from a herd in the United States that was infected with a parainfluenza virus type 3 (PIV-3), although its ability to consistently cause clinical disease or its pathogenic potential has not been confirmed. Another Paramyxovirus belonging to the species parainfluenza virus type 5 (PIV-5) was isolated from the lung of swine experiencing respiratory illness in Korea in 2013, although again, the significance of detecting this virus was not confirmed. A report from Hong Kong in 2013 also described a parainfluenza virus belonging to the family Respirovirus that was detected and sequenced from samples collected from deceased swine. PPIV-1 has also been detected in veterinary diagnostic labs in the United States. Although previous evidence suggests PPIV-1 may cause clinical respiratory disease, little is known about its epidemiology or role as a pathogen in the PRDC.

BRIEF SUMMARY OF THE INVENTION

The present invention encompasses immunogenic compositions comprising porcine parainfluenza virus type 1 (PPIV-1) strains. The PPIV-1 strains may be used, in one embodiment, as inactivated or live, attenuated vaccines. Thus, the invention comprises an immunogenic composition, suitable to be used as a vaccine, which comprises a PPIV-1 strain of the invention, preferably live and attenuated, or an immunogenic fragment thereof, one or more adjuvants, and optionally one or more excipients, in an amount effective to elicit production of neutralizing antibodies in swine.

The immunogenic compositions of the invention protect swine from infection by PPIV-1. The present invention includes novel nucleotide and amino acid sequences of PPIV-1, including novel genotypes thereof, all of which are useful in the preparation of vaccines for treating and preventing diseases in swine and other animals. Diagnostic and therapeutic polyclonal and monoclonal antibodies are also a feature of the present invention, as are infectious clones useful in the propagation of the virus and in the preparation of vaccines. The invention also provides the full length genomic sequences of PPIV-1 strains at different passages in cell culture.

The present invention provides methods for inducing an immune response against PPIV-1 and methods of treating or preventing a disease in an animal caused by infection with PPIV-1, including disease states that are directly caused by PPIV-1, and disease states contributed to or potentiated by PPIV-1. Disease states in swine that may be potentiated by PPIV-1, and which may also be treated or prevented according to the practice of the invention, include those associated with porcine respiratory disease complex (PRDC) such as porcine reproductive and respiratory syndrome virus (PRRSV) and influenza A virus (IAV). The present invention also includes the option to administer a combination vaccine, that is, a bivalent or multivalent combination of antigens, which may include live, modified live, or inactivated antigens against the non-PPIV-1 pathogen, with appropriate choice of adjuvant. The present invention also provides methods for determining if a population of swine is in need of vaccination against PPIV-1 infection.

Representative embodiments of the invention include an isolated polynucleotide sequence that includes a genomic polynucleotide which encodes PPIV-1 proteins which are attenuated and may be used as an immunogenic composition. This can include whole genome sequences selected from:

(a) SEQ ID NOs: 1, 14, or 15 or an immunogenic fragment thereof that encodes the PPIV-1 virus;

(b) the complement of any sequence in (a);

(c) a polynucleotide that hybridizes with a sequence of (a) or (b) under stringent conditions defined as hybridizing to filter bound DNA in 0.5M $NaHPO_4$, 7% SDS, 1 mM EDTA at 65° C., and washing in 0.1×SSC/0.1% SDS at 68° C.

(d) a polynucleotide that is at least 70% identical to the polynucleotide of (a) or (b);

(e) a polynucleotide that is at least 80% identical to the polynucleotide of (a) or (b);

(f) a polynucleotide that is at least 90% identical to the polynucleotide of (a) or (b);

(g) a polynucleotide that is at least 95% identical to the polynucleotide of (a) or (b);

(h) a polynucleotide that is at least 98% identical to the polynucleotide of (a) or (b); and (i) a polynucleotide that is at least 99% identical to the polynucleotide of (a) or (b).

The invention further provides RNA and DNA molecules, their complements, fragments and vectors and plasmids for the expression of any such RNA or DNA polynucleotides, and for PPIV-1 virus that is expressed from such nucleotide sequences, wherein said virus is live, or fully or partially attenuated.

Methods of preparing a live, attenuated PPIV-1 such that the virus fails to cause clinical signs of PPIV-1 when administered to a swine but is capable of inducing an immune response that immunizes the swine against pathogenic forms of PPIV-1 are also provided.

The invention also provides a vaccine that comprises a polynucleotide sequence as aforementioned, and corresponding nucleotide sequences that may function as infectious clones.

The invention further provides nucleic acid sequences and resultant protein variants that have amino acid substitutions, and which reduce virulence, cause attenuation and allow the compositions to be used safely as immunogenic compositions and as vaccines. In at least some embodiments the nucleic acid and protein sequences include at least one base or amino acid change such that the sequence is not a naturally occurring sequence.

While multiple embodiments are disclosed, still other embodiments of the present invention will become apparent to those skilled in the art from the following detailed description, which shows and describes illustrative embodiments of the invention. Accordingly, the figures and detailed description are to be regarded as illustrative in nature and not restrictive.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

FIG. 7A shows non-challenged piglet with no lesions; FIG. 7B shows PPIV-1 challenged piglet with mild peribronchiolar lymphocytic cuffing (arrow); FIG. 7C shows PPIV-1 challenged piglet with bronchiolar epithelial changes including proliferation (arrow).

FIG. 8A shows non-challenged piglet with no lesions; FIG. 8B shows PPIV-1 challenged piglet with mild lymphoplasmacytic inflammation in the submucosa (arrow); FIG. 8C shows PPIV-1 challenged piglet with epithelial attenuation and necrosis of the nasal turbinate (arrow).

FIG. 9A shows non-challenged piglet with no lesions; FIG. 9B shows PPIV-1 challenged piglet with PPIV-1 IHC signals in bronchiolar epithelium (arrow); FIG. 9C shows PPIV-1 challenged piglet with PPIV-1 IHC signals in pulmonary parenchyma (arrow).

FIG. 10A shows non-challenged piglet with no lesions; FIG. 10B shows PPIV-1 challenged piglet with PPIV-1 IHC signals in trachea epithelium (arrow); FIG. 10C shows PPIV-1 challenged piglet with PPIV-1 IHC signals in nasal turbinate epithelium (arrow).

DETAILED DESCRIPTION OF THE INVENTION

Figure 1:
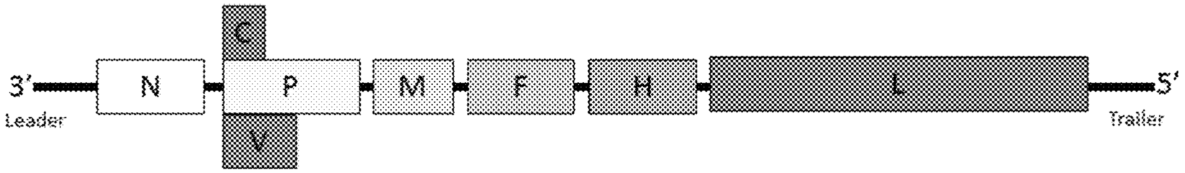
FIG. 1 shows a diagrammatic representation of the Parainfluenza genome and representative open reading frames and their locations in the genome. Parainfluenza is a negative-sense, single-stranded RNA virus of approximately 15 kb in length that encodes eight different proteins.

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

The singular terms "a", "an", and "the" include plural referents unless context clearly indicates otherwise. Similarly, the word "or" is intended to include "and" unless the context clearly indicate otherwise. The word "or" means any one member of a particular list and also includes any combination of members of that list.

Numeric ranges recited within the specification, including ranges of "greater than," "at least," or "less than" a numeric value, are inclusive of the numbers defining the range and include each integer within the defined range.

The term "about," as used herein, refers to variation in the numerical quantity that can occur, for example, through typical measuring techniques and equipment, with respect to any quantifiable variable, including, but not limited to, mass, volume, time, distance, wave length, frequency, voltage, current, and electromagnetic field. Further, given solid and liquid handling procedures used in the real world, there is certain inadvertent error and variation that is likely through differences in the manufacture, source, or purity of the ingredients used to make the compositions or carry out the methods and the like. The term "about" also encompasses amounts that differ due to different equilibrium conditions for a composition resulting from a particular initial mixture. The term "about" also encompasses these variations. Whether or not modified by the term "about," the claims include equivalents to the quantities.

The term "adjuvant" refers to a compound that enhances the effectiveness of the vaccine and may be added to the formulation that includes the immunizing agent. Adjuvants provide enhanced immune response even after administration of only a single dose of the vaccine. Adjuvants may include, for example, aluminum hydroxide and aluminum phosphate, saponins e.g., Quil A, QS-21 (Cambridge Biotech Inc., Cambridge Mass.), GPI-0100 (Galenica Pharmaceuticals, Inc., Birmingham, Ala.), non-metabolizable oil, mineral and/or plant/vegetable and/or animal oils, polymers, carbomers, surfactants, natural organic compounds, plant extracts, carbohydrates, cholesterol, lipids, water-in-oil emulsion, oil-in-water emulsion, water-in-oil-in-water emulsion, HRA-3 (acrylic acid saccharide cross-linked polymer), HRA-3 with cottonseed oil (CSO), or preferably an acrylic acid polyol cross-linked polymer. The emulsion can be based in particular on light liquid paraffin oil (European Pharmacopeia type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the PLURONIC® brand products, especially L121. See Hunter et al., The Theory and Practical Application of Adjuvants (Ed. Stewart-Tull, D. E. S.) John Wiley and Sons, NY, pp 51-94 (1995) and Todd et al., Vaccine 15:564-570 (1997). In a preferred embodiment the adjuvant is at a concentration of about 0.01 to about 50%, preferably at a concentration of about 2% to 30%, more preferably at a concentration of about 5% to about 25%, still more preferably at a concentration of about 7% to about 22%, and most preferably at a concentration of about 10% to about 20% by volume of the final product. Examples of suitable adjuvants are described in U.S. Patent Application Publication No. US2004/0213817 A1. "Adjuvanted" refers to a composition that incorporates or is combined with an adjuvant.

"Antibodies" refers to polyclonal and monoclonal antibodies, chimeric, and single chain antibodies, as well as Fab fragments, including the products of a Fab or other immunoglobulin expression library. With respect to antibodies, the term, "immunologically specific" refers to antibodies that bind to one or more epitopes of a protein of interest, but which do not substantially recognize and bind other molecules in a sample containing a mixed population of antigenic biological molecules.

An "attenuated" PPIV-1 as used herein refers to a PPIV-1 which is capable of infecting and/or replicating in a susceptible host but is non-pathogenic or less-pathogenic to the susceptible host. For example, the attenuated virus may cause no observable/detectable clinical manifestations, or less clinical manifestations, or less severe clinical manifestations, or exhibit a reduction in virus replication efficiency and/or infectivity, as compared with the related field isolated strains. The clinical manifestations of PPIV-1 infection can include, without limitation, flu-like symptoms, i.e. sore throat, fever, and chills.

The term "inactivated" and "inactivated virus" refers to a previously virulent virus that has been irradiated (UV. X-ray or gamma radiation), heated or chemically treated to inactivate, kill, or otherwise modify the virus to substantially eliminate its virulent properties while retaining its immunogenicity. In a preferred embodiment, the inactivated viruses disclosed herein are inactivated by treatment with an inactivating agent. Suitable inactivating agents include beta propiolactone, binary or beta-ethyleneimine (BEI), glutaraldehyde, ozone, and Formalin (formaldehyde).

"Diluents" can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others.

An "epitope" is an antigenic determinant that is immunologically active in the sense that once administered to the host, it is able to evoke an immune response of the humoral (B cells) and/or cellular type (T cells). These are particular chemical groups or peptide sequences on a molecule that are antigenic. An antibody specifically binds a particular antigenic epitope on a polypeptide. In the animal, most antigens will present several or even many antigenic determinants simultaneously. Such a polypeptide may also be qualified as an immunogenic polypeptide and the epitope may be identified as described further.

An "immunogenic or immunological composition" refers to a composition of matter that comprises at least one antigen, which elicits an immunological response in the host of a cellular and/or antibody-mediated immune response to the composition or vaccine of interest. Usually, an "immunological response" includes but is not limited to one or more of the following effects: the production or activation of antibodies, B cells, helper T cells, suppressor T cells, and/or cytotoxic T cells and/or gamma-delta T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of clinical signs normally displayed by an infected host, a quicker recovery time and/or a lowered duration or bacterial titer in the tissues or body fluids or excretions of the infected host compared to a healthy control. Preferably said reduction in symptoms is statistically significant when compared to a control.

The term "immunogenic fragment" as used herein refers to a polypeptide or a fragment of a polypeptide, or a nucleotide sequence encoding the same which comprises an allele-specific motif, an epitope or other sequence such that the polypeptide or the fragment will bind an MHC molecule and induce a cytotoxic T lymphocyte ("CTL") response, and/or a B cell response (for example, antibody production), and/or T-helper lymphocyte response, and/or a delayed type hypersensitivity (DTH) response against the antigen from which the immunogenic polypeptide or the immunogenic fragment is derived. A DTH response is an immune reaction in which T cell-dependent macrophage activation and inflammation cause tissue injury. A DTH reaction to the subcutaneous injection of antigen is often used as an assay for cell-mediated immunity.

An "infectious DNA molecule", for purposes of the present invention, is a DNA molecule that encodes the necessary elements for viral replication, transcription, and translation into a functional virion in a suitable host cell.

The term "isolated" is used to indicate that a cell, peptide, or nucleic acid is separated from its native environment. Isolated peptides and nucleic acids may be substantially pure, i.e. essentially free of other substances with which they may be bound in nature.

For purposes of the present invention, the nucleotide sequence of a second polynucleotide molecule (either RNA or DNA) is "homologous" to the nucleotide sequence of a first polynucleotide molecule, or has "identity" to said first polynucleotide molecule, where the nucleotide sequence of the second polynucleotide molecule encodes the same polyaminoacid as the nucleotide sequence of the first polynucleotide molecule as based on the degeneracy of the genetic code, or when it encodes a polyaminoacid that is sufficiently similar to the polyaminoacid encoded by the nucleotide sequence of the first polynucleotide molecule so as to be useful in practicing the present invention. Homologous polynucleotide sequence also refers to sense and antisense strands, and in all cases to the complement of any such strands. For purposes of the present invention, a polynucleotide molecule is useful in practicing the present invention, and is therefore homologous or has identity, where it can be used as a diagnostic probe to detect the presence of PPIV-1 or viral polynucleotide in a fluid or tissue sample of an infected pig, e.g. by standard hybridization or amplification techniques. Generally, the nucleotide sequence of a second polynucleotide molecule is homologous to the nucleotide sequence of a first polynucleotide molecule if it has at least about 70% nucleotide sequence identity to the nucleotide sequence of the first polynucleotide molecule as based on the BLASTN algorithm (National Center for Biotechnology Information, otherwise known as NCBI, (Bethesda, Md., USA) of the United States National Institute of Health). In a specific example for calculations according to the practice of the present invention, reference is made to BLASTP 2.2.6 [Tatusova T A and TL Madden, "BLAST 2 sequences—a new tool for comparing protein and nucleotide sequences." (1999) FEMS Microbiol Lett. 174:247-2501. Briefly, two amino acid sequences are aligned to optimize the alignment scores using a gap opening penalty of 10, a gap extension penalty of 0.1, and the "blosum62" scoring matrix of Henikoff and Henikoff (Proc. Nat. Acad. Sci. USA 325 89:10915-10919. 1992). The percent identity is then calculated as: Total number of identical matches X 100/divided by the length of the longer sequence+number of gaps introduced into the longer sequence to align the two sequences.

Preferably, a homologous nucleotide sequence has at least about 75% nucleotide sequence identity, even more preferably at least about 80%, 85%, 90%, 95%, 96%, 97%, 98%, 99%, and 99.5% nucleotide sequence identity. Since the genetic code is degenerate, a homologous nucleotide sequence can include any number of "silent" base changes, i.e. nucleotide substitutions that nonetheless encode the same amino acid.

A homologous nucleotide sequence can further contain non-silent mutations, i.e. base substitutions, deletions, or additions resulting in amino acid differences in the encoded polyaminoacid, so long as the sequence remains at least about 70% identical to the polyaminoacid encoded by the first nucleotide sequence or otherwise is useful for practicing the present invention. In this regard, certain conservative amino acid substitutions may be made which are generally recognized not to inactivate overall protein function: such as in regard of positively charged amino acids (and vice versa), lysine, arginine and histidine; in regard of negatively charged amino acids (and vice versa), aspartic acid and glutamic acid; and in regard of certain groups of neutrally charged amino acids (and in all cases, also vice versa), (1) alanine and serine, (2) asparagine, glutamine, and histidine, (3) cysteine and serine, (4) glycine and proline, (5) isoleucine, leucine and valine, (6) methionine, leucine and isoleucine, (7) phenylalanine, methionine, leucine, and tyrosine, (8) serine and threonine, (9) tryptophan and tyrosine, (10) and for example tyrosine, tyrptophan and phenylalanine. Amino acids can be classified according to physical properties and contribution to secondary and tertiary protein structure. A conservative substitution is thus recognized in the art as a substitution of one amino acid for another amino acid that has similar properties, and exemplary conservative substitutions may be found in WO 97/09433, page 10, published Mar. 13, 1997 (PCT/GB96/02197, filed Sep. 6, 1996). Alternatively, conservative amino acids can be grouped as described in Lehninger, (Biochemistry, Second Edition; Worth Publishers, Inc. NY:New York (1975), pp. 71-77). Protein sequences can be aligned using both Vector NTI Advance 11.5 and CLUSTAL 2.1 multiple sequence alignment. As used herein the recitation of a particular amino acid or nucleotide sequence shall include all silent mutations with respect to nucleic acid sequence and any and all conservatively modified variants with respect to amino acid sequences.

Homologous nucleotide sequences can be determined by comparison of nucleotide sequences, for example by using BLASTN, above. Alternatively, homologous nucleotide sequences can be determined by hybridization under selected conditions. For example, the nucleotide sequence of a second polynucleotide molecule is homologous to SEQ ID NO:1 (or any other particular polynucleotide sequence) if it hybridizes to the complement of SEQ ID NO:1 under moderately stringent conditions, e.g., hybridization to filter-bound DNA in 0.5 M $NaHPO_4$, 7% sodium dodecyl sulfate (SDS), 1 mM EDTA at 65° C., and washing in 0.2×SSC/0.1% SDS at 42° C. (see Ausubel et al editors, Protocols in Molecular Biology, Wiley and Sons, 1994, pp. 6.0.3 to 6.4.10), or conditions which will otherwise result in hybridization of sequences that encode a PPIV-1 virus. Modifications in hybridization conditions can be empirically determined or precisely calculated based on the length and percentage of guanosine/cytosine (GC) base pairing of the probe. The hybridization conditions can be calculated as described in Sambrook, et al., (Eds.), Molecular Cloning: A Laboratory Manual, Cold Spring Harbor Laboratory Press: Cold Spring Harbor, N.Y. (1989), pp. 9.47 to 9.51.

In another embodiment, a second nucleotide sequence is homologous to SEQ ID NO: 1 (or any other sequence disclosed herein) if it hybridizes to the complement of SEQ ID NO: 1 under highly stringent conditions, e.g. hybridization to filter-bound DNA in 0.5 M $NaHPO_4$, 7% SDS, 1 mM EDTA at 65° C., and washing in 0.1×SSC/0.1% SDS at 68° C., as is known in the art.

It is furthermore to be understood that the isolated polynucleotide molecules and the isolated RNA molecules of the present invention include both synthetic molecules and molecules obtained through recombinant techniques, such as by in vitro cloning and transcription.

"Mammals" include any warm-blooded vertebrates of the Mammalia class, including humans. The terms "porcine" and "swine" are used interchangeably herein and refer to any animal that is a member of the family Suidae such as, for example, a pig.

As used herein, "a pharmaceutically acceptable carrier" or "pharmaceutical carrier" includes any and all excipients, solvents, growth media, dispersion media, coatings, adjuvants, stabilizing agents, diluents, preservatives, inactivating agents, antimicrobial, antibacterial and antifungal agents, isotonic agents, adsorption delaying agents, and the like. Such ingredients include those that are safe and appropriate for use in veterinary applications. Pharmaceutically acceptable carriers are typically non-toxic, inert, solid or liquid carriers.

A "susceptible" host as used herein refers to a cell or an animal that can be infected by PPIV-1. When introduced to a susceptible animal, an attenuated PPIV-1 may also induce an immunological response against the PPIV-1 or its antigen, and thereby render the animal immunity against PPIV-1 infection.

The term "vaccine" refers to an antigenic preparation used to produce immunity to a disease, in order to prevent or ameliorate the effects of infection. Vaccines are typically prepared using a combination of an immunologically effective amount of an immunogen together with an adjuvant effective for enhancing the immune response of the vaccinated subject against the immunogen.

Vaccine formulations will contain a "therapeutically effective amount" of the active ingredient, that is, an amount capable of eliciting an induction of an immunoprotective response in a subject to which the composition is administered. In the treatment and prevention of PPIV-1, for example, a "therapeutically effective amount" would preferably be an amount that enhances resistance of the vaccinated subject to new infection and/or reduces the clinical severity of the disease. Such protection will be demonstrated by either a reduction or lack of symptoms normally displayed by a subject infected with PPIV-1, a quicker recovery time and/or a lowered count of virus particles. Vaccines can be administered prior to infection, as a preventative measure against PPIV-1. Alternatively, vaccines can be administered after the subject already has contracted a disease. Vaccines given after exposure to PPIV-1 may be able to attenuate the disease, triggering a superior immune response than the natural infection itself.

The present invention provides for reduction of the incidence of and/or severity of clinical symptoms associated with PPIV-1 infection. Preferably, the severity and/or incidence of clinical symptoms in animals receiving the immunogenic composition of the present invention are reduced at least 10% in comparison to animals not receiving such an administration when both groups (animals receiving and animals not receiving the composition) are challenged with or exposed to infection by PPIV-1. More preferably, the incidence or severity is reduced at least 20%, even more preferably, at least 30%, still more preferably, at least 40%, even more preferably, at least 50%, still more preferably, at least 60%, even more preferably, at least 70%, still more preferably, at least 80%, even more preferably, at least 90%, still more preferably, at least 95%, and most preferably, at least 100%, wherein the animals receiving the composition of the present invention exhibit no clinical symptoms, or alternatively exhibit clinical symptoms of reduced severity.

For the purpose of the practice of all aspects of the invention, it is well known to those skilled in the art that there is no absolute immunological boundary in immunological assays in regard of animals that are seronegative for exposure to a particular antigen or pathogen, and those that are seropositive (having been exposed to a vaccine or pathogen). Nonetheless, those skilled in the art would recognize that in serum neutralization assays, seropositive animals would generally be detected at least up to a 1:1000 serum dilution, whereas a seronegative animal would be expected not to neutralize at a higher dilution than about 1:20 or 1:10.

Vaccine & Immunogenic Compositions

The invention also relates to an immunogenic composition, suitable to be used as a vaccine, which comprises a PPIV-1 strain according to the invention. The immunogenic compositions according to the invention elicit a specific humoral immune response toward the PPIV-1 comprising neutralizing antibodies.

The preferred immunogenic compositions based upon the variant strains disclosed herein can provide live, attenuated viruses which exhibit high immunogenicity while at the same time not producing dangerous pathogenic or lethal effects.

The immunogenic and vaccine compositions of this invention are not, however, restricted to any particular type or method of preparation. These include, but are not limited to, infectious DNA vaccines (i.e., using plasmids, vectors or other conventional carriers to directly inject DNA into pigs), live vaccines, modified live vaccines, inactivated vaccines, subunit vaccines, attenuated vaccines, genetically engineered vaccines, etc. These vaccines are prepared by standard methods known in the art.

The present invention preferably includes immunogenic compositions comprising a live, attenuated PPIV-1 of the invention and a pharmaceutically acceptable carrier. As used herein, the expression "live, attenuated PPIV-1 of the invention" encompasses any live, attenuated PPIV-1 strain that includes one or more of the variations described herein. The pharmaceutically acceptable carrier can be, e.g., water, a stabilizer, a preservative, culture medium, or a buffer. Immunogenic and vaccine compositions comprising the attenuated PPIV-1 of the invention can be prepared in the form of a suspension or in a lyophilized form or, alternatively, in a frozen form. If frozen, glycerol or other similar agents may be added to enhance stability when frozen. The advantages of live attenuated viruses, in general, include the presentation of all the relevant immunogenic determinants of an infectious agent in its natural form to the host's immune system, and the need for relatively small amounts of the immunizing agent due to the ability of the agent to multiply in the vaccinated host.

Attenuation of the virus for a live vaccine, so that it is insufficiently pathogenic to substantially harm the vaccinated target animal, may be accomplished by known procedures, including preferably by serial passaging. The following references provide various general methods for attenuation, and are suitable for attenuation or further attenuation of any of the strains useful in the practice of the present invention: B. Neuman et al., Journal of Virology, vol. 79, No. 15, pp. 9665-9676, 2005; J. Netland et al., Virology, v 399(1), pp. 120-128, 2010; Y-P Huang et al., "Sequence changes of infectious bronchitis virus isolates in the 3' 7.3 kb of the genome after attenuating passage in embryonated eggs, Avian Pathology, v. 36 (1), (Abstract), 2007; and S. Hingley et al., Virology, v. 200(1) 1994, pp. 1-10; see U.S. Pat. No. 3,914,408; and Ortego et al., Virology, vol. 308 (1), pp. 13-22, 2003. In some embodiments, the live, attenuated PPIV-1 is attenuated by passaging in cell culture such that when the attenuated virus is administered to a swine it fails to cause clinical signs of PPIV-1 but is capable of inducing an immune response that immunizes the swine against pathogenic forms of PPIV-1. In some embodiments, the PPIV-1 is passaged in LLC-MK2 cells.

In some embodiments, the live, attenuated PPIV-1 comprises a substitution at one or more of the following positions: position 898 of phosphoprotein gene as determined by reference to SEQ ID NO: 4; position 129 of matrix protein gene as determined by reference to SEQ ID NO: 6; or position 305, 729, 1045, 1217, or 1379 of hemagglutinin-neuraminidase gene as determined by reference to SEQ ID NO: 10. Preferably, the live, attenuated PPIV-1 comprises one of more of the following nucleotide substitutions: an A at position 898 of phosphoprotein gene as determined by reference to SEQ ID NO: 4; a G at position 129 of matrix protein gene as determined by reference to SEQ ID NO: 6; or a T at position 305, a C at position 729, a G at position 1045, a C at position 1217, or a T at position 1379 of hemagglutinin-neuraminidase gene as determined by reference to SEQ ID NO: 10.

In some embodiments, the live, attenuated PPIV-1 encodes one or more of the following proteins with amino acid substitutions at one or more of the following positions: position 300 of phosphoprotein as determined by reference to SEQ ID NO: 5; or position 102, 349, 406, or 460 of hemagglutinin-neuraminidase protein as determined by reference to SEQ ID NO: 11. Preferably, the live, attenuated PPIV-1 comprises a nucleotide sequence which encodes one or more of the following proteins with one or more of the following amino acid substitutions: a lysine at position 300 of phosphoprotein as determined by reference to SEQ ID NO: 5; or an isoleucine at position 102, an aspartic acid at position 349, a threonine at position 406, or an isoleucine at position 460 of hemagglutinin-neuraminidase protein as determined by reference to SEQ ID NO: 11.

In some embodiments, the live, attenuated PPIV-1 comprises an RNA nucleotide sequence that is at least 90%, 95%, 96%, 97%, 98%, 99%, or 99.5% identical to the DNA sequence set forth in SEQ ID NOs: 14 or 15. Preferably, the live, attenuated PPIV-1 comprises an RNA nucleotide sequence that is at least 90%, 95%, 96%, 97%, 98%, 99%, or 99.5% identical to the DNA sequence set forth in SEQ ID NOs: 14 or 15 and includes an A at position 2690, a G at position 3764, a T at position 6928, a C at position 7352, a G at position 7668, a C at position 7840, and/or a T at position 8002. More preferably, the live, attenuated virus PPIV-1 comprises an RNA nucleotide sequence that corresponds to the DNA sequence set forth in SEQ ID NOs:14 or 15.

Additional genetically engineered vaccines, which are desirable in the present invention, are produced by techniques known in the art. Such techniques involve, but are not limited to, further manipulation of recombinant DNA, modification of or substitutions to the amino acid sequences of the recombinant proteins and the like.

Genetically engineered vaccines based on recombinant DNA technology are made, for instance, by identifying alternative portions of the viral gene encoding proteins responsible for inducing a stronger immune or protective response in pigs (e.g., proteins derived from N, P, M, F, HN, or L, etc.). Various subtypes or isolates of the viral protein genes can be subjected to the DNA-shuffling method. The resulting heterogeneous chimeric viral proteins can be used broad protecting subunit vaccines. Alternatively, such chimeric viral genes or immuno-dominant fragments can be cloned into standard protein expression vectors, such as the baculovirus vector, and used to infect appropriate host cells (see, for example, O'Reilly et al., "Baculovirus Expression Vectors: A Lab Manual," Freeman & Co., 1992). The host cells are cultured, thus expressing the desired vaccine proteins, which can be purified to the desired extent and formulated into a suitable vaccine product.

If the clones retain any undesirable natural abilities of causing disease, it is also possible to pinpoint the nucleotide sequences in the viral genome responsible for any residual virulence, and genetically engineer the virus avirulent through, for example, site-directed mutagenesis. Site-directed mutagenesis is able to add, delete or change one or more nucleotides (see, for instance, Zoller et al., DNA 3:479-488, 1984). An oligonucleotide is synthesized containing the desired mutation and annealed to a portion of single stranded viral DNA. The hybrid molecule, which results from that procedure, is employed to transform bacteria. Then double-stranded DNA, which is isolated containing the appropriate mutation, is used to produce full-length DNA by ligation to a restriction fragment of the latter that is subsequently transfected into a suitable cell culture. Ligation of the genome into the suitable vector for transfer may be accomplished through any standard technique known to those of ordinary skill in the art. Transfection of the vector into host cells for the production of viral progeny may be done using any of the conventional methods such as calcium-phosphate or DEAE-dextran mediated transfection, electroporation, protoplast fusion and other well-known techniques (e.g., Sambrook et al., "Molecular Cloning: A Laboratory Manual," Cold Spring Harbor Laboratory Press, 1989). The cloned virus then exhibits the desired mutation. Alternatively, two oligonucleotides can be synthesized which contain the appropriate mutation. These may be annealed to form double-stranded DNA that can be inserted in the viral DNA to produce full-length DNA.

An immunologically effective amount of the vaccines of the present invention is administered to a pig in need of protection against viral infection. The immunologically effective amount or the immunogenic amount that inoculates the pig can be easily determined or readily titrated by routine testing. An effective amount is one in which a sufficient immunological response to the vaccine is attained to protect the pig exposed to the PPIV-1 virus. Preferably, the pig is protected to an extent in which one to all of the adverse physiological symptoms or effects of the viral disease are significantly reduced, ameliorated or totally prevented.

The vaccine or immunogenic compositions of the present invention can be formulated following accepted convention to include acceptable carriers for animals, such as standard buffers, stabilizers, diluents, preservatives, and/or solubilizers, and can also be formulated to facilitate sustained release. Diluents include water, saline, dextrose, ethanol, glycerol, and the like. Additives for isotonicity include sodium chloride, dextrose, mannitol, sorbitol, and lactose, among others. Stabilizers include albumin, among others. Other suitable vaccine vehicles and additives, including those that are particularly useful in formulating modified live vaccines, are known or will be apparent to those skilled in the art. See, e.g., Remington's Pharmaceutical Science, 18th ed., 1990, Mack Publishing, which is incorporated herein by reference.

The vaccine or immunogenic compositions of the present invention may further comprise one or more additional immunomodulatory components such as, e.g., an adjuvant or cytokine, among others. Non-limiting examples of adjuvants that can be used in the vaccine of the present invention include the RIBI adjuvant system (Ribi Inc., Hamilton, Mont.), alum, mineral gels such as aluminum hydroxide gel, oil-in-water emulsions, water-in-oil emulsions such as, e.g., Freund's complete and incomplete adjuvants, Block copolymer (CytRx, Atlanta Ga.), QS-21 (Cambridge Biotech Inc., Cambridge Mass.), SAF-M (Chiron, Emeryville Calif.), AMPHIGEN® adjuvant, saponin, Quil A or other saponin fraction, monophosphoryl lipid A, ionic polysaccharides, and Avridine lipid-amine adjuvant. Non-limiting examples of oil-in-water emulsions useful in the vaccine of the invention include modified SEAM62 and SEAM 1/2 formulations. Modified SEAM62 is an oil-in-water emulsion containing 5% (v/v) squalene (Sigma), 1% (v/v) SPAN® 85 detergent (ICI Surfactants), 0.7% (v/v) TWEEN® 80 detergent (ICI Surfactants), 2.5% (v/v) ethanol, 200 μg/ml Quil A, 100 μg/ml cholesterol, and 0.5% (v/v) lecithin. Modified SEAM 1/2 is an oil-in-water emulsion comprising 5% (v/v) squalene, 1% (v/v) SPAN® 85 detergent, 0.7% (v/v) Tween 80 detergent, 2.5% (v/v) ethanol, 100 μg/ml Quil A, and 50 μg/ml cholesterol. Other immunomodulatory agents that can be included in the vaccine include, e.g., one or more interleukins, interferons, or other known cytokines. Additional adjuvant systems permit for the combination of both T-helper and B-cell epitopes, resulting in one or more types of covalent T-B epitope linked structures, which may be additionally lipidated, such as those described in WO2006/084319, WO2004/014957, and WO2004/014956.

At least one vaccine or immunogenic composition of the present invention can be administered by any means that achieve the intended purpose, using a composition as described herein. For example, route of administration of such a composition can be by parenteral, oral, oronasal, intranasal, intratracheal, topical, subcutaneous, intramuscular, transcutaneous, intradermal, intraperitoneal, intraocular, and intravenous administration. In one embodiment of the present invention, the composition is administered by intramuscularly. Parenteral administration can be by bolus injection or by gradual perfusion over time. Any suitable device may be used to administer the compositions, including syringes, droppers, needleless injection devices, patches, and the like. The route and device selected for use will depend on the composition of the adjuvant, the antigen, and the subject, and such are well known to the skilled artisan. Administration that is oral, or alternatively, subcutaneous, is preferred. Oral administration may be direct, via water, or via feed (solid or liquid feed). When provided in liquid form, the vaccine may be lyophilized with reconstitution, or provided as a paste, for direct addition to feed (mix in or top dress) or otherwise added to water or liquid feed.

The appropriate dose of the immunogenic composition of the present invention depends on several variables such as the formulation, the route of administration, the animal's age, the animal's weight, the time of administration, the excretion rate, and reaction irritability. One of ordinary skill in the art can determine the appropriate dose by administering the antigen to the animal and assaying for an increase or, if applicable, a decrease in the immune response.

The immunogenic compositions may comprise proteins and/or antigens from at least one additional pathogen ("non-PPIV-1"). The additional pathogen may be any pathogen that causes illness and/or an infection in a porcine subject. Exemplary pathogens include, but are not limited to, porcine reproductive and respiratory syndrome virus (PRRSV), *Mycoplasma hyopneumoniae, Mycoplasma hyosynoviae, Mycoplasma rhinitis, Clostridium tetani, Clostridium perfringens*, porcine parvovirus, *Erysipelothrix rhusiopathiae, Leptospira pomona, Leptospira grippotyphosa, Leptospira hardjo, Leptospira canicola, Leptospira icterohaemorrhagiae, Leptospira Bratislava*, porcine circovirus, *Lawsonia intracellularis, Escherchia coli, Actinobacillus pleuropneumoniae, Haemophilus parasuis, Salmonella choleraesuis, Salmonella typhimurium, Streptococcus suis, Pasteurella multocida, Bordetella bronchiseptica, Actinobacillus pleuropneumoniae, Serpulina hyodysenteriae*, encephalomyocarditis virus, swine influenza virus, transmissible gastroenteritis virus (TGE), swine delta coronavirus, rotavirus diarrhea, foot and mouth disease virus, classical swine fever virus, pseudorabies virus, Japanese encephalitis virus (JEV), encephalomyocarditis virus, or a combination thereof. In other embodiments, the additional pathogen includes those associated with porcine respiratory disease complex (PRDC) such as porcine reproductive and respiratory syndrome virus (PRRSV) and influenza A virus (IAV).

Embodiments herein relating to "vaccine compositions" of the invention are also applicable to embodiments relating to "immunogenic compositions" of the invention, and vice versa.

Polypeptides and Polynucleotides of the Invention

Representative embodiments of the invention include an isolated polynucleotide sequence that comprises a polynucleotide selected from: (a) SEQ ID NOs: 1, 14, or 15; (b) the complement of any sequence in (a); (c) a polynucleotide that hybridizes with a sequence of (a) or (b) under stringent conditions defined as hybridizing to filter bound DNA in 0.5M $NaHPO_4$, 7% SDS, 1 mM EDTA at 65° C., and washing in 0.1×SSC/0.1% SDS at 68° C.; (d) a polynucleotide that is at least 70% identical to the polynucleotide of (a) or (b); (e) a polynucleotide that is at least 80% identical to the polynucleotide of (a) or (b); (f) a polynucleotide that is at least 90% identical to the polynucleotide of (a) or (b); (g) a polynucleotide that is at least 95% identical to the polynucleotide of (a) or (b); (h) a polynucleotide that is at least 98% identical to the polynucleotide of (a) or (b); and (i) a polynucleotide that is at least 99% identical to the polynucleotide of (a) or (b).

The invention also provides a polypeptide encoded by any of the open reading frames of SEQ ID NOs: 1, 14, or 15, combinations thereof, or a polypeptide that is at least 90% identical thereto, domains thereof, or to a fragment thereof, including the option that additional otherwise identical amino acids are replaced by conservative substitutions. The invention also provides a polypeptide encoded by any of the open reading frames of the PPIV-1 strains of the invention as set forth in SEQ ID NOs: 3, 5, 7, 9, 11, or 13, or a polypeptide that is at least 90% identical thereto, or to a fragment thereof, including the option that additional otherwise identical amino acids are replaced by conservative substitutions. In some embodiments, the polypeptides comprise one or more of the following amino acid substitutions: a lysine at position 300 of phosphoprotein as determined by reference to SEQ ID NO: 5; or an isoleucine at position 102, an aspartic acid at position 349, a threonine at position 406, or an isoleucine at position 460 of hemagglutinin-neuraminidase protein as determined by reference to SEQ ID NO: 11.

In some embodiments, the polynucleotide comprises a substitution at one or more of the following positions: position 898 of phosphoprotein gene as determined by reference to SEQ ID NO: 4; position 129 of matrix protein gene as determined by reference to SEQ ID NO: 6; or position 305, 729, 1045, 1217, or 1379 of hemagglutinin-neuraminidase gene as determined by reference to SEQ ID NO: 10. Preferably, the polynucleotide comprises one of more of the following nucleotide substitutions: an A at position 898 of phosphoprotein gene as determined by reference to SEQ ID NO: 4; a G at position 129 of matrix protein gene as determined by reference to SEQ ID NO: 6; or a T at position 305, a C at position 729, a G at position 1045, a C at position 1217, or a T at position 1379 of hemagglutinin-neuraminidase gene as determined by reference to SEQ ID NO: 10.

In some embodiments, the polynucleotide encodes one or more of the following polypeptides with amino acid substitutions at one or more of the following positions: position 300 of phosphoprotein as determined by reference to SEQ ID NO: 5; or position 102, 349, 406, or 460 of hemagglutinin-neuraminidase protein as determined by reference to SEQ ID NO: 11. Preferably, the polynucleotide comprises a nucleotide sequence which encodes one or more of the following polypeptides with one or more of the following amino acid substitutions: a lysine at position 300 of phosphoprotein as determined by reference to SEQ ID NO: 5; or an isoleucine at position 102, an aspartic acid at position 349, a threonine at position 406, or an isoleucine at position 460 of hemagglutinin-neuraminidase protein as determined by reference to SEQ ID NO: 11.

In some embodiments, the polynucleotide comprises an RNA nucleotide sequence that is at least 90%, 95%, 96%, 97%, 98%, 99%, or 99.5% identical to the DNA sequence set forth in SEQ ID NOs: 14 or 15. Preferably, the polynucleotide comprises an RNA nucleotide sequence that is at least 90%, 95%, 96%, 97%, 98%, 99%, or 99.5% identical to the DNA sequence set forth in SEQ ID NOs: 14 or 15 and includes an A at position 2690, a G at position 3764, a T at position 6928, a C at position 7352, a G at position 7668, a C at position 7840, and/or a T at position 8002.

Further Genetic Manipulations

The polynucleotide and amino acid sequence information provided by the present invention also makes possible the systematic analysis of the structure and function of the viral genes and their encoded gene products. Knowledge of a polynucleotide encoding a viral gene product of the invention also makes available anti-sense polynucleotides which recognize and hybridize to polynucleotides encoding a polypeptide of the invention, or a fragment thereof. Full length and fragment anti-sense polynucleotides are useful in this respect. The worker of ordinary skill will appreciate that fragment anti-sense molecules of the invention include (i) those which specifically recognize and hybridize to a specific RNA (as determined by sequence comparison of DNA encoding a viral polypeptide of the invention as well as (ii) those which recognize and hybridize to RNA encoding variants of the encoded proteins. Antisense polynucleotides that hybridize to RNA/DNA encoding other PPIV-1 peptides are also identifiable through sequence comparison to identify characteristic, or signature sequences for the family of molecules, further of use in the study of antigenic domains in PPIV-1 polypeptides, and may also be used to distinguish between infection of a host animal with remotely related non-PPIV-1 members of the Paramyxovirus family.

Antibodies

Also contemplated by the present invention are anti-PPIV-1 antibodies (e.g., monoclonal and polyclonal antibodies, single chain antibodies, chimeric antibodies, humanized, human, porcine, and CDR-grafted antibodies, including compounds which include CDR sequences which specifically recognize a PPIV-1 polypeptide of the invention. The term “specific for” indicates that the variable regions of the antibodies of the invention recognize and bind a PPIV-1 polypeptide exclusively (i.e., are able to distinguish a single PPIV-1 polypeptide from related polypeptides despite sequence identity, homology, or similarity found in the family of polypeptides), and which are permitted (optionally) to interact with other proteins (for example, *S. aureus* protein A or other antibodies in ELISA techniques) through interactions with sequences outside the variable region of the antibodies, and in particular, in the constant region of the Ab molecule. Screening assays to determine binding specificity of an antibody of the invention are well known and routinely practiced in the art. For a comprehensive discussion of such assays, see Harlow et al. (Eds), Antibodies A Laboratory Manual; Cold Spring Harbor Laboratory; Cold Spring Harbor, N.Y. (1988), Chapter 6. Antibodies that recognize and bind fragments of the PPIV-1 polypeptides of the invention are also contemplated, provided that the antibodies are first and foremost specific for, as defined above, a PPIV-1 polypeptide of the invention from which the fragment was derived.

For the purposes of clarity, “antibody” refers to an immunoglobulin molecule that can bind to a specific antigen as the result of an immune response to that antigen. Immunoglobulins are serum proteins composed of “light” and “heavy” polypeptide chains having “constant” and “variable” regions and are divided into classes (e.g., IgA, IgD, IgE, IgG, and IgM) based on the composition of the constant regions. Antibodies can exist in a variety of forms including, for example, as, Fv, Fab', F(ab')2, as well as in single chains, and include synthetic polypeptides that contain all or part of one or more antibody single chain polypeptide sequences.

Diagnostic Kits

The present invention also provides diagnostic kits. The kit can be valuable for differentiating between porcine animals naturally infected with a field strain of a PPIV-1 and porcine animals administered with any of the PPIV-1 vaccine or immunogenic compositions described herein. The kits can also be of value because animals potentially infected with field strains of PPIV-1 virus can be detected prior to the existence of clinical symptoms and removed from the herd, or kept in isolation away from naive or vaccinated animals. The kits include reagents for analyzing a sample from a porcine animal for the presence of antibodies to a particular component of a specified PPIV-1 virus. Diagnostic kits of the present invention can include as a component a peptide or peptides from the PPIV-1 strains of the invention which is present in a field strain but not in the vaccine or immunogenic composition of interest, or vice versa, and selection of such suitable peptide domains is made possible by the extensive amino acid sequencing. As is known in the art, kits of the present invention can alternatively include as a component a peptide which is provided via a fusion protein. The term “fusion peptide” or “fusion protein” for purposes of the present invention means a single polypeptide chain consisting of at least a portion of a PPIV-1 protein and a heterologous peptide or protein.

All publications, patents and patent applications identified herein are incorporated by reference, as though set forth herein in full. The invention being thus described, it will be apparent to those skilled in the art that the same may be varied in many ways without departing from the spirit and scope of the invention. Such variations are included within the scope of the following claims.

The invention is further illustrated by the following specific examples which are not intended in any way to limit the scope of the invention.

EXAMPLES

Example 1: Prevalence of Porcine Parainfluenza Virus Type 1 (PPIV-1) in Diagnostic Specimens The Iowa State University Veterinary Diagnostic Laboratory (ISU-VDL) received several diagnostic submissions from swine experiencing respiratory disease, lethargy, coughing, and sneezing with microscopic lesions consistent with bronchointerstitial pneumonia. Lung lesions also included bronchiolitis with bronchiolar epithelial necrosis, a common lesion caused by infection with IAV. Lung tissue, nasal swabs, and oral fluids submitted with these accessions were PCR negative for pathogens commonly associated with the PRDC, including influenza, which prompted further investigations. Additional diagnostics using genus-level PCR assays detected an amplicon with genetic similarity to a porcine parainfluenza virus type 1 reported in Hong Kong, suggesting an association between PPIV-1 and respiratory disease in swine.

Figure 2:
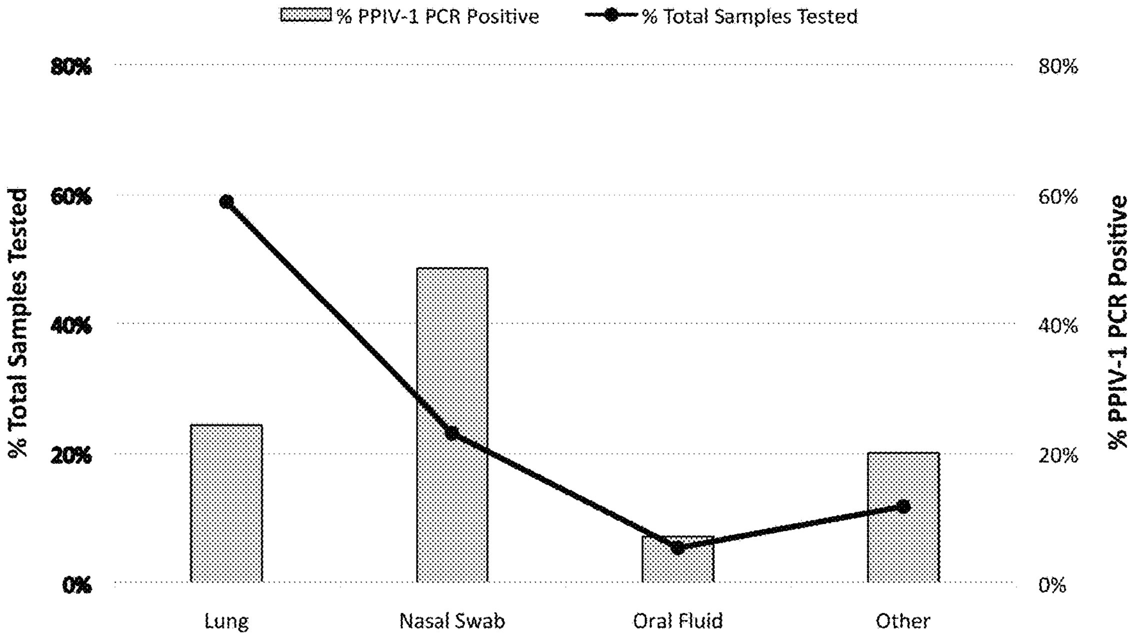
FIG. 2 shows the percent of PPIV-1 PCR positive accessions based on sample type and submitted to the Iowa State University Veterinary Diagnostic Laboratory with a clinical history of respiratory disease.
Figure 3:
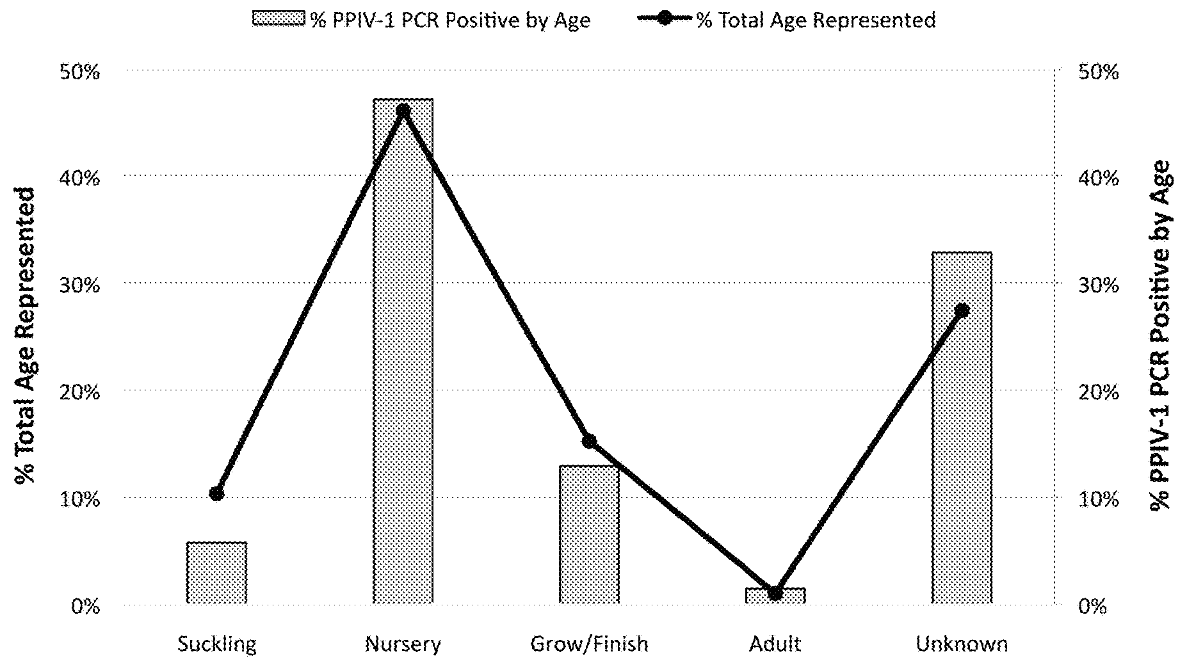
FIG. 3 shows the percent of PPIV-1 PCR positive accessions based on age and submitted to the Iowa State University Veterinary Diagnostic Laboratory with a clinical history of respiratory disease.

A real-time reverse transcription PCR (qRT-PCR) was developed for PPIV-1 to help analyze 204 swine accessions submitted to the ISU-VDL since 2014. Accessions were submitted from swine of different ages with a complaint of PRD that demonstrated similar characteristics as described above and including a request to test for PPIV-1 among other differentials typical for respiratory disease in swine. Accessions included a full complement of fresh and formalin-fixed tissues from nine states (Iowa, Ill., Mich., Minn., Neb., Ohio, Okla., S.D., Texas). Of 204 accessions, 34% (70/204) were PPIV-1 PCR positive. Samples included lung, nasal swabs, oral fluids, bronchoalveolar lavage, and various other samples. Total positive included 24% (17/70) lung, 49% (34/70) nasal swab, 7% (5/70) oral fluid, and 20% (14/70) other (FIG. 2). The following accessions were dual positive with an additional respiratory pathogen: 5 with IAV, 6 with PRRSV, and 4 with systemic pathogens (*S. suis, H. parasuis*, etc.). Three accessions diagnosed tracheitis, and one case demonstrated rhinitis. Pig ages represented included 10% (21/204) suckling piglets, 46% (94/204) nursery pigs, 15% (31/204) grow/finish swine, 1% (2/204) adult swine, and 27% (56/204) of unknown age. Percent of PPIV-1 PCR positive accessions by age included 6% (4/70) suckling piglets, 47% (33/70) nursery pigs, 13% (9/70) grow/finish swine, 1% (1/70) adult, and 33% (23/70) of unknown age (FIG. 3).

Figure 4:
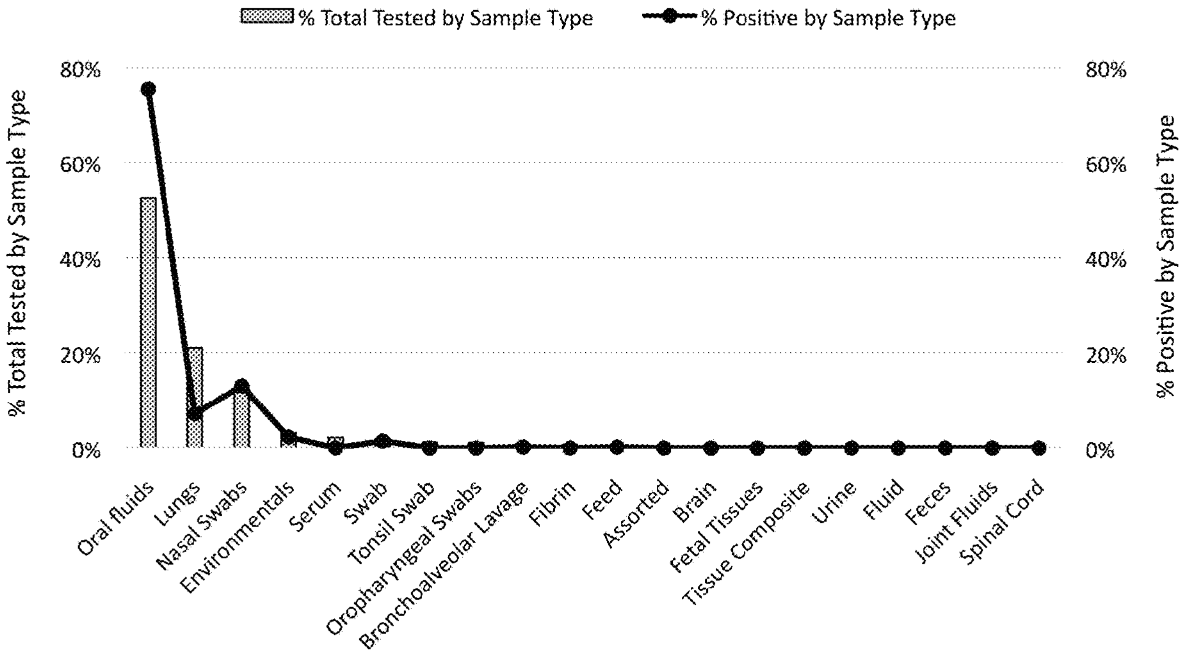
FIG. 4 shows the percent of porcine samples submitted to the Iowa State University Veterinary Diagnostic Laboratory and analyzed for the presence of PPIV-1 RNA regardless of clinical history.
Figure 5:
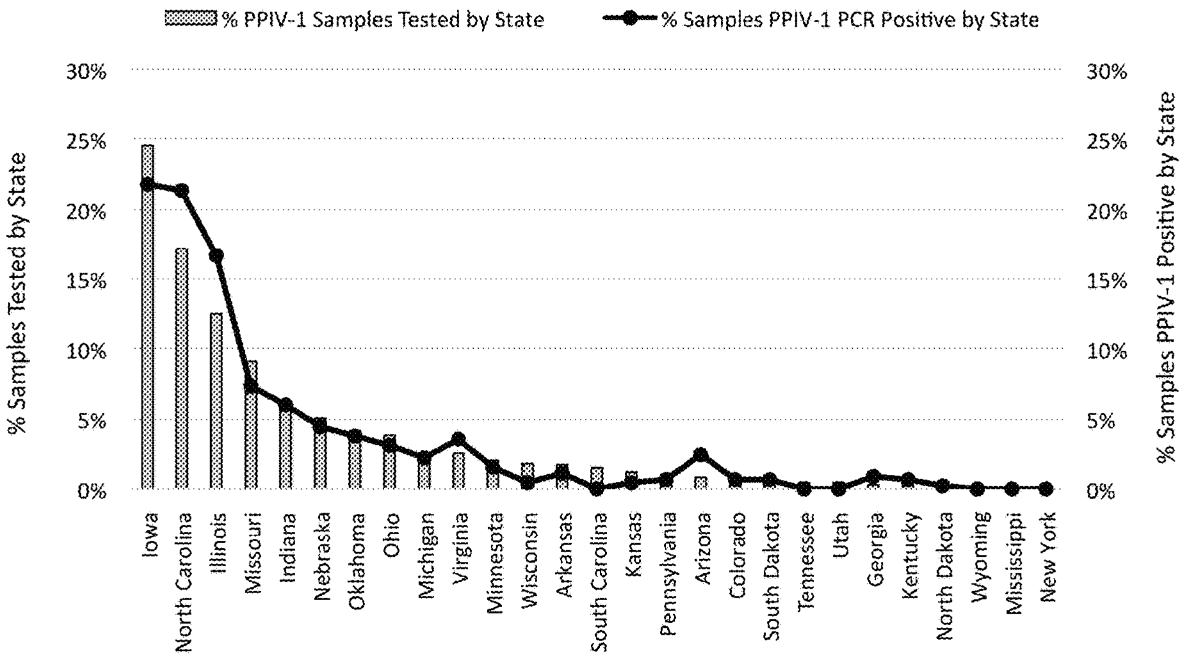
FIG. 5 shows the States evaluated for PPIV-1 in samples submitted to the Iowa State University Veterinary Diagnostic Laboratory and percent of porcine samples PCR positive for PPIV-1 regardless of clinical disease.

The ISU-VDL also conducted a prospective PPIV-1 prevalence evaluation in diagnostic samples collected from swine and submitted for PCR. Samples were tested by PCR to detect the presence of PPIV-1 regardless of clinical history. Samples included oral fluid, lung, nasal swab, environmental sample, serum, tonsil swab, oropharyngeal swab, bronchoalveolar lavage, fibrin, feed, brain, fetal tissues, tissue composite, urine, undesignated fluids, feces, joint fluid, and spinal cord. A total of 1385 samples were tested and 34% (472/1385) were PCR positive for PPIV-1. The diagnostic samples that tested positive included oral fluid (75.4%), lung (7.2%), nasal swab (13.1%), environmental (2.3%), undesignated swab (1.5%), bronchoalveolar lavage (0.2%), and a feed sample (0.2%) (FIG. 4). Samples originated from 27 states with Iowa, North Carolina, and Illinois representing the largest number of accessions and largest number PPIV-1 positive (FIG. 5). Some samples were also tested by PCR for IAV, and 21.1% (115/544) oral fluid, 4.5% (12/269) lung, and 7.4% (13/176) nasal swabs were PCR positive for both pathogens. These results suggest that PPIV-1 detection, but not necessarily clinical disease, may be widespread in the U.S. pig population. Based on sample type, oral fluid is the most likely to be PPIV-1 PCR positive compared to lung and nasal swabs. However, in cases submitted with a specific history of respiratory disease, nasal swabs were more likely to be positive for the presence of PPIV-1 compared to other sample types.

PPIV-1 can be detected in swine of all ages regardless of clinical history and is widespread in the U.S. swine population. PPIV-1 has been primarily detected in nursery and grow-finish swine and has been detected most often in the upper respiratory tract. Although PPIV-1 may be highly prevalent in swine, clinical significance remains unknown and requires further evaluation under experimental conditions. Virus isolates are needed to characterize PPIV-1 pathogenesis, clinical disease, and lesions.

Example 2: Pathogenesis of a Porcine Parainfluenza Virus-1 Isolate (USA/MN25890NS/2016) in Conventional and CDCD Piglets Detection of this new paramyxovirus spurred many veterinary diagnostic labs in the United States to develop PPIV-1-specific detection methods; e.g., real-time reverse transcriptase polymerase chain reactions (RT-qPCR) and enzyme-linked immunosorbent assay (ELISA). However, it had been unclear whether PPIV-1 contributed significantly to the porcine respiratory disease complex (PRDC), since the virus had been detected in both symptomatic and asymptomatic herds. The objective of this study was to evaluate the pathogenesis of a PPIV-1 isolate (USA/MN25890NS/2016) in weaned and caesarian derived, colostrum deprived (CDCD) piglets.

Two PPIV-1 pathogenesis studies were conducted that included 50 conventional and 14 caesarian derived, colostrum deprived piglets. Results indicate that PPIV-1 replicates extensively in the respiratory tract based on RT-qPCR and IHC. Mild lung consolation was observed in conventional piglets but was not observed in CDCD piglets. However, marked quantities of viral antigen were detected by IHC in the respiratory epithelium of nasal turbinate, trachea, bronchi, and bronchioles. Microscopic lung lesions consisted of mild interstitial pneumonia with peribronchiolar cuffing, suppurative bronchiolitis, and epithelial necrosis. Serum neutralizing antibodies were detected in CDCD piglets at 28 days post infection and conventional piglets at 21 days post infection. Clinical respiratory disease was not induced under experimental conditions, suggesting PPIV-1 may not be a primary pathogen in the PRDC. However, it may be involved in porcine respiratory disease in some capacity that requires additional studies or investigations using coinfections with other PRDC agents.

Materials and Methods

Virus and Cell Lines:

An isolate USA/MN25890NS/2016 was passaged in LLC-MK2 (ATCC® CCL-7™). The cells were maintained with M199 medium (Gibco™, Waltham Mass.) supplemented with 1% equine serum (SigmaAldrich®) and 1% penicillin-streptomycin antibiotics (Gibco™, Waltham Mass.). Virus post inoculation media (PIM) consisted of α-Minimum Essential Media (α-MEM) (Gibco™, Waltham Mass.) supplemented with 2 μg/mL L-1-tosylamido-2-phenylethyl chloromethyl ketone (TPCK) treated trypsin and 1% penicillin-streptomycin antibiotics (PIM) (Gibco™, Waltham Mass.). The conventional piglets were challenged with $2\times10^4$ tissue culture infectious dose 50/mL ($TCID_{50}$/mL) of virus, 2 mL intratracheal and 1 mL divided between each nostril (Study 1). CDCD piglets were inoculated with $6.3\times10^4$ $TCID_{50}$/mL in a similar manner (Study 2). Viral titers were calculated using the Reed-Muench method.

Animal Study Design: Study 1

Fifty piglets approximately 28 days old were screened and confirmed negative for PPIV-1 antibody using a prototype whole-virus ELISA developed at the ISU-VDL. The piglets were also determined to be PCR negative for *Mycoplasma* hyopneumoniae, Influenza A virus (IAV), porcine circovirus type 2 (PCV2) and Porcine reproductive and respiratory syndrome virus (PRRSV) by PCR on nasal swabs or serum. The piglets were blocked by weight and litter prior to randomization into challenge (Ch), non-challenge (NCh), and contact groups (Cont). Thirty Ch piglets were intranasally and intratracheally inoculated with PPIV-1 strain USA/MN25890NS/2016 on 0 days post inoculation (DPI). Five Cont piglets were introduced into a separate pen sharing the same airspace approximately 3 feet apart without nose-to-nose contact to evaluate indirect transmission. Nasal swabs were collected daily for the first five days and then periodically until the final necropsy from all groups. Blood was collected from all groups using BD Vacutainer™ SST™ tubes via the anterior vena cava and spun down at 3000×g for ten minutes. Cotton ropes were hung and oral fluids were collected from each pen. See Table 1 for daily sample collection.

TABLE 1

| Sample Type | DPI collected |
|---|---|
| Nasal Swab (NS) | Study 1: D 0, 1, 2, 3, 4, 5, 7, 9, 14, 16, 21<br>Study 2: D 0, 1, 2, 3, 4, 5, 6, 7, 9, 11, 13, 15, 16, 17, 19, 21, 24, 27 |
| Oral fluid (OF) | Study 1: D 0, 1, 2, 3, 4, 5, 7, 9, 14, 16, 21<br>Study 2: (Not collected) |
| Serum | Study 1: D 3, 7, 9, 14, 16, and 21<br>Study 2: 0, 3, 5, 7, 9, 13, 16, 21, 24, 27 |

Clinical observations and rectal temperatures were collected daily from all groups. Respiratory distress scores were assigned on an ascending scale from 0-3: 0-normal, 1-mild increase in respiratory rate, 2-moderate dyspnea and notable increase in respiratory rate, 3-severe with thumping and exaggerated abdominal breathing. Coughing was evaluated as either present or absent. Weight was measured prior to challenge and at necropsy.

Ten piglets from Ch and five piglets from NCh were necropsied at 2, 5, and 21 DPI (see Table 2 showing the treatment groups and necropsy schedule). Fresh and fixed tissues representing the upper (URT) and lower respiratory tract (LRT) were collected from each animal. Fixed tissues collected included lung (right apical, right cardiac, intermediate, right proximal diaphragmatic, and right distal diaphragmatic lobes), nasal turbinate, and trachea. Fresh tissues consisted of proximal and distal trachea, right cardiac lung, and nasal turbinate. The proximal and distal trachea were swabbed and placed in 2 mL of α-MEM. The lung was lavaged with 50 mL of α-MEM and approximately 10-20 mL of BALF was collected. Each lobe surface was evaluated for gross consolidation, and the individual surface areas were summated to determine pneumonia.

TABLE 2

| Group | Number of Animals | Necropsy Schedule |
|---|---|---|
| Challenge (Ch) | 30 | Study 1: n = 10 on 2, 5, and 21 DPI<br>Study 2: n = 3/4/4 on 2, 5, and 27 DPI respectively |
| Negative Control (NCh) | 15 | Study 1: n = 5 Piglets on 2, 5, and 21 DPI<br>Study 2: n = 1/1/2 on 2, 5, and 27 DPI respectively |
| Contact (Con) | 5 | Study 1: n = 5 Piglets on 21 DPI<br>Study 2: not evaluated |

Animal Study Design: Study 2

Isolate USA/MN25890NS/2016 was used to inoculate 10 CDCD Ch piglets. All necropsy samples, clinical observations, lung scoring, and weights were obtained in the same manner to Study 1 although OF were not collected. All samples were processed identical to Study 1. See table 1 and table 2 for complete necropsy and sample collection schedule.

Sample Processing for Nucleic Acid Extraction and Virus Isolation

Tissues were processed consistent with ISU-VDL standard operating procedures for nucleic acid extraction and PCR. Fresh lung was processed by placing 1 g of tissue into 9 mL of Earle's balanced salt solution (Earle's) (Sigma-Aldrich®, St. Luis, Mo.) to create a ten percent weight to volume tissue homogenate. Nasal turbinate was processed using a disposable tissue grinder system. One-half gram of tissue was placed into 5 mL of Earle's and vigorously ground for 30 seconds to create a 10% w:v homogenate. Nasal and tracheal swabs required no additional sample preparation before extraction.

Magnetic Bead Viral RNA Extraction

Nucleic acid was extracted from clinical samples using the 5XAmbion® MagMAX™-96 Viral RNA Kit and automated Kingfisher 96® magnetic particle processor (ThermoFisher™ Scientific, Waltham Mass.) per manufacturer specifications. A standard extraction was performed on nasal swabs, serum, BALF, and lung tissue. A "high volume" extraction was performed on OF per ISU-VDL protocols. Samples extracted by either standard or high volume extraction were eluted into 90 μl of elution buffer and tested immediately after extraction.

Detection of PPIV-1 by RT-qPCR

Viral RNA was detected using an Ambion® Path-ID™ RT-qPCR Kit (Life Technologies, Carlsbad Calif.) with primers designed to target the N-gene of PPIV-1. The probe contained a 5'fluorophore and 3'Iowa Black® quencher. Signal amplification was monitored using a 7500 RT-qPCR Thermocycler (Applied Biosystems®, Foster City Calif.). Cycle threshold (Ct) values >40 were considered negative. All Cts were converted into genomic copies per mL (GC/mL) based on standards developed at the ISU-VDL.

PPIV-1 Virus Isolation and Titration

Virus isolation was performed on Study 1 and Study 2 BALF, NS, OF, and nasal turbinate based on RT-qPCR results. Negative PCR samples with Ct>40 were also considered VI negative. One milliliter of sample was first filtered using a 0.45 μm Millex® MF-Millipore™ membrane filter (Merck KGaA, Darmstadt Germany). Confluent LLC-MK2 monolayers grown in 96-Well Microtiter™ Microplates (96-well plates) (ThermoFisher™ Scientific, Waltham Mass.) were washed twice with 125 μl α-MEM base medium. Next, 100 μl of sample was adsorbed onto the cells for two hours in a 37° C. incubator. The supernatant was removed, 100 μl of PIM was added, and the cells were incubated at 37° C. for 72 hours. The cells were fixed in 100 μl of 80% acetone at −20 C diluted in distilled water for 15 minutes. The virus was visualized with an inverted light microscope using a previously described horseradish peroxidase (HRP) based immunocytochemistry assay (ICC).

The positive samples were added in triplicate to 96-well plates and 10-fold serially titrated in PIM starting at a 1:10 dilution. Samples negative by virus isolation were not titrated. The infected LLC-MK2 monolayers were incubated at 37° C. for 72 hours and monitored for development of cytopathic effect (CPE). The 96-well plates were fixed, stained, and viewed under a light microscope. Virus titers were determined using the Reed-Muench method. The limit of detection was determined to be <2.25 $TCID_{50}$/mL.

Detection of PPIV-1 Neutralizing Antibodies by Serum Virus Neutralization Assay

A prototype serum virus neutralization (SVN) assay was developed based on an IAV SVN protocol. Serum volume of 250 μl was aliquoted into a MagMax™ Express Microtiter 96 Deep Well Plate (DW plate) (Applied Biosystems®, Foster City Calif.) and heat inactivated in a 56° C. hot water bath for 30 minutes. Next, 100 μl of PIM was added to rows B-H of an empty microtiter plate, and 180 μl was added to wells A3-A12. Rows 1 and 2 were left as cell and virus controls, respectively. Next, 20 μl of heat inactivated serum was added to wells A3-A12, and two-fold serial dilutions were made down the plate (100 μl of serum virus mixture into 100 μl of PIM, first dilution 1:10). Ten serum samples could be tested per plate. Virus USA/MN25890NS/2016 was diluted to 4,000 $TCID_{50}$/mL (200 $TCID_{50}$/50 μl) and was added to rows 2-12 and 100 μl of PIM containing only antibiotics was added to row 1. The serum virus mixture was allowed to incubate for 60 min at 37° C.

During incubation, confluent LLC-MK2 monolayers in 96-well plates were washed two times with 125 μl α-MEM base medium without antibiotics or TPCK trypsin. The last wash was left on the cells until the end of the serum virus mixture incubation. After 60 minutes, the base media was decanted and the serum virus mixture was transferred to the cell plate in order of decreasing virus concentration (rows A-H). The remaining virus not neutralized by serum antibodies was then adsorbed for 2 hr at 37° C. At the end of the incubation, the mixture was removed, the cells were washed two times with 125 α-MEM base medium, and 100 μl of PIM was transferred onto the cells.

Statistical Analysis

A generalized linear mixed model (GLIMMIX) was used to analyze nasal swab shedding, SVN antibody titers, IHC scores, and necropsy samples with statistical analysis system (SAS) version 9.4 (SAS Institute, Cary, N.C.). The IHC data were analyzed using DPI, treatment, and anatomic location as fixed effects with the animal identifier nested within the DPI*treatment interaction. Necropsy samples were analyzed in a similar manner with DPI and physiologic location as fixed effects and the animal identifier nested within DPI. Daily nasal swab samples were analyzed using DPI as the fixed effect and the animal identifier as random effect. SVN data were analyzed with DPI and treatment as fixed effects and the animal identifier nested in treatment.

Results

Clinical Signs and Gross Lesions

Figure 6:
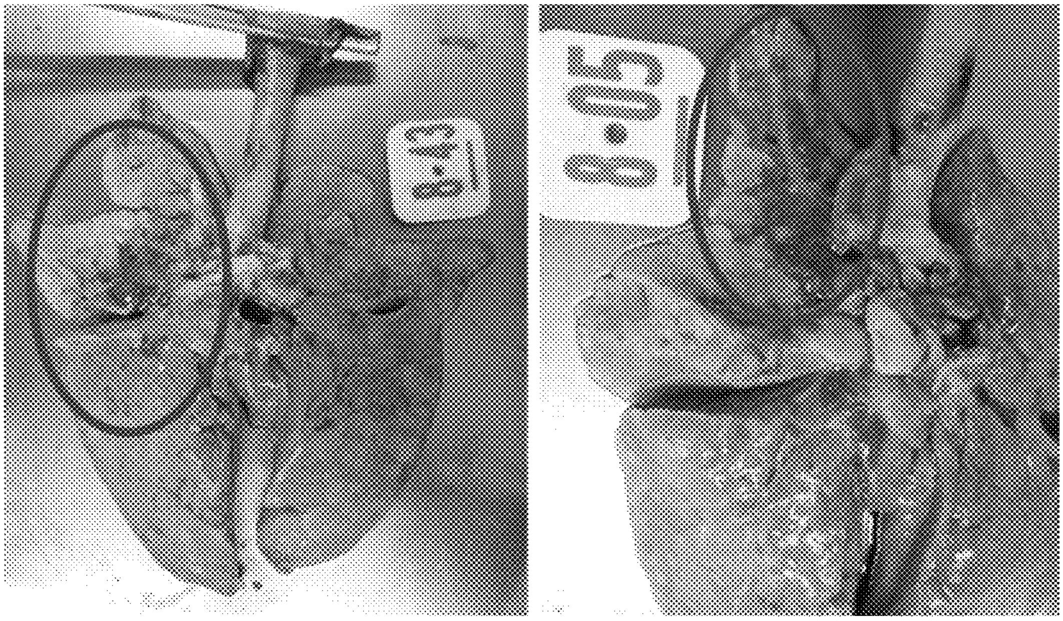
FIG. 6 shows macroscopic lung lesions observed at 5 DPI in two conventional pigs challenged with PPIV-1 demonstrating mild lung consolidation. Macroscopic lung lesions were not observed in PPIV-1 challenged CDCD piglets.

PPIV-1 infection caused minimal clinical disease under experimental conditions, even though large amounts of viral RNA were shed in nasal secretions as detected by RT-qPCR. No differences were observed in Study 2 between the Ch and NCh groups 0-5 DPI for clinical signs or gross lesions that would suggest viruses or bacteria. No statistically significant differences were observed in Study 1 for weight gain and mean coughing and respiratory distress scores from 0-5 DPI. Very mild consolidation was observed in the Ch piglets on D5 and D21 necropsy, with maximum mean lung consolidation scores only totaling 4%. Lung lesions were localized in the cranioventral lobes typical of a mild bronchopneumonia (FIG. 6).

Microscopic Lesions

Figure 7A:
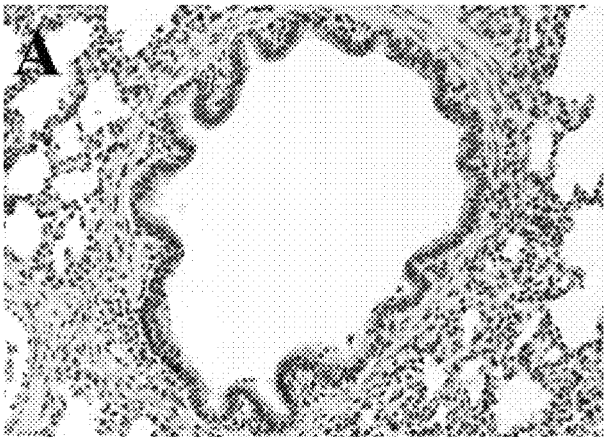
FIGS. 7A-C show microscopic lung lesions at 5 DPI.
Figure 7B:
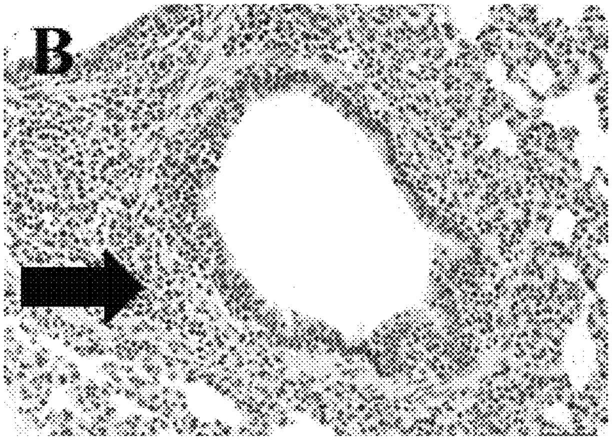
Figure 7C:
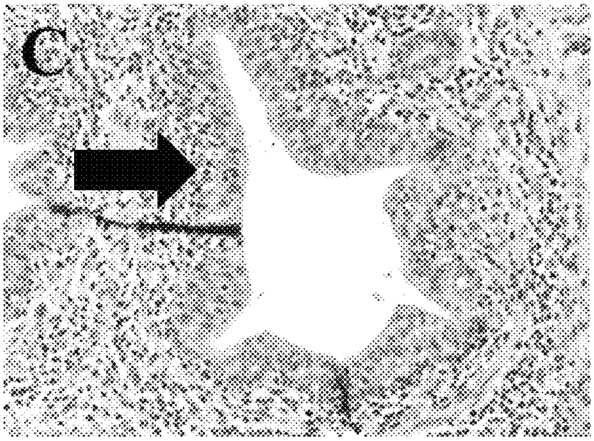

Hematoxylin and eosin (H&E) slides were prepared and evaluated for presence of histologic lesions. Similar microscopic lesions were observed in both studies. Mild epithelial attenuation and loss of goblet cells were observed in the turbinate and trachea at 5 DPI. A mild infiltrate was observed in the propria submucosa of affected piglet lungs consisting of lymphocytes, plasma cells, and macrophages and peribronchiolar lymphocytic cuffing was mild. Occasionally, the alveolar septa were expanded by plasma cells and lymphocytes. Epithelial necrosis and mild degenerative changes were also observed in the bronchiolar epithelium of CH piglets in both studies, consistent with lesions expected from an epitheliotropic virus. (FIG. 7).

Figure 8A:
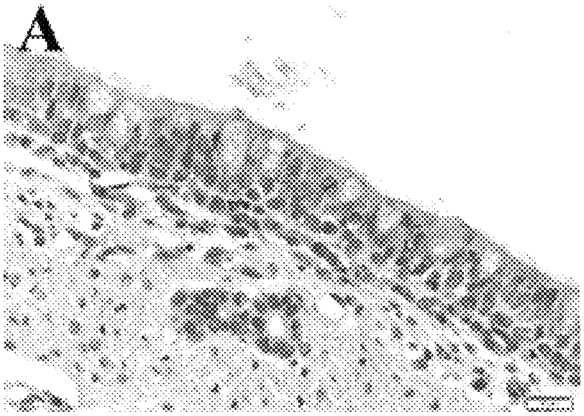
FIGS. 8A-C show microscopic trachea lesions at 5 DPI.
Figure 8B:
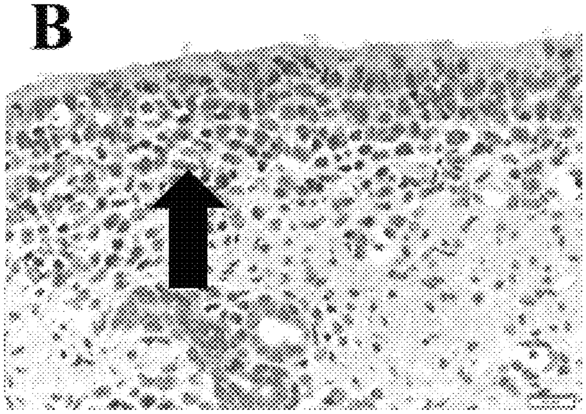
Figure 8C:
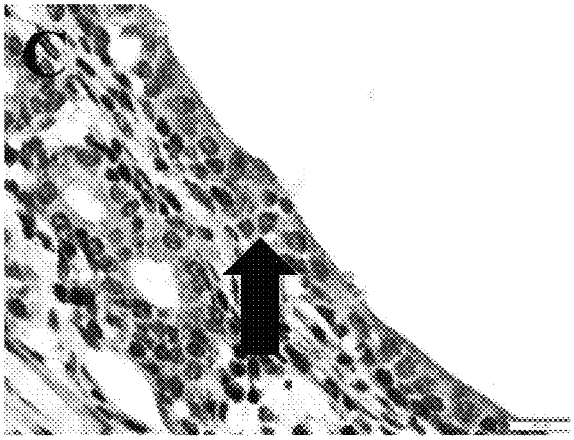

The propria submucosa of the trachea was moderately expanded by mononuclear cells and epithelial attenuation was observed in some challenged pigs (FIG. 8).

Immunohistochemistry

Figure 9A:
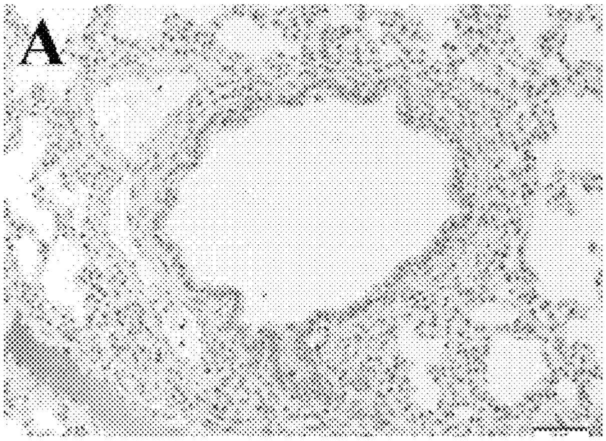
FIGS. 9A-C show immunohistochemistry PPIV-1 signals represented at 5 DPI.
Figure 9B:
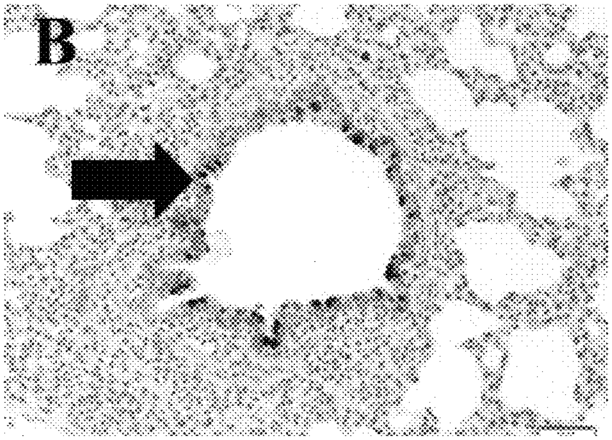
Figure 9C:
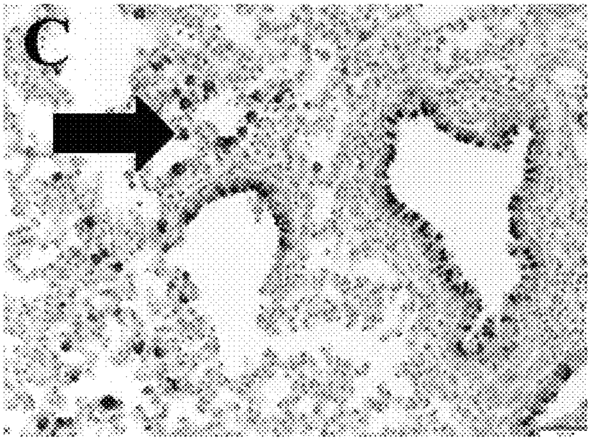

Marked IHC signals were observed in the respiratory epithelium of the trachea, nasal turbinate, bronchi, and bronchioles. Similar results were observed in both Study 1 and Study 2. There was no statistically significant difference in mean IHC signal scores between nasal turbinate and trachea at 2 and 5 DPI in Study 1. PPIV-1 signals were not observed in NCH pigs. In contrast, large amounts of PPIV-1 signals were observed in the bronchiolar/bronchi epithelium at 5 DPI. Mild PPIV-1 signals were detected in the lung parenchyma on 2 and 5 DPI, indicating low levels of viral antigen can occasionally be found outside the respiratory epithelium (FIG. 9).

Figure 10A:
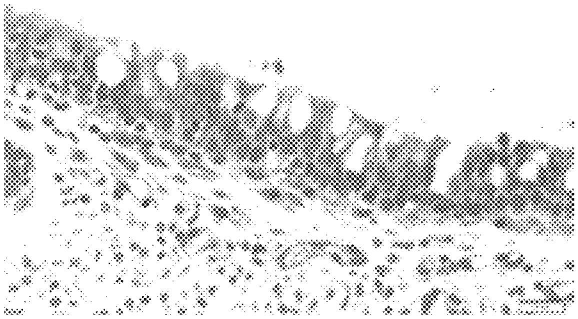
FIGS. 10A-C show immunohistochemistry PPIV-1 signals in trachea and nasal turbinate.
Figure 10B:
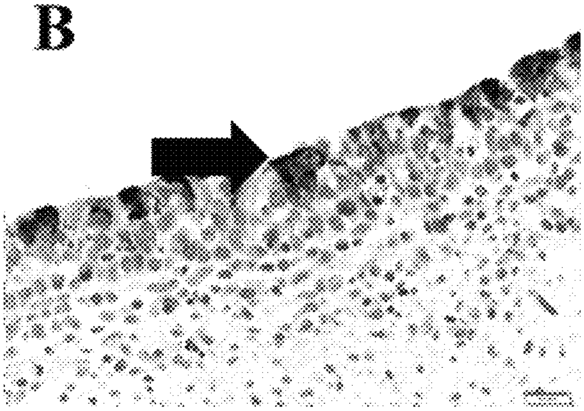
Figure 10C:
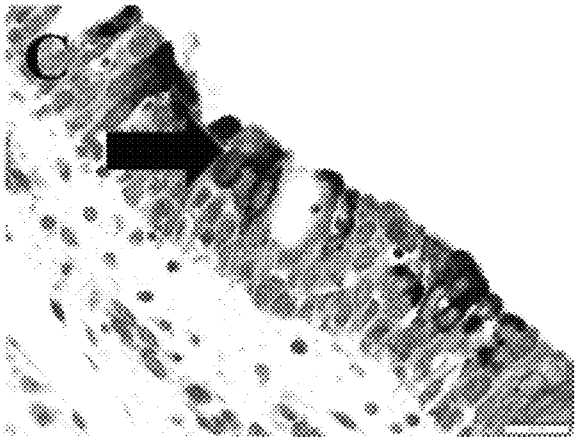

Prominent PPIV-1 IHC signals were observed at 5 DPI in trachea turbinate epithelium (FIG. 10). No staining was observed 21 or 28 DPI in either Study 1 or Study 2.

PPIV-1 Shedding in Nasal Swabs and Oral Fluids

Figure 11:
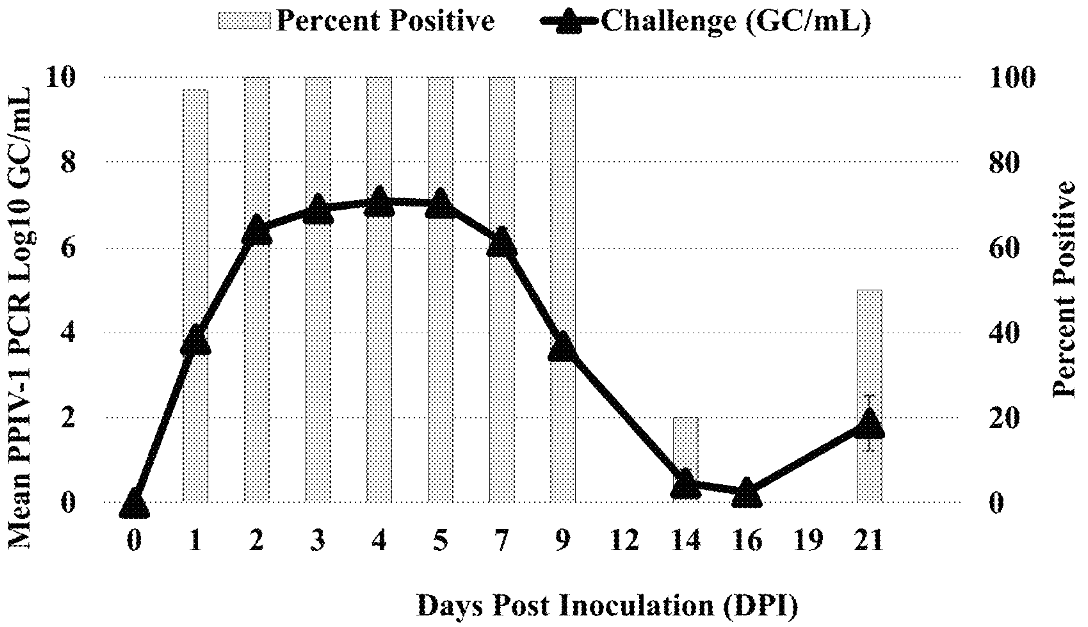
FIG. 11 shows nasal swab PPIV-1 positive RT-qPCR shedding at 1-21 DPI in conventional piglets.
Figure 12:
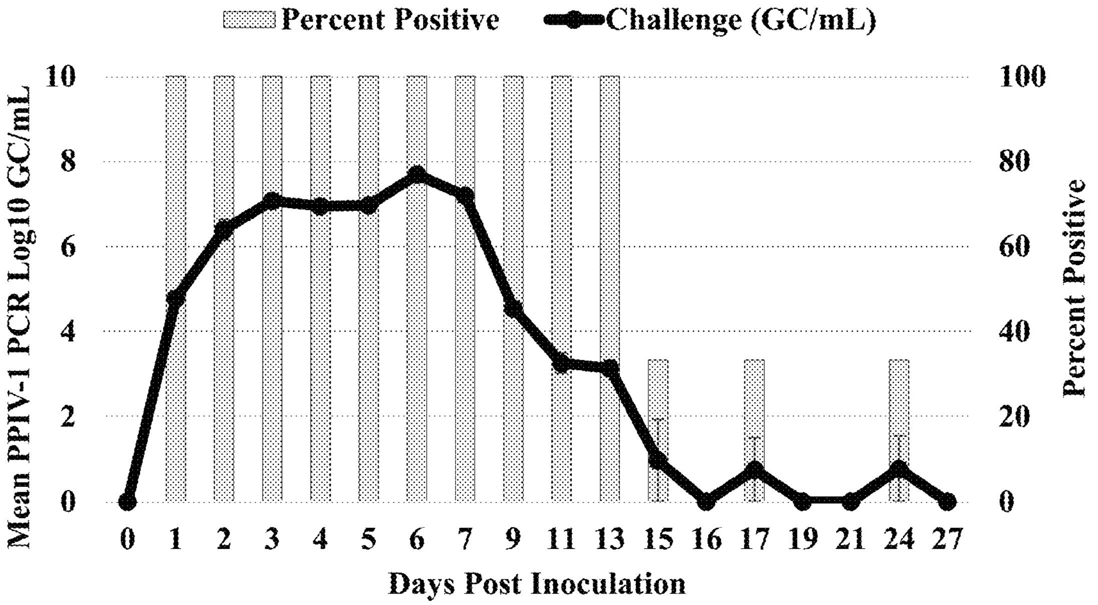
FIG. 12 shows nasal swab PPIV-1 positive RT-qPCR shedding at 1-27 DPI in CDCD piglets.

All piglets were confirmed negative by RT-qPCR for viral nucleic acid on 0 DPI. The onset of viral shedding was rapid in both conventional and CDCD piglets, with 29/30 (FIG. 11) and 10/10 (FIG. 12) Ch piglets shedding virus 1 DPI in both studies, respectively. Viral titers in Ch piglets of both Study 1 and Study 2 reached a maximum from 2-7 DPI and decreased on 9 DPI, and were detected at statistically insignificant levels from 14-16 DPI. There was a statistically significant increase at 21 DPI found in the conventional piglets not seen in the CDCD piglets, but the viral concentration was below 2 log 10 GC/ml. Small amounts of virus were detected from CDCD Ch piglets between 15-27 DPI.

Figure 13:
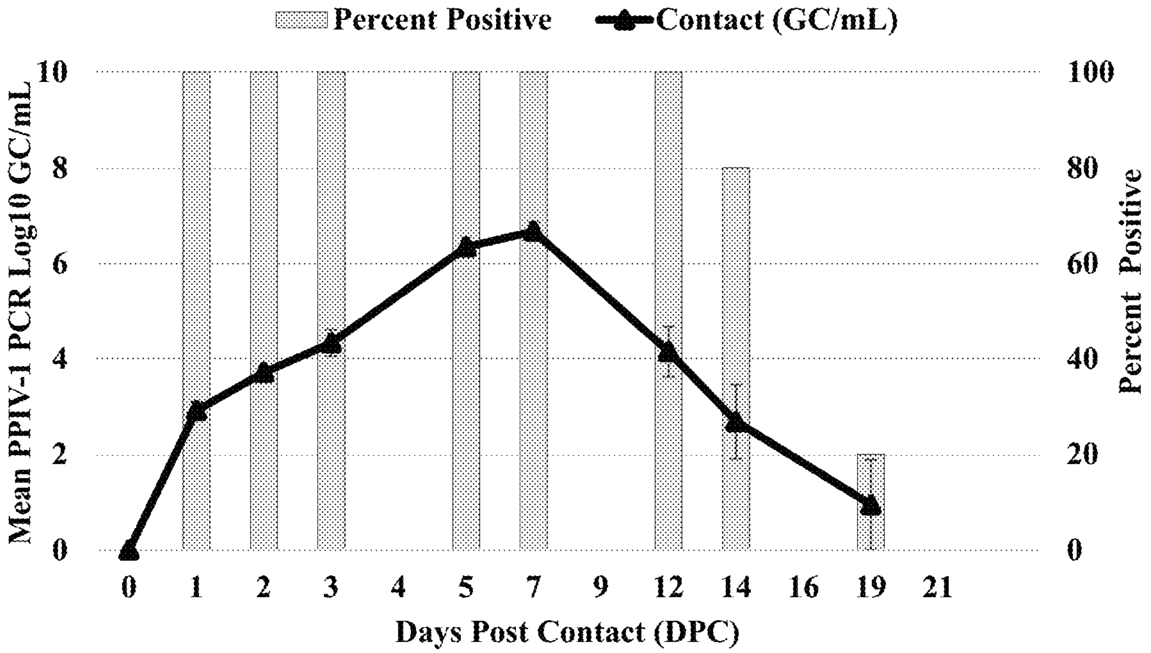
FIG. 13 shows nasal swab PPIV-1 positive RT-qPCR shedding at 1-21 DPI in conventional contact piglets.

All piglets in the Cont group of Study 1 were shedding virus by 1 DPC at low levels. Maximum virus levels were detected on 5 and 7 DPC. There was no statistically significant difference in virus shedding on 0 DPC and 19 DPC in NS. The duration of shedding in Cont piglets was between 14 and 16 DPC, comparable to the Ch piglets in Study 1 and Study 2 (FIG. 13).

Figure 14:
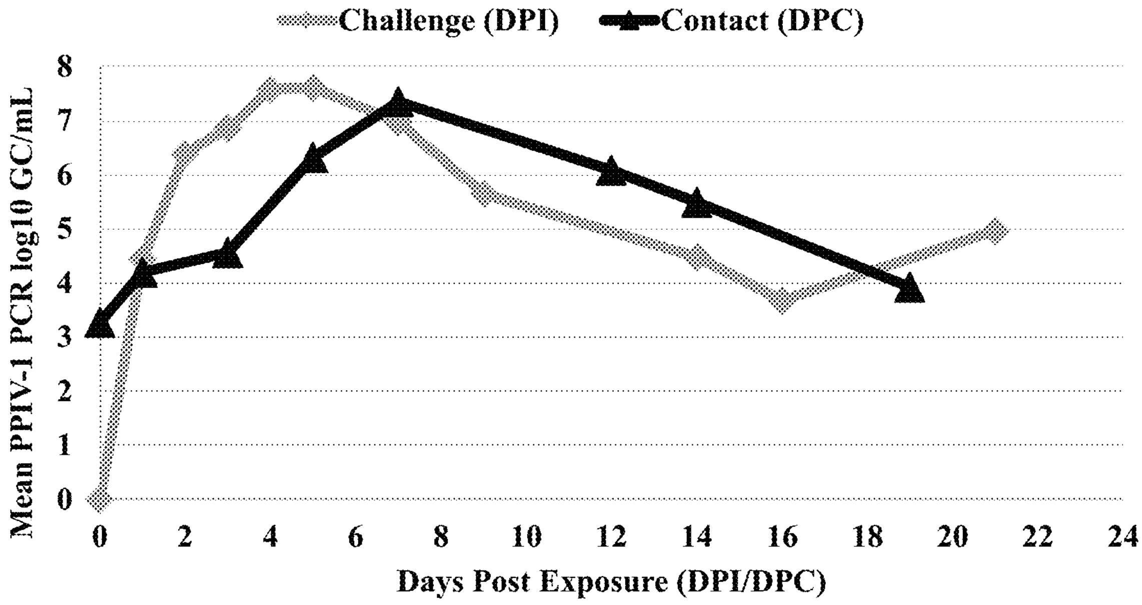
FIG. 14 shows oral fluid PPIV-1 positive RT-qPCR at 1-21 DPI in conventional and contact piglets.

Oral fluids were collected from Study 1 per pen. There were two pens of Ch piglets and one pen of Cont piglets in the Ch room. Lack of replication hindered statistical analysis; however, viral RNA was detected in OF by RT-qPCR and appeared to follow a similar pattern of shedding as seen in NS (FIG. 14).

PPIV-1 Viral RNA Detection at Necropsy

Figure 15:
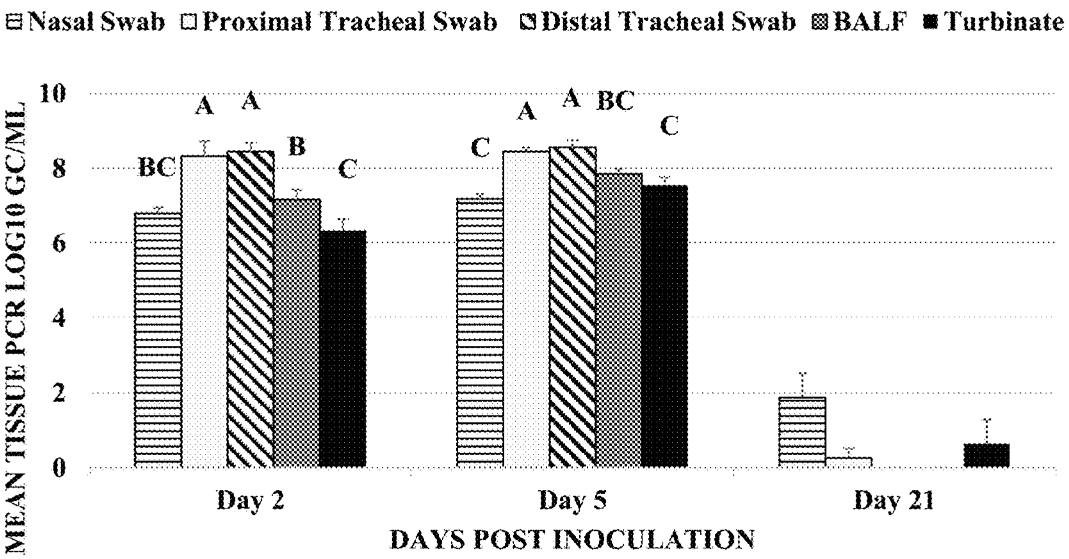
FIG. 15 shows PPIV-1 positive RT-qPCR in nasal swab, proximal tracheal swab, distal tracheal swab, BALF and nasal turbinate at 2, 5, and 21 DPI in conventional piglets.

Significant levels of PPIV-1 viral RNA were detected by RT-qPCR throughout the URT and LRT at 2 and 5 DPI. The main effects of sample type and DPI were statistically significant in the model in Study 1 and Study 2. More genetic material was detected in the proximal (PTS) and distal tracheal swabs (DTS) than was detected in NS and turbinate in Study 1 on both 2 and 5 DPI. Similar to Study 1, PTS and DTS consistently had higher viral loads than NS (FIG. 15).

There was no difference between turbinate and BALF in Study 2 in contrast to results found in Study 1. Mean viral concentrations in CDCD and conventional Ch piglets ranged from approximately 6-8 log 10 GC/ml, with a maximum mean difference of 100-fold in the Study 1 and 1000 fold difference Study 2. This difference was not as pronounced by RT-qPCR results at 5 DPI compared to 2 DPI necropsy samples in both studies.

Virus Isolation

The PPIV-1 was successfully isolated from a variety of experimental samples, including NS, turbinate, BALF, and tracheal swabs. Some samples were able to produce relatively high titers, reaching above 4 lop) TCID50/mL in some cases. This data supports Koch's postulates, even though viral titers in cell culture were low overall. The highest titers were consistently found in TS and BALF samples, and no titers above 3 $\log_{10}$ TCID50/ml were found in NS samples.

Serum Virus Neutralization

In Study 2, there was clear evidence of seroconversion, starting on 7 DPI. The Ch group had significantly higher Ab titers than the Neg group at every time point after 7 DPI except for 14 DPI where the p-value was 0.08. This discrepancy is most likely due to lack of replicates. The Ch piglets in Study 1 took longer to develop Ab titers relative to the (Lau et al., 2013) controls compared with Study 2. Seroconversion did occur in the Ch group by 14 DPI, and Cont group by 21 DPI. The Ch and Cont groups had higher titers on 21 DPI than the controls, with the Ch group also having higher titers at 14 DPI.

Discussion

A pathogenesis study was needed for elucidating the relationship between PPIV-1 and clinical disease. The objectives of this study were to 1) evaluate the pathogenesis of PPIV-1 isolate USA/MN25890NS/2016 in weaned and caesarian derived colostrum deprived piglets 2) evaluate aerosol transmission through indirect contact with PPIV-1 challenged piglets and 3) validate Koch's postulates and determine if PPIV-1 is a contributing agent to the PRDC. Our findings indicate that experimental infection with PPIV-1 does not produce significant clinical signs or lesions, despite significant virus detection from nasal secretions and lung homogenates. This is consistent with findings from experimentally infected calves, where it is commonly accepted that BPI-3 only causes a mild infection in the most severe cases. Clinical signs in cattle are most commonly associated with coinfection with other viral and bacterial agents, so is therefore considered an integral component of the bovine respiratory disease complex in feedlot cattle and enzootic pneumonia in calves. Similarly, human parainfluenza viruses are common agents of coinfection, with some reports indicating that 33.3-63.2% of samples tested positive for another human respiratory pathogen.

In both pathogenesis studies, large quantities of virus were detected by RT-qPCR throughout the respiratory tract. On 2 DPI and 5 DPI, significantly more virus was detected in the proximal and distal tracheal swabs than the other sample types in Study 1 and Study 2. The IHC scores followed a similar pattern to the RT-qPCR necropsy results. Significant amounts of viral antigen were observed in the respiratory epithelium throughout the respiratory tract. Interestingly, low levels of viral antigen was observed in the pulmonary interstitium outside of the respiratory tract, localized primarily in macrophages on 5 DPI in the Ch group of both studies.

PPIV-1 appears to be mostly confined to the respiratory tract and no viremia was observed in serum on 3 DPI. Some have proposed that the immune response restricts parainfluenza virus infection to the respiratory epithelium. Ultrastructural studies indicate that BPIV-3 preferentially buds from the apical surface, but basolateral production of virus occurs as well. However, in humans, in-vitro apically inoculated human airway epithelium cultures only produced virus from the luminal surface, contrary to what has been reported in cattle. It is unclear in human patients whether systemic infection is caused by loss of respiratory epithelium integrity or increased ability of virus to escape the respiratory tract in lymphocytes. There are host proteases with the ability to cleave $F_0$ into $F_1$ and $F_2$ that are ubiquitously produced in the body and they may cause systemic infection. In mice, F-protein specific host range mutants of SeV have been shown to cause generalized infection through cleavage by ubiquitous proteases. Additionally, instances of systemic parainfluenza virus infection have been documented in children with severe combined immunodeficiency and other cell-mediated immunity disorders.

Seroconversion occurred in both studies by 21 DPI. In Study 2, there was a significant SVN response by 9 DPI in the Ch group, corresponding to a decrease in virus shedding in NS detected by RT-qPCR. Development of a neutralizing antibody response was slower in Study 1 compared to Study 2, with significant differences compared to Neg piglets occurring after 14 DPI and 21 DPI in the Ch and Cont groups respectively. The absolute magnitude of the neutralizing response appeared lower in Study 1 compared to Study 2. There were VN titers in some of the piglets at 0 DPI in Study 1, which most likely can be attributed to low residual levels of maternal antibody originally not detected by our provisional wv-ELISA. However, these levels appeared not to be protective or affect study results as 29/30 piglets in the Ch group were positive by PPIV-1 RT-qPCR by 1 DPI. Additionally, all of the Cont group piglets were shedding virus in NS by RT-qPCR one day post exposure. These results are consistent with established literature in other host species like mice, humans, and cattle. The lower magnitude of neutralization titers in Study 1 is consistent with reports in humans where maternal antibody can cause immunosuppressive effects against nonviable parenteral and live mucosal vaccines.

Virus isolation was also performed in both studies on all nasal swabs and necropsy samples positive by RT-qPCR. Virus was isolated from all sample types. The highest virus titers were observed in BALF and TS samples. The virus isolation results prove that PPIV-1 inoculation produces viable virus into the environment. The inconsistency in virus isolation results can likely be attributed to lack of cellular permissiveness to infection and the difficulty in growing PPIV-1 in cell culture.

The isolate (USA/MN25890NS/2016) does not cause significant clinical disease under experimental conditions despite high levels of viral replication throughout the respiratory tract. Not much is currently known about the epidemiology of PPIV-1, and the lack of clinical signs could also be attributed to strain variation. Clinical reports suggest that PPIV-1 might cause clinical disease in the absence of other respiratory viruses. The large amounts of viral replication and shedding as well as microscopic lesions indicate that PPIV-1 likely has a contributing role in the PRDC.

Example 3: Complete Genome Sequence of Porcine Respirovirus 1 Strain USA/MN25890NS/2016, Isolated in the United States Obtaining a PPIV-1 isolate propagated in cell culture is critical for experimental challenge to evaluate the pathogenesis and clinical significance of viral infection in swine. In addition, the availability of a PPIV-1 isolate can help develop and validate virological and serological diagnostic assays and assist vaccine development.

Figure 16:
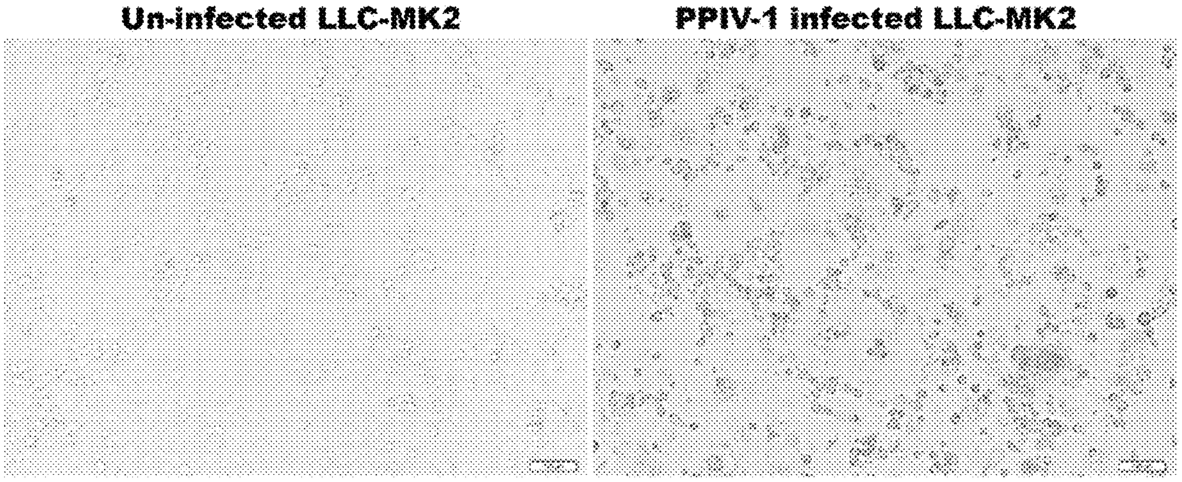
FIG. 16 shows the formation of syncytia caused by PPIV-1 infection in LLC-MK2 cells.

Virus isolation was attempted using rRT-PCR-positive respiratory samples from random submissions with a history of respiratory disease. Lung homogenate and nasal swabs were resuspended to 10% (w/v) suspensions in Earles's balanced salt solution (Sigma-Aldrich, St. Louis, Mo.). The suspensions were clarified at 10,000 rpm for 5 min and filtered through 0.2 micron membrane filter and then inoculated onto LLC-MK2 cell monolayers (ATCC CCL-7) for 2 hours at 37.0 in a humidified 5% CO2 incubator. The inoculum was removed and minimum essential medium (MEM) supplemented with Penicillin-Streptomycin solution and 2 ug/ml of TPCK-trypsin was added. Blind passages of the samples were carried out until the cytopathic effect (CPE) appeared. A distinct cytopathic effect, which is the formation of syncytia, was detected after two or three passages of four different clinical samples. The infected cells show multi-nucleate enlarged cells and a rounded appearance ultimately causing cell detachment from the culture plate (FIG. 16).

A porcine parainfluenza virus type 1 (species Porcine respirovirus 1) cell culture isolate, USA/MN25890NS/2016, was obtained from porcine nasal swabs, and its complete genome sequence was determined to help further characterize this virus. The complete genome of PPIV-1 isolate USA/MN25890NS/2016 was acquired using next-generation sequencing (NGS) technology on an Illumina MiSeq platform and analyzed using the DNASTAR Lasergene 12. The sequence consists of 15,334 nucleotides and encodes six open reading frames (3'-N-P-M-F-HN-L-5').

The viral genome is a negative-sense, single-stranded RNA virus of approximately 15 kb in length. The genome consists of six genes that encode six major proteins and two accessory proteins associated with the phosphoprotein that are translated through a process known as RNA editing. Two PPIV-1 proteins important for virus replication in host cells include the fusion (F) protein, which induces fusion between the viral envelope and the host cell membrane, and the hemagglutinin-neuraminidase (HN) gene, which encodes the cell attachment protein and facilitates viral entry into a host cell. In addition to the HN and F proteins are the matrix (M), nucleoprotein (NP), phosphoprotein (P), and large protein (L) with two small accessory proteins (C, V).

The full genome sequence of this PPIV-1 isolate is more closely related to PPIV-1 strains detected in the United States in 2016 (GenBank accession numbers KT749882 and KT749883), forming a clade with 98.1% and 98.2% nucleotide homology in a phylogenetic analysis using Clustal W in DNASTAR Lasergene 12. In contrast, the PPIV-1 whole genome demonstrated 91.3%, 95.9%, and 96% identities with virus strains detected in Hong Kong in 2013 (accession numbers JX857410, JX857409, and JX857411, respectively). These data suggest that the PPIV-1 virus is genetically evolving over time and at different geographic locations.

The complete genome sequence of PPIV-1 isolate USA/MN25890NS/2016 has been deposited in GenBank under the accession number MF681710.

| Sequences |
|---|
| >USA/MN25890NS/2016-P3, complete genome<br>(SEQ ID NO: 1)<br>GGTTAAAGTATTAACCTCAAAAGGACAGATCAGGAACTTTGATTTCTTAGCATAGTGCCAAAATGGCAGGGTT<br>ATTAAGTGTCTTTGACACATTTAGTTCTAAAAGGAGTGAAAGCATAAATAGAGGAGGTGGTGGTGCGGTTATA<br>CCTGGACAAAAGAACACCGTCTCAGTATTTGTCCTAGGGTCAAGTATTGTAGACGACAGCGATAAGTTAGCTA<br>TAGCACTCATGTTTTTAACACATGCTCTTGATACTGACAAGCAACACTCACAAAGAAGCGGTTTCCTGGTTTC<br>ATTAATGGCAATGGCATATAGTAGTCCTGAATTATATCTAACAACTAATGGAGTTAATGCAGATGTTAAGTAT<br>GTTATCTACACAATTGAGCATGATCCCCAGAGGACAACCCATAATGGGTTCATTGTTAGGACAAGAGATATGG<br>ACTATGAAAAGACAACAGAGTGGCTATTCAGCCGTATAACTAATAAATACCCACTACTTCAGGGACAAAAAGA<br>CACTCATGATCCAGAATCACTACTCCAGACTTATGGATATCCCTCATGTTTAGGAGCATTGATAATCCAGGTT<br>TGGATTGTCTTGGTCAAAGCAATTACAAGTAGTGCTGGATTGAAGAAAGGATTCTTCAATAGACTTGAAGCCT<br>TCAGGCAGGATGGAACAGTTAGAAGCTCACTAGTCTTCAGTGGGGAGACAGTTGAGGGGATTGGGTCAGTGAT<br>GAGATCTCAGCAGAGTTTGGTGTCCTTAATGGTAGAGACTCTAGTTACCATGAACACGGCCAGATCTGACTTG<br>ACCACTCTAGAAAAGAATATTCAGATTGTTGGGAATTACATCAGGGATGCAGGTCTTGCTTCATTCATGAACA<br>CGATTAGATATGGTGTGGAGACTAAGATGGCAGCACTTACATTATCTAATCTTAGACCTGATATTAATAAACT<br>AAAGAGTCTAATTGACATCTACTTATCCAAAGGTGCAAGAGCCCCCTTCATATGCATATTACGTGATCCGGTA<br>CACGGAGAATTTGCTCCTGGAAATTATCCAGCATTGTGGAGTTATGCTATGGGGGTCGCAGTAGTCCAGAACA<br>AAGCCATGCAGCAGTATGTGACAGGGAGGACTTATCTGGATATGGAAATGTTCCTTCTTGGTCAAGCAGTAGC<br>TAAAGACGCAGAATCTAAGATCAGTAATGCATTAGAGGATGAATTAGGTATAACTGAAAATGCCAAAGACAGG<br>CTCAAACATCATCTTGCTAACCTTTCTGGAGGTGATGGAGCTTATCACAAACCCACTGGTGGAGGAGCAATAG<br>AAGTTATAATTGACAATGCAGACATAGATCTCAGGACAGAGGAAACCACAGAAGAATCTTCAATCAGGCTTTC<br>CAATATTAGAGAAAACAAAGGGAGAATAGCAGACGGGCAGAGGAGATGGGAAACAACCAGATCCATTGGTGAT<br>GACCCCAATCCAGACAACACCACTGACGATGAAGTATCCGCCGCAGAAAGGAGGATTGCAGAAAGACTGGCAA<br>AAAAGGAGGGGAAGAATACCAGGTCGGATATACTCATTACCGATGGTATGACTGAAGATACAGATAACGATGA<br>TGATATAATGAGAATGAATGCACTAGGAGGAATATAATAAATCCAAACAAAGGGTTTTATATATTGGTTAGTA<br>AGAAAAACTTAGGGTGAAAGAATAGCTCCTAGATACTAGGAACTCTATCACTCCCAAAGACAGGATCTCAAAC |

-continued

| Sequences |
|---|
| TGGCCACCCACAAAAGAATCCCCCAAAATCCAGATACCAAATGGATCAAGATGCCCTCTTTTCTGAAGAATCT |
| ATGGAGGATCAGAAGGAGGGACACTCAACAACCAGCACACTCACCAGTGCAGTCGGACTCATTGACATCATCC |
| TTGCCAGTGAGCCCACAGACATTAGAAAAGACAGAAAACACCTATGTGAGCCCATCACAGCCTGGGGAAAATC |
| AGAAGCAAGCAAGATTTCCAAGGATACAGTCTGTGAAGAAAACCCAAGAACAGAAAGGGAAGATTATGGACAA |
| AGTAAAAAGAGTGGAATTCCTAGGGAGTCAAACAAGTTCGAAGCAGAAGTTTCTTTTAGAGAAACTCATAGCT |
| CAGGTACATCATGGAGGGCTTGGAGAAGAAGTAGTGCAAACTCTATACTTGAGAATATGGGCAATGGATCCGA |
| CTCCTATGGCAACGAAATTACTGGAAATGGAGGAGGAAACCAGAGACAAAGTCCTGAAGCTAAAGTTGGAGAG |
| ATGGATCCGAGTTCTAATACGAGGAGAAAAGACAAAACTGAGGGACTTCCAGAAGAGATACGAGGAGGTTCAC |
| CCATATCTAATGACGGAGAAGGTGGAAGAAATAATAATGGAGGAAGCCTGGAGTCTGTCAGCACACATAATCC |
| AAGAGTAGAAAACAACATTATGGATCCAACTCATCATCTTGAAGAAGAGGTACTTAAGAGGAACAAGCCACGG |
| GAGATGAATGCTACAAGTCAATGGTCGGGTGGATACAAGACTGATCAACAAGACGGTAAACATGAATTGATAA |
| CCAATCCAATATTTTCAAATCAAAATAGGTCACAGGACACAAAAAAGGGAAAAGGGAAAGAATCAACTGTAAA |
| GCCCAAGACCAGAAAATCTAAAATATCCTTTGAAGACACAAGAAGCACAGATCACATCTACGAAGACTCTCAA |
| GAACATACAAGAAGAAAGAAAACAGACAACGAACCATCACAAAAGATTGGTAAAAAGGGCACAGAAGAGAATA |
| CCTTATATACAGAAGAGGTGATCAAATTGTTAGTGAGTCTTGGTGTAATCCCATCTGTAGCCGCATTCAACCA |
| ATCCCGAAACATATGCCATGTATTTGCAAAACGTGTCCTCAATTCTGTGAACTCTGCAGAAATGACAGCTAAT |
| ATGTGCGGATTATTGCTGTCTGTTGAGAAATCAGTATCAGACCATATTGAAGAAAATAAGACACTAATAAATC |
| AGATTATAAGTGATTTAAGTACAGGTAGGGAAGTGCAGAAACGTTTCACTGAGTATCAAAAGGAACAGAATTC |
| ATTGATTATGTCAAATCTGGCGACACTTCATATCATAACAGATAGAGGAGGAAAGAACAACAGCATGGATACA |
| GGGGAGAGGACACCATCAATCAGGACCAAGGGGAAGGAGCCAACACAGAGAACACAAAGATTTGATCCATCTA |
| TGGAATTCACCGAGGAGATTAAGTACAAGCCCGATCTATACAGGGAAGACACATTGAGACAAAGAATAACAAA |
| CCCTGTTCTTGATGAGAGCGCAGAGAGAATCGACAATTCGAATGCCGCGAGACTGATACCTTGCAAAGAAAAA |
| TCAACACTGCGTTCACTCAAATTAATTATTGAGAACAGCAATTTGAGCAGAGCAGACAAAATTGCCTATATCA |
| GGTCATTATCAAAATGCAAAGATGACAAAGAGGTAGAATCAGTAATGAAACTATTTGAAGAAGATATAGAATC |
| AAGTAATGAATAATCACTGATCAGTATATCCAGAAAACGTCAAGACAAGAGTGTACTGTGATGAGTAATGACT |
| CTCCAAATACCTAATAAGAAAAACTTAGGGTGCAAGACTCACCAACCAAGCCAAGCAAATGGCCGAGATCTAC |
| AAGTTCCCCAAGCTATCATATGAGGAACATGGATATATGGAACCTCTACCACTAAGGACTGGCCCAGATAAGA |
| AGGCAGTCCCACATATAAGGATAATCAAGATAGGGGACCCACCGAAGCATGGAAATCGATATCTTGATATTCT |
| CTTACTTGGGTTTTATGAGATACCCAAAGAAGTTGGAACATACGGTAGTGTATCAGATTTGACGAGACCCACG |
| GGATACACAATCTGCGGTTCAGGATCATTACCTATTGGAATTGCTAGGTACTTAGGTACAGATCAGGAACTAC |
| TCAAAGCATCAGTAGAGCTAAAAGTGACAGTGAGAAGGACAGTAAGGTCAAGTGAGATGATTGTGTATATGGT |
| AGATACCATACCACCAGCAATGATGGCTTGGGCTTCCAGGTTGAAACGAGGCATGATATTCAATGCGAATAAA |
| GTAGCTCTAGCTCCTCAATGTCTACCTATAGATAAAGATATAAGATTCAGAGTTGTCTTTGTCAATGGCACTT |
| CTCTAGGTTCCATCACAATAGCAAAAGTTCCCAAGACATTAGCCGATCTTGCTTTACCGAATTCCATATCGGT |
| CAATTTAATGGTCTCACTCAAGACTGGTGCGTCAACTGAGTCCAAGGGCATTATTCCTACGCTAAACGAAAAG |
| GGCGACAAGGTACTAAACTTTATGGTACACCTTGGATTAATACATAGGAAAGTCGGAAGGGTGTATTCAATGG |
| AGTATTGCAAGGGTAAAATAGAGAAGATGCGGCTGATCTTCTCATTAGGACTGGTTGGAGGAATCAGTTTCCA |
| TGTTCAGCTTACAGGTGTGGTATCTAAATCCTTTGTTGGTCAGCTTGGAGGGAGGAAGGAAATATGTTACCCT |
| TTGATGGATGTAAACCCACACATGAATTTAGTTATCTGGGCTGCTTCCGTTGAAATCACTGGCGTGGATGCTG |
| TTTTCCAACCTTCCATACCAAGAGATTTCAAATACTACCCGAATGTGGTGGCAAAAAATATTGGGAAAATAAA |
| AGCTTAGAGATCCAAAGCCACTGTAACCCCAGACATCCCAACACTAGACTGGTAAGTGTCATTATATGATCAG |
| CATCATTCATCAGAAATAAGAAAAACTTAGGGTACAAGTTATCCAAAAAAGACAGAACAGAACAAACAGATCA |
| AGACAAGACATCACAAAATGCAAATCATCATCCTCAGACCAGCCATAATACTAAGCATAGTACTATTAGTGAC |
| CAGTCAAGTCCCTAGAGATAAACTAGCCAATTTAGGGATCATCATTAAGGACAGCAAAGCACTCAAAATTGCA |
| GGATCTTATGAAAACAGATACATAGTCTTAAACCTTGTACCAACAATAGAAAATGTGGGTGGGTGTGGTTCCA |
| TCCAAATAGCAAAATATAAAGAGATGCTTGAAAGGTTGTTAATACCGATAAAAGATGCACTAGATTTACAAGA |
| GTCTTTGATAATGATTGATAATGAAACCGTCAACAACAATTATCGTCCTCAGTATAGATTTGTTGGTGCAATT |
| ATTGGGACTATAGCCCTTGGGGTAGCAACTGCGGCCCAAGTTACAGCAGGGGTGGCACTGATGGAGGCAAGAG |
| AGGCCAAAAGAGATATATCAGTGTTAAAAGAAGCAATTGGAAAGACTCAAAACTCAATTGAAAAATTACAGAA |
| TTCTGCAGGTGAACAGATACTGGCTCTCAAAATGCTCCAGGATTATGTCAATGGAGAGATTAAACCAGCTATT |
| GAAGAACTTGGATGTGAGACTGCTGCACTTAAATTAGGAATTGCACTTACACAACACTACACAGAGCTCACAA |
| ATGCCTTTGGGTCGAATCTAGGTTCCATAGGAGAGAAGAGCTTAACATTACAGGCCCTATCATCATTATACAA |
| GACCAATATAACTGATATACTGACAACAACTAATCTCGGGAAAACAGATATTTATGATATTATATATGCTGAG |
| CAAGTTAAAGGAAGAGTAATAGATGTCGATCTTAGACGATATATGGTTACAATATCTGTTAAGATACCAATAT |
| TATCAGAAATACCAGGAGTATTGATCTATGAAGTCTCCTCTATATCTTATAATATAGATGGAACAGAATGGTA |
| TGCCGCTGTACCTGACCACATATTAAGTAAATCCGCATATATAGGGGGTGCAGATATAAGTGATTGTATAGAA |
| TCTGGATTGACATATATTTGTCCGCGAGATCCTGCTCAGATTATAGCGGATAACCAACAGCAATGTTTTTAG |
| GTCATCTTGACAAGTGCCCTATAACTAAAGTAGTTGATAATCTTGTGCCTAAATTTGCATTCATAAATGGTGG |
| AGTAGTTGCAAACTGTATAGCCTCTACATGTACCTGTGGAGAAGAGAGGGTCCAGGTCTCTCAAGATAGAAAT |
| AAAGGAGTAACCTTTTTGACTCATAATAATTGTGGATTAATAGGGATAAACGGGATGGAATTTCATGCTAACA |
| AGAAAGGGAGTGATGCTACTTGGAATGTCTCCCCCATAAGAGCAGGGCCAGCGGTATCGTTAAGACCAGTAGA |
| TATATCTTTACAAATAGTTTCTGCTACTAATTTTCTAAACTCATCAAGAAAAGATCTTATGAAGGCAAAAGAG |
| ATCTTAAACCAGGTAGGAAATCTTAGAGATTTAACCGTCATAACGATAATTAATATAGTAATTATAGCTGTAT |
| TACTTATATGTGTAACTGGATTAGGCGTACTGTATCACCAATTGAGAAGTGCACTAGTGATGAGAGACAAGAT |
| GTCAGTATTAAATAATAGTTCCTATTCTTTAGAACCAAGAACCACCCAGGTACAAGTAATTAAGCCTACTAGT |
| TTCATGAGATAAACTATAAAAATATATTTTAATCCATCCTCATTAATCAAAGTAAAGAAAACTTAGGGTGCAC |
| GACAGTAACTCACCACCAAAGGAGAAATAGATCAGAGACCAACACACCAAGAGATGGAAGGGGCCAAAGTTAA |
| GACATCAGGGTACTGGGCCAAGAGTCCTCAAATTCACGCAACAAATAATCCTAACGTACAAAACAGAGAGAAG |
| ATCAAGGAAACATTAACAATTTTAATATCATTCATTTCTTTCCTATCTCTTGTACTGGTTATAGCTGTACTGA |
| TAATGCAATCTTTACATAACGGCACAATACTAAGGTGTAAAGATGTAGGCCTAGAATCTATCAATAAATCCAC |
| TTACTCTATATCTAATGCAATTCTGGATGTCATCAAACAAGAGCTGATAACTCGTATAATAAATACTCAAAGT |
| TCTGTGCAGGTAGCCCTCCCGGTCTTAATTAACAAGAAAATCCAGGATCTCTCACTAACCATTGAGAAAAGTT |
| CAAAAGTGCATCAAAATTCTCCTACTTGTAGTGGTGTGGCTGCCCTGACACATGTGGAAGGGATAAAACCTTT |
| GGATCCAGACGATTACTGGAGGTGTCCAAGTGGGGAACCATATCTAGAGGATGAATTGACATTAAGTCTTATC |
| CCTGGACCTAGTATGCTAGCTGGAACCTCTACCATCGATGGCTGTGTAAGATTACCATCTCTTGCAATAGGAA |
| AATCGCTATATGCCTATAGTTCCAACCTTATAACTAAGGGTTGTCAAGATATAGGGAAATCCTATCAAGTGCT |
| ACAGTTAGGTATTATAACTCTGAATTCAGACTTACATCCTGATTTAAATCCTATAATATCACATACTTATGAT |

-continued

| Sequences |
| --- |
| ATAAATGATAATAGAAAGTCCTGTTCTGTTGCTGTATCAGAAACTAAAGGATACCAATTATGCTCGATGCCGC<br>GTGTCAATGAAAAAACAGATTACACTAGTGATGGTATTGAAGATATAGTTTTTGATGTACTTGATCTCAAAGG<br>GTCCTCTAGAAGTTTCAAATTTTCAAACAATGATATAAACTTTGATCATCCTTTTTCAGCGTTATACCCTAGT<br>GTAGGAAGTGGTATTATATGGGAAAATGAACTGTATTTCCTAGGTTACGGGGCTCTGACAACTGCACTTCAAG<br>GGAATACAAAATGTAATTTAATGGGATGTCCAGGAGCAACACAAAACAACTGCAACAAGTTCATCTCTAGTTC<br>ATGGTTATACAGCAAACAGATGGTTAATGTACTGATACAGGTTAAGGGGTATTTATCTAACAAGCCAAGTATT<br>ATAGTTAGAACAATCCCAATAACGGAAAATTATGTAGGAGCAGAAGGGAAACTAGTGGGAACACGTGAGAGAA<br>TATATATATATACAAGATCAACGGGTTGGCATGCCAATTTACAAATAGGAGTACTTAATATAAATCATCCAAT<br>AACCATAACTTGGAAAGATCACAAAGTACTATCAAGACCAGGAAGAAGTCCTTGTGCCTGGAATAACAAATGC<br>CCTAGAAATTGTACTACTGGTGTATACACAGATGCTTATCCTATATCGCCTGATGCTAATTATGTTGCTAGAG<br>TTACTCTATTATCTAATTCAACACGAACTAATCCTACTATTATGTATTCATCTTCTGATAGAGTATATAACAT<br>GTTAAGATTAAGAAATACTGAATTAGAAGCTGCATACACAACCACGTCTTGTATTGTCCACTTTGATAGAGGT<br>TATTGTTTTCATATTATAGAAATTAATCAAAAAGGACTGAATACACTACAGCCTATGCTCTTTAAGACTGCAA<br>TTCCTAAAGCTTGCAGGATAAGCAATTTATAAGACACCCATTGAAATAATAATTTGTATCTAATTACTTAAAA<br>GGGTGACTGTGCATGACTTAGAGATAAGTGACCTGTGGACATAAATCATACAGGTCATTAAATAGCATATAAT<br>ACACCTAATAAGAAAAACTTAGGTTGAATGCCAAAGCATTCAGCCAGAATGGATCATTTCAATATGTCTCAAA<br>ATCCAAGTGATATACTATACCCTGAATGCCACTTGAACTCTCCAGTTGTGAAAGGGAAGATCGCTCAGCTACA<br>TGTCTTGTTAGATATTAATCAGCCGTATGAAATGAGGGACCCTAGTATAATAGAAATCACAAAAGTTAAAATT<br>AAATCTGGAGGGTTAAATCAAAGGTTAATCAGAATCAGATCTTTAGGGAAAGAGATGAGGAGAATCATATTTG<br>ATTTTGATAAGTATACATTCGAACCTTACCCAATATTTTCTAAAGAATTATTTAGATTAGAGATACCAGAGAT<br>TTGTGATAAAATTCAATCAGTTTTTGCAGTGTCGGATAGGTTAAGCAAAGATATATCCCAGCCATTACAATAC<br>TTATGGAGAGATGTGCGTAGGCAGTTGGGAGGGGATTGTTCCAAGGATCTTTCTAACAATGAGATTGATATAC<br>ACAAAATTCCTGAAATCCATACTAAATTCACCAGAAATAACTGGTATAAACCATTCATGACATGGTTTAGTAT<br>TAAATATGATATGAGAAGATGTCAAAAGAATAGGGAAAACATAAACTTAGACAGTAGGCAATCATATAATTAT<br>CTTAACTGTAAATACTATTTTATAATTATCCACCCGGATCTCTTAATGATATTGGACAAGATCAAATACACGG<br>GATACTTACTGACACCAGAATTAGTGCTAATGTACTGTGATGTGGTCGAAGGTAGATGGAATATGTCTGCTGC<br>TGGACAATTAGATGACAAATCACACAAAATAACATTGAAAGGAGAAGAATTGTGGGGCAGGATAGATGAATTA<br>TTCAAGATAATCGGGGAAGAGACATTTAATATCATATCACTATTGGAGCCATTATCTTTAGCATTGATACAAT<br>TAACAGATCCTGTTATGTCTTTAAAAGGTGCATTTATGAGACATGTCATCTCAGAAATGAGTGAAATATTGGG<br>TAAATGTGGAAATCTAACTGAACTTGAGGTGGATCACATAATGGATTCAATCCTTAACATTTTTATGGATACA<br>ACAGTAGATGAGAAAGCAGAGATATTCTCCTTCTTTAGGACATTTGGTCATCCTAGCCTTGAGGCCTCCATAG<br>CTGCTGAAAAAGTTAGGCAACATATGTATGCGCAGAAAAGTATAAAATATAAGACCTTATGTGAGTGTCACGC<br>TATATTTTGTACAATTATAATAAACGGATATAGAGACAGACATGGAGGACAGTGGCCCCCCTGTCAGTTCCCA<br>GATCATGTGTGTCAAGAACTCAGAAATTCTCAAGGATCTAATTCAGCTATATCTTATGAAACAGCCGTTGACA<br>ATTTCGAGAGCTTTATAGGTTTCAGATTCGAGAAGTTCATAGACCCTCAATTAGATGAAGATCTCACTATTTA<br>CATGAGAGATAAAGCATTGTCTCCAAGAAGAGAAGCCTGGGATTCTGTGTATCCAGATGGCAATCTGCTGTAT<br>AAAGTGCCGTTCTCTGAAGAAACAAGGAGATTGATAGAAGTCTTTATTAGTGATTCTAATTTCAATCCAGAAG<br>ACATTATACAATATGTAGAGACAGGAGAATGGTTGAACGATGATACTTTCAACATATCTTATAGCCTAAAAGA<br>AAAGGAGATCAAACAAGAGGGTCGATTGTTTGCCAAGATGACATACAAAATGAGAGCAGTCCAAGTATTGGCA<br>GAAACTTTGCTAGCAAAAGGAATAGGGGGTTTATTTAATGAAAATGGTATGGTTAAAGGTGAAATCGATTTAC<br>TAAAGAGTCTAACTACTTTATCTATATCAGGAGTTCCAAGGACTAGCGAGATTTATAATGAATCAGTTAGTGA<br>AGAAGCTGATAGGAGAAGATGGGAAAGGAAAATTCCTCATACTATTGGGATAAAAGAAAAAAATCAAAACAT<br>GAGTTCAAAGCCACAGACTCATCTACTAACGGCTATGAGACTCTAAGCTGTTTTCTTACTACGGACTTGAAAA<br>AATATTGTCTAAATTGGAGGTTTGAGAGTACATCTCTATTCGGGCAGAGATGTAACGAAATATTTGGGTTCAA<br>GAGATTCTTCAACTGGATGCATCCTGTATTGGAAGAATGTACAATATATGTGGGTGATCCTTACTGTCCCGTG<br>CCCGATAAAATCCACAAGAATTTAGAAGATCATGAAGATTCAGGCATCTTTATACATAGACCGAGGGGTGGGA<br>TAGAAGGTTATTGTCAAAAACTTTGGACTCTCATATCCATAAGTGCAATTCATCTAGCTGCTGTCAAGGTCGG<br>GGTTAGAGTATCAGCTATGGTACAAGGTGACAACCAAGCAATTGCCGTGACATCTAGGGTACCAGTGACGGCC<br>ACGTATAAGTTCAAAAAAGAGCAGGTATATACGGAGATCACTAAGTATTTTAGGTCTTTAAGAGATGTGATGT<br>CTGATTTAGGACATGAACTCAAACTCAACGAGACAATTATAAGTAGCAAGATGTTCGTGTATAGTAAGCGGAT<br>ATATTATGATGGTAAAATACTACCCCAATGTTTAAAAGCACTTACAAGGTGTGTTTTTTGGTCTGAGACCTTG<br>GTGGATGAAAACAGGTCTGCTTGTTCCAATCTTGCAACTGCTATAGCCAAAGCTATAGAAAATGGCTATTCAC<br>CAATATTAGGTTACTCAATAGCTCTGTATAAGACTTGTCAGCAAGTATGTATCTCATTAGGGATGACTATCAA<br>TCCTACAATAACACCTAATATAAGAGACCAATATTATTTAGGGAAGAATTGGCTTAGATGTGCAGTTTTGATA<br>CCTGCTAATGTTGGGGGATTTAACTACATGGCAATGTCTAGATGCTTCGTCAGAAATATAGGCGACCCTGCAG<br>TAGCTGCTCTAGCAGACCTCAAAAGGTTTATCCGAGCAGGACTATTGGACAAGCAGATTTTGTACCGTGTAAT<br>GAATCAAGAATCTGGGGAGTCTAATTTCTTAGACTGGGCATCTGATCCATACTCATGTAATTTACCACATTCG<br>CAGAGTATCACAACAATTATAAAGAATATTACAGCTCGTTCAGTTCTCCAAGAGTCACCAAATCCTCTACTGT<br>CAGGTTTATTTACATGTGACAGTAAAGAAGAAGACTTAAATTTAGCGACATTTCTGATGGACAGGAAGGTCAT<br>ATTGCCAAGAGTTGCACATGAGATACTAGACAACTCTTTGACAGGGATCAGAGAATCCATCGCAGGAATGCTG<br>GATACTACAAAATCATTAGTACGGGTTAGTATTAGAAAAGGGGGTTTATCATACAATCTCTTAAGAAAGCTGA<br>TAAATTATGACTTATTACAATATGAAACATTAACCAGGACTTTAAGGAAAGTCGTCACAAATAACATTGAATA<br>TGAATATATGTGTTCTGTGGAATTAGCAATTGGATTAAGGCAAAAAATGTGGTCACATCTAACATATGGGAGA<br>CCTATACATGGATTAGAAACACCTGATCCTCTAGAACTCCTTAAAGGAACATTCATCAAAGGATCTGAGGTTT<br>GCAAAATATGCAGGTCTGAAGGTGATAATCCTATATATACTTGGTTTTATTTACCTGAGGAAATAGATCTGGA<br>TAACCTAGAACAAGGAAATCCATCTATAAGAATACCTTACTTTGGGTCTACTACTGACGAAAGATCAGAAGCA<br>CAACTGGGTTATGTTAAAACACTGAGTAAACCTGCTAAAGCAGCGATTAGGATTGCTATGATATATACTTGGG<br>CTTATGGTACTGATGAGATATCATGGATGGAAGCGGCTCAGATTGCACAAACAAGAGCAAATTTAAGTCTTGA<br>TAATTTGAAACTTCTGACTCCGGTATCAACATCTACAAATCTGTCCCATAGATTAAAGGACACTGCTACCCAG<br>ATGAAATTCTCAAGTGCAACTCTAGTTAGAGCTAGTAGATTTATTACTATATCAAATGATAAGATGGCTCTGA<br>AGGAGGCAGGTGAGACAAAGGATACTAATTTAATATATCAGCAGATAATGTTGACAGGACTTAGTGTTTTTGA<br>ATTCAATACCAGATACATTAAAGGTAAGACTAAACAACCAATGATCCTACACTTACATTTAAACAATGGCTGC<br>TGCATTATGGAATCACCACAAGAGACTTGTATCCCTCCTAAATCTACTCTAGACTTAGAGGTAACCAATGAAG<br>AAAATAAATTAATATATGATAATAATCCATTAAAAAATGTTGATCTCGGTATTTTCCAAAAAATTAGAGATAT<br>CGTACACACTGTAGATATGACTTTCTGGTCTGATTTGGAAATAATGAGAGCAGTTACTATTTGTACATCTATG<br>ACAATAGCAGACACCATGTCTCAATTGGATAGAGATAACCTTAAAGAAGTAATTGTTCTTGCGAATGATGATG<br>ACATTAATAGCTTAATAACAGAGTTTATGATAATAGACATCCCGCTCTTTTGCTCAACATTCGGAGGAATCTT |

-continued

Sequences

AGTAAATCAGTTTGCCTATGCATTATACGGTCTAAATATAAGAGGTAGAGAAGAAATATGGGGTTACATTACA
CGGACTTTGAAAGATACTTCTCATGCTGTGTTAAAGGTACTTGCTAATGCATTATCACATCCAAAGGTGTTCA
AGAGATTCTGGGATTTCGGTATTTTAGAGCCTGTATATGGACCTAATTTATCCAACCAAGATAAGATAATGTT
AGCATTATCTGTTTGTGAGTACTCAATAGACTTATTCATGAGGGACTGGCAAAGCGGAATACCTCTAGAAACC
TTTATATGTGACAATGATCCAGAAGTAGTTGAATTAAGAAAAGGTGCCTACTTGGCAAGACATTTAGCATATT
TATGCAGCTTAGGAGAGATTTCCTCATATGGTCCTAGATTAGAAACTCTAACATCATTAGAAAGGTTAGAGGT
TCTTAAAAGCTACCTAGAGATATCTTGTTTAGAGGATCCAACATTGAGATACAGTCAGGTTACAGGGCTGGTA
TTAAAAGTGTTCCCATCAACAGTAGTATATATCAGGAAGTTAGCTATAAAGATGTTGAGGATTAGGGGCATAG
GGGTGCCAGAGGTGTTAGAAGACTGGGATCCCAGTCATGAACAAGCTCTACTAGATAATATAGCTCAAGAGAT
CCAACATAATATCCCAATAAACCAATCTATCAAGACACCTTTCTGGGGGCTCAAAGTCAATAATTCCCAAGTC
TTACGTCTAAGGGGATATAAGGAGGTTAAGGATAGGAAATCAGGGCGATCAGGAGTAGGTCTAACACTTCCAT
GTGATAATAGGTACTTATCCCATCAGATAAGACTTTTCGGGATTAATAGTACTAGCTGCCTGAAAGCTTTGGA
GTTAACATATTTAATAGGACCATTGATAGATAAAAGTAAAGATAGATTATTCTTAGGGGAAGGTGCAGGTGCT
ATGTTGTCATGTTATGATGCAACGTTAGGACCTTCAATGAACTATTATAACTCAGGTGTCTCATCATATGATA
TAAATGGTCAGAGGGAATTAGGGATCTATCCATCTGAGGCTGCATTAGTGGCAAAGAAATTGAATAATGTAAC
TAATTTGGGTCAGAGAATTAAGGTGCTGTTCAACGGAAACCCTGGGTCTACATGGGTTGGCAACCAGGAATGC
GAAACATTAATTTGGAGTGAATTACAGGACAAATCAATCGGCTTGATACATTGTGACCTAGAAGGTGGAGAAC
TAAAAGATACACAAACAGTACTGCATGAACATTATAGCATAATTAGGATAGCATACTTAGTAGGAGATAACGA
TGTTTTATTAGTGACTAAAATTGCACCTAAATTGGGTACAGATTGGACTCAGCAACTATGCTTGTATCTAAGA
TATTGGAATGAAGTCAATTTAGTTGTTCTTAAGACATCTAATCCTTCTTCTACTGAGATGTATTTGTTATCAA
GGAATCCAAGTAAAGATGTGATTGAAGATAGTCTAACAGTAATCTCAGACCTAAAGCCATTGTCTAAAAAAGA
TAGTATACAATTAGAAAAGTGGATTTTGGTTGAGAAAGACAAAGTTAAGGAATGGCTAATTAAAGAATTAAGA
GAGGGAGAACTAATGTCAGGTTCACTTAGGCCTTATCACCAAGCACTTCAGATTTTTGGATTTGAGGCCAACT
TGCACAAATTGTGTAGAGACTTCTTATCAACTATGAGTATTTCAGATATCCAGATGTGTATAAATTCATTCTA
CAGAGTTTTAAAGGACACAATATTTGAGTGGAGTCGGGTAACAAATGATCATAAGACATGTAAACTCACAGGG
AAATATGAGTTATATCCTATAAGAGACAGTGGAAAGTTGAAAGTGATATCAAGAAGGCTTATAATATCCTGGA
TTGCTTTATCCATGTCTACTAGACTGTTAACAGGCGCTTTCCCTGATATTAAGTTTGAGTCCAGATTGAATAT
AGGTTTAGTCTCCTTATCTACGAATGAGATCAAATCACTTAAACTTATATCCAAGGCTACGGTGGATAGGTTT
CAAGAAGTGATTCACAGTGTATCCTACAGATTCTTGACTAAAGAAATTAAAATACTCATGAAGATACTTGGAG
CTGTTAAATTATTTGGTGCAAGACAGACTTATAACCATTTAGCTTTAACACCAGAACCTCTATCTGATATAGA
GGGATATTTAGATGATTAGCTCGAATATCAACAGTAAACAGCTAAGAATCATTAAGAAGACTATCTGGATCCA
GACCTAAATGAAAGAATAAGAAAAACTTATTTAAACAATCAAAGATCCAAGCAAAATGATATGTCTTAAACTC
TTGT

>USA/MN25890NS/2016-P3 nucleocapsid protein (N) nucleotide sequence
(SEQ ID NO: 2)
ATGGCAGGGTTATTAAGTGTCTTTGACACATTTAGTTCTAAAAGGAGTGAAAGCATAAATAGAGGAGGTGGTG
GTGCGGTTATACCTGGACAAAAGAACACCGTCTCAGTATTTGTCCTAGGGTCAAGTATTGTAGACGACAGCGA
TAAGTTAGCTATAGCACTCATGTTTTTAACACATGCTCTTGATACTGACAAGCAACACTCACAAAGAAGCGGT
TTCCTGGTTTCATTAATGGCAATGGCATATAGTAGTCCTGAATTATATCTAACAACTAATGGAGTTAATGCAG
ATGTTAAGTATGTTATCTACACAATTGAGCATGATCCCCAGAGGACAACCCATAATGGGTTCATTGTTAGGAC
AAGAGATATGGACTATGAAAAGACAACAGAGTGGCTATTCAGCCGTATAACTAATAAATACCCACTACTTCAG
GGACAAAAAGACACTCATGATCCAGAATCACTACTCCAGACTTATGGATATCCCTCATGTTTAGGAGCATTGA
TAATCCAGGTTTGGATTGTCTTGGTCAAAGCAATTACAAGTAGTGCTGGATTGAAGAAAGGATTCTTCAATAG
ACTTGAAGCCTTCAGGCAGGATGGAACAGTTAGAAGCTCACTAGTCTTCAGTGGGGAGACAGTTGAGGGGATT
GGGTCAGTGATGAGATCTCAGCAGAGTTTGGTGTCCTTAATGGTAGAGACTCTAGTTACCATGAACACGGCCA
GATCTGACTTGACCACTCTAGAAAAGAATATTCAGATTGTTGGGAATTACATCAGGGATGCAGGTCTTGCTTC
ATTCATGAACACGATTAGATATGGTGTGGAGACTAAGATGGCAGCACTTACATTATCTAATCTTAGACCTGAT
ATTAATAAACTAAAGAGTCTAATTGACATCTACTTATCCAAAGGTGCAAGAGCCCCCTTCATATGCATATTAC
GTGATCCGGTACACGGAGAATTTGCTCCTGGAAATTATCCAGCATTGTGGAGTTATGCTATGGGGGTCGCAGT
AGTCCAGAACAAAGCCATGCAGCAGTATGTGACAGGGAGGACTTATCTGGATATGGAAATGTTCCTTCTTGGT
CAAGCAGTAGCTAAAGACGCAGAATCTAAGATCAGTAATGCATTAGAGGATGAATTAGGTATAACTGAAAATG
CCAAAGACAGGCTCAAACATCATCTTGCTAACCTTTCTGGAGGTGATGGAGCTTATCACAAACCCACTGGTGG
AGGAGCAATAGAAGTTATAATTGACAATGCAGACATAGATCTCAGGACAGAGGAAACCACAGAAGAATCTTCA
ATCAGGCTTTCCAATATTAGAGAAAACAAAGGGAGAATAGCAGACGGGCAGAGGAGATGGGAAACAACCAGAT
CCATTGGTGATGACCCCAATCCAGACAACACCACTGACGATGAAGTATCCGCCGCAGAAAGGAGGATTGCAGA
AAGACTGGCAAAAAAGGAGGGGAAGAATACCAGGTCGGATATACTCATTACCGATGGTATGACTGAAGATACA
GATAACGATGATGATATAATGAGAATGAATGCACTAGGAGGAATATAA >USA/MN25890NS/2016-P3 nucleocapsid protein (N) amino acid sequence
(SEQ ID NO: 3)
MAGLLSVFDTFSSKRSESINRGGGGAVIPGQKNTVSVFVLGSSIVDDSDKLAIALMFLTHALDTDKQHSQRSG
FLVSLMAMAYSSPELYLTTNGVNADVKYVIYTIEHDPQRTTHNGFIVRTRDMDYEKTTEWLFSRITNKYPLLQ
GQKDTHDPESLLQTYGYPSCLGALIIQVWIVLVKAITSSAGLKKGFFNRLEAFRQDGTVRSSLVFSGETVEGI
GSVMRSQQSLVSLMVETLVTMNTARSDLTTLEKNIQIVGNYIRDAGLASFMNTIRYGVETKMAALTLSNLRPD
INKLKSLIDIYLSKGARAPFICILRDPVHGEFAPGNYPALWSYAMGVAVVQNKAMQQYVTGRTYLDMEMFLLG
QAVAKDAESKISNALEDELGITENAKDRLKHHLANLSGGDGAYHKPTGGGAIEVIIDNADIDLRTEETTEESS
IRLSNIRENKGRIADGQRRWETTRSIGDDPNPDNTTDDEVSAAERRIAERLAKKEGKNTRSDILITDGMTEDT
DNDDDIMRMNALGGI >USA/MN25890NS/2016-P3 phosphoprotein (P) nucleotide sequence
(SEQ ID NO: 4)
ATGGATCAAGATGCCCTCTTTTCTGAAGAATCTATGGAGGATCAGAAGGAGGGACACTCAACAACCAGCACAC
TCACCAGTGCAGTCGGACTCATTGACATCATCCTTGCCAGTGAGCCCACAGACATTAGAAAAGACAGAAAACA
CCTATGTGAGCCCATCACAGCCTGGGGAAAATCAGAAGCAAGCAAGATTTCCAAGGATACAGTCTGTGAAGAA
AACCCAAGAACAGAAAGGGAAGATTATGGACAAAGTAAAAAGAGTGGAATTCCTAGGGAGTCAAACAAGTTCG
AAGCAGAAGTTTCTTTTAGAGAAACTCATAGCTCAGGTACATCATGGAGGGCTTGGAGAAGAAGTAGTGCAAA -continued

| Sequences |
| --- |

CTCTATACTTGAGAATATGGGCAATGGATCCGACTCCTATGGCAACGAAATTACTGGAAATGGAGGAGGAAAC
CAGAGACAAAGTCCTGAAGCTAAAGTTGGAGAGATGGATCCGAGTTCTAATACGAGGAGAAAAGACAAAACTG
AGGGACTTCCAGAAGAGATACGAGGAGGTTCACCCATATCTAATGACGGAGAAGGTGGAAGAAATAATAATGG
AGGAAGCCTGGAGTCTGTCAGCACACATAATCCAAGAGTAGAAAACAACATTATGGATCCAACTCATCATCTT
GAAGAAGAGGTACTTAAGAGGAACAAGCCACGGGAGATGAATGCTACAAGTCAATGGTCGGGTGGATACAAGA
CTGATCAACAAGACGGTAAACATGAATTGATAACCAATCCAATATTTTCAAATCAAAATAGGTCACAGGACAC
AAAAAAGGGAAAAGGGAAAGAATCAACTGTAAAGCCCAAGACCAGAAAATCTAAAATATCCTTTGAAGACACA
AGAAGCACAGATCACATCTACGAAGACTCTCAAGAACATACAAGAAGAAAGAAAACAGACAACGAACCATCAC
AAAAGATTGGTAAAAAGGGCACAGAAGAGAATACCTTATATACAGAAGAGGTGATCAAATTGTTAGTGAGTCT
TGGTGTAATCCCATCTGTAGCCGCATTCAACCAATCCCGAAACATATGCCATGTATTTGCAAAACGTGTCCTC
AATTCTGTGAACTCTGCAGAAATGACAGCTAATATGTGCGGATTATTGCTGTCTGTTGAGAAATCAGTATCAG
ACCATATTGAAGAAAATAAGACACTAATAAATCAGATTATAAGTGATTTAAGTACAGGTAGGGAAGTGCAGAA
ACGTTTCACTGAGTATCAAAAGGAACAGAATTCATTGATTATGTCAAATCTGGCGACACTTCATATCATAACA
GATAGAGGAGGAAAGAACAACAGCATGGATACAGGGGAGAGGACACCATCAATCAGGACCAAGGGGAAGGAGC
CAACACAGAGAACACAAAGATTTGATCCATCTATGGAATTCACCGAGGAGATTAAGTACAAGCCCGATCTATA
CAGGGAAGACACATTGAGACAAAGAATAACAAACCCTGTTCTTGATGAGAGCGCAGAGAGAATCGACAATTCG
AATGCCGCGAGACTGATACCTTGCAAAGAAAAATCAACACTGCGTTCACTCAAATTAATTATTGAGAACAGCA
ATTTGAGCAGAGCAGACAAAATTGCCTATATCAGGTCATTATCAAAATGCAAAGATGACAAAGAGGTAGAATC
AGTAATGAAACTATTTGAAGAAGATATAGAATCAAGTAATGAATAA

>USA/MN25890NS/2016-P3 phosphoprotein (P) amino acid sequence
(SEQ ID NO: 5)
MDQDALFSEESMEDQKEGHSTTSTLTSAVGLIDIILASEPTDIRKDRKHLCEPITAWGKSEASKISKDTVCEE
NPRTEREDYGQSKKSGIPRESNKFEAEVSFRETHSSGTSWRAWRRSSANSILENMGNGSDSYGNEITGNGGGN
QRQSPEAKVGEMDPSSNTRRKDKTEGLPEEIRGGSPISNDGEGGRNNNGGSLESVSTHNPRVENNIMDPTHHL
EEEVLKRNKPREMNATSQWSGGYKTDQQDGKHELITNPIFSNQNRSQDTKKGKGKESTVKPKTRKSKISFEDT
RSTDHIYEDSQEHTRRKKTDNEPSQKIGKKGTEENTLYTEEVIKLLVSLGVIPSVAAFNQSRNICHVFAKRVL
NSVNSAEMTANMCGLLLSVEKSVSDHIEENKTLINQIISDLSTGREVQKRFTEYQKEQNSLIMSNLATLHIIT
DRGGKNNSMDTGERTPSIRTKGKEPTQRTQRFDPSMEFTEEIKYKPDLYREDTLRQRITNPVLDESAERIDNS
NAARLIPCKEKSTLRSLKLIIENSNLSRADKIAYIRSLSKCKDDKEVESVMKLFEEDIESSNE >USA/MN25890NS/2016-P3 matrix protein (M) nucleotide sequence
(SEQ ID NO: 6)
ATGGCCGAGATCTACAAGTTCCCCAAGCTATCATATGAGGAACATGGATATATGGAACCTCTACCACTAAGGA
CTGGCCCAGATAAGAAGGCAGTCCCACATATAAGGATAATCAAGATAGGGGACCCACCGAAGCATGGAAATCG
ATATCTTGATATTCTCTTACTTGGGTTTTATGAGATACCCAAAGAAGTTGGAACATACGGTAGTGTATCAGAT
TTGACGAGACCCACGGGATACACAATCTGCGGTTCAGGATCATTACCTATTGGAATTGCTAGGTACTTAGGTA
CAGATCAGGAACTACTCAAAGCATCAGTAGAGCTAAAAGTGACAGTGAGAAGGACAGTAAGGTCAAGTGAGAT
GATTGTGTATATGGTAGATACCATACCACCAGCAATGATGGCTTGGGCTTCCAGGTTGAAACGAGGCATGATA
TTCAATGCGAATAAAGTAGCTCTAGCTCCTCAATGTCTACCTATAGATAAAGATATAAGATTCAGAGTTGTCT
TTGTCAATGGCACTTCTCTAGGTTCCATCACAATAGCAAAAGTTCCCAAGACATTAGCCGATCTTGCTTTACC
GAATTCCATATCGGTCAATTTAATGGTCTCACTCAAGACTGGTGCGTCAACTGAGTCCAAGGGCATTATTCCT
ACGCTAAACGAAAAGGGCGACAAGGTACTAAACTTTATGGTACACCTTGGATTAATACATAGGAAAGTCGGAA
GGGTGTATTCAATGGAGTATTGCAAGGGTAAAATAGAGAAGATGCGGCTGATCTTCTCATTAGGACTGGTTGG
AGGAATCAGTTTCCATGTTCAGCTTACAGGTGTGGTATCTAAATCCTTTGTTGGTCAGCTTGGAGGGAGGAAG
GAAATATGTTACCCTTTGATGGATGTAAACCCACACATGAATTTAGTTATCTGGGCTGCTTCCGTTGAAATCA
CTGGCGTGGATGCTGTTTTCCAACCTTCCATACCAAGAGATTTCAAATACTACCCGAATGTGGTGGCAAAAAA
TATTGGGAAAATAAAAGCTTAG >USA/MN25890NS/2016-P3 matrix protein (M) amino acid sequence
(SEQ ID NO: 7)
MAEIYKFPKLSYEEHGYMEPLPLRTGPDKKAVPHIRIIKIGDPPKHGNRYLDILLLGFYEIPKEVGTYGSVSD
LTRPTGYTICGSGSLPIGIARYLGTDQELLKASVELKVTVRRTVRSSEMIVYMVDTIPPAMMAWASRLKRGMI
FNANKVALAPQCLPIDKDIRFRVVFVNGTSLGSITIAKVPKTLADLALPNSISVNLMVSLKTGASTESKGIIP
TLNEKGDKVLNFMVHLGLIHRKVGRVYSMEYCKGKIEKMRLIFSLGLVGGISFHVQLTGVVSKSFVGQLGGRK
EICYPLMDVNPHMNLVIWAASVEITGVDAVFQPSIPRDFKYYPNVVAKNIGKIKA >USA/MN25890NS/2016-P3 fusion protein (F) nucleotide sequence
(SEQ ID NO: 8)
ATGCAAATCATCATCCTCAGACCAGCCATAATACTAAGCATAGTACTATTAGTGACCAGTCAAGTCCCTAGAG
ATAAACTAGCCAATTTAGGGATCATCATTAAGGACAGCAAAGCACTCAAAATTGCAGGATCTTATGAAAACAG
ATACATAGTCTTAAACCTTGTACCAACAATAGAAAATGTGGGTGGGTGTGGTTCCATCCAAATAGCAAAATAT
AAAGAGATGCTTGAAAGGTTGTTAATACCGATAAAAGATGCACTAGATTTACAAGAGTCTTTGATAATGATTG
ATAATGAAACCGTCAACAACAATTATCGTCCTCAGTATAGATTTGTTGGTGCAATTATTGGGACTATAGCCCT
TGGGGTAGCAACTGCGGCCCAAGTTACAGCAGGGGTGGCACTGATGGAGGCAAGAGAGGCCAAAAGAGATATA
TCAGTGTTAAAAGAAGCAATTGGAAAGACTCAAAACTCAATTGAAAAATTACAGAATTCTGCAGGTGAACAGA
TACTGGCTCTCAAAATGCTCCAGGATTATGTCAATGGAGAGATTAAACCAGCTATTGAAGAACTTGGATGTGA
GACTGCTGCACTTAAATTAGGAATTGCACTTACACAACACTACACAGAGCTCACAAATGCCTTTGGGTCGAAT
CTAGGTTCCATAGGAGAGAAGAGCTTAACATTACAGGCCCTATCATCATTATACAAGACCAATATAACTGATA
TACTGACAACAACTAATCTCGGGAAAACAGATATTTATGATATTATATATGCTGAGCAAGTTAAAGGAAGAGT
AATAGATGTCGATCTTAGACGATATATGGTTACAATATCTGTTAAGATACCAATATTATCAGAAATACCAGGA
GTATTGATCTATGAAGTCTCCTCTATATCTTATAATATAGATGGAACAGAATGGTATGCCGCTGTACCTGACC
ACATATTAAGTAAATCCGCATATATAGGGGGTGCAGATATAAGTGATTGTATAGAATCTGGATTGACATATAT
TTGTCCGCGAGATCCTGCTCAGATTATAGCGGATAACCAACAGCAATGTTTTTTAGGTCATCTTGACAAGTGC
CCTATAACTAAAGTAGTTGATAATCTTGTGCCTAAATTTGCATTCATAAATGGTGGAGTAGTTGCAAACTGTA
TAGCCTCTACATGTACCTGTGGAGAAGAGAGGGTCCAGGTCTCTCAAGATAGAAATAAAGGAGTAACCTTTTT
GACTCATAATAATTGTGGATTAATAGGGATAAACGGGATGGAATTTCATGCTAACAAGAAAGGGAGTGATGCT -continued

| Sequences |
| --- |
| ACTTGGAATGTCTCCCCCATAAGAGCAGGGCCAGCGGTATCGTTAAGACCAGTAGATATATCTTTACAAATAG<br>TTTCTGCTACTAATTTTCTAAACTCATCAAGAAAAGATCTTATGAAGGCAAAAGAGATCTTAAACCAGGTAGG<br>AAATCTTAGAGATTTAACCGTCATAACGATAATTAATATAGTAATTATAGCTGTATTACTTATATGTGTAACT<br>GGATTAGGCGTACTGTATCACCAATTGAGAAGTGCACTAGTGATGAGAGACAAGATGTCAGTATTAAATAATA<br>GTTCCTATTCTTTAGAACCAAGAACCACCCAGGTACAAGTAATTAAGCCTACTAGTTTCATGAGA |
| >USA/MN25890NS/2016-P3 fusion protein (F) amino acid sequence<br>(SEQ ID NO: 9)<br>MQIIILRPAIIISIVLLVTSQVPRDKLANLGIIIKDSKALKIAGSYENRYIVLNLVPTIENVGGCGSIQIAKY<br>KEMLERLLIPIKDALDLQESLIMIDNETVNNNYRPQYRFVGAIIGTIALGVATAAQVTAGVALMEAREAKRDI<br>SVLKEAIGKTQNSIEKLQNSAGEQILALKMLQDYVNGEIKPAIEELGCETAALKLGIALTQHYTELTNAFGSN<br>LGSIGEKSLTLQALSSLYKTNITDILTTTNLGKTDIYDIIYAEQVKGRVIDVDLRRYMVTISVKIPILSEIPG<br>VLIYEVSSISYNIDGTEWYAAVPDHILSKSAYIGGADISDCIESGLTYICPRDPAQIIADNQQQCFLGHLDKC<br>PITKVVDNLVPKFAFINGGVVANCIASTCTCGEERVQVSQDRNKGVTFLTHNNCGLIGINGMEFHANKKGSDA<br>TWNVSPIRAGPAVSLRPVDISLQIVSATNFLNSSRKDLMKAKEILNQVGNLRDLTVITIINIVIIAVLLICVT<br>GLGVLYHQLRSALVMRDKMSVLNNSSYSLEPRTTQVQVIKPTSFMR |
| >USA/MN25890NS/2016-P3 hemagglutinin-neuraminidase (HN) nucleotide sequence<br>(SEQ ID NO: 10)<br>ATGGAAGGGGCCAAAGTTAAGACATCAGGGTACTGGGCCAAGAGTCCTCAAATTCACGCAACAAATAATCCTA<br>ACGTACAAAACAGAGAGAAGATCAAGGAAACATTAACAATTTTAATATCATTCATTTCTTTCCTATCTCTTGT<br>ACTGGTTATAGCTGTACTGATAATGCAATCTTTACATAACGGCACAATACTAAGGTGTAAAGATGTAGGCCTA<br>GAATCTATCAATAAATCCACTTACTCTATATCTAATGCAATTCTGGATGTCATCAAACAAGAGCTGATAACTC<br>GTATAATAAATACTCAAAGTTCTGTGCAGGTAGCCCTCCCGGTCTTAATTAACAAGAAAATCCAGGATCTCTC<br>ACTAACCATTGAGAAAAGTTCAAAAGTGCATCAAAATTCTCCTACTTGTAGTGGTGTGGCTGCCCTGACACAT<br>GTGGAAGGGATAAAACCTTTGGATCCAGACGATTACTGGAGGTGTCCAAGTGGGGAACCATATCTAGAGGATG<br>AATTGACATTAAGTCTTATCCCTGGACCTAGTATGCTAGCTGGAACCTCTACCATCGATGGCTGTGTAAGATT<br>ACCATCTCTTGCAATAGGAAAATCGCTATATGCCTATAGTTCCAACCTTATAACTAAGGGTTGTCAAGATATA<br>GGGAAATCCTATCAAGTGCTACAGTTAGGTATTATAACTCTGAATTCAGACTTACATCCTGATTTAAATCCTA<br>TAATATCACATACTTATGATATAAATGATAATAGAAAGTCCTGTTCTGTTGCTGTATCAGAAACTAAAGGATA<br>CCAATTATGCTCGATGCCGCGTGTCAATGAAAAAACAGATTACACTAGTGATGGTATTGAAGATATAGTTTTT<br>GATGTACTTGATCTCAAAGGGTCCTCTAGAAGTTTCAAATTTTCAAACAATGATATAAACTTTGATCATCCTT<br>TTTCAGCGTTATACCCTAGTGTAGGAAGTGGTATTATATGGGAAAATGAACTGTATTTCCTAGGTTACGGGGC<br>TCTGACAACTGCACTTCAAGGGAATACAAAATGTAATTTAATGGGATGTCCAGGAGCAACACAAAACAACTGC<br>AACAAGTTCATCTCTAGTTCATGGTTATACAGCAAACAGATGGTTAATGTACTGATACAGGTTAAGGGGTATT<br>TATCTAACAAGCCAAGTATTATAGTTAGAACAATCCCAATAACGGAAAATTATGTAGGAGCAGAAGGGAAACT<br>AGTGGGAACACGTGAGAGAATATATATATATACAAGATCAACGGGTTGGCATGCCAATTTACAAATAGGAGTA<br>CTTAATATAAATCATCCAATAACCATAACTTGGAAAGATCACAAAGTACTATCAAGACCAGGAAGAAGTCCTT<br>GTGCCTGGAATAACAAATGCCCTAGAAATTGTACTACTGGTGTATACACAGATGCTTATCCTATATCGCCTGA<br>TGCTAATTATGTTGCTACAGTTACTCTATTATCTAATTCAACACGAACTAATCCTACTATTATGTATTCATCT<br>TCTGATAGAGTATATAACATGTTAAGATTAAGAAATACTGAATTAGAAGCTGCATACACAACCACGTCTTGTA<br>TTGTCCACTTTGATAGAGGTTATTGTTTTCATATTATAGAAATTAATCAAAAAGGACTGAATACACTACAGCC<br>TATGCTCTTTAAGACTGCAATTCCTAAAGCTTGCAGGATAAGCAATTTATAA |
| >USA/MN25890NS/2016-P3 hemagglutinin-neuraminidase (HN) amino acid sequence<br>(SEQ ID NO: 11)<br>MEGAKVKTSGYWAKSPQIHATNNPNVQNREKIKETLTILISFISFLSLVLVIAVLIMQSLHNGTILRCKDVGL<br>ESINKSTYSISNAILDVIKQELITRIINTQSSVQVALPVLINKKIQDLSLTIEKSSKVHQNSPTCSGVAALTH<br>VEGIKPLDPDDYWRCPSGEPYLEDELTLSLIPGPSMLAGTSTIDGCVRLPSLAIGKSLYAYSSNLITKGCQDI<br>GKSYQVLQLGIITLNSDLHPDLNPIISHTYDINDNRKSCSVAVSETKGYQLCSMPRVNEKTDYTSDGIEDIVF<br>DVLDLKGSSRSFKFSNNDINFDHPFSALYPSVGSGIIWENELYFLGYGALTTALQGNTKCNLMGCPGATQNNC<br>NKFISSSWLYSKQMVNVLIQVKGYLSNKPSIIVRTIPITENYVGAEGKLVGTRERIYIYTRSTGWHANLQIGV<br>LNINHPITITWKDHKVLSRPGRSPCAWNNKCPRNCTTGVYTDAYPISPDANYVATVTLLSNSTRTNPTIMYSS<br>SDRVYNMLRLRNTELEAAYTTTSCIVHFDRGYCFHIIEINQKGLNTLQPMLFKTAIPKACRISNL |
| >USA/MN25890NS/2016-P3 large protein (L) nucleotide sequence<br>(SEQ ID NO: 12)<br>ATGCCAAAGCATTCAGCCAGAATGGATCATTTCAATATGTCTCAAAATCCAAGTGATATACTATACCCTGAAT<br>GCCACTTGAACTCTCCAGTTGTGAAAGGGAAGATCGCTCAGCTACATGTCTTGTTAGATATTAATCAGCCGTA<br>TGAAATGAGGGACCCTAGTATAATAGAAATCACAAAAGTTAAAATTAAATCTGGAGGGTTAAATCAAAGGTTA<br>ATCAGAATCAGATCTTTAGGGAAAGAGATGAGGAGAATCATATTTGATTTTGATAAGTATACATTCGAACCTT<br>ACCCAATATTTTCTAAAGAATTATTTAGATTAGAGATACCAGAGATTTGTGATAAAATTCAATCAGTTTTTGC<br>AGTGTCGGATAGGTTAAGCAAAGATATATCCCAGCCATTACAATACTTATGGAGAGATGTGCGTAGGCAGTTG<br>GGAGGGGATTGTTCCAAGGATCTTTCTAACAATGAGATTGATATACACAAAATTCCTGAAATCCATACTAAAT<br>TCACCAGAAATAACTGGTATAAACCATTCATGACATGGTTTAGTATTAAATATGATATGAGAAGATGTCAAAA<br>GAATAGGGAAAACATAAACTTAGACAGTAGGCAATCATATAATTATCTTAACTGTAAATACTATTTTATAATT<br>ATCCACCCGGATCTCTTAATGATATTGGACAAGATCAAATACACGGGATACTTACTGACACCAGAATTAGTGC<br>TAATGTACTGTGATGTGGTCGAAGGTAGATGGAATATGTCTGCTGCTGGACAATTAGATGACAAATCACACAA<br>AATAACATTGAAAGGAGAAGAATTGTGGGGCAGGATAGATGAATTATTCAAGATAATCGGGGAAGAGACATTT<br>AATATCATATCACTATTGGAGCCATTATCTTTAGCATTGATACAATTAACAGATCCTGTTATGTCTTTAAAAG<br>GTGCATTTATGAGACATGTCATCTCAGAAATGAGTGAAATATTGGGTAAATGTGGAAATCTAACTGAACTTGA<br>GGTGGATCACATAATGGATTCAATCCTTAACATTTTTATGGATACAACAGTAGATGAGAAAGCAGAGATATTC<br>TCCTTCTTTAGGACATTTGGTCATCCTAGCCTTGAGGCCTCCATAGCTGCTGAAAAAGTTAGGCAACATATGT<br>ATGCGCAGAAAAGTATAAAATATAAGACCTTATGTGAGTGTCACGCTATATTTTGTACAATTATAATAAACGG<br>ATATAGAGACAGACATGGAGGACAGTGGCCCCCCTGTCAGTTCCCAGATCATGTGTGTCAAGAACTCAGAAAT<br>TCTCAAGGATCTAATTCAGCTATATCTTATGAAACAGCCGTTGACAATTTCGAGAGCTTTATAGGTTTCAGAT<br>TCGAGAAGTTCATAGACCCTCAATTAGATGAAGATCTCACTATTTACATGAGAGATAAAGCATTGTCTCCAAG |

-continued

| Sequences |
|---|
| AAGAGAAGCCTGGGATTCTGTGTATCCAGATGGCAATCTGCTGTATAAAGTGCCGTTCTCTGAAGAAACAAGG |
| AGATTGATAGAAGTCTTTATTAGTGATTCTAATTTCAATCCAGAAGACATTATACAATATGTAGAGACAGGAG |
| AATGGTTGAACGATGATACTTTCAACATATCTTATAGCCTAAAAGAAAAGGAGATCAAACAAGAGGGTCGATT |
| GTTTGCCAAGATGACATACAAAATGAGAGCAGTCCAAGTATTGGCAGAAACTTTGCTAGCAAAAGGAATAGGG |
| GGTTTATTTAATGAAAATGGTATGGTTAAAGGTGAAATCGATTTACTAAAGAGTCTAACTACTTTATCTATAT |
| CAGGAGTTCCAAGGACTAGCGAGATTTATAATGAATCAGTTAGTGAAGAAGCTGATAGGAGAAGATGGGAAAG |
| GGAAAATTCCTCATACTATTGGGATAAAAGAAAAAAATCAAAACATGAGTTCAAAGCCACAGACTCATCTACT |
| AACGGCTATGAGACTCTAAGCTGTTTTCTTACTACGGACTTGAAAAAATATTGTCTAAATTGGAGGTTTGAGA |
| GTACATCTCTATTCGGGCAGAGATGTAACGAAATATTTGGGTTCAAGAGATTCTTCAACTGGATGCATCCTGT |
| ATTGGAAGAATGTACAATATATGTGGGTGATCCTTACTGTCCCGTGCCCGATAAAATCCACAAGAATTTAGAA |
| GATCATGAAGATTCAGGCATCTTTATACATAGACCGAGGGGTGGGATAGAAGGTTATTGTCAAAAACTTTGGA |
| CTCTCATATCCATAAGTGCAATTCATCTAGCTGCTGTCAAGGTCGGGGTTAGAGTATCAGCTATGGTACAAGG |
| TGACAACCAAGCAATTGCCGTGACATCTAGGGTACCAGTGACGGCCACGTATAAGTTCAAAAAAGAGCAGGTA |
| TATACGGAGATCACTAAGTATTTTAGGTCTTTAAGAGATGTGATGTCTGATTTAGGACATGAACTCAAACTCA |
| ACGAGACAATTATAAGTAGCAAGATGTTCGTGTATAGTAAGCGGATATATTATGATGGTAAAATACTACCCCA |
| ATGTTTAAAAGCACTTACAAGGTGTGTTTTTTGGTCTGAGACCTTGGTGGATGAAAACAGGTCTGCTTGTTCC |
| AATCTTGCAACTGCTATAGCCAAAGCTATAGAAAATGGCTATTCACCAATATTAGGTTACTCAATAGCTCTGT |
| ATAAGACTTGTCAGCAAGTATGTATCTCATTAGGGATGACTATCAATCCTACAATAACACCTAATATAAGAGA |
| CCAATATTATTTAGGGAAGAATTGGCTTAGATGTGCAGTTTTGATACCTGCTAATGTTGGGGGATTTAACTAC |
| ATGGCAATGTCTAGATGCTTCGTCAGAAATATAGGCGACCCTGCAGTAGCTGCTCTAGCAGACCTCAAAAGGT |
| TTATCCGAGCAGGACTATTGGACAAGCAGATTTTGTACCGTGTAATGAATCAAGAATCTGGGGAGTCTAATTT |
| CTTAGACTGGGCATCTGATCCATACTCATGTAATTTACCACATTCGCAGAGTATCACAACAATTATAAAGAAT |
| ATTACAGCTCGTTCAGTTCTCCAAGAGTCACCAAATCCTCTACTGTCAGGTTTATTTACATGTGACAGTAAAG |
| AAGAAGACTTAAATTTAGCGACATTTCTGATGGACAGGAAGGTCATATTGCCAAGAGTTGCACATGAGATACT |
| AGACAACTCTTTGACAGGGATCAGAGAATCCATCGCAGGAATGCTGGATACTACAAAATCATTAGTACGGGTT |
| AGTATTAGAAAAGGGGGTTTATCATACAATCTCTTAAGAAAGCTGATAAATTATGACTTATTACAATATGAAA |
| CATTAACCAGGACTTTAAGGAAAGTCGTCACAAATAACATTGAATATGAATATATGTGTTCTGTGGAATTAGC |
| AATTGGATTAAGGCAAAAAATGTGGTCACATCTAACATATGGGAGACCTATACATGGATTAGAAACACCTGAT |
| CCTCTAGAACTCCTTAAAGGAACATTCATCAAAGGATCTGAGGTTTGCAAAATATGCAGGTCTGAAGGTGATA |
| ATCCTATATATACTTGGTTTTATTTACCTGAGGAAATAGATCTGGATAACCTAGAACAAGGAAATCCATCTAT |
| AAGAATACCTTACTTTGGGTCTACTACTGACGAAAGATCAGAAGCACAACTGGGTTATGTTAAAACACTGAGT |
| AAACCTGCTAAAGCAGCGATTAGGATTGCTATGATATATACTTGGGCTTATGGTACTGATGAGATATCATGGA |
| TGGAAGCGGCTCAGATTGCACAAACAAGAGCAAATTTAAGTCTTGATAATTTGAAACTTCTGACTCCGGTATC |
| AACATCTACAAATCTGTCCCATAGATTAAAGGACACTGCTACCCAGATGAAATTCTCAAGTGCAACTCTAGTT |
| AGAGCTAGTAGATTTATTACTATATCAAATGATAAGATGGCTCTGAAGGAGGCAGGTGAGACAAAGGATACTA |
| ATTTAATATATCAGCAGATAATGTTGACAGGACTTAGTGTTTTTGAATTCAATACCAGATACATTAAAGGTAA |
| GACTAAACAACCAATGATCCTACACTTACATTTAAACAATGGCTGCTGCATTATGGAATCACCACAAGAGACT |
| TGTATCCCTCCTAAATCTACTCTAGACTTAGAGGTAACCAATGAAGAAAATAAATTAATATATGATAATAATC |
| CATTAAAAAATGTTGATCTCGGTATTTTCCAAAAAATTAGAGATATCGTACACACTGTAGATATGACTTTCTG |
| GTCTGATTTGGAAATAATGAGAGCAGTTACTATTTGTACATCTATGACAATAGCAGACACCATGTCTCAATTG |
| GATAGAGATAACCTTAAAGAAGTAATTGTTCTTGCGAATGATGATGACATTAATAGCTTAATAACAGAGTTTA |
| TGATAATAGACATCCCGCTCTTTTGCTCAACATTCGGAGGAATCTTAGTAAATCAGTTTGCCTATGCATTATA |
| CGGTCTAAATATAAGAGGTAGAGAAGAAATATGGGGTTACATTACACGGACTTTGAAAGATACTTCTCATGCT |
| GTGTTAAAGGTACTTGCTAATGCATTATCACATCCAAAGGTGTTCAAGAGATTCTGGGATTTCGGTATTTTAG |
| AGCCTGTATATGGACCTAATTTATCCAACCAAGATAAGATAATGTTAGCATTATCTGTTTGTGAGTACTCAAT |
| AGACTTATTCATGAGGGACTGGCAAAGCGGAATACCTCTAGAAACCTTTATATGTGACAATGATCCAGAAGTA |
| GTTGAATTAAGAAAAGGTGCCTACTTGGCAAGACATTTAGCATATTTATGCAGCTTAGGAGAGATTTCCTCAT |
| ATGGTCCTAGATTAGAAACTCTAACATCATTAGAAAGGTTAGAGGTTCTTAAAAGCTACCTAGAGATATCTTG |
| TTTAGAGGATCCAACATTGAGATACAGTCAGGTTACAGGGCTGGTATTAAAAGTGTTCCCATCAACAGTAGTA |
| TATATCAGGAAGTTAGCTATAAAGATGTTGAGGATTAGGGGCATAGGGGTGCCAGAGGTGTTAGAAGACTGGG |
| ATCCCAGTCATGAACAAGCTCTACTAGATAATATAGCTCAAGAGATCCAACATAATATCCCAATAAACCAATC |
| TATCAAGACACCTTTCTGGGGGCTCAAAGTCAATAATTCCCAAGTCTTACGTCTAAGGGGATATAAGGAGGTT |
| AAGGATAGGAAATCAGGGCGATCAGGAGTAGGTCTAACACTTCCATGTGATAATAGGTACTTATCCCATCAGA |
| TAAGACTTTTCGGGATTAATAGTACTAGCTGCCTGAAAGCTTTGGAGTTAACATATTTAATAGGACCATTGAT |
| AGATAAAAGTAAAGATAGATTATTCTTAGGGGAAGGTGCAGGTGCTATGTTGTCATGTTATGATGCAACGTTA |
| GGACCTTCAATGAACTATTATAACTCAGGTGTCTCATCATATGATATAAATGGTCAGAGGGAATTAGGGATCT |
| ATCCATCTGAGGCTGCATTAGTGGCAAAGAAATTGAATAATGTAACTAATTTGGGTCAGAGAATTAAGGTGCT |
| GTTCAACGGAAACCCTGGGTCTACATGGGTTGGCAACCAGGAATGCGAAACATTAATTTGGAGTGAATTACAG |
| GACAAATCAATCGGCTTGATACATTGTGACCTAGAAGGTGGAGAACTAAAAGATACACAAACAGTACTGCATG |
| AACATTATAGCATAATTAGGATAGCATACTTAGTAGGAGATAACGATGTTTTATTAGTGACTAAAATTGCACC |
| TAAATTGGGTACAGATTGGACTCAGCAACTATGCTTGTATCTAAGATATTGGAATGAAGTCAATTTAGTTGTT |
| CTTAAGACATCTAATCCTTCTTCTACTGAGATGTATTTGTTATCAAGGAATCCAAGTAAAGATGTGATTGAAG |
| ATAGTCTAACAGTAATCTCAGACCTAAAGCCATTGTCTAAAAAAGATAGTATACAATTAGAAAAGTGGATTTT |
| GGTTGAGAAAGACAAAGTTAAGGAATGGCTAATTAAAGAATTAAGAGAGGGAGAACTAATGTCAGGTTCACTT |
| AGGCCTTATCACCAAGCACTTCAGATTTTTGGATTTGAGGCCAACTTGCACAAATTGTGTAGAGACTTCTTAT |
| CAACTATGAGTATTTCAGATATCCAGATGTGTATAAATTCATTCTACAGAGTTTTAAAGGACACAATATTTGA |
| GTGGAGTCGGGTAACAAATGATCATAAGACATGTAAACTCACAGGGAAATATGAGTTATATCCTATAAGAGAC |
| AGTGGAAAGTTGAAAGTGATATCAAGAAGGCTTATAATATCCTGGATTGCTTTATCCATGTCTACTAGACTGT |
| TAACAGGCGCTTTCCCTGATATTAAGTTTGAGTCCAGATTGAATATAGGTTTAGTCTCCTTATCTACGAATGA |
| GATCAAATCACTTAAACTTATATCCAAGGCTACGGTGGATAGGTTTCAAGAAGTGATTCACAGTGTATCCTAC |
| AGATTCTTGACTAAAGAAATTAAAATACTCATGAAGATACTTGGAGCTGTTAAATTATTTGGTGCAAGACAGA |
| CTTATAACCATTTAGCTTTAACACCAGAACCTCTATCTGATATAGAGGGATATTTAGATGATTAG |
| |
| >USA/MN25890NS/2016-P3 large protein (L) amino acid sequence |
| (SEQ ID NO: 13) |
| MPKHSARMDHFNMSQNPSDILYPECHLNSPVVKGKIAQLHVLLDINQPYEMRDPSIIEITKVKIKSGGLNQRL |
| IRIRSLGKEMRRIIFDFDKYTFEPYPIFSKELFRLEIPEICDKIQSVFAVSDRLSKDISQPLQYLWRDVRRQL |

-continued

| Sequences |
|---|
| GGDCSKDLSNNEIDIHKIPEIHTKFTRNNWYKPFMTWFSIKYDMRRCQKNRENINLDSRQSYNYLNCKYYFII<br>IHPDLLMILDKIKYTGYLLTPELVLMYCDVVEGRWNMSAAGQLDDKSHKITLKGEELWGRIDELFKIIGEETF<br>NIISLLEPLSLALIQLTDPVMSLKGAFMRHVISEMSEILGKCGNLTELEVDHIMDSILNIFMDTTVDEKAEIF<br>SFFRTFGHPSLEASIAAEKVRQHMYAQKSIKYKTLCECHAIFCTIIINGYRDRHGGQWPPCQFPDHVCQELRN<br>SQGSNSAISYETAVDNFESFIGFRFEKFIDPQLDEDLTIYMRDKALSPRREAWDSVYPDGNLLYKVPFSEETR<br>RLIEVFISDSNFNPEDIIQYVETGEWLNDDTFNISYSLKEKEIKQEGRLFAKMTYKMRAVQVLAETLLAKGIG<br>GLFNENGMVKGEIDLLKSLTTLSISGVPRTSEIYNESVSEEADRRRWERENSSYYWDKRKKSKHEFKATDSST<br>NGYETLSCFLTTDLKKYCLNWRFESTSLFGQRCNEIFGFKRFFNWMHPVLEECTIYVGDPYCPVPDKIHKNLE<br>DHEDSGIFIHRPRGGIEGYCQKLWTLISISAIHLAAVKVGVRVSAMVQGDNQAIAVTSRVPVTATYKFKKEQV<br>YTEITKYFRSLRDVMSDLGHELKLNETIISSKMFVYSKRIYYDGKILPQCLKALTRCVFWSETLVDENRSACS<br>NLATAIAKAIENGYSPILGYSIALYKTCQQVCISLGMTINPTITPNIRDQYYLGKNWLRCAVLIPANVGGFNY<br>MAMSRCFVRNIGDPAVAALADLKRFIRAGLLDKQILYRVMNQESGESNFLDWASDPYSCNLPHSQSITTIIKN<br>ITARSVLQESPNPLLSGLFTCDSKEEDLNLATFLMDRKVILPRVAHEILDNSLTGIRESIAGMLDTTKSLVRV<br>SIRKGGLSYNLLRKLINYDLLQYETLTRTLRKVVTNNIEYEYMCSVELAIGLRQKMWSHLTYGRPIHGLETPD<br>PLELLKGTFIKGSEVCKICRSEGDNPIYTWFYLPEEIDLDNLEQGNPSIRIPYFGSTTDERSEAQLGYVKTLS<br>KPAKAAIRIAMIYTWAYGTDEISWMEAAQIAQTRANLSLDNLKLLTPVSTSTNLSHRLKDTATQMKFSSATLV<br>RASRFITISNDKMALKEAGETKDTNLIYQQIMLTGLSVFEFNTRYIKGKTKQPMILHLHLNNGCCIMESPQET<br>CIPPKSTLDLEVTNEENKLIYDNNPLKNVDLGIFQKIRDIVHTVDMTFWSDLEIMRAVTICTSMTIADTMSQL<br>DRDNLKEVIVLANDDDINSLITEFMIIDIPLFCSTFGGILVNQFAYALYGLNIRGREEIWGYITRTLKDTSHA<br>VLKVLANALSHPKVFKRFWDFGILEPVYGPNLSNQDKIMLALSVCEYSIDLFMRDWQSGIPLETFICDNDPEV<br>VELRKGAYLARHLAYLCSLGEISSYGPRLETLTSLERLEVLKSYLEISCLEDPTLRYSQVTGLVLKVFPSTVV<br>YIRKLAIKMLRIRGIGVPEVLEDWDPSHEQALLDNIAQEIQHNIPINQSIKTPFWGLKVNNSQVLRLRGYKEV<br>KDRKSGRSGVGLTLPCDNRYLSHQIRLFGINSTSCLKALELTYLIGPLIDKSKDRLFLGEGAGAMLSCYDATL<br>GPSMNYYNSGVSSYDINGQRELGIYPSEAALVAKKLNNVTNLGQRIKVLFNGNPGSTWVGNQECETLIWSELQ<br>DKSIGLIHCDLEGGELKDTQTVLHEHYSIIRIAYLVGDNDVLLVTKIAPKLGTDWTQQLCLYLRYWNEVNLVV<br>LKTSNPSSTEMYLLSRNPSKDVIEDSLTVISDLKPLSKKDSIQLEKWILVEKDKVKEWLIKELREGELMSGSL<br>RPYHQALQIFGFEANLHKLCRDFLSTMSISDIQMCINSFYRVLKDTIFEWSRVTNDHKTCKLTGKYELYPIRD<br>SGKLKVISRRLIISWIALSMSTRLLTGAFPDIKFESRLNIGLVSLSTNEIKSLKLISKATVDRFQEVIHSVSY<br>RFLTKEIKILMKILGAVKLFGARQTYNHLALTPEPLSDIEGYLDD |

Example 4: Attenuation of Strain USA/MN25890NS/2016

The PPIV-1 isolate USA/MN25890NS/2016 was serially passed in LLC-MK2 cells, and the whole genome sequence of the viruses at the passages P25 and P50 were determined. Comparison of the whole genome sequences revealed nucleotide and amino acid changes located in phosphoprotein (P), matrix protein (M), and hemagglutinin-neuraminidase (HN). There are five non-synonymous and two synonymous amino acid changes.

P Gene: 1725 Bases (position numbering relative to passage 3, SEQ ID NOs: 4 and 5)

| | |
|---|---|
| PPIV-1 MN16 p3 #898 G | Glutamine300 |
| PPIV-1 MN16 p25 #898 G | Glutamine |
| PPIV-1 MN16 p50 #898 A | Lysine |

M Gene: 1044 bases (position numbering relative to passage 3, SEQ ID NOs: 6 and 7)

| | |
|---|---|
| PPIV-1 MN16 p3 #129 A | Proline43 |
| PPIV-1 MN16 p25 #129 A | Proline |
| PPIV-1 MN16 p50 #129 G | Proline |

HN Gene: 1731 bases (position numbering relative to passage 3, SEQ ID NOs: 10 and 11)

| | |
|---|---|
| PPIV-1 MN16 p3 #305 C | Threonine 102 |
| PPIV-1 MN16 p25 #305 T | Isoleucine |
| PPIV-1 MN16 p50 #305 T | Isoleucine |
| PPIV-1 MN16 p3 #729 T | Proline243 |
| PPIV-1 MN16 p25 #729 T | Proline |
| PPIV-1 MN16 p50 #729 C | Proline |
| PPIV-1 MN16 p3 #1045 A | Asparagine349 |
| PPIV-1 MN16 p25 #1045 A | Asparagine |
| PPIV-1 MN16 p50 #1045 G | Aspartic acid |
| PPIV-1 MN16 p3 #1217 A | Asparagine406 |
| PPIV-1 MN16 p25 #1217 C | Threonine |
| PPIV-1 MN16 p50 #1217 C | Threonine |
| PPIV-1 MN16 p3 #1379 G | Arginine460 |
| PPIV-1 MN16 p25 #1379 G | Arginine |
| PPIV-1 MN16 p50 #1379 T | Isoleucine |

Continuous passage of the virus in cell culture is needed to obtain a fully attenuated vaccine candidate virus. This study provides a strong basis for developing a PPIV-1 vaccine and for understanding virus attenuation.

Nucleotides changes relative to SEQ ID NO:1 are indicated in bold.

>USA/MN25890NS/2016-P25, complete genome
(SEQ ID NO: 14)
GGTTAAAGTATTAACCTCAAAAGGACAGATCAGGAACTTTGATTTCTTAGCATAGTGCCAAAATGGCAGGGTT
ATTAAGTGTCTTTGACACATTTAGTTCTAAAAGGAGTGAAAGCATAAATAGAGGAGGTGGTGGTGCGGTTATA
CCTGGACAAAAGAACACCGTCTCAGTATTTGTCCTAGGGTCAAGTATTGTAGACGACAGCGATAAGTTAGCTA
TAGCACTCATGTTTTTAACACATGCTCTTGATACTGACAAGCAACACTCACAAAGAAGCGGTTTCCTGGTTTC
ATTAATGGCAATGGCATATAGTAGTCCTGAATTATATCTAACAACTAATGGAGTTAATGCAGATGTTAAGTAT -continued GTTATCTACACAATTGAGCATGATCCCCAGAGGACAACCCATAATGGGTTCATTGTTAGGACAAGAGATATGG
ACTATGAAAAGACAACAGAGTGGCTATTCAGCCGTATAACTAATAAATACCCACTACTTCAGGGACAAAAAGA
CACTCATGATCCAGAATCACTACTCCAGACTTATGGATATCCCTCATGTTTAGGAGCATTGATAATCCAGGTT
TGGATTGTCTTGGTCAAAGCAATTACAAGTAGTGCTGGATTGAAGAAAGGATTCTTCAATAGACTTGAAGCCT
TCAGGCAGGATGGAACAGTTAGAAGCTCACTAGTCTTCAGTGGGGAGACAGTTGAGGGGATTGGGTCAGTGAT
GAGATCTCAGCAGAGTTTGGTGTCCTTAATGGTAGAGACTCTAGTTACCATGAACACGGCCAGATCTGACTTG
ACCACTCTAGAAAAGAATATTCAGATTGTTGGGAATTACATCAGGGATGCAGGTCTTGCTTCATTCATGAACA
CGATTAGATATGGTGTGGAGACTAAGATGGCAGCACTTACATTATCTAATCTTAGACCTGATATTAATAAACT
AAAGAGTCTAATTGACATCTACTTATCCAAAGGTGCAAGAGCCCCCTTCATATGCATATTACGTGATCCGGTA
CACGGAGAATTTGCTCCTGGAAATTATCCAGCATTGTGGAGTTATGCTATGGGGGTCGCAGTAGTCCAGAACA
AAGCCATGCAGCAGTATGTGACAGGGAGGACTTATCTGGATATGGAAATGTTCCTTCTTGGTCAAGCAGTAGC
TAAAGACGCAGAATCTAAGATCAGTAATGCATTAGAGGATGAATTAGGTATAACTGAAAATGCCAAAGACAGG
CTCAAACATCATCTTGCTAACCTTTCTGGAGGTGATGGAGCTTATCACAAACCCACTGGTGGAGGAGCAATAG
AAGTTATAATTGACAATGCAGACATAGATCTCAGGACAGAGGAAACCACAGAAGAATCTTCAATCAGGCTTTC
CAATATTAGAGAAAACAAAGGGAGAATAGCAGACGGGCAGAGGAGATGGGAAACAACCAGATCCATTGGTGAT
GACCCCAATCCAGACAACACCACTGACGATGAAGTATCCGCCGCAGAAAGGAGGATTGCAGAAAGACTGGCAA
AAAAGGAGGGGAAGAATACCAGGTCGGATATACTCATTACCGATGGTATGACTGAAGATACAGATAACGATGA
TGATATAATGAGAATGAATGCACTAGGAGGAATATAATAAATCCAAACAAAGGGTTTTATATATTGGTTAGTA
AGAAAAACTTAGGGTGAAAGAATAGCTCCTAGATACTAGGAACTCTATCACTCCCAAAGACAGGATCTCAAAC
TGGCCACCCACAAAAGAATCCCCCAAAATCCAGATACCAAATGGATCAAGATGCCCTCTTTTCTGAAGAATCT
ATGGAGGATCAGAAGGAGGGACACTCAACAACCAGCACACTCACCAGTGCAGTCGGACTCATTGACATCATCC
TTGCCAGTGAGCCCACAGACATTAGAAAAGACAGAAAACACCTATGTGAGCCCATCACAGCCTGGGGAAAATC
AGAAGCAAGCAAGATTTCCAAGGATACAGTCTGTGAAGAAAACCCAAGAACAGAAAGGGAAGATTATGGACAA
AGTAAAAAGAGTGGAATTCCTAGGGAGTCAAACAAGTTCGAAGCAGAAGTTTCTTTTAGAGAAACTCATAGCT
CAGGTACATCATGGAGGGCTTGGAGAAGAAGTAGTGCAAACTCTATACTTGAGAATATGGGCAATGGATCCGA
CTCCTATGGCAACGAAATTACTGGAAATGGAGGAGGAAACCAGAGACAAAGTCCTGAAGCTAAAGTTGGAGAG
ATGGATCCGAGTTCTAATACGAGGAGAAAAGACAAAACTGAGGGACTTCCAGAAGAGATACGAGGAGGTTCAC
CCATATCTAATGACGGAGAAGGTGGAAGAAATAATAATGGAGGAAGCCTGGAGTCTGTCAGCACACATAATCC
AAGAGTAGAAAACAACATTATGGATCCAACTCATCATCTTGAAGAAGAGGTACTTAAGAGGAACAAGCCACGG
GAGATGAATGCTACAAGTCAATGGTCGGGTGGATACAAGACTGATCAACAAGACGGTAAACATGAATTGATAA
CCAATCCAATATTTTCAAATCAAAATAGGTCACAGGACACAAAAAAGGGAAAAGGGAAAGAATCAACTGTAAA
GCCCAAGACCAGAAAATCTAAAATATCCTTTGAAGACACAAGAAGCACAGATCACATCTACGAAGACTCTCAA
GAACATACAAGAAGAAAGAAAACAGACAACGAACCATCACAAAAGATTGGTAAAAAGGGCACAGAAGAGAATA
CCTTATATACAGAAGAGGTGATCAAATTGTTAGTGAGTCTTGGTGTAATCCCATCTGTAGCCGCATTCAACCA
ATCCCGAAACATATGCCATGTATTTGCAAAACGTGTCCTCAATTCTGTGAACTCTGCAGAAATGACAGCTAAT
ATGTGCGGATTATTGCTGTCTGTTGAGAAATCAGTATCAGACCATATTGAAGAAAATAAGACACTAATAAATC
AGATTATAAGTGATTTAAGTACAGGTAGGGAAGTGCAGAAACGTTTCACTGAGTATCAAAAGGAACAGAATTC
ATTGATTATGTCAAATCTGGCGACACTTCATATCATAACAGATAGAGGAGGAAAGAACAACAGCATGGATACA
GGGGAGAGGACACCATCAATCAGGACCAAGGGGAAGGAGCCAACACAGAGAACACAAAGATTTGATCCATCTA
TGGAATTCACCGAGGAGATTAAGTACAAGCCCGATCTATACAGGGAAGACACATTGAGACAAAGAATAACAAA
CCCTGTTCTTGATGAGAGCGCAGAGAGAATCGACAATTCGAATGCCGCGAGACTGATACCTTGCAAAGAAAAA
TCAACACTGCGTTCACTCAAATTAATTATTGAGAACAGCAATTTGAGCAGAGCAGACAAAATTGCCTATATCA
GGTCATTATCAAAATGCAAAGATGACAAAGAGGTAGAATCAGTAATGAAACTATTTGAAGAAGATATAGAATC
AAGTAATGAATAATCACTGATCAGTATATCCAGAAAACGTCAAGACAAGAGTGTACTGTGATGAGTAATGACT
CTCCAAATACCTAATAAGAAAAACTTAGGGTGCAAGACTCACCAACCAAGCCAAGCAAATGGCCGAGATCTAC
AAGTTCCCCAAGCTATCATATGAGGAACATGGATATATGGAACCTCTACCACTAAGGACTGGCCCAGATAAGA
AGGCAGTCCCACATATAAGGATAATCAAGATAGGGGACCCACCGAAGCATGGAAATCGATATCTTGATATTCT
CTTACTTGGGTTTTATGAGATACCCAAAGAAGTTGGAACATACGGTAGTGTATCAGATTTGACGAGACCCACG
GGATACACAATCTGCGGTTCAGGATCATTACCTATTGGAATTGCTAGGTACTTAGGTACAGATCAGGAACTAC
TCAAAGCATCAGTAGAGCTAAAAGTGACAGTGAGAAGGACAGTAAGGTCAAGTGAGATGATTGTGTATATGGT
AGATACCATACCACCAGCAATGATGGCTTGGGCTTCCAGGTTGAAACGAGGCATGATATTCAATGCGAATAAA
GTAGCTCTAGCTCCTCAATGTCTACCTATAGATAAAGATATAAGATTCAGAGTTGTCTTTGTCAATGGCACTT
CTCTAGGTTCCATCACAATAGCAAAAGTTCCCAAGACATTAGCCGATCTTGCTTTACCGAATTCCATATCGGT
CAATTTAATGGTCTCACTCAAGACTGGTGCGTCAACTGAGTCCAAGGGCATTATTCCTACGCTAAACGAAAAG
GGCGACAAGGTACTAAACTTTATGGTACACCTTGGATTAATACATAGGAAAGTCGGAAGGGTGTATTCAATGG
AGTATTGCAAGGGTAAAATAGAGAAGATGCGGCTGATCTTCTCATTAGGACTGGTTGGAGGAATCAGTTTCCA
TGTTCAGCTTACAGGTGTGGTATCTAAATCCTTTGTTGGTCAGCTTGGAGGGAGGAAGGAAATATGTTACCCT
TTGATGGATGTAAACCCACACATGAATTTAGTTATCTGGGCTGCTTCCGTTGAAATCACTGGCGTGGATGCTG
TTTTCCAACCTTCCATACCAAGAGATTTCAAATACTACCCGAATGTGGTGGCAAAAAATATTGGGAAAATAAA
AGCTTAGAGATCCAAAGCCACTGTAACCCCAGACATCCCAACACTAGACTGGTAAGTGTCATTATATGATCAG
CATCATTCATCAGAAATAAGAAAAACTTAGGGTACAAGTTATCCAAAAAAGACAGAACAGAACAAACAGATCA
AGACAAGACATCACAAAATGCAAATCATCATCCTCAGACCAGCCATAATACTAAGCATAGTACTATTAGTGAC
CAGTCAAGTCCCTAGAGATAAACTAGCCAATTTAGGGATCATCATTAAGGACAGCAAAGCACTCAAAATTGCA
GGATCTTATGAAAACAGATACATAGTCTTAAACCTTGTACCAACAATAGAAAATGTGGGTGGGTGTGGTTCCA
TCCAAATAGCAAAATATAAAGAGATGCTTGAAAGGTTGTTAATACCGATAAAAGATGCACTAGATTTACAAGA
GTCTTTGATAATGATTGATAATGAAACCGTCAACAACAATTATCGTCCTCAGTATAGATTTGTTGGTGCAATT
ATTGGGACTATAGCCCTTGGGGTAGCAACTGCGGCCCAAGTTACAGCAGGGGTGGCACTGATGGAGGCAAGAG
AGGCCAAAAGAGATATATCAGTGTTAAAAGAAGCAATTGGAAAGACTCAAAACTCAATTGAAAAATTACAGAA
TTCTGCAGGTGAACAGATACTGGCTCTCAAAATGCTCCAGGATTATGTCAATGGAGAGATTAAACCAGCTATT
GAAGAACTTGGATGTGAGACTGCTGCACTTAAATTAGGAATTGCACTTACACAACACTACACAGAGCTCACAA
ATGCCTTTGGGTCGAATCTAGGTTCCATAGGAGAGAAGAGCTTAACATTACAGGCCCTATCATCATTATACAA
GACCAATATAACTGATATACTGACAACAACTAATCTCGGGAAAACAGATATTTATGATATTATATATGCTGAG
CAAGTTAAAGGAAGAGTAATAGATGTCGATCTTAGACGATATATGGTTACAATATCTGTTAAGATACCAATAT
TATCAGAAATACCAGGAGTATTGATCTATGAAGTCTCCTCTATATCTTATAATATAGATGGAACAGAATGGTA
TGCCGCTGTACCTGACCACATATTAAGTAAATCCGCATATATAGGGGGTGCAGATATAAGTGATTGTATAGAA
TCTGGATTGACATATATTTGTCCGCGAGATCCTGCTCAGATTATAGCGGATAACCAACAGCAATGTTTTTTAG
GTCATCTTGACAAGTGCCCTATAACTAAAGTAGTTGATAATCTTGTGCCTAAATTTGCATTCATAAATGGTGG
AGTAGTTGCAAACTGTATAGCCTCTACATGTACCTGTGGAGAAGAGAGGGTCCAGGTCTCTCAAGATAGAAAT
AAAGGAGTAACCTTTTTGACTCATAATAATTGTGGATTAATAGGGATAAACGGGATGGAATTTCATGCTAACA -continued AGAAAGGGAGTGATGCTACTTGGAATGTCTCCCCCATAAGAGCAGGGCCAGCGGTATCGTTAAGACCAGTAGA
TATATCTTTACAAATAGTTTCTGCTACTAATTTTCTAAACTCATCAAGAAAAGATCTTATGAAGGCAAAAGAG
ATCTTAAACCAGGTAGGAAATCTTAGAGATTTAACCGTCATAACGATAATTAATATAGTAATTATAGCTGTAT
TACTTATATGTGTAACTGGATTAGGCGTACTGTATCACCAATTGAGAAGTGCACTAGTGATGAGAGACAAGAT
GTCAGTATTAAATAATAGTTCCTATTCTTTAGAACCAAGAACCACCCAGGTACAAGTAATTAAGCCTACTAGT
TTCATGAGATAAACTATAAAAATATATTTTAATCCATCCTCATTAATCAAAGTAAAGAAAACTTAGGGTGCAC
GACAGTAACTCACCACCAAAGGAGAAATAGATCAGAGACCAACACACCAAGAGATGGAAGGGGCCAAAGTTAA
GACATCAGGGTACTGGGCCAAGAGTCCTCAAATTCACGCAACAAATAATCCTAACGTACAAAACAGAGAGAAG
ATCAAGGAAACATTAACAATTTTAATATCATTCATTTCTTTCCTATCTCTTGTACTGGTTATAGCTGTACTGA
TAATGCAATCTTTACATAACGGCACAATACTAAGGTGTAAAGATGTAGGCCTAGAATCTATCAATAAATCCAC
TTACTCTATATCTAATGCAATTCTGGATGTCATCAAACAAGAGCTGATAACTCGTATAATAAATATTCAAAGT
TCTGTGCAGGTAGCCCTCCCGGTCTTAATTAACAAGAAAATCCAGGATCTCTCACTAACCATTGAGAAAAGTT
CAAAAGTGCATCAAAATTCTCCTACTTGTAGTGGTGTGGCTGCCCTGACACATGTGGAAGGGATAAAACCTTT
GGATCCAGACGATTACTGGAGGTGTCCAAGTGGGGAACCATATCTAGAGGATGAATTGACATTAAGTCTTATC
CCTGGACCTAGTATGCTAGCTGGAACCTCTACCATCGATGGCTGTGTAAGATTACCATCTCTTGCAATAGGAA
AATCGCTATATGCCTATAGTTCCAACCTTATAACTAAGGGTTGTCAAGATATAGGGAAATCCTATCAAGTGCT
ACAGTTAGGTATTATAACTCTGAATTCAGACTTACATCCTGATTTAAATCCTATAATATCACATACTTATGAT
ATAAATGATAATAGAAAGTCCTGTTCTGTTGCTGTATCAGAAACTAAAGGATACCAATTATGCTCGATGCCGC
GTGTCAATGAAAAAACAGATTACACTAGTGATGGTATTGAAGATATAGTTTTTGATGTACTTGATCTCAAAGG
GTCCTCTAGAAGTTTCAAATTTTCAAACAATGATATAAACTTTGATCATCCTTTTTCAGCGTTATACCCTAGT
GTAGGAAGTGGTATTATATGGGAAAATGAACTGTATTTCCTAGGTTACGGGGCTCTGACAACTGCACTTCAAG
GGAATACAAAATGTAATTTAATGGGATGTCCAGGAGCAACACAAAACAACTGCAACAAGTTCATCTCTAGTTC
ATGGTTATACAGCAAACAGATGGTTAATGTACTGATACAGGTTAAGGGGTATTTATCTAACAAGCCAAGTATT
ATAGTTAGAACAATCCCAATAACGGAAACTTATGTAGGAGCAGAAGGGAAACTAGTGGGAACACGTGAGAGAA
TATATATATATACAAGATCAACGGGTTGGCATGCCAATTTACAAATAGGAGTACTTAATATAAATCATCCAAT
AACCATAACTTGGAAAGATCACAAAGTACTATCAAGACCAGGAAGAAGTCCTTGTGCCTGGAATAACAAATGC
CCTAGAAATTGTACTACTGGTGTATACACAGATGCTTATCCTATATCGCCTGATGCTAATTATGTTGCTACAG
TTACTCTATTATCTAATTCAACACGAACTAATCCTACTATTATGTATTCATCTTCTGATAGAGTATATAACAT
GTTAAGATTAAGAAATACTGAATTAGAAGCTGCATACACAACCACGTCTTGTATTGTCCACTTTGATAGAGGT
TATTGTTTTCATATTATAGAAATTAATCAAAAAGGACTGAATACACTACAGCCTATGCTCTTTAAGACTGCAA
TTCCTAAAGCTTGCAGGATAAGCAATTTATAAGACACCCATTGAAATAATAATTTGTATCTAATTACTTAAAA
GGGTGACTGTGCATGACTTAGAGATAAGTGACCTGTGGACATAAATCATACAGGTCATTAAATAGCATATAAT
ACACCTAATAAGAAAAACTTAGGTTGAATGCCAAAGCATTCAGCCAGAATGGATCATTTCAATATGTCTCAAA
ATCCAAGTGATATACTATACCCTGAATGCCACTTGAACTCTCCAGTTGTGAAAGGGAAGATCGCTCAGCTACA
TGTCTTGTTAGATATTAATCAGCCGTATGAAATGAGGGACCCTAGTATAATAGAAATCACAAAAGTTAAAATT
AAATCTGGAGGGTTAAATCAAAGGTTAATCAGAATCAGATCTTTAGGGAAAGAGATGAGGAGAATCATATTTG
ATTTTGATAAGTATACATTCGAACCTTACCCAATATTTTCTAAAGAATTATTTAGATTAGAGATACCAGAGAT
TTGTGATAAAATTCAATCAGTTTTTGCAGTGTCGGATAGGTTAAGCAAAGATATATCCCAGCCATTACAATAC
TTATGGAGAGATGTGCGTAGGCAGTTGGGAGGGGATTGTTCCAAGGATCTTTCTAACAATGAGATTGATATAC
ACAAAATTCCTGAAATCCATACTAAATTCACCAGAAATAACTGGTATAAACCATTCATGACATGGTTTAGTAT
TAAATATGATATGAGAAGATGTCAAAAGAATAGGGAAAACATAAACTTAGACAGTAGGCAATCATATAATTAT
CTTAACTGTAAATACTATTTTATAATTATCCACCCGGATCTCTTAATGATATTGGACAAGATCAAATACACGG
GATACTTACTGACACCAGAATTAGTGCTAATGTACTGTGATGTGGTCGAAGGTAGATGGAATATGTCTGCTGC
TGGACAATTAGATGACAAATCACACAAAATAACATTGAAAGGAGAAGAATTGTGGGGCAGGATAGATGAATTA
TTCAAGATAATCGGGGAAGAGACATTTAATATCATATCACTATTGGAGCCATTATCTTTAGCATTGATACAAT
TAACAGATCCTGTTATGTCTTTAAAAGGTGCATTTATGAGACATGTCATCTCAGAAATGAGTGAAATATTGGG
TAAATGTGGAAATCTAACTGAACTTGAGGTGGATCACATAATGGATTCAATCCTTAACATTTTTATGGATACA
ACAGTAGATGAGAAAGCAGAGATATTCTCCTTCTTTAGGACATTTGGTCATCCTAGCCTTGAGGCCTCCATAG
CTGCTGAAAAAGTTAGGCAACATATGTATGCGCAGAAAAGTATAAAATATAAGACCTTATGTGAGTGTCACGC
TATATTTTGTACAATTATAATAAACGGATATAGAGACAGACATGGAGGACAGTGGCCCCCCTGTCAGTTCCCA
GATCATGTGTGTCAAGAACTCAGAAATTCTCAAGGATCTAATTCAGCTATATCTTATGAAACAGCCGTTGACA
ATTTCGAGAGCTTTATAGGTTTCAGATTCGAGAAGTTCATAGACCCTCAATTAGATGAAGATCTCACTATTTA
CATGAGAGATAAAGCATTGTCTCCAAGAAGAGAAGCCTGGGATTCTGTGTATCCAGATGGCAATCTGCTGTAT
AAAGTGCCGTTCTCTGAAGAAACAAGGAGATTGATAGAAGTCTTTATTAGTGATTCTAATTTCAATCCAGAAG
ACATTATACAATATGTAGAGACAGGAGAATGGTTGAACGATGATACTTTCAACATATCTTATAGCCTAAAAGA
AAAGGAGATCAAACAAGAGGGTCGATTGTTTGCCAAGATGACATACAAAATGAGAGCAGTCCAAGTATTGGCA
GAAACTTTGCTAGCAAAAGGAATAGGGGGTTTATTTAATGAAAATGGTATGGTTAAAGGTGAAATCGATTTAC
TAAAGAGTCTAACTACTTTATCTATATCAGGAGTTCCAAGGACTAGCGAGATTTATAATGAATCAGTTAGTGA
AGAAGCTGATAGGAGAAGATGGGAAAGGGAAAATTCCTCATACTATTGGGATAAAAGAAAAAAATCAAAACAT
GAGTTCAAAGCCACAGACTCATCTACTAACGGCTATGAGACTCTAAGCTGTTTTCTTACTACGGACTTGAAAA
AATATTGTCTAAATTGGAGGTTTGAGAGTACATCTCTATTCGGGCAGAGATGTAACGAAATATTTGGGTTCAA
GAGATTCTTCAACTGGATGCATCCTGTATTGGAAGAATGTACAATATATGTGGGTGATCCTTACTGTCCCGTG
CCCGATAAAATCCACAAGAATTTAGAAGATCATGAAGATTCAGGCATCTTTATACATAGACCGAGGGGTGGGA
TAGAAGGTTATTGTCAAAAACTTTGGACTCTCATATCCATAAGTGCAATTCATCTAGCTGCTGTCAAGGTCGG
GGTTAGAGTATCAGCTATGGTACAAGGTGACAACCAAGCAATTGCCGTGACATCTAGGGTACCAGTGACGGCC
ACGTATAAGTTCAAAAAAGAGCAGGTATATACGGAGATCACTAAGTATTTTAGGTCTTTAAGAGATGTGATGT
CTGATTTAGGACATGAACTCAAACTCAACGAGACAATTATAAGTAGCAAGATGTTCGTGTATAGTAAGCGGAT
ATATTATGATGGTAAAATACTACCCCAATGTTTAAAAGCACTTACAAGGTGTGTTTTTTGGTCTGAGACCTTG
GTGGATGAAAACAGGTCTGCTTGTTCCAATCTTGCAACTGCTATAGCCAAAGCTATAGAAAATGGCTATTCAC
CAATATTAGGTTACTCAATAGCTCTGTATAAGACTTGTCAGCAAGTATGTATCTCATTAGGGATGACTATCAA
TCCTACAATAACACCTAATATAAGAGACCAATATTATTTAGGGAAGAATTGGCTTAGATGTGCAGTTTTGATA
CCTGCTAATGTTGGGGGATTTAACTACATGGCAATGTCTAGATGCTTCGTCAGAAATATAGGCGACCCTGCAG
TAGCTGCTCTAGCAGACCTCAAAAGGTTTATCCGAGCAGGACTATTGGACAAGCAGATTTTGTACCGTGTAAT
GAATCAAGAATCTGGGGAGTCTAATTTCTTAGACTGGGCATCTGATCCATACTCATGTAATTTACCACATTCG
CAGAGTATCACAACAATTATAAAGAATATTACAGCTCGTTCAGTTCTCCAAGAGTCACCAAATCCTCTACTGT
CAGGTTTATTTACATGTGACAGTAAAGAAGAAGACTTAAATTTAGCGACATTTCTGATGGACAGGAAGGTCAT
ATTGCCAAGAGTTGCACATGAGATACTAGACAACTCTTTGACAGGGATCAGAGAATCCATCGCAGGAATGCTG
GATACTACAAAATCATTAGTACGGGTTAGTATTAGAAAAGGGGGTTTATCATACAATCTCTTAAGAAAGCTGA
TAAATTATGACTTATTACAATATGAAACATTAACCAGGACTTTAAGGAAAGTCGTCACAAATAACATTGAATA -continued TGAATATATGTGTTCTGTGGAATTAGCAATTGGATTAAGGCAAAAAATGTGGTCACATCTAACATATGGGAGA
CCTATACATGGATTAGAAACACCTGATCCTCTAGAACTCCTTAAAGGAACATTCATCAAAGGATCTGAGGTTT
GCAAAATATGCAGGTCTGAAGGTGATAATCCTATATATACTTGGTTTTATTTACCTGAGGAAATAGATCTGGA
TAACCTAGAACAAGGAAATCCATCTATAAGAATACCTTACTTTGGGTCTACTACTGACGAAAGATCAGAAGCA
CAACTGGGTTATGTTAAAACACTGAGTAAACCTGCTAAAGCAGCGATTAGGATTGCTATGATATATACTTGGG
CTTATGGTACTGATGAGATATCATGGATGGAAGCGGCTCAGATTGCACAAACAAGAGCAAATTTAAGTCTTGA
TAATTTGAAACTTCTGACTCCGGTATCAACATCTACAAATCTGTCCCATAGATTAAAGGACACTGCTACCCAG
ATGAAATTCTCAAGTGCAACTCTAGTTAGAGCTAGTAGATTTATTACTATATCAAATGATAAGATGGCTCTGA
AGGAGGCAGGTGAGACAAAGGATACTAATTTAATATATCAGCAGATAATGTTGACAGGACTTAGTGTTTTTGA
ATTCAATACCAGATACATTAAAGGTAAGACTAAACAACCAATGATCCTACACTTACATTTAAACAATGGCTGC
TGCATTATGGAATCACCACAAGAGACTTGTATCCCTCCTAAATCTACTCTAGACTTAGAGGTAACCAATGAAG
AAAATAAATTAATATATGATAATAATCCATTAAAAAATGTTGATCTCGGTATTTTCCAAAAAATTAGAGATAT
CGTACACACTGTAGATATGACTTTCTGGTCTGATTTGGAAATAATGAGAGCAGTTACTATTTGTACATCTATG
ACAATAGCAGACACCATGTCTCAATTGGATAGAGATAACCTTAAAGAAGTAATTGTTCTTGCGAATGATGATG
ACATTAATAGCTTAATAACAGAGTTTATGATAATAGACATCCCGCTCTTTTGCTCAACATTCGGAGGAATCTT
AGTAAATCAGTTTGCCTATGCATTATACGGTCTAAATATAAGAGGTAGAGAAGAAATATGGGGTTACATTACA
CGGACTTTGAAAGATACTTCTCATGCTGTGTTAAAGGTACTTGCTAATGCATTATCACATCCAAAGGTGTTCA
AGAGATTCTGGGATTTCGGTATTTTAGAGCCTGTATATGGACCTAATTTATCCAACCAAGATAAGATAATGTT
AGCATTATCTGTTTGTGAGTACTCAATAGACTTATTCATGAGGGACTGGCAAAGCGGAATACCTCTAGAAACC
TTTATATGTGACAATGATCCAGAAGTAGTTGAATTAAGAAAAGGTGCCTACTTGGCAAGACATTTAGCATATT
TATGCAGCTTAGGAGAGATTTCCTCATATGGTCCTAGATTAGAAACTCTAACATCATTAGAAAGGTTAGAGGT
TCTTAAAAGCTACCTAGAGATATCTTGTTTAGAGGATCCAACATTGAGATACAGTCAGGTTACAGGGCTGGTA
TTAAAAGTGTTCCCATCAACAGTAGTATATATCAGGAAGTTAGCTATAAAGATGTTGAGGATTAGGGGCATAG
GGGTGCCAGAGGTGTTAGAAGACTGGGATCCCAGTCATGAACAAGCTCTACTAGATAATATAGCTCAAGAGAT
CCAACATAATATCCCAATAAACCAATCTATCAAGACACCTTTCTGGGGGCTCAAAGTCAATAATTCCCAAGTC
TTACGTCTAAGGGGATATAAGGAGGTTAAGGATAGGAAATCAGGGCGATCAGGAGTAGGTCTAACACTTCCAT
GTGATAATAGGTACTTATCCCATCAGATAAGACTTTTCGGGATTAATAGTACTAGCTGCCTGAAAGCTTTGGA
GTTAACATATTTAATAGGACCATTGATAGATAAAAGTAAAGATAGATTATTCTTAGGGGAAGGTGCAGGTGCT
ATGTTGTCATGTTATGATGCAACGTTAGGACCTTCAATGAACTATTATAACTCAGGTGTCTCATCATATGATA
TAAATGGTCAGAGGGAATTAGGGATCTATCCATCTGAGGCTGCATTAGTGGCAAAGAAATTGAATAATGTAAC
TAATTTGGGTCAGAGAATTAAGGTGCTGTTCAACGGAAACCCTGGGTCTACATGGGTTGGCAACCAGGAATGC
GAAACATTAATTTGGAGTGAATTACAGGACAAATCAATCGGCTTGATACATTGTGACCTAGAAGGTGGAGAAC
TAAAAGATACACAAACAGTACTGCATGAACATTATAGCATAATTAGGATAGCATACTTAGTAGGAGATAACGA
TGTTTTATTAGTGACTAAAATTGCACCTAAATTGGGTACAGATTGGACTCAGCAACTATGCTTGTATCTAAGA
TATTGGAATGAAGTCAATTTAGTTGTTCTTAAGACATCTAATCCTTCTTCTACTGAGATGTATTTGTTATCAA
GGAATCCAAGTAAAGATGTGATTGAAGATAGTCTAACAGTAATCTCAGACCTAAAGCCATTGTCTAAAAAAGA
TAGTATACAATTAGAAAAGTGGATTTTGGTTGAGAAAGACAAAGTTAAGGAATGGCTAATTAAAGAATTAAGA
GAGGGAGAACTAATGTCAGGTTCACTTAGGCCTTATCACCAAGCACTTCAGATTTTTGGATTTGAGGCCAACT
TGCACAAATTGTGTAGAGACTTCTTATCAACTATGAGTATTTCAGATATCCAGATGTGTATAAATTCATTCTA
CAGAGTTTTAAAGGACACAATATTTGAGTGGAGTCGGGTAACAAATGATCATAAGACATGTAAACTCACAGGG
AAATATGAGTTATATCCTATAAGAGACAGTGGAAAGTTGAAAGTGATATCAAGAAGGCTTATAATATCCTGGA
TTGCTTTATCCATGTCTACTAGACTGTTAACAGGCGCTTTCCCTGATATTAAGTTTGAGTCCAGATTGAATAT
AGGTTTAGTCTCCTTATCTACGAATGAGATCAAATCACTTAAACTTATATCCAAGGCTACGGTGGATAGGTTT
CAAGAAGTGATTCACAGTGTATCCTACAGATTCTTGACTAAAGAAATTAAAATACTCATGAAGATACTTGGAG
CTGTTAAATTATTTGGTGCAAGACAGACTTATAACCATTTAGCTTTAACACCAGAACCTCTATCTGATATAGA
GGGATATTTAGATGATTAGCTCGAATATCAACAGTAAACAGCTAAGAATCATTAAGAAGACTATCTGGATCCA
GACCTAAATGAAAGAATAAGAAAAACTTATTTAAACAATCAAAGATCCAAGCAAAATGATATGTCTTAAACTC
TTGT >USA/MN25890NS/2016-P50, complete genome (SEQ ID NO: 15)
GGTTAAAGTATTAACCTCAAAAGGACAGATCAGGAACTTTGATTTCTTAGCATAGTGCCAAAATGGCAGGGTT
ATTAAGTGTCTTTGACACATTTAGTTCTAAAAGGAGTGAAAGCATAAATAGAGGAGGTGGTGGTGCGGTTATA
CCTGGACAAAAGAACACCGTCTCAGTATTTGTCCTAGGGTCAAGTATTGTAGACGACAGCGATAAGTTAGCTA
TAGCACTCATGTTTTTAACACATGCTCTTGATACTGACAAGCAACACTCACAAAGAAGCGGTTTCCTGGTTTC
ATTAATGGCAATGGCATATAGTAGTCCTGAATTATATCTAACAACTAATGGAGTTAATGCAGATGTTAAGTAT
GTTATCTACACAATTGAGCATGATCCCCAGAGGACAACCCATAATGGGTTCATTGTTAGGACAAGAGATATGG
ACTATGAAAAGACAACAGAGTGGCTATTCAGCCGTATAACTAATAAATACCCACTACTTCAGGGACAAAAAGA
CACTCATGATCCAGAATCACTACTCCAGACTTATGGATATCCCTCATGTTTAGGAGCATTGATAATCCAGGTT
TGGATTGTCTTGGTCAAAGCAATTACAAGTAGTGCTGGATTGAAGAAAGGATTCTTCAATAGACTTGAAGCCT
TCAGGCAGGATGGAACAGTTAGAAGCTCACTAGTCTTCAGTGGGGAGACAGTTGAGGGGATTGGGTCAGTGAT
GAGATCTCAGCAGAGTTTGGTGTCCTTAATGGTAGAGACTCTAGTTACCATGAACACGGCCAGATCTGACTTG
ACCACTCTAGAAAAGAATATTCAGATTGTTGGGAATTACATCAGGGATGCAGGTCTTGCTTCATTCATGAACA
CGATTAGATATGGTGTGGAGACTAAGATGGCAGCACTTACATTATCTAATCTTAGACCTGATATTAATAAACT
AAAGAGTCTAATTGACATCTACTTATCCAAAGGTGCAAGAGCCCCCTTCATATGCATATTACGTGATCCGGTA
CACGGAGAATTTGCTCCTGGAAATTATCCAGCATTGTGGAGTTATGCTATGGGGGTCGCAGTAGTCCAGAACA
AAGCCATGCAGCAGTATGTGACAGGGAGGACTTATCTGGATATGGAAATGTTCCTTCTTGGTCAAGCAGTAGC
TAAAGACGCAGAATCTAAGATCAGTAATGCATTAGAGGATGAATTAGGTATAACTGAAAATGCCAAAGACAGG
CTCAAACATCATCTTGCTAACCTTTCTGGAGGTGATGGAGCTTATCACAAACCCACTGGTGGAGGAGCAATAG
AAGTTATAATTGACAATGCAGACATAGATCTCAGGACAGAGGAAACCACAGAAGAATCTTCAATCAGGCTTTC
CAATATTAGAGAAAACAAAGGGAGAATAGCAGACGGGCAGAGGAGATGGGAAACAACCAGATCCATTGGTGAT
GACCCCAATCCAGACAACACCACTGACGATGAAGTATCCGCCGCAGAAAGGAGGATTGCAGAAAGACTGGCAA
AAAAGGAGGGGAAGAATACCAGGTCGGATATACTCATTACCGATGGTATGACTGAAGATACAGATAACGATGA
TGATATAATGAGAATGAATGCACTAGGAGGAATATAATAAATCCAAACAAAGGGTTTTATATATTGGTTAGTA
AGAAAAACTTAGGGTGAAAGAATAGCTCCTAGATACTAGGAACTCTATCACTCCCAAAGACAGGATCTCAAAC
TGGCCACCGACAAAAGAATCCCCCAAAATCCAGATACCAAATGGATCAAGATGCCCTCTTTTCTGAAGAATCT
ATGGAGGATCAGAAGGAGGGACACTCAACAACCAGCACACTCACCAGTGCAGTCGGACTCATTGACATCATCC
TTGCCAGTGAGCCCACAGACATTAGAAAAGACAGAAAACACCTATGTGAGCCCATCACAGCCTGGGGAAAATC
AGAAGCAAGCAAGATTTCCAAGGATACAGTCTGTGAAGAAAACCCAAGAACAGAAAGGGAAGATTATGGACAA
AGTAAAAAGAGTGGAATTCCTAGGGAGTCAAACAAGTTCGAAGCAGAAGTTTCTTTTAGAGAAACTCATAGCT -continued CAGGTACATCATGGAGGGCTTGGAGAAGAAGTAGTGCAAACTCTATACTTGAGAATATGGGCAATGGATCCGA
CTCCTATGGCAACGAAATTACTGGAAATGGAGGAGGAAACCAGAGACAAAGTCCTGAAGCTAAAGTTGGAGAG
ATGGATCCGAGTTCTAATACGAGGAGAAAAGACAAAACTGAGGGACTTCCAGAAGAGATACGAGGAGGTTCAC
CCATATCTAATGACGGAGAAGGTGGAAGAAATAATAATGGAGGAAGCCTGGAGTCTGTCAGCACACATAATCC
AAGAGTAGAAAACAACATTATGGATCCAACTCATCATCTTGAAGAAGAGGTACTTAAGAGGAACAAGCCACGG
GAGATGAATGCTACAAGTCAATGGTCGGGTGGATACAAGACTGATCAACAAGACGGTAAACATGAATTGATAA
CCAATCCAATATTTTCAAATCAAAATAGGTCACAGGACACAAAAAAGGGAAAAGGGAAAGAATCAACTGTAAA
GCCCAAGACCAGAAAATCTAAAATATCCTTTGAAGACACAAGAAGCACAGATCACATCTACAAAGACTCTCAA
GAACATACAAGAAGAAAGAAAACAGACAACGAACCATCACAAAAGATTGGTAAAAAGGGCACAGAAGAGAATA
CCTTATATACAGAAGAGGTGATCAAATTGTTAGTGAGTCTTGGTGTAATCCCATCTGTAGCCGCATTCAACCA
ATCCCGAAACATATGCCATGTATTTGCAAAACGTGTCCTCAATTCTGTGAACTCTGCAGAAATGACAGCTAAT
ATGTGCGGATTATTGCTGTCTGTTGAGAAATCAGTATCAGACCATATTGAAGAAAATAAGACACTAATAAATC
AGATTATAAGTGATTTAAGTACAGGTAGGGAAGTGCAGAAACGTTTCACTGAGTATCAAAAGGAACAGAATTC
ATTGATTATGTCAAATCTGGCGACACTTCATATCATAACAGATAGAGGAGGAAAGAACAACAGCATGGATACA
GGGGAGAGGACACCATCAATCAGGACCAAGGGGAAGGAGCCAACACAGAGAACACAAAGATTTGATCCATCTA
TGGAATTCACCGAGGAGATTAAGTACAAGCCCGATCTATACAGGGAAGACACATTGAGACAAAGAATAACAAA
CCCTGTTCTTGATGAGAGCGCAGAGAGAATCGACAATTCGAATGCCGCGAGACTGATACCTTGCAAAGAAAAA
TCAACACTGCGTTCACTCAAATTAATTATTGAGAACAGCAATTTGAGCAGAGCAGACAAAATTGCCTATATCA
GGTCATTATCAAAATGCAAAGATGACAAAGAGGTAGAATCAGTAATGAAACTATTTGAAGAAGATATAGAATC
AAGTAATGAATAATCACTGATCAGTATATCCAGAAAACGTCAAGACAAGAGTGTACTGTGATGAGTAATGACT
CTCCAAATACCTAATAAGAAAAACTTAGGGTGCAAGACTCACCAACCAAGCCAAGCAAATGGCCGAGATCTAC
AAGTTCCCCAAGCTATCATATGAGGAACATGGATATATGGAACCTCTACCACTAAGGACTGGCCCAGATAAGA
AGGCAGTCCCACATATAAGGATAATCAAGATAGGGGACCCGCCGAAGCATGGAAATCGATATCTTGATATTCT
CTTACTTGGGTTTTATGAGATACCCAAAGAAGTTGGAACATACGGTAGTGTATCAGATTTGACGAGACCCACG
GGATACACAATCTGCGGTTCAGGATCATTACCTATTGGAATTGCTAGGTACTTAGGTACAGATCAGGAACTAC
TCAAAGCATCAGTAGAGCTAAAAGTGACAGTGAGAAGGACAGTAAGGTCAAGTGAGATGATTGTGTATATGGT
AGATACCATACCACCAGCAATGATGGCTTGGGCTTCCAGGTTGAAACGAGGCATGATATTCAATGCGAATAAA
GTAGCTCTAGCTCCTCAATGTCTACCTATAGATAAAGATATAAGATTCAGAGTTGTCTTTGTCAATGGCACTT
CTCTAGGTTCCATCACAATAGCAAAAGTTCCCAAGACATTAGCCGATCTTGCTTTACCGAATTCCATATCGGT
CAATTTAATGGTCTCACTCAAGACTGGTGCGTCAACTGAGTCCAAGGGCATTATTCCTACGCTAAACGAAAAG
GGCGACAAGGTACTAAACTTTATGGTACACCTTGGATTAATACATAGGAAAGTCGGAAGGGTGTATTCAATGG
AGTATTGCAAGGGTAAAATAGAGAAGATGCGGCTGATCTTCTCATTAGGACTGGTTGGAGGAATCAGTTTCCA
TGTTCAGCTTACAGGTGTGGTATCTAAATCCTTTGTTGGTCAGCTTGGAGGGAGGAAGGAAATATGTTACCCT
TTGATGGATGTAAACCCACACATGAATTTAGTTATCTGGGCTGCTTCCGTTGAAATCACTGGCGTGGATGCTG
TTTTCCAACCTTCCATACCAAGAGATTTCAAATACTACCCGAATGTGGTGGCAAAAAATATTGGGAAAATAAA
AGCTTAGAGATCCAAAGCCACTGTAACCCCAGACATCCCAACACTAGACTGGTAAGTGTCATTATATGATCAG
CATCATTCATCAGAAATAAGAAAAACTTAGGGTACAAGTTATCCAAAAAAGACAGAACAGAACAAACAGATCA
AGACAAGACATCACAAAATGCAAATCATCATCCTCAGACCAGCCATAATACTAAGCATAGTACTATTAGTGAC
CAGTCAAGTCCCTAGAGATAAACTAGCCAATTTAGGGATCATCATTAAGGACAGCAAAGCACTCAAAATTGCA
GGATCTTATGAAAACAGATACATAGTCTTAAACCTTGTACCAACAATAGAAAATGTGGGTGGGTGTGGTTCCA
TCCAAATAGCAAAATATAAAGAGATGCTTGAAAGGTTGTTAATACCGATAAAAGATGCACTAGATTTACAAGA
GTCTTTGATAATGATTGATAATGAAACCGTCAACAACAATTATCGTCCTCAGTATAGATTTGTTGGTGCAATT
ATTGGGACTATAGCCCTTGGGGTAGCAACTGCGGCCCAAGTTACAGCAGGGGTGGCACTGATGGAGGCAAGAG
AGGCCAAAAGAGATATATCAGTGTTAAAAGAAGCAATTGGAAAGACTCAAAACTCAATTGAAAAATTACAGAA
TTCTGCAGGTGAACAGATACTGGCTCTCAAAATGCTCCAGGATTATGTCAATGGAGAGATTAAACCAGCTATT
GAAGAACTTGGATGTGAGACTGCTGCACTTAAATTAGGAATTGCACTTACACAACACTACACAGAGCTCACAA
ATGCCTTTGGGTCGAATCTAGGTTCCATAGGAGAGAAGAGCTTAACATTACAGGCCCTATCATCATTATACAA
GACCAATATAACTGATATACTGACAACAACTAATCTCGGGAAAACAGATATTTATGATATTATATATGCTGAG
CAAGTTAAAGGAAGAGTAATAGATGTCGATCTTAGACGATATATGGTTACAATATCTGTTAAGATACCAATAT
TATCAGAAATACCAGGAGTATTGATCTATGAAGTCTCCTCTATATCTTATAATATAGATGGAACAGAATGGTA
TGCCGCTGTACCTGACCACATATTAAGTAAATCCGCATATATAGGGGGTGCAGATATAAGTGATTGTATAGAA
TCTGGATTGACATATATTTGTCCGCGAGATCCTGCTCAGATTATAGCGGATAACCAACAGCAATGTTTTTAG
GTCATCTTGACAAGTGCCCTATAACTAAAGTAGTTGATAATCTTGTGCCTAAATTTGCATTCATAAATGGTGG
AGTAGTTGCAAACTGTATAGCCTCTACATGTACCTGTGGAGAAGAGAGGGTCCAGGTCTCTCAAGATAGAAAT
AAAGGAGTAACCTTTTTGACTCATAATAATTGTGGATTAATAGGGATAAACGGGATGGAATTTCATGCTAACA
AGAAAGGGAGTGATGCTACTTGGAATGTCTCCCCCATAAGAGCAGGGCCAGCGGTATCGTTAAGACCAGTAGA
TATATCTTTACAAATAGTTTCTGCTACTAATTTTCTAAACTCATCAAGAAAAGATCTTATGAAGGCAAAAGAG
ATCTTAAACCAGGTAGGAAATCTTAGAGATTTAACCGTCATAACGATAATTAATATAGTAATTATAGCTGTAT
TACTTATATGTGTAACTGGATTAGGCGTACTGTATCACCAATTGAGAAGTGCACTAGTGATGAGAGACAAGAT
GTCAGTATTAAATAATAGTTCCTATTCTTTAGAACCAAGAACCACCCAGGTACAAGTAATTAAGCCTACTAGT
TTCATGAGATAAACTATAAAAATATATTTTAATCCATCCTCATTAATCAAAGTAAAGAAAACTTAGGGTGCAC
GACAGTAACTCACCACCAAAGGAGAAATAGATCAGAGACCAACACACCAAGAGATGGAAGGGGCCAAAGTTAA
GACATCAGGGTACTGGGCCAAGAGTCCTCAAATTCACGCAACAAATAATCCTAACGTACAAAACAGAGAGAAG
ATCAAGGAAACATTAACAATTTTAATATCATTCATTTCTTTCCTATCTCTTGTACTGGTTATAGCTGTACTGA
TAATGCAATCTTTACATAACGGCACAATACTAAGGTGTAAAGATGTAGGCCTAGAATCTATCAATAAATCCAC
TTACTCTATATCTAATGCAATTCTGGATGTCATCAAACAAGAGCTGATAACTCGTATAATAAATATTCAAAGT
TCTGTGCAGGTAGCCCTCCCGGTCTTAATTAACAAGAAAATCCAGGATCTCTCACTAACCATTGAGAAAAGTT
CAAAAGTGCATCAAAATTCTCCTACTTGTAGTGGTGTGGCTGCCCTGACACATGTGGAAGGGATAAAACCTTT
GGATCCAGACGATTACTGGAGGTGTCCAAGTGGGGAACCATATCTAGAGGATGAATTGACATTAAGTCTTATC
CCTGGACCTAGTATGCTAGCTGGAACCTCTACCATCGATGGCTGTGTAAGATTACCATCTCTTGCAATAGGAA
AATCGCTATATGCCTATAGTTCCAACCTTATAACTAAGGGTTGTCAAGATATAGGGAAATCCTATCAAGTGCT
ACAGTTAGGTATTATAACTCTGAATTCAGACTTACATCCTGATTTAAATCCCATAATATCACATACTTATGAT
ATAAATGATAATAGAAAGTCCTGTTCTGTTGCTGTATCAGAAACTAAAGGATACCAATTATGCTCGATGCCGC
GTGTCAATGAAAAAACAGATTACACTAGTGATGGTATTGAAGATATAGTTTTTGATGTACTTGATCTCAAAGG
GTCCTCTAGAAGTTTCAAATTTTCAAACAATGATATAAACTTTGATCATCCTTTTTCAGCGTTATACCCTAGT
GTAGGAAGTGGTATTATATGGGAAAATGAACTGTATTTCCTAGGTTACGGGGCTCTGACAACTGCACTTCAAG
GGGATACAAAATGTAATTTAATGGGATGTCCAGGAGCAACACAAAACAACTGCAACAAGTTCATCTCTAGTTC
ATGGTTATACAGCAAACAGATGGTTAATGTACTGATACAGGTTAAGGGGTATTTATCTAACAAGCCAAGTATT
ATAGTTAGAACAATCCCAATAACGGAAACTTATGTAGGAGCAGAAGGGAAACTAGTGGGAACACGTGAGAGAA -continued TATATATATATACAAGATCAACGGGTTGGCATGCCAATTTACAAATAGGAGTACTTAATATAAATCATCCAAT
AACCATAACTTGGAAAGATCACAAAGTACTATCAAGACCAGGAATAAGTCCTTGTGCCTGGAATAACAAATGC
CCTAGAAATTGTACTACTGGTGTATACACAGATGCTTATCCTATATCGCCTGATGCTAATTATGTTGCTACAG
TTACTCTATTATCTAATTCAACACGAACTAATCCTACTATTATGTATTCATCTTCTGATAGAGTATATAACAT
GTTAAGATTAAGAAATACTGAATTAGAAGCTGCATACACAACCACGTCTTGTATTGTCCACTTTGATAGAGGT
TATTGTTTTCATATTATAGAAATTAATCAAAAAGGACTGAATACACTACAGCCTATGCTCTTTAAGACTGCAA
TTCCTAAAGCTTGCAGGATAAGCAATTTATAAGACACCCATTGAAATAATAATTTGTATCTAATTACTTAAAA
GGGTGACTGTGCATGACTTAGAGATAAGTGACCTGTGGACATAAATCATACAGGTCATTAAATAGCATATAAT
ACACCTAATAAGAAAAACTTAGGTTGAATGCCAAAGCATTCAGCCAGAATGGATCATTTCAATATGTCTCAAA
ATCCAAGTGATATACTATACCCTGAATGCCACTTGAACTCTCCAGTTGTGAAAGGGAAGATCGCTCAGCTACA
TGTCTTGTTAGATATTAATCAGCCGTATGAAATGAGGGACCCTAGTATAATAGAAATCACAAAAGTTAAAATT
AAATCTGGAGGGTTAAATCAAAGGTTAATCAGAATCAGATCTTTAGGGAAAGAGATGAGGAGAATCATATTTG
ATTTTGATAAGTATACATTCGAACCTTACCCAATATTTTCTAAAGAATTATTTAGATTAGAGATACCAGAGAT
TTGTGATAAAATTCAATCAGTTTTTGCAGTGTCGGATAGGTTAAGCAAAGATATATCCCAGCCATTACAATAC
TTATGGAGAGATGTGCGTAGGCAGTTGGGAGGGGATTGTTCCAAGGATCTTTCTAACAATGAGATTGATATAC
ACAAAATTCCTGAAATCCATACTAAATTCACCAGAAATAACTGGTATAAACCATTCATGACATGGTTTAGTAT
TAAATATGATATGAGAAGATGTCAAAAGAATAGGGAAAACATAAACTTAGACAGTAGGCAATCATATAATTAT
CTTAACTGTAAATACTATTTTATAATTATCCACCCGGATCTCTTAATGATATTGGACAAGATCAAATACACGG
GATACTTACTGACACCAGAATTAGTGCTAATGTACTGTGATGTGGTCGAAGGTAGATGGAATATGTCTGCTGC
TGGACAATTAGATGACAAATCACACAAAATAACATTGAAAGGAGAAGAATTGTGGGGCAGGATAGATGAATTA
TTCAAGATAATCGGGGAAGAGACATTTAATATCATATCACTATTGGAGCCATTATCTTTAGCATTGATACAAT
TAACAGATCCTGTTATGTCTTTAAAAGGTGCATTTATGAGACATGTCATCTCAGAAATGAGTGAAATATTGGG
TAAATGTGGAAATCTAACTGAACTTGAGGTGGATCACATAATGGATTCAATCCTTAACATTTTTATGGATACA
ACAGTAGATGAGAAAGCAGAGATATTCTCCTTCTTTAGGACATTTGGTCATCCTAGCCTTGAGGCCTCCATAG
CTGCTGAAAAAGTTAGGCAACATATGTATGCGCAGAAAAGTATAAAATATAAGACCTTATGTGAGTGTCACGC
TATATTTTGTACAATTATAATAAACGGATATAGAGACAGACATGGAGGACAGTGGCCCCCCTGTCAGTTCCCA
GATCATGTGTGTCAAGAACTCAGAAATTCTCAAGGATCTAATTCAGCTATATCTTATGAAACAGCCGTTGACA
ATTTCGAGAGCTTTATAGGTTTCAGATTCGAGAAGTTCATAGACCCTCAATTAGATGAAGATCTCACTATTTA
CATGAGAGATAAAGCATTGTCTCCAAGAAGAGAAGCCTGGGATTCTGTGTATCCAGATGGCAATCTGCTGTAT
AAAGTGCCGTTCTCTGAAGAAACAAGGAGATTGATAGAAGTCTTTATTAGTGATTCTAATTTCAATCCAGAAG
ACATTATACAATATGTAGAGACAGGAGAATGGTTGAACGATGATACTTTCAACATATCTTATAGCCTAAAAGA
AAAGGAGATCAAACAAGAGGGTCGATTGTTTGCCAAGATGACATACAAAATGAGAGCAGTCCAAGTATTGGCA
GAAACTTTGCTAGCAAAAGGAATAGGGGGTTTATTTAATGAAAATGGTATGGTTAAAGGTGAAATCGATTTAC
TAAAGAGTCTAACTACTTTATCTATATCAGGAGTTCCAAGGACTAGCGAGATTTATAATGAATCAGTTAGTGA
AGAAGCTGATAGGAGAAGATGGGAAAGGAAAATTCCTCATACTATTGGGATAAAAGAAAAAAATCAAAACAT
GAGTTCAAAGCCACAGACTCATCTACTAACGGCTATGAGACTCTAAGCTGTTTTCTTACTACGGACTTGAAAA
AATATTGTCTAAATTGGAGGTTTGAGAGTACATCTCTATTCGGGCAGAGATGTAACGAAATATTTGGGTTCAA
GAGATTCTTCAACTGGATGCATCCTGTATTGGAAGAATGTACAATATATGTGGGTGATCCTTACTGTCCCGTG
CCCGATAAAATCCACAAGAATTTAGAAGATCATGAAGATTCAGGCATCTTTATACATAGACCGAGGGGTGGGA
TAGAAGGTTATTGTCAAAAACTTTGGACTCTCATATCCATAAGTGCAATTCATCTAGCTGCTGTCAAGGTCGG
GGTTAGAGTATCAGCTATGGTACAAGGTGACAACCAAGCAATTGCCGTGACATCTAGGGTACCAGTGACGGCC
ACGTATAAGTTCAAAAAAGAGCAGGTATATACGGAGATCACTAAGTATTTTAGGTCTTTAAGAGATGTGATGT
CTGATTTAGGACATGAACTCAAACTCAACGAGACAATTATAAGTAGCAAGATGTTCGTGTATAGTAAGCGGAT
ATATTATGATGGTAAAATACTACCCCAATGTTTAAAAGCACTTACAAGGTGTGTTTTTTGGTCTGAGACCTTG
GTGGATGAAAACAGGTCTGCTTGTTCCAATCTTGCAACTGCTATAGCCAAAGCTATAGAAAATGGCTATTCAC
CAATATTAGGTTACTCAATAGCTCTGTATAAGACTTGTCAGCAAGTATGTATCTCATTAGGGATGACTATCAA
TCCTACAATAACACCTAATATAAGAGACCAATATTATTTAGGGAAGAATTGGCTTAGATGTGCAGTTTTGATA
CCTGCTAATGTTGGGGGATTTAACTACATGGCAATGTCTAGATGCTTCGTCAGAAATATAGGCGACCCTGCAG
TAGCTGCTCTAGCAGACCTCAAAAGGTTTATCCGAGCAGGACTATTGGACAAGCAGATTTTGTACCGTGTAAT
GAATCAAGAATCTGGGGAGTCTAATTTCTTAGACTGGGCATCTGATCCATACTCATGTAATTTACCACATTCG
CAGAGTATCACAACAATTATAAAGAATATTACAGCTCGTTCAGTTCTCCAAGAGTCACCAAATCCTCTACTGT
CAGGTTTATTTACATGTGACAGTAAAGAAGAAGACTTAAATTTAGCGACATTTCTGATGGACAGGAAGGTCAT
ATTGCCAAGAGTTGCACATGAGATACTAGACAACTCTTTGACAGGGATCAGAGAATCCATCGCAGGAATGCTG
GATACTACAAAATCATTAGTACGGGTTAGTATTAGAAAAGGGGGTTTATCATACAATCTCTTAAGAAAGCTGA
TAAATTATGACTTATTACAATATGAAACATTAACCAGGACTTTAAGGAAAGTCGTCACAAATAACATTGAATA
TGAATATATGTGTTCTGTGGAATTAGCAATTGGATTAAGGCAAAAAATGTGGTCACATCTAACATATGGGAGA
CCTATACATGGATTAGAAACACCTGATCCTCTAGAACTCCTTAAAGGAACATTCATCAAAGGATCTGAGGTTT
GCAAAATATGCAGGTCTGAAGGTGATAATCCTATATATACTTGGTTTTATTTACCTGAGGAAATAGATCTGGA
TAACCTAGAACAAGGAAATCCATCTATAAGAATACCTTACTTTGGGTCTACTACTGACGAAAGATCAGAAGCA
CAACTGGGTTATGTTAAAACACTGAGTAAACCTGCTAAAGCAGCGATTAGGATTGCTATGATATATACTTGGG
CTTATGGTACTGATGAGATATCATGGATGGAAGCGGCTCAGATTGCACAAACAAGAGCAAATTTAAGTCTTGA
TAATTTGAAACTTCTGACTCCGGTATCAACATCTACAAATCTGTCCCATAGATTAAAGGACACTGCTACCCAG
ATGAAATTCTCAAGTGCAACTCTAGTTAGAGCTAGTAGATTTATTACTATATCAAATGATAAGATGGCTCTGA
AGGAGGCAGGTGAGACAAAGGATACTAATTTAATATATCAGCAGATAATGTTGACAGGACTTAGTGTTTTTGA
ATTCAATACCAGATACATTAAAGGTAAGACTAAACAACCAATGATCCTACACTTACATTTAAACAATGGCTGC
TGCATTATGGAATCACCACAAGAGACTTGTATCCCTCCTAAATCTACTCTAGACTTAGAGGTAACCAATGAAG
AAAATAAATTAATATATGATAATAATCCATTAAAAAATGTTGATCTCGGTATTTTCCAAAAAATTAGAGATAT
CGTACACACTGTAGATATGACTTTCTGGTCTGATTTGGAAATAATGAGAGCAGTTACTATTTGTACATCTATG
ACAATAGCAGACACCATGTCTCAATTGGATAGAGATAACCTTAAAGAAGTAATTGTTCTTGCGAATGATGATG
ACATTAATAGCTTAATAACAGAGTTTATGATAATAGACATCCCGCTCTTTTGCTCAACATTCGGAGGAATCTT
AGTAAATCAGTTTGCCTATGCATTATACGGTCTAAATATAAGAGGTAGAGAAGAAATATGGGGTTACATTACA
CGGACTTTGAAAGATACTTCTCATGCTGTGTTAAAGGTACTTGCTAATGCATTATCACATCCAAAGGTGTTCA
AGAGATTCTGGGATTTCGGTATTTTAGAGCCTGTATATGGACCTAATTTATCCAACCAAGATAAGATAATGTT
AGCATTATCTGTTTGTGAGTACTCAATAGACTTATTCATGAGGGACTGGCAAAGCGGAATACCTCTAGAAACC
TTTATATGTGACAATGATCCAGAAGTAGTTGAATTAAGAAAAGGTGCCTACTTGGCAAGACATTTAGCATATT
TATGCAGCTTAGGAGAGATTTCCTCATATGGTCCTAGATTAGAAACTCTAACATCATTAGAAAGGTTAGAGGT
TCTTAAAAGCTACCTAGAGATATCTTGTTTAGAGGATCCAACATTGAGATACAGTCAGGTTACAGGGCTGGTA
TTAAAAGTGTTCCCATCAACAGTAGTATATATCAGGAAGTTAGCTATAAAGATGTTGAGGATTAGGGGCATAG
GGGTGCCAGAGGTGTTAGAAGACTGGGATCCCAGTCATGAACAAGCTCTACTAGATAATATAGCTCAAGAGAT -continued

```
CCTACATAATATCCCAATAAACCAATCTATCAAGACACCTTTCTGGGGGCTCAAAGTCAATAATTCCCAAGTC
TTACGTCTAAGGGGATATAAGGAGGTTAAGGATAGGAAATCAGGGCGATCAGGAGTAGGTCTAACACTTCCAT
GTGATAATAGGTACTTATCCCATCAGATAAGACTTTTCGGGATTAATAGTACTAGCTGCCTGAAAGCTTTGGA
GTTAACATATTTAATAGGACCATTGATAGATAAAAGTAAAGATAGATTATTCTTAGGGGAAGGTGCAGGTGCT
ATGTTGTCATGTTATGATGCAACGTTAGGACCTTCAATGAACTATTATAACTCAGGTGTCTCATCATATGATA
TAAATGGTCAGAGGGAATTAGGGATCTATCCATCTGAGGCTGCATTAGTGGCAAAGAAATTGAATAATGTAAC
TAATTTGGGTCAGAGAATTAAGGTGCTGTTCAACGGAAACCCTGGGTCTACATGGGTTGGCAACCAGGAATGC
GAAACATTAATTTGGAGTGAATTACAGGACAAATCAATCGGCTTGATACATTGTGACCTAGAAGGTGGAGAAC
TAAAAGATACACAAACAGTACTGCATGAACATTATAGCATAATTAGGATAGCATACTTAGTAGGAGATAACGA
TGTTTTATTAGTGACTAAAATTGCACCTAAATTGGGTACAGATTGGACTCAGCAACTATGCTTGTATCTAAGA
TATTGGAATGAAGTCAATTTAGTTGTTCTTAAGACATCTAATCCTTCTTCTACTGAGATGTATTTGTTATCAA
GGAATCCAAGTAAAGATGTGATTGAAGATAGTCTAACAGTAATCTCAGACCTAAAGCCATTGTCTAAAAAAGA
TAGTATACAATTAGAAAAGTGGATTTTGGTTGAGAAAGACAAAGTTAAGGAATGGCTAATTAAAGAATTAAGA
GAGGGAGAACTAATGTCAGGTTCACTTAGGCCTTATCACCAAGCACTTCAGATTTTTGGATTTGAGGCCAACT
TGCACAAATTGTGTAGAGACTTCTTATCAACTATGAGTATTTCAGATATCCAGATGTGTATAAATTCATTCTA
CAGAGTTTTAAAGGACACAATATTTGAGTGGAGTCGGGTAACAAATGATCATAAGACATGTAAACTCACAGGG
AAATATGAGTTATATCCTATAAGAGACAGTGGAAAGTTGAAAGTGATATCAAGAAGGCTTATAATATCCTGGA
TTGCTTTATCCATGTCTACTAGACTGTTAACAGGCGCTTTCCCTGATATTAAGTTTGAGTCCAGATTGAATAT
AGGTTTAGTCTCCTTATCTACGAATGAGATCAAATCACTTAAACTTATATCCAAGGCTACGGTGGATAGGTTT
CAAGAAGTGATTCACAGTGTATCCTACAGATTCTTGACTAAAGAAATTAAAATACTCATGAAGATACTTGGAG
CTGTTAAATTATTTGGTGCAAGACAGACTTATAACCATTTAGCTTTAACACCAGAACCTCTATCTGATATAGA
GGGATATTTAGATGATTAGCTCGAATATCAACAGTAAACAGCTAAGAATCATTAAGAAGACTATCTGGATCCA
GACCTAAATGAAAGAATAAGAAAAACTTATTTAAACAATCAAAGATCCAAGCAAAATGATATGTCTTAAACTC
TTGT
```

What is claimed is:

1. An immunogenic composition comprising an inactivated or live, attenuated porcine parainfluenza virus type 1 (PPIV-1), wherein said virus comprises an RNA nucleotide sequence that is at least 90%, 95%, 96%, 97%, 98%, 99%, or 99.5% identical to the DNA sequence set forth in SEQ ID NOs: 1, 14, or 15, and wherein the nucleotide sequence encodes one or more of the following proteins with one or more of the following amino acid substitutions:
 - a lysine at position 300 of phosphoprotein as determined by reference to SEQ ID NO: 5; or
 - an isoleucine at position 102, an aspartic acid at position 349, a threonine at position 406, or an isoleucine at position 460 of hemagglutinin-neuraminidase protein as determined by reference to SEQ ID NO: 11.

2. The immunogenic composition of claim 1, wherein said virus comprises an RNA nucleotide sequence that corresponds to the DNA sequence set forth in SEQ ID NOs: 1, 14 or 15.

3. The immunogenic composition of claim 1, wherein said virus is inactivated.

4. The immunogenic composition of claim 1, wherein said virus is a live, attenuated virus.

5. The immunogenic composition of claim 4, wherein said virus is attenuated by passaging in cell culture such that when the attenuated virus is administered to a swine it fails to cause clinical signs of PPIV-1 but is capable of inducing an immune response that immunizes the swine against pathogenic forms of PPIV-1.

6. The immunogenic composition of claim 1, wherein said virus comprises a substitution at one or more of the following positions:
 - position 898 of phosphoprotein gene as determined by reference to SEQ ID NO: 4;
 - position 129 of matrix protein gene as determined by reference to SEQ ID NO: 6; or
 - position 305, 729, 1045, 1217, or 1379 of hemagglutinin-neuraminidase gene as determined by reference to SEQ ID NO: 10.

7. The immunogenic composition of claim 4, wherein said virus comprises an RNA nucleotide sequence that corresponds to the DNA sequence set forth in SEQ ID NOs: 14 or 15.

8. The immunogenic composition of claim 1, further comprising a suitable pharmaceutical carrier.

9. The immunogenic composition of claim 8, wherein said suitable pharmaceutical carrier is selected from a diluent, adjuvant, antimicrobial agent, preservative, inactivating agent, or combinations thereof.

10. The immunogenic composition of claim 1, further comprising one or more non-PPIV-1 inactivated or attenuated pathogens or antigenic material thereof.

11. A method for inducing an immune response against porcine parainfluenza virus type 1 (PPIV-1) in swine comprising:
 - administering to a swine an immunogenic composition comprising an inactivated or live, attenuated porcine parainfluenza virus type 1 (PPIV-1), wherein said virus comprises an RNA nucleotide sequence that is at least 90%, 95%, 96%, 97%, 98%, 99%, or 99.5% identical to the DNA sequence set forth in SEQ ID NOs: 1, 14, or 15, and wherein the nucleotide sequence encodes one or more of the following proteins with one or more of the following amino acid substitutions:
 - a lysine at position 300 of phosphoprotein as determined by reference to SEQ ID NO: 5; or
 - an isoleucine at position 102, an aspartic acid at position 349, a threonine at position 406, or an isoleucine at position 460 of hemagglutinin-neuraminidase protein as determined by reference to SEQ ID NO: 11.

12. The method of claim 11, wherein said virus comprises an RNA nucleotide sequence that corresponds to the DNA sequence set forth in SEQ ID NOs: 14 or 15.

13. The method of claim 11, wherein said virus is inactivated.

14. The method of claim 11, wherein said virus is a live, attenuated virus.

15. The method of claim 14, wherein said virus is attenuated by passaging in cell culture such that when the attenuated virus is administered to a swine it fails to cause clinical signs of PPIV-1 but is capable of inducing an immune response that immunizes the swine against pathogenic forms of PPIV-1.

16. The method of claim 11, wherein said virus comprises a substitution at one or more of the following positions:
 - position 898 of phosphoprotein gene as determined by reference to SEQ ID NO: 4;
 - position 129 of matrix protein gene as determined by reference to SEQ ID NO: 6; or
 - position 305, 729, 1045, 1217, or 1379 of hemagglutinin-neuraminidase gene as determined by reference to SEQ ID NO: 10.

17. The method of claim 14, wherein said virus comprises an RNA nucleotide sequence that corresponds to the DNA sequence set forth in SEQ ID NOs: 14 or 15.

18. The method of claim 11, wherein said immunogenic composition further comprises a suitable pharmaceutical carrier.

19. The method of claim 18, wherein said suitable pharmaceutical carrier is selected from a diluent, adjuvant, antimicrobial agent, preservative, inactivating agent, or combinations thereof.

20. The method of claim 11, wherein said immunogenic composition further comprises one or more non-PPIV-1 inactivated or attenuated pathogens or antigenic material thereof.

21. The method of claim 11, wherein said swine include any of sows, gilts, boars, hogs, and piglets.

22. An isolated porcine parainfluenza virus type 1 (PPIV-1), wherein said virus comprises an RNA nucleotide sequence that is at least 95% identical to the DNA nucleotide sequence set forth in SEQ ID NO: 15, and that encodes one or more of the following amino acid substitutions:
(a) a lysine at position 300 of phosphoprotein as determined by reference to SEQ ID NO: 5;
(b) an isoleucine at position 102 of hemagglutinin-neuraminidase protein as determined by reference to SEQ ID NO: 11;
(c) an aspartic acid at position 349 of hemagglutinin-neuraminidase protein as determined by reference to SEQ ID NO: 11;
(d) a threonine at position 406 of hemagglutinin-neuraminidase protein as determined by reference to SEQ ID NO: 11; and/or
(e) an isoleucine at position 460 of hemagglutinin-neuraminidase protein as determined by reference to SEQ ID NO: 11.

23. The virus of claim 22, wherein said virus comprises an RNA nucleotide sequence that is at least 98% identical to the DNA nucleotide sequence set forth in SEQ ID NO: 13.

24. The virus of claim 22, wherein said virus comprises an RNA nucleotide sequence that is at least 99% identical to the DNA nucleotide sequence set forth in SEQ ID NO: 15.

25. The virus of claim 22, wherein said virus comprises an RNA nucleotide sequence that is at least 99.5% identical to the DNA nucleotide sequence set forth in SEQ ID NO: 15.

26. A vaccine composition comprising an inactivated or live, attenuated porcine parainfluenza virus type 1 (PPIV-1) and a suitable pharmaceutical carrier, wherein said virus comprises an RNA nucleotide sequence that is at least 90%, 95%, 96%, 97%, 98%, 99%, or 99.5% identical to the DNA sequence set forth in SEQ ID NOs: 1, 14, or 15, and
wherein the nucleotide sequence encodes one or more of the following proteins with one or more of the following amino acid substitutions:
a lysine at position 300 of phosphoprotein as determined by reference to SEQ ID NO: 5; or
an isoleucine at position 102, an aspartic acid at position 349, a threonine at position 406, or an isoleucine at position 460 of hemagglutinin-neuraminidase protein as determined by reference to SEQ ID NO: 11.

27. The vaccine composition of claim 26, wherein said virus comprises an RNA nucleotide sequence that corresponds to the DNA sequence set forth in SEQ ID NOs: 14 or 15.

28. The vaccine composition of claim 26, wherein said virus is inactivated.

29. The vaccine composition of claim 26, wherein said virus is a live, attenuated virus.

30. The vaccine composition of claim 29, wherein said virus is attenuated by passaging in cell culture such that when the attenuated virus is administered to a swine it fails to cause clinical signs of PPIV-1 but is capable of inducing an immune response that immunizes the swine against pathogenic forms of PPIV-1.

31. The vaccine composition of claim 26, wherein said suitable pharmaceutical carrier is selected from a diluent, adjuvant, antimicrobial agent, preservative, inactivating agent, or combinations thereof.

32. The vaccine composition of claim 26, wherein said suitable pharmaceutical carrier is a diluent.

33. The vaccine composition of claim 26, further comprising an adjuvant.

34. The vaccine composition of claim 26, further comprising one or more non-PPIV-1 inactivated or attenuated pathogens or antigenic material thereof.

35. The vaccine composition of claim 26, wherein said vaccine is effective in a single dose program.

36. The vaccine composition of claim 26, wherein said vaccine is effective in a two-dose program.

37. A vaccine composition comprising an attenuated strain of porcine parainfluenza virus type 1 (PPIV-1) and a suitable pharmaceutical carrier, wherein said strain of PPIV-1 comprises a nucleic acid sequence that is at least 95% identical to SEQ ID NO: 15, and that encodes one or more of the following amino acid substitutions:
(a) a lysine at position 300 of phosphoprotein as determined by reference to SEQ ID NO: 5;
(b) an isoleucine at position 102 of hemagglutinin-neuraminidase protein as determined by reference to SEQ ID NO: 11;
(c) an aspartic acid at position 349 of hemagglutinin-neuraminidase protein as determined by reference to SEQ ID NO: 11;
(d) a threonine at position 406 of hemagglutinin-neuraminidase protein as determined by reference to SEQ ID NO: 11; and/or
(e) an isoleucine at position 460 of hemagglutinin-neuraminidase protein as determined by reference to SEQ ID NO: 11.

38. A method of treating or preventing disease caused by porcine parainfluenza virus type 1 (PPIV-1) comprising:
administering an effective amount of the vaccine composition of claim 26 to a swine in need thereof.

39. The method of claim 38, wherein said swine include any of sows, gilts, boars, hogs, and piglets.

40. A method of preparing a live, attenuated porcine parainfluenza virus type 1 (PPIV-1) comprising:
passaging a virus in cell culture, wherein said virus comprises an RNA nucleotide sequence that is at least 90%, 95%, 96%, 97%, 98%, 99%, or 99.5% identical to the DNA sequence set forth in SEQ ID NOs: 1, 14, or 15, and wherein the nucleotide sequence encodes one or more of the following proteins with one or more of the following amino acid substitutions:
a lysine at position 300 of phosphoprotein as determined by reference to SEQ ID NO: 5; or
an isoleucine at position 102, an aspartic acid at position 349, a threonine at position 406, or an isoleucine at position 460 of hemagglutinin-neuraminidase protein as determined by reference to SEQ ID NO: 11.

41. The method of claim 40, wherein the virus is passaged such that the virus fails to cause clinical signs of PPIV-1 when administered to a swine but is capable of inducing an immune response that immunizes the swine against pathogenic forms of PPIV-1.

42. The method of claim 40, wherein the virus is passaged in LLC-MK2 cells.

43. A method for determining if a population of swine is in need of vaccination against porcine parainfluenza virus type 1 (PPIV-1) infection:
collecting a biological sample from one or more swine of said population; and
detecting the presence of said virus in said biological sample, wherein said virus comprises an RNA nucleotide sequence that is at least 90%, 95%, 96%, 97%, 98%, 99%, or 99.5% identical to the DNA sequence set forth in SEQ ID NO: 1, and administering the vaccine composition of claim 26 to said population if the virus is detected.

44. The method of claim 43, wherein said detecting is accomplished by polymerase chain reaction.

45. The method of claim 43, wherein said detecting is accomplished by immunohistochemistry.

* * * * *